United States Patent [19]

Lay et al.

[11] Patent Number: 5,095,054

[45] Date of Patent: Mar. 10, 1992

[54] POLYMER COMPOSITIONS CONTAINING DESTRUCTURIZED STARCH

[75] Inventors: Gustav Lay, Bad Bellingen; Johannes Rehm, Bad Krozingen, both of Fed. Rep. of Germany; Robert F. Stepto, Cheshire, United Kingdom; Markus Thoma, Reihen; Jean-Pierre Sachetto, Arlesheim, both of Switzerland; David J. Lentz, Randolph, N.J.; Jakob Silbiger, Basel, Switzerland

[73] Assignee: Warner-Lambert Company, Morris Plains, N.J.

[21] Appl. No.: 539,846

[22] Filed: Jun. 18, 1990

Related U.S. Application Data

[63] Continuation-in-part of Ser. No. 431,715, Oct. 2, 1989, abandoned, and Ser. No. 430,764, Oct. 2, 1989, abandoned, and Ser. No. 431,672, Oct. 2, 1989, abandoned, and Ser. No. 449,313, Dec. 8, 1989, abandoned, and Ser. No. 447,741, Dec. 8, 1989, abandoned, and Ser. No. 440,955, Dec. 22, 1989, abandoned, and Ser. No. 447,979, Dec. 8, 1989, abandoned, and Ser. No. 449,095, Dec. 8, 1989, abandoned, and Ser. No. 447,747, Dec. 8, 1989, abandoned, and Ser. No. 449,314, Dec. 8, 1989, abandoned, and Ser. No. 443,791, Oct. 22, 1989, abandoned, and Ser. No. 447,730, Dec. 8, 1989, abandoned, and Ser. No. 298,603, Jan. 18, 1989, abandoned, said Ser. No. 431,715, is a continuation-in-part of Ser. No. 368,486, Jun. 19, 1989, abandoned, said Ser. No. 430,764, is a continuation-in-part of Ser. No. 369,978, Jun. 22, 1989, abandoned, said Ser. No. 431,672, is a continuation-in-part of Ser. No. 369,983, Jun. 22, 1989, abandoned, said Ser. No. 449,313, is a continuation-in-part of Ser. No. 407,643, Jul. 18, 1989, abandoned, said Ser. No. 447,741, is a continuation-in-part of Ser. No. 376,057, Jul. 6, 1989, abandoned, said Ser. No. 440,955, is a continuation-in-part of Ser. No. 378,120, Jul. 11, 1989, abandoned, said Ser. No. 447,979, is a continuation-in-part of Ser. No. 377,981, Jul. 11, 1989, said Ser. No. 447,747, is a continuation-in-part of Ser. No. 381,620, Jul. 18, 1989, abandoned, said Ser. No. 449,314, is a continuation-in-part of Ser. No. 407,644, Jul. 18, 1989, abandoned, said Ser. No. 443,791, is a continuation-in-part of Ser. No. 382,870, Jul. 20, 1989, abandoned.

[30] Foreign Application Priority Data

Feb. 3, 1988 [GB] United Kingdom ................. 8802313

[51] Int. Cl.⁵ ..................... C08L 89/06; C08L 101/00; C09H 9/02; B29C 45/00
[52] U.S. Cl. ........................................ 524/47; 524/52; 524/53; 264/328.14; 424/451; 427/2
[58] Field of Search ............................. 524/47, 52, 53; 264/328.14; 424/451; 427/2

[56] References Cited

U.S. PATENT DOCUMENTS 2,676,929 4/1954 Duddly .................................. 524/47
3,081,183 3/1963 Roscelli et al. ...................... 106/197

(List continued on next page.)

FOREIGN PATENT DOCUMENTS 0304401 2/1969 European Pat. Off. .
A0032802 7/1981 European Pat. Off. .

(List continued on next page.)

OTHER PUBLICATIONS

Ind. Eng. Chem. Res., vol. 26, 1987, pp. 1659-63.
Ing. Eng. Chem. Prod. Res. Dev., vol. 23, 1984, pp. 594-95.

(List continued on next page.)

Primary Examiner—Nathan M. Nutter
Attorney, Agent, or Firm—Daniel A. Scola, Jr.

[57] ABSTRACT

A thermoplastic polymer composition comprising:

(a) a destructurized starch, and either (b) an effective amount of at least one compound selected from the following: (1) a polymer which contains at least two different types of functional groups, one of said types of these groups being hydroxyl groups; (2) at least one polymer which does not contain hydroxyl groups and is selected from the group consisting of polymers which contain at least two types of functional groups bound to the same molecule one type of these groups being carboxylate groups; (3) at least one polymer selected from the group consisting of polymers which contain tertiary amino groups and/or salts thereof and/or quaternary ammonium groups; (4) at least one polymer selected from the group of polysaccharides which have been chemically modified to contain added hydroxyalkyl groups and/or contain alkyl ether groups, and/or contain ester groups; (5) at least one compound selected from the group consisting of copolymers of vinyl pyrrolidone; (6) at least one compound selected from the group consisting of cationically modified polysaccharides; (7) at least one compound selected from the group consisting of anionically modified polysaccharides; (8) at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group; (9) at least one compound selected from the group consisting of polysaccharide graft copolymers and graft copolymers of polysaccharide derivatives; (10) at least one compound selected from the group consisting of polyalkyleneimine polymers and polyalkyleneimine copolymers; (11) at least one compound selected from the group consisting of styrene sulfonic acid polymers, styrene sulfonic acid copolymers, and salts thereof; and (12) at least one compound selected from the group consisting of polymers and copolymers which contain carboxylic groups which partially or wholly are present in the form of their salts and wherein said polymers or copolymers do not contain further functional groups; or (c) At least one substantially water-insoluble thermoplastic polymer. combinations of (a), (b) and (c) are also disclosed.

868 Claims, 4 Drawing Sheets

U.S. PATENT DOCUMENTS

| | | | |
|---|---|---|---|
| 3,165,508 | 1/1965 | Otey et al. | 536/111 |
| 3,243,308 | 3/1966 | Barger et al. | 106/213 |
| 3,320,118 | 5/1967 | Black | 524/47 |
| 3,436,309 | 4/1969 | Ottinger et al. | 536/111 |
| 3,467,647 | 9/1969 | Bennings | 260/207 |
| 3,485,777 | 12/1969 | Gaylor | 524/47 |
| 3,524,827 | 9/1970 | Johnson et al. | 524/47 |
| 3,611,733 | 10/1971 | Eilers et al. | 61/36 R |
| 3,652,542 | 3/1972 | Hjermstad et al. | 524/47 |
| 3,865,603 | 2/1975 | Szymanski et al. | 106/130 |
| 3,892,905 | 7/1975 | Albert | 428/220 |
| 3,949,145 | 4/1976 | Otey et al. | 428/423 |
| 3,976,605 | 8/1976 | Matsunaga et al. | 524/13 |
| 3,976,608 | 8/1976 | Buckler et al. | 524/47 |
| 4,016,117 | 4/1977 | Griffin | 524/47 |
| 4,021,260 | 5/1977 | Crill | 106/213 |
| 4,021,388 | 5/1977 | Griffin | 524/47 |
| 4,045,388 | 8/1977 | Matsunaga et al. | 524/47 |
| 4,076,846 | 2/1978 | Nakatsuka et al. | 426/62 |
| 4,133,784 | 1/1979 | Otey et al. | 524/47 |
| 4,156,073 | 5/1979 | Login | 528/295 |
| 4,218,350 | 8/1980 | Griffin | 524/47 |
| 4,329,181 | 5/1982 | Chiu et al. | 106/213 |
| 4,337,181 | 6/1982 | Otey et al. | 523/128 |
| 4,339,364 | 7/1982 | Krankkala | 524/44 |
| 4,393,202 | 7/1983 | Breuninger | 536/102 |
| 4,446,261 | 5/1984 | Yamasaki et al. | 524/40 |
| 4,454,268 | 6/1984 | Otey et al. | 524/47 |
| 4,483,950 | 11/1984 | Fanta et al. | 524/48 |
| 4,492,714 | 1/1985 | Cooper et al. | 426/602 |
| 4,529,539 | 7/1985 | Monma et al. | 252/518 |
| 4,547,540 | 10/1985 | Yeoman | 524/130 |
| 4,600,440 | 7/1986 | Guevarra et al. | 106/211 |
| 4,663,159 | 5/1987 | Brode, II et al. | 424/70 |
| 4,673,438 | 6/1987 | Wittwer et al. | 106/126 |
| 4,873,270 | 10/1989 | Aime | 524/35 |
| 4,900,361 | 2/1990 | Sachetto et al. | 106/213 |
| 4,952,402 | 8/1990 | Sparks et al. | 424/419 |

FOREIGN PATENT DOCUMENTS

| | | |
|---|---|---|
| A0087847 | 9/1983 | European Pat. Off. |
| A0132299 | 1/1985 | European Pat. Off. |
| 0045621 | 10/1985 | European Pat. Off. |
| A0253490 | 1/1988 | European Pat. Off. |
| 0298920 | 1/1989 | European Pat. Off. |
| 0301542 | 2/1989 | European Pat. Off. |
| A0327505 | 8/1989 | European Pat. Off. |
| A0344118 | 11/1989 | European Pat. Off. |
| A0400532 | 5/1990 | European Pat. Off. |
| A0739630 | 9/1943 | Fed. Rep. of Germany |
| A1470846 | 2/1696 | Fed. Rep. of Germany |
| A1314474 | 12/1962 | France |
| A2617857 | 1/1989 | France |
| 53-049190A | 5/1978 | Japan |
| 57305 | 8/1988 | Japan |
| 63-304061A | 12/1988 | Japan |
| A0422323 | 4/1967 | Switzerland |
| A1055648 | 1/1967 | United Kingdom |
| 1247474 | 9/1971 | United Kingdom |
| A2009762 | 1/1979 | United Kingdom |
| 2029836B | 3/1980 | United Kingdom |
| 1600496 | 10/1981 | United Kingdom |
| A2091276 | 7/1982 | United Kingdom |
| A2190093 | 11/1987 | United Kingdom |
| 2205102A | 11/1988 | United Kingdom |
| 2214920 | 9/1989 | United Kingdom |
| 2220944A | 1/1990 | United Kingdom |
| A8500176 | 1/1985 | World Int. Prop. O. |
| 89/10381 | 11/1989 | World Int. Prop. O. |

OTHER PUBLICATIONS

Menglin et al., Polymeric Materials Science & Engr.; No. 4:47–52 (1988), and Applicant's Translation thereof.

Plastics Design & Processing 18(3):50–54 (1978).

Swanson et al., Proceedings, Corn Utilization Conference II, pp. 1–24; Aug. 16, 1988.

Fanta et al., J. Appl. Polymer Sci. 40:811–21 (1990).

Roper et al.; Starke 42N.4 S123–130 (1990).

Griffin, G.; Possible Solutions to Disposal Problems, Held Oct. 18, 1989.

Fanta et al.; Amer. Chem. Soc. 29(2):453–54 (1988).

Res. Disclosure; Abstract No. 19800, Feb. 1980.

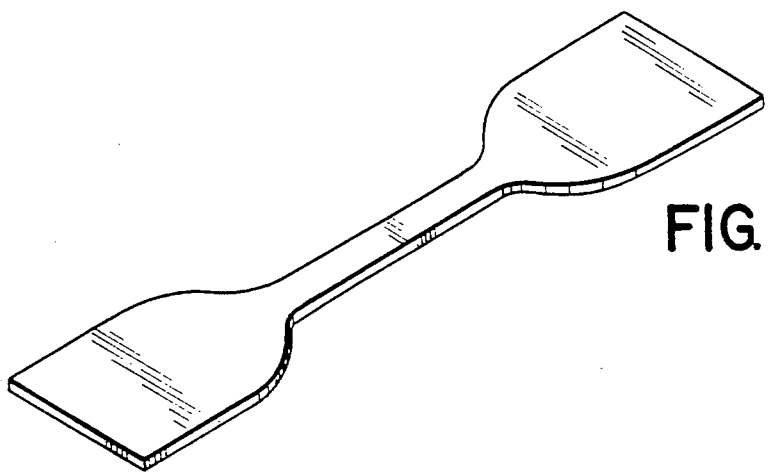
FIG. 1.1
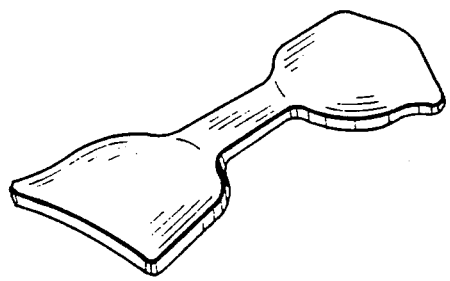
FIG. 1.2
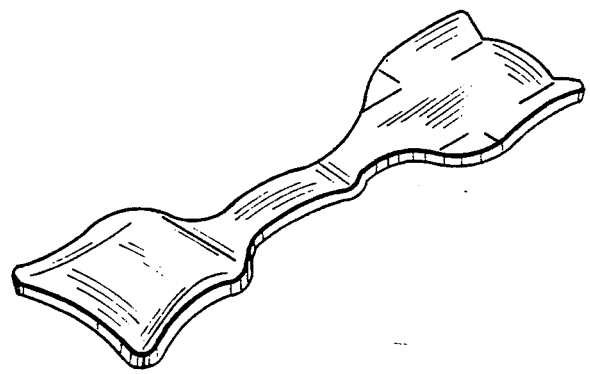
FIG. 1.3
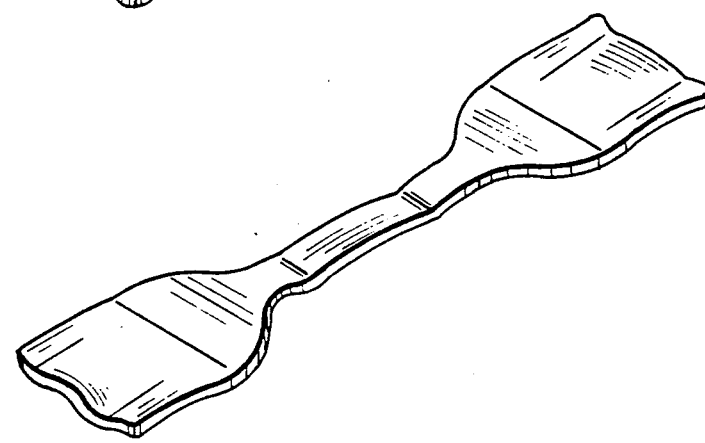
FIG. 1.4

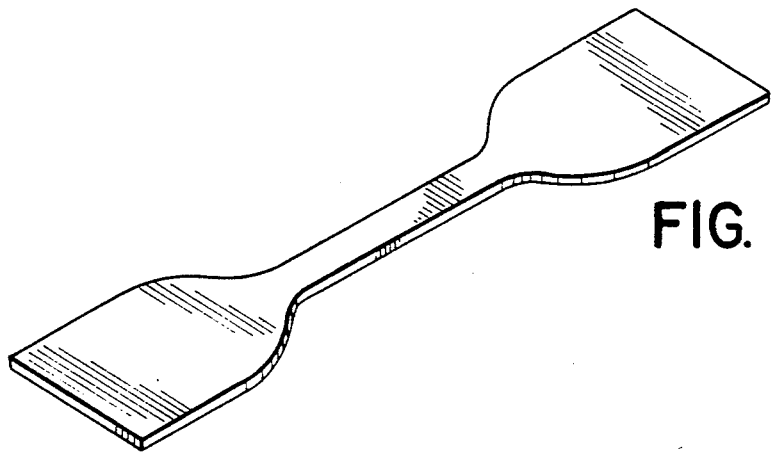
FIG. 2.1
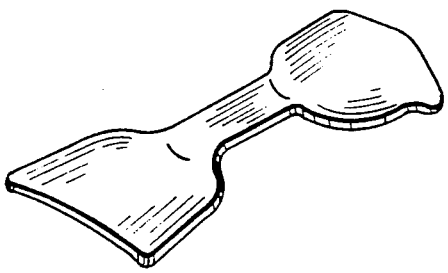
FIG. 2.2
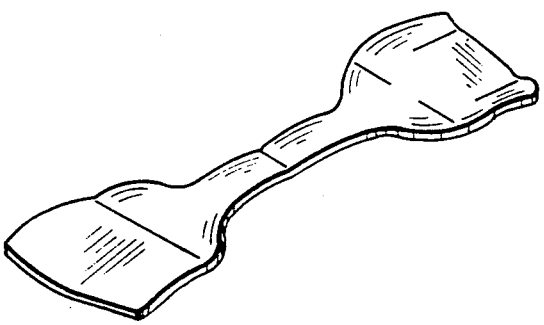
FIG. 2.3
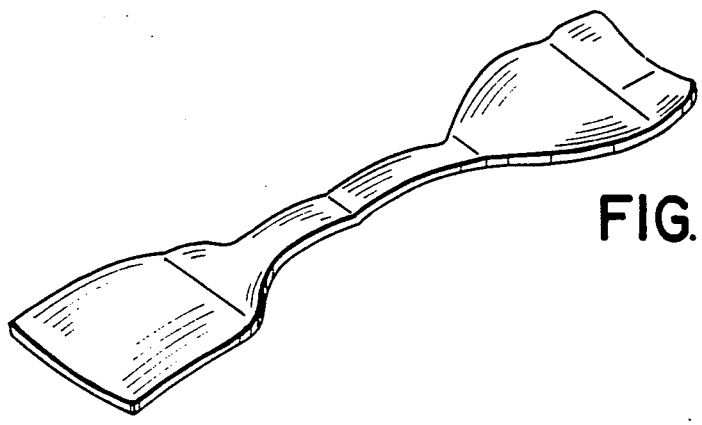
FIG. 2.4

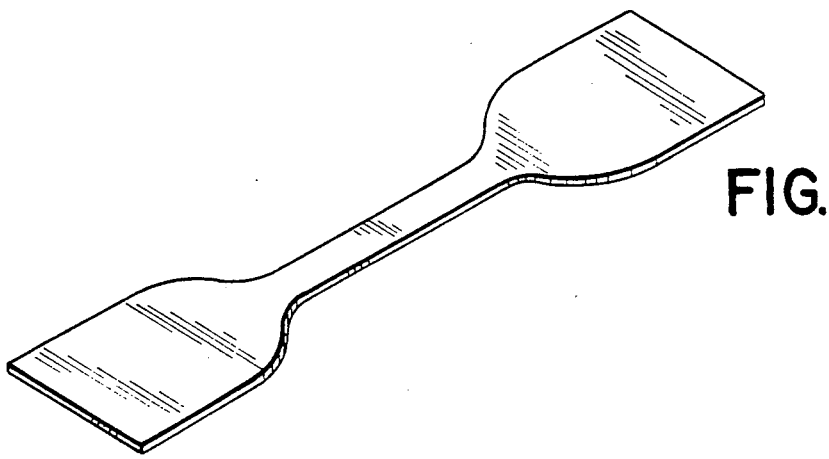
FIG. 3.1
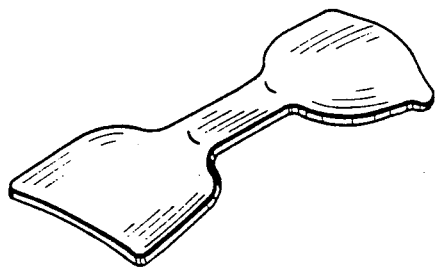
FIG. 3.2
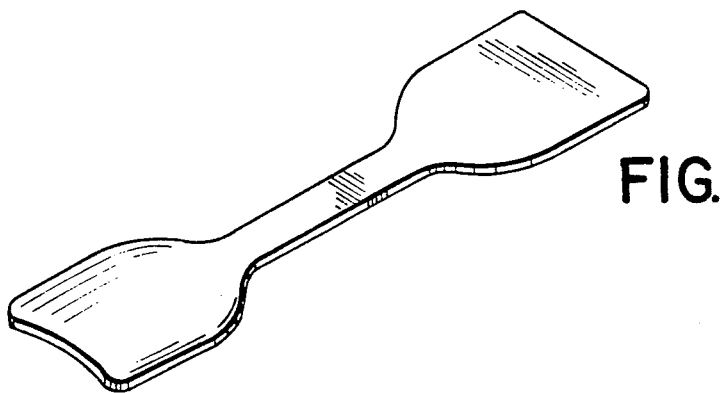
FIG. 3.3
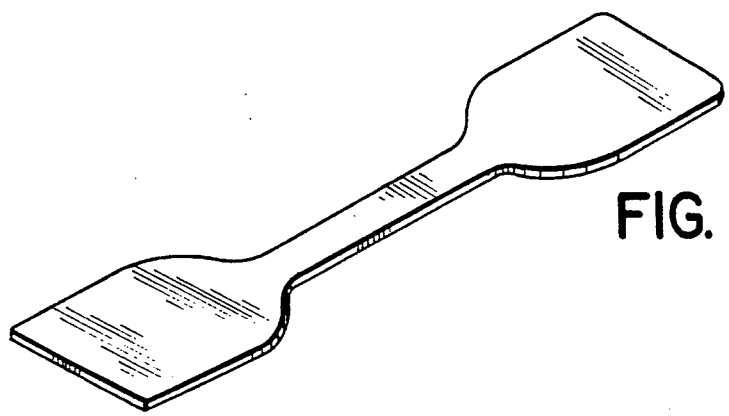
FIG. 3.4

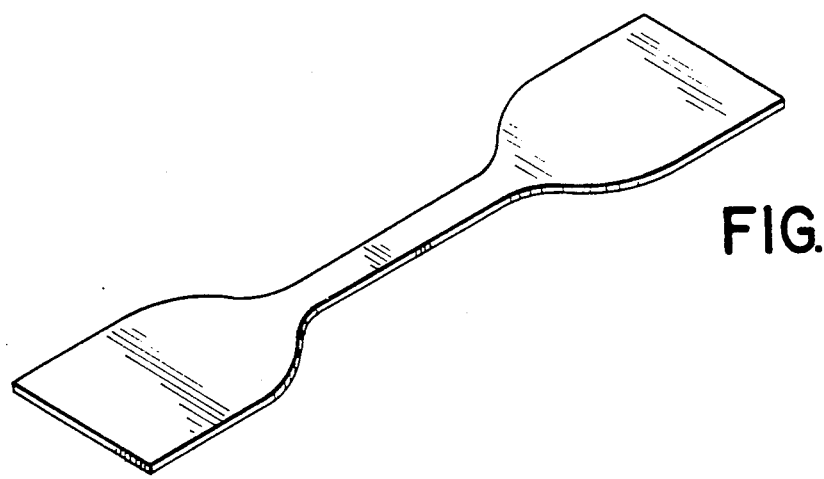
FIG. 4.1
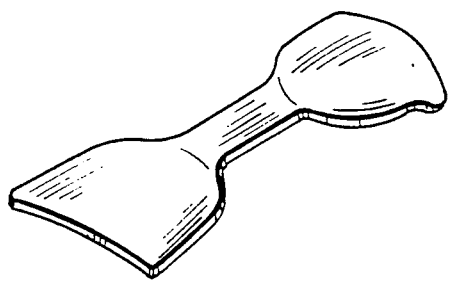
FIG. 4.2
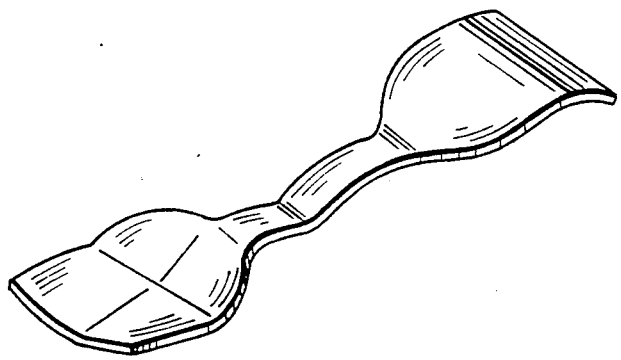
FIG. 4.3
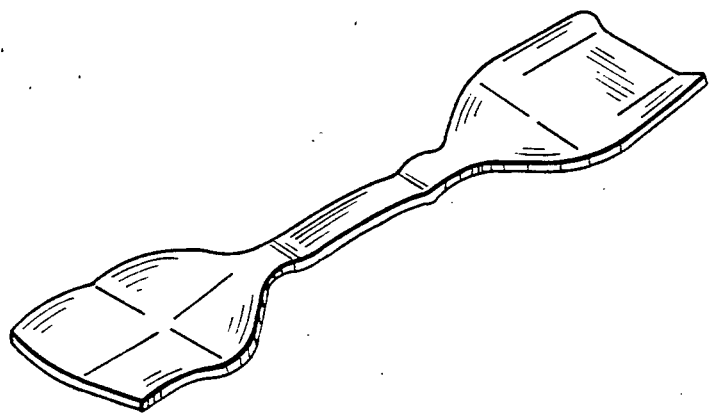
FIG. 4.4

POLYMER COMPOSITIONS CONTAINING DESTRUCTURIZED STARCH

REFERENCE TO RELATED APPLICATIONS

This application is a continuation-in-part of each of the following applications, now abandoned: (1) Ser. No. 431,715 filed Oct. 2, 1989, which in turn is a continuation-in-part of Ser. No. 368,486 filed June 19, 1989; (2) Ser. No. 430,764 filed Oct. 2, 1989, which in turn is a continuation-in-part of Ser. No. 369,978 filed June 22, 1989; (3) Ser. No. 431,672 filed Oct. 2, 1989, which in turn is a continuation-in-part of Ser. No. 369,983 filed June 22, 1989; (4) Ser. No. 449,313 filed Dec. 8, 1989, which in turn is a continuation-in-part of Ser. No. 407,643 filed July 18, 1989; (5) Ser. No. 447,741 filed Dec. 8, 1989, which in turn is a continuation-in-part of Ser. No. 376,057 filed July 6, 1989; (6) Ser. No. 440,955 filed Dec. 22, 1989, which in turn is a continuation-in-part of Ser. No. 378,120 filed July 11, 1989; (7) Ser. No. 447,979 filed Dec. 8, 1989, which in turn is a continuation-in-part of Ser. No. 377,981 filed July 11, 1989; (8) Ser. No. 449,095 filed Dec. 8, 1989, which in turn is a continuation-in-part of Ser. No. 378,536 filed July 11, 1989; (9) Ser. No. 447,747 filed Dec. 8, 1989, which in turn is a continuation-in-part of Ser. No. 381,620 filed July 18, 1989; (10) Ser. No. 449,314 filed Dec. 8, 1989, which in turn is a continuation-in-part of Ser. No. 407,644 filed July 18, 1989; (11) Ser. No. 443,791 filed Oct. 22, 1989, which in turn is a continuation-in-part of Ser. No. 382,870 filed July 20, 1989; (12) Ser. No. 447,730 filed Dec. 8, 1989, which in turn is a continuation-in-part of Ser. No. 382,869 filed July 20, 1989; and Ser. No. 298,603 filed Jan. 18, 1989 which is based on United Kingdom Application No. 8802313, filed Feb. 3, 1988. All of these applications are hereby incorporated by reference herein.

FIELD OF THE INVENTION

The present invention relates to polymer compositions capable of being formed by heat and pressure into articles having dimensional stability and enhanced physical properties, and to pre-mixes useful for preparing these compositions. These compositions and pre-mixes comprise destructurized starch and other polymers as described herein.

BACKGROUND OF THE INVENTION

It is known that natural starch found in vegetable products that contains a defined amount of water can be treated at an elevated temperature and in a closed volume, thereby at elevated pressures, to form a melt. The process is conveniently carried out in an injection molding machine or extruder. The starch is fed through the hopper onto a rotating, reciprocating screw. The feed material moves along the screw towards the tip. During this process, the temperature of the material is increased by means of external heaters around the outside of the barrel and by the shearing action of the screw. Starting in the feed zone and continuing in the compression zone, the particulate feed becomes gradually molten. It is then conveyed through the metering zone, where homogenization of the melt occurs, and then to the end of the screw. The molten material at the tip can then be treated further by injection molding or extrusion or any other known technique to treat thermoplastic melts, to obtain shaped articles.

This treatment, which is described in U.S. Pat. No. 4,673,438, which patent is incorporated herein by reference, yields a substantially destructurized starch. As described in the above-mentioned patent, the reason for the destructurizing is that the starch is heated above the glass transition and the melting temperatures of its components. As a consequence, a melting and disordering of the molecular structure of the starch granules takes place, so that a substantially destructurized starch is obtained. The expression "destructurized starch" defines starch obtained by such thermoplastic melt formation. Reference is also made to U.S. patent application Ser. No. 209,151, filed June 20, 1988, now U.S. Pat. No. 4,900,361, Ser. No. 209,402, filed June 20, 1988 and now abandoned and Ser. No. 278,116, filed Nov. 30, 1988 and now abandoned, which further describe destructurized starch, methods for making it, and uses of it. These applications are also incorporated herein by reference.

It is preferred that the destructurized starch used in the present invention has been heated to a high enough temperature and for a time long enough so that the specific endothermic transition analysis as represented by a differential scanning calorimetry (DSC) curve indicates that a specific relatively narrow peak just prior to oxidative and thermal degradation has disappeared, as described in the above-mentioned application Ser. No. 278,116.

Destructurized starch is a new and useful material for many applications. An important property is its biodegradability. In humid air, however, destructurized starch takes up water from the air, thereby increasing its moisture content. As a consequence, a shaped article made from destructurized starch may lose its dimensional stability under such conditions. On the other hand, such an article may dry out in low humidity and become brittle.

Thermoplastic starch has a unique set of properties and, while these properties make destructurized starch very useful, these same properties may limit the utility of destructurized starch in cases where a softer, more resilient or a harder, tougher polymer is desired.

Thermoplastic starch, as mentioned, can be extruded and molded into numerous useful shapes, profiles and products. However, the processing parameters such as water content, temperature, and pressure must be narrowly controlled to achieve reproducible quality products. This is a further disadvantage for many commercial applications.

To overcome these potential limitations, it would be useful to increase the dimensional stability over a wide humidity range; to increase the toughness (measured as break energy); to increase the elasticity (measured as elongation); to decrease polymer stiffness (measured as Young's modulus) and to increase the hardness.

By broadening the processing latitude it is possible to increase the variety of shapes and composites that can be made on a commercial basis and to decrease the need for close controls. It would therefore also be useful to improve the control of the melt strength, e.g. increasing the processing latitude for extruding, injection molding, film blowing or fiber drawing and to control surface tack and adhesion to other substrates.

Conventional thermoplastic materials are hydrophobic, substantially water-insoluble polymers that are conventionally processed in the absence of water and volatile materials. Starch, on the other hand, forms a melt in the presence of water but decomposes at elevated temperature. i.e. around 240° C. Therefore, it was expected, in view of its hydrophilic nature and chemical structure that such a starch melt would not be useful as a thermoplastic component together with hydrophobic, substantially water-insoluble polymeric materials.

It has now been found that starch, when heated in a closed volume at proper moisture and temperature conditions as described above to form a melt of destructurized starch, is substantially compatible in its processing with melts formed by hydrophobic substantially water-insoluble thermoplastic polymers and that the two types of molten materials show an interesting combination of properties, especially after the melt has solidified.

One very important aspect is the surprisingly improved dimensional stability of such destructurized starch blended with such hydrophobic thermoplastic materials. For example, by blending destructurized starch with merely 1% by weight of a thermoplastic synthetic polymer (component (c)), without the use of component (b), a shrinkage of less than 4% is observed after two days in shaped articles such as long, narrow rods. This is to be compared to a shrinkage of up to 40% in length when such articles are comprised only of destructurized starch and are exposed to humidity in the air. Shrinkage in these instances may occur within a few hours. Such polymer compositions are described in copending U.S. patent application Ser. No. 298,603, filed Jan. 18, 1989.

Although articles made from such compositions, components (a) and (c) admixed, possess better dimensional stability than those made from destructurized starch alone (component (a)), the physical properties of the therein-described compositions, while useful for certain important applications, are not as good as might be desired for other end uses. In particular, it is important that articles made from destructurized starch compositions retain sufficient strength and dimensional stability to perform their desired functions while still being biodegradable after disposal.

It has now been found that articles made from such destructurized starch blended with specific hydrophobic thermoplastic materials as described herein show a surprising increase in all or a part of their physical properties and behavior of their melts and overcome the limitations explained above. Moreover, and surprisingly, many of the blends described herein show a significantly improved dimensional stability in humid air compared with non-blended destructurized starch while retaining a surprisingly high degree of disintegration in contact with liquid water, which in consequence leads to a high degree of biodegradability.

SUMMARY OF THE INVENTION

The present invention has several embodiments that solve the difficulties set out above.

A first embodiment of the invention comprises: (a) destructurized starch, (b) at least one polymer which contains at least two different types of functional groups, one of said types being hydroxyl groups (referred to herein as "component b-1"), and, optionally, (c) a substantially water-insoluble polymer different from those defined as component b-1. In one aspect, the present invention relates to a composition comprising destructurized starch and component b-1. This composition is useful itself for making finished articles, but it is primarily useful as a "pre-mix" for combining with a substantially water-insoluble polymer. In a second aspect, the first embodiment of the invention comprises the ternary composition of: destructurized starch, component b-1, and at least one substantially water-insoluble polymer (component (c)). These compositions may be in the form of powdery mixtures of the components, melts, or solid forms. The invention also includes methods for making and using both above-described compositions and shaped articles made therefrom.

In a second embodiment of the invention, it has been found useful to make polymer compositions comprising: (a) destructurized starch, (b) at least one polymer which does not contain hydroxyl groups and is selected from the group consisting of polymers which contain at least two types of functional groups bound to the same molecule one type of these groups being carboxylate groups (referred to herein as "component b-2"), and optionally (c) a substantially water-insoluble polymer different from those defined as component b-2. In one aspect, the present invention relates to a composition comprising destructurized starch and component b-2. This composition is useful itself for making finished articles, but it is primarily useful as a "pre-mix" for combining with a substantially water-insoluble polymer. In a second aspect, the invention comprises the ternary composition of destructurized starch, component b-2, and at least one substantially water-insoluble polymer (component (c)). These compositions may be in the form of powdery mixtures of the components, melts, or solid forms. The invention also includes methods for making and using both above-described compositions and shaped articles made therefrom.

In a third embodiment of the invention, it has been found useful to make polymer compositions comprising: (a) destructurized starch, (b) at least one polymer selected from the group consisting of polymers which contain tertiary amino groups and/or salts thereof and/or quaternary ammonium groups (referred to herein as "component b-3"), and optionally (c) a substantially water-insoluble polymer different from those defined as component b-3. In one aspect, the present invention relates to a composition comprising destructurized starch and component b-3. This composition is useful itself for making finished articles, but it is primarily useful as a "pre-mix" for combining with a substantially water-insoluble polymer. In a second aspect, the third embodiment of the invention comprises the ternary composition of destructurized starch, component b-3, and at least one substantially water-insoluble polymer (component (c)). These compositions may be in the form of powdery mixtures of the components, melts, or solid forms. The invention also includes methods for making and using both above described compositions and shaped articles made therefrom.

In a fourth embodiment of the invention, it has been found useful to make polymer compositions comprising: (a) destructurized starch, (b) at least one polymer selected from the group of polysaccharides which have been chemically modified to contain added hydroxyalkyl groups and/or contain alkyl ether groups, and/or contain ester groups (referred to herein as "component b-4"), and, optionally, (c) a substantially water-insoluble polymer different from those defined as component b-4. In one aspect, the present invention relates to a composition comprising destructurized starch and component b-4. This composition is useful itself for making finished articles, but it is primarily useful as a "pre-mix" for combining with a substantially water-insoluble polymer. In a second aspect, the invention comprises the ternary composition of destructurized starch, component b-4, and at least one substantially water-insoluble polymer (component (c)). These compositions may be in the form of powdery mixtures of the components, melts, or solid forms. The invention also includes methods for making and using both above-described compositions and shaped articles made therefrom.

In a fifth embodiment of the invention, it has been found useful to make polymer compositions comprising: (a) destructurized starch, (b) at least one compound selected from the group consisting of copolymers of vinyl pyrrolidone (referred to herein as "component b-5"), and optionally (c) a substantially water-insoluble polymer different from those defined as component b-5. In one aspect, the present invention relates to a composition comprising destructurized starch and component b-5. This composition is useful itself for making finished articles, but it is primarily useful as a "pre-mix" for combining with a substantially water-insoluble polymer. In a second aspect, the invention comprises the ternary composition of destructurized starch, component b-5, and at least one substantially water-insoluble polymer (component (c)). These compositions may be in the form of powdery mixtures of the components, melts, or solid forms. The invention also includes methods for making and using both above-described compositions and shaped articles made therefrom.

In a sixth embodiment of the invention, it has been found useful to make polymer compositions comprising: (a) destructurized starch, (b) at least one compound selected from the group consisting of cationically modified polysaccharides (referred to herein as "component b-6"), and, optionally, (c) a substantially water-insoluble polymer different from those defined as component b-6. In one aspect, the present invention relates to a composition comprising destructurized starch and component b-6. This composition is useful itself for making finished articles, but it is primarily useful as a "pre-mix" for combining with a substantially water-insoluble polymer. In a second aspect, the invention comprises the ternary composition of destructurized starch, component b-6, and at least one substantially water-insoluble polymer (component (c)). These compositions may be in the form of powdery mixtures of the components, melts, or solid forms. The invention also includes methods for making and using both above described compositions and shaped articles made therefrom.

In a seventh embodiment of the invention, it has been found useful to make polymer compositions comprising: (a) destructurized starch, (b) at least one compound selected from the group consisting of anionically modified polysaccharides (referred to herein as "component b-7"), and optionally (c) a substantially water-insoluble polymer different from those defined as component b-7. In one aspect, the present invention relates to a composition comprising destructurized starch and component b-7. This composition is useful itself for making finished articles, but it is primarily useful as a "pre-mix" for combining with the substantially water-insoluble polymer. In a second aspect, the invention comprises the ternary composition of destructurized starch, component b-7, and at least one substantially water-insoluble polymer (component (c)). These compositions may be in the form of powdery mixtures of the components, melts, or solid forms. The invention also includes methods for making and using both above-described compositions and shaped articles made therefrom.

In an eighth embodiment of the invention, it has been found useful to make polymer compositions comprising: (a) destructurized starch, (b) at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group, (referred to herein as "component b-8"), and optionally (c) a substantially water-insoluble polymer different from those defined as component b-8. In one aspect, the present invention relates to a composition comprising destructurized starch and component b-8. This composition is useful itself for making finished articles, but it is primarily useful as a "pre-mix" for combining with the substantially water-insoluble polymer. In a second aspect, the invention comprises the ternary composition of destructurized starch, component b-8, and at least one substantially water-insoluble polymer (component (c)). These compositions may be in the form of powdery mixtures of the components, melts, or solid forms. The invention also includes methods for making and using both above described compositions and shaped articles made therefrom.

In a ninth embodiment of the invention, it has been found useful to make polymer compositions comprising: (a) destructurized starch, (b) at least one compound selected from the group consisting of polysaccharide graft copolymers and graft copolymers of polysaccharide derivatives (referred to herein as "component b-9"), and optionally (c) a substantially water-insoluble polymer different from those defined as component b-9. In one aspect, the present invention relates to a composition comprising destructurized starch and component b-9. This composition is useful itself for making finished articles, but it is primarily useful as a "pre-mix" for combining with the substantially water-insoluble polymer. In a second aspect, the invention comprises the ternary composition of destructurized starch, component b-9, and at least one substantially water-insoluble polymer (component (c)). These compositions may be in the form of powdery mixtures of the components, melts, or solid forms. The invention also includes methods for making and using both above-described compositions and shaped articles made therefrom.

In a tenth embodiment of the invention, it has been found useful to make polymer compositions comprising: (a) destructurized starch, (b) at least one compound selected from the group consisting of polyalkyleneimine polymers and polyalkyleneimine copolymers (referred to herein as "component b-10"), and optionally (c) a substantially water-insoluble polymer different from those defined as component b-10. In one aspect, the present invention relates to a composition comprising destructurized starch and component b-10. This composition is useful itself for making finished articles, but it is primarily useful as a "pre-mix" for combining with the substantially water-insoluble polymer. In a second aspect, the invention comprises the ternary composition of destructurized starch, component b-10, and at least one substantially water-insoluble polymer (component (c)). These compositions may be in the form of powdery mixtures of the components, melts, or solid forms. The invention also includes methods for making and using both above-described compositions and shaped articles made therefrom.

In an eleventh embodiment of the invention, it has been found useful to make polymer compositions comprising: (a) destructurized starch, (b) at least one compound selected from the group consisting of styrene sulfonic acid polymers, styrene sulfonic acid copolymers, and salts thereof (referred to herein as "component b-11"), and optionally (c) a substantially water-insoluble polymer different from those defined as component b-11. In one aspect, the present invention relates to a composition comprising destructurized starch and component b-11. This composition is useful itself for making finished articles, but it is primarily useful as a "pre-mix" for combining with the substantially water-insoluble polymer. In a second aspect, the invention comprises the ternary composition of destructurized starch, component b-11, and at least one substantially water-insoluble polymer (component (c)). These compositions may be in the form of powdery mixtures of the components, melts, or solid forms. The invention also includes methods for making and using both above-described compositions and shaped articles made therefrom.

In a twelfth embodiment of the invention, it has been found useful to make polymer compositions comprising: (a) destructurized starch, (b) at least one compound selected from the group consisting of polymers and copolymers which contain carboxylic groups which partially or wholly are present in the form of their salts and wherein said polymers or copolymers do not contain further functional groups (referred to herein as "component b-12"), and optionally (c) a substantially water-insoluble polymer different from those defined as component b-12. In one aspect, the present invention relates to a composition comprising destructurized starch and component b-12. This composition is useful itself for making finished articles, but it is primarily useful as a "pre-mix" for combining with the substantially water-insoluble polymer. In a second aspect, the invention comprises the ternary composition of destructurized starch, component b-12, and at least one substantially water-insoluble polymer (component (c)). These compositions may be in the form of powdery mixtures of the components, melts, or solid forms. The invention also includes methods for making and using both above-described compositions and shaped articles made therefrom.

In a thirteenth embodiment, the present invention concerns blended polymeric compositions comprising (a) destructurized starch (component (a)) and (c) at least one essentially water insoluble hydrophobic thermoplastic polymer (component (c)). In this emobiment, component (b), as described in other embodiments, has been omitted. Specifically, the thirteenth embodiment also refers to a method of producing polymeric materials comprising a modified destructurized starch and an essentially water insoluble synthetic thermoplastic polymer by heating starches having a water content of 5% to 30% by weight based on the starch/water component in a closed volume to elevated temperatures thereby at elevated pressures for a time long enough to form a melt, characterized in that said starch/water material is mixed with at least one essentially water-insoluble synthetic thermoplastic polymer before or during melting formation. Preferably the synthetic thermoplastic polymer is added before melting is initiated.

BRIEF DESCRIPTION OF THE DRAWINGS

FIGS. 1.1 to 1.4 show comparative tests results for untreated starch, blended starch containing 1% of polyethylene and 5% of polyethylene when stored three days according to Example (c-1)-1(d). Dimensional changes are apparent from the drawings.

FIGS. 2.1 to 2.4 show comparative test results for untreated starch, blended starch containing 1% of polyacetal and 5% of polyacetal when stored three days according to Example (c1)-1(d). Dimensional changes are apparent from the drawings.

FIGS. 3.1 to 3.4 show comparative test results for untreated starch, blended starch containing 1% of EAA (ethylene/acrylic acid-copolymer) and 5% of EAA (ethylene/acrylic acid-copolymer) when stored three days according to Example (C-1)-1(d). Dimensional changes are apparent from the drawings.

FIGS. 4.1 to 4.4 show comparative test results for untreated starch, blended starch containing 1% of EVA (ethylene/vinyl acetate-copolymer) and 5% of EVA (ethylene/vinyl acetate-copolymer) when stored three days according to Example (c-1)-1(d). Dimensional changes are apparent from the drawings.

DETAILED DESCRIPTION OF THE INVENTION

The compositions of the first aspect of the invention comprise:

(a) destructurized starch, and (b-1) at least one polymer which contains at least two different types of functional groups, one of said types being hydroxyl groups.

Such a polymer composition may optionally contain further additives.

Specifically, one aspect of this embodiment of the invention is a polymer composition capable of being formed into articles having substantial dimensional stability comprising:

(a) destructurized starch, and (b-1) at least one polymer which contains at least two different types of functional groups, one of said types being hydroxyl groups; said polymer being present in an amount effective to enhance the physical properties of said articles (which amount is sometimes referred to herein as an "effective amount" of component b-1).

Preferably this polymer composition additionally comprises at least one component (c):

(c) a substantially water-insoluble thermoplastic polymer which does not fall within the definition of those compounds defined herein as component b-1.

The compositions of the second aspect of the invention comprise:

(a) destructurized starch, and (b-2) at least one polymer which does not contain hydroxyl groups and is selected from the group consisting of polymers which contain at least two types of functional groups bound to the same molecule one type of these groups being carboxylate groups.

Such polymer composition may optionally contain further additives.

Specifically, one aspect of this embodiment of the invention is a polymer composition capable of being formed into articles having substantial dimensional stability comprising:

(a) destructurized starch, and (b-2) at least one polymer which does not contain hydroxyl groups and is selected from the group consisting of polymers which contain at least two types of functional groups bound to the same molecule one type of these groups being carboxylate groups: said polymer being present in an amount effective to enhance the physical properties of said articles (which amount is sometimes referred to herein as an "effective amount" of component b-2).

Preferably this polymer composition additionally comprises at least one component (c):

(c) a substantially water-insoluble thermoplastic polymer which does not fall within the definition of those compounds defined herein as component b-2.

The compositions of the third aspect of the invention comprise:

(a) destructurized starch, and (b-3) at least one polymer selected from the group consisting of polymers which contain tertiary amino groups and/or salts thereof and/or quaternary ammonium groups.

Such a polymer composition may optionally contain further additives.

Specifically, one aspect of this embodiment of the invention is a polymer composition capable of being formed into articles having substantial dimensional stability comprising:

(a) destructurized starch, and (b-3) at least one polymer selected from the group consisting of polymers which contain tertiary amino groups and/or salts thereof and/or quaternary ammonium groups; said polymer being present in an amount effective to enhance the physical properties of said articles (which amount is sometimes referred to herein as an "effective amount" of component b-3).

Preferably this polymer composition additionally comprises at least one component (c):

(c) a substantially water-insoluble thermoplastic polymer which does not fall within the definition of those compounds defined herein as component b-3.

The composition of the fourth aspect of the invention comprises:

(a) destructurized starch, and (b-4) at least one polymer selected from the group of polysaccharides which have been chemically modified to contain added hydroxyalkyl groups and/or contain alkyl ether groups, and/or contain ester groups.

Such a polymer composition may optionally contain further additives.

Specifically, one aspect of this embodiment of the invention is a polymer composition capable of being formed into articles having substantial dimensional stability comprising:

(a) destructurized starch, and (b-4) at least one polymer selected from the group of polysaccharides which have been chemically modified to contain added hydroxyalkyl groups and/or contain alkyl ether groups, and/or contain ester groups; said polymer being present in an amount effective to enhance the physical properties of said articles (which amount is sometimes referred to herein as an "effective amount" of component b-4).

Preferably this polymer composition additionally comprises at least one component (c):

(c) a substantially water-insoluble thermoplastic polymer which does not fall within the definition of those compounds defined herein as component b-4.

The compositions of the fifth aspect of the invention comprise:

(a) destructurized starch, and (b-5) at least one compound selected from the group consisting of copolymers of vinyl pyrrolidone.

Such polymer composition may optionally contain further additives.

Specifically, one aspect of this embodiment of the invention is a polymer composition capable of being formed into articles having substantial dimensional stability comprising:

(a) destructurized starch, and (b-5) at least one compound selected from the group consisting of copolymers of vinyl pyrrolidone; said copolymers being present in an amount effective to enhance the physical properties of said articles (which amount is sometimes referred to herein as an "effective amount" of component b-5).

Preferably this polymer composition additionally comprises at least one component (c):

(c) a substantially water-insoluble thermoplastic polymer which does not fall within the definition of those compounds defined herein as component b-5.

The compositions of the sixth aspect of the invention comprise:

(a) destructurized starch, and (b-6) at least one compound selected from the group consisting of cationically modified polysaccharides.

Such a polymer composition may optionally contain further additives.

Specifically, one aspect of this embodiment of the invention is a polymer composition capable of being formed into articles having substantial dimensional stability comprising:

(a) destructurized starch, and (b-6) at least one compound selected from the group consisting of cationically modified polysaccharides; said modified polysaccharide being present in an amount effective to enhance the physical properties of said articles (which amount is sometimes referred to herein as an "effective amount" of component b-6).

Preferably this polymer composition additionally comprises at least one component (c):

(c) a substantially water-insoluble thermoplastic polymer which does not fall within the definition of those compounds defined herein as component b-6.

The compositions of the seventh aspect of the invention comprise:

(a) destructurized starch, and (b-7) at least one compound selected from the group consisting of anionically modified polysaccharides.

Such polymer compositions may optionally contain further additives.

Specifically, one aspect of this embodiment of the invention is a polymer composition capable of being formed into articles having substantial dimensional stability comprising:

(a) destructurized starch, and (b-7) at least one compound selected from the group consisting of anionically modified polysaccharides; said modified polysaccharide being present in an amount effective to enhance the physical properties of said articles (which amount is sometimes referred to herein as an "effective amount" of component b-7).

Preferably this polymer composition additionally comprises at least one component (c):

(c) a substantially water-insoluble thermoplastic polymer which does not fall within the definition of those compounds defined herein as component b-7.

The compositions of the eighth aspect of the invention comprise:

(a) destructurized starch, and (b-8) at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group.

Such a polymer composition may optionally contain further additives.

Specifically, one aspect of this embodiment of the invention is a polymer composition capable of being formed into articles having substantial dimensional stability comprising:

(a) destructurized starch, and (b-8) at least one polymer selected from the group of copolymers containing vinyl alcohol units together with aliphatic chain units as are obtained by copolymerization of vinyl esters, preferably vinyl acetate, with an unsaturated monomers containing no functional group with subsequent hydrolysis of the vinyl ester groups; said polymer being present in an amount effective to enhance the physical properties of said articles (which amount is sometimes referred to herein as an "effective amount" of component b-8).

Preferably this polymer composition additionally comprises at least one component (c):

(c) a substantially water-insoluble thermoplastic polymer which does not fall within the definition of those compounds defined herein as component b-8.

The compositions of the ninth aspect of the invention comprise:

(a) destructurized starch, and (b-9) at least one compound selected from the group consisting of polysaccharide graft copolymers and graft copolymers of polysaccharide derivatives.

Such a polymer composition may optionally contain further additives.

Specifically, one aspect of this embodiment of the invention is a polymer composition capable of being formed into articles having substantial dimensional stability comprising:

(a) destructurized starch, and (b-9) at least one compound selected from the group consisting of polysaccharide graft copolymers and graft copolymers of polysaccharide derivatives; said compound being present in an amount effective to enhance the physical properties of said articles (which amount is sometimes referred to herein as an "effective amount" of component b-9).

Preferably this polymer composition additionally comprises at least one component (c):

(c) a substantially water-insoluble thermoplastic polymer which does not fall within the definition of those compounds defined herein as component b-9.

The compositions of the tenth aspect of the invention comprise:

(a) destructurized starch, and (b-10) at least one compound selected from the group consisting of polyalkyleneimine polymers and polyalkyleneimine copolymers.

Such a polymer composition may optionally contain further additives.

Specifically, one aspect of this embodiment of the invention is a polymer composition capable of being formed into articles having substantial dimensional stability comprising:

(a) destructurized starch, and (b-10) at least one compound selected from the group consisting of polyalkyleneimine polymers and polyalkyleneimine copolymers said modified polysaccharide being present in an amount effective to enhance the physical properties of said articles (which amount is sometimes referred to herein as an "effective amount" of component b-10).

Preferably this polymer composition additionally comprises at least one component (c):

(c) a substantially water-insoluble thermoplastic polymer which does not fall within the definition of those compounds defined herein as component b-10.

The compositions of the eleventh aspect of the invention comprise:

(a) destructurized starch, and (b-11) at least one compound selected from the group consisting of styrene sulfonic acid polymers, styrene sulfonic acid copolymers, and salts thereof.

Such a polymer composition may optionally contain further additives.

Specifically, one aspect of this embodiment of the invention is a polymer composition capable of being formed into articles having substantial dimensional stability comprising:

(a) destructurized starch, and (b-11) at least one compound selected from the group consisting of styrene sulfonic acid polymers, styrene sulfonic acid copolymers, and salts thereof; said compound being present in an amount effective to enhance the physical properties of said articles (which amount is sometimes referred to herein as an "effective amount" of component b-11).

Preferably this polymer composition additionally comprises at least one component (c):

(c) a substantially water-insoluble thermoplastic polymer which does not fall within the definition of those compounds defined herein as component b-11.

The compositions of the twelfth aspect of the invention comprise:

(a) destructurized starch, and (b-12) at least one compound selected from the group consisting of polymers and copolymers which contain carboxylic groups which partially or wholly are present in the form of their salts and wherein said polymers or copolymers do not contain further functional groups.

Such a polymer composition may optionally contain further additives.

Specifically, one aspect of this embodiment of the invention is a polymer composition capable of being formed into articles having substantial dimensional stability comprising:

(a) destructurized starch, and (b-12) at least one compound selected from the group consisting of polymers and copolymers which contain carboxylic groups which partially or wholly are present in the form of their salts and wherein said polymers or copolymers do not contain further functional groups. Said polymers and copolymers being present in an amount effective to enhance the physical properties of said articles (which amount is sometimes referred to herein as an "effective amount" of component b-12).

Preferably this polymer composition additionally comprises at least one component (c):

(c) a substantially water-insoluble thermoplastic polymer which does not fall within the definition of those compounds defined herein as component b-12.

The compositions of the thirteenth aspect of the invention comprise:

(a) destructurized starch, and (c) at least one substantially water-insoluble thermoplastic polymer.

Such a polymer composition may optionally contain further additives.

The present invention includes any of the said polymer compositions described herein in the form of powdery mixtures of their components, in the form of melts, or in solidified form. Mixtures of the polymer compositions are contemplated in any of these forms.

Unless specifically stated otherwise, the use of the term "component (b)" means any of the "(b)" components described as b-1, b-2, b-3, b-4, b-5, b-6, b-7, b-8, b-9, b-10, b-11, b-12 as well as mixtures thereof.

Component (b) is chosen as described herein to be substantially compatible with the starch and also to promote the compatibility of component (c) with the combination of starch and component (b).

The present invention further comprises methods of producing the polymer compositions in the molten or solid form as well as a method of producing shaped articles from said polymer compositions, and to the resulting shaped articles made therefrom.

The polymer compositions of the present invention are prepared by admixing destructurized starch, component (b) and optionally component (c), and any further additives. This mixture is then heated in a closed volume to elevated temperatures until a homogeneous melt is obtained, and shaped articles can be formed therefrom.

An alternative method of producing the polymer compositions of the present invention comprises: (1) heating starch which is in a condition to be destructurized in a closed volume to elevated temperatures and at elevated pressures for a time sufficient to destructurize the starch and form a melt; (2) adding component (b) as well as other polymer or polymers and/or additives before, during or after such starch destructurization; and (3) continuing to heat the mixture until a homogenous melt is obtained. It is preferred that component (b) and, if desired, component (c), as well as other additives be combined with the starch and the combination formed into a melt. The starch in this combination may be already wholly or partially destructurized or the destructurization may take place during melt formation.

The present invention further refers to the process of working said polymer compositions under controlled water content, temperature and pressure conditions as a thermoplastic melt wherein said working process is any known process, such as, for example injection molding, blow molding, extrusion, coextrusion, compression molding, vacuum forming, thermoforming or foaming. All of these processes are collectively referred to herein as "forming".

As used herein a "substantially water-insoluble thermoplastic polymer" is a polymer which absorbs less than 10% of water, preferably less than 5%, per 100 grams of the polymer at room temperature and more preferably less than 2% per 100 grams of the polymer at room temperature.

The term "functional group" as used herein includes known polar groups that may be bound to the polymer chain such as, for example, hydroxy, alkoxy, carboxy, carboxyalkyl, alkyl carboxy, halo, pyrrolidono, acetal and the like. These groups should be selected from those which will not degrade the starch.

The term "unsaturated monomers containing no functional group" includes for example alkenes such ethylene, isobutylene and propylene. It also includes styrene, as the benzene nucleus is not considered to be a functional group within the scope of this invention.

The term "carboxylate" as used herein includes groups of the formula

wherein $Me^+$ signifies $NH_4^+$, or a mono- or polyvalent metallic cation, preferably an alkali or earth alkali cation or zinc, preferably sodium, magnesium or zinc.

The term "starch" as used herein includes chemically substantially non-modified starches as, for example generally, carbohydrates of natural, vegetable origin, composed mainly of amylose and/or amylopectin. They can be extracted from various plants, examples being potatoes, rice, tapioca, corn (maize), pea, and cereals such as rye, oats and wheat. Preferred is starch made from potatoes, corn, wheat or rice. Mixtures of starches obtained from these sources are contemplated. "Starch" further includes physically modified starches such as gelatinized or cooked starches, starches with a modified acid value (pH), e.g. where acid has been added to lower the acid value of a starch to a range of about 3 to about 6. Further included are starches, e.g. potato starch, in which the divalent ions like $Ca^{+2}$ or $Mg^{+2}$-ions associated with the phosphate groups in the potato starch have been partially or completely washed out from the starch or optionally wherein the ions present in the starch have been replaced partially or wholly by the same or different mono- or polyvalent ions. It further includes pre-extruded starches, as described in the above-referenced U.S. patent application Ser. No. 209,402, filed June 20, 1988.

As described above, it has been found that starches, e.g. with a water content within the range of about 5 to about 40% by weight based on the weight of the composition, undergo a specific narrow endothermic transition on heating to elevated temperatures in a closed volume just prior to the endotherm change characteristic of oxidative and thermal degradation. The specific endothermic transition can be determined by differential scanning calorimetric analysis (DSC) and is indicated on the DSC-diagram by a specific relatively narrow peak just prior to the endotherm characteristic of oxidative and thermal degradation. The peak disappears as soon as the mentioned specific endothermic transition has been undergone. The term "starch" includes also treated starches wherein said specific endothermic transition has been undergone. Such starch is described in U.S. patent application Ser. No. 278,116 filed Nov. 30, 1988.

Although at the current time, destructurization of starch requires the presence of water in ranges disclosed herein, the present compositions also contemplate the use of destructurized starch prepared by other methods, e.g. without the use of water.

The water content of such a starch/water composition is preferably about 5 to about 40% water by weight of the starch/water component and preferably about 5–30%. However, in order to work with the material near its equilibrium water content to which it gets when it is finally exposed to the free atmosphere, a water content of about 10 to about 22%, preferably of about 14 to about 18% by weight, based on the starch/water component, should be used in processing and is preferred.

First Embodiment (b-1)

The polymer of component b-1 is preferably a polymer containing vinyl alcohol units. More preferably component b-1 is a poly(vinyl ester) wherein the ester groups are partially hydrolyzed or a copolymer containing vinyl alcohol units as well as other units such as are obtained by copolymerization of vinyl esters, preferably vinyl acetate, with monomers such as ethylene, vinyl chloride, vinyl ethers, acrylo-nitrile, acryl amide, omega-octadecene, vinyl-butyl ether, vinyl-octadecyl ether, vinyl pyrrolidone and other known monomers, with subsequent hydrolysis of at least some of the vinyl-ester groups.

These polymers of component b-1 have preferably from about 20 to about 99 mol % hydroxyl containing units such as vinyl alcohol units, preferably from about 30 to about 99 mol % and most preferably from 40 to 95 mol % of the hydroxyl containing unit, the remaining units being as mentioned above.

In addition, component b-1 can be a polymer or copolymer as obtained from polymerizing or copolymerizing monomers of the formula:

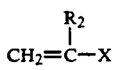

wherein $R_2$ is hydrogen or methyl,

X does not form a vinyl alcohol and is an organic moiety with up to 8 carbon atoms substituted by 1 to 3 hydroxyl groups and/or containing 1 or 2 carboxylate groups.

X can be exemplified by the moiety $X_1$ wherein $X_1$ is $—CH_2OH$, $—O—CH_2—CH_2OH$, $—C(O)OCH_2—CH_2OH$ or $—C_6H_4—O—CH_2—CH_2OH$.

Component b-1 may also be an ester derivative of maleic acid or fumaric acid that optionally contains hydroxyl groups, such as $$HOCH_2—CH_2—O(O)C—HC\!=\!HC—C(O)O—CH_2—CH_2OH \quad (Ia)$$

(cis or trans)

The monomers of the compounds of formula $CH_2\!=\!C(R_2)X$ or said derivatives of maleic or fumaric acid may be copolymerized with vinyl esters, preferably vinyl acetate and/or with monomers such as ethylene, vinyl chloride, vinyl ethers, acrylic acid esters, acrylonitrile, methacrylic acid esters, maleic acid esters, acrylamide, omega-octadecene, vinyl butyl ether, vinyloctadecyl ether, vinyl pyrrolidone and other known monomers. Such polymers and copolymers are known.

It is preferred that the polymer does not contain hydroxyl groups together with carboxyl groups bound directly to the same main polymer chain because cross-linking may occur prior to or during processing. However, this does not necessarily always happen and such useful combinations are included within the scope of the present invention.

The amount of hydroxyl-containing monomer will depend on the type of copolymer used carrying the other functional group. The preferred molar ratios are given above and are generally applicable. However, if the monomer carrying the functional group that is not hydroxyl has an elevated molecular weight compared to the hydroxyl carrying moiety, then a higher proportion of the latter moiety will be required. It is therefore recommended that the weight % of the hydroxyl moiety (—OH) is from 4.5 to 35 and preferably from 9.0 to 25 weight percent of component b-1. If the monomer carries a hydroxyl and at the same time another functional group, e.g., an ester group, no comonomer may be needed because the homopolymer carries two different functional groups. The person skilled in the art can optimize component b-1, e.g., by combining different molar ratios of known monomers or combining other monomers that have not been set out here. Many of these polymers and copolymers are known.

The repeating units in the polymer of component b-1 can be exemplified by the following formulas:

wherein R is alkyl, preferably methyl, ethyl, propyl, butyl or octadecyl;

wherein $R_1$ is a saturated or unsaturated $C_1$-$C_{21}$ hydrocarbon, preferably methyl, ethyl, propyl or butyl;

wherein $R_2$ is H or $CH_3$ and $R_1$ is as mentioned above; and

The polymers of component (b-1) may have a general formula wherein the number of repeating units varies for each individual type of copolymer and is known per se as, e.g., described in "Encyclopaedia of Polymer Science and Technology, Interscience Publ. Vol. 14, 1971." These copolymers may be described by the following general formulas VII to XII incorporating the mer units described above. The units within the brackets represent the individual mer units within each copolymer. These units may be combined in any known fashion, including random or block copolymerization. The molecular weight of the copolymer may be within known ranges.

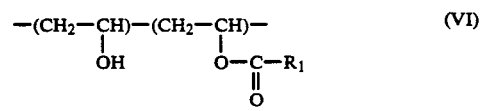

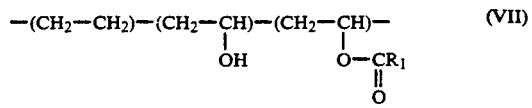

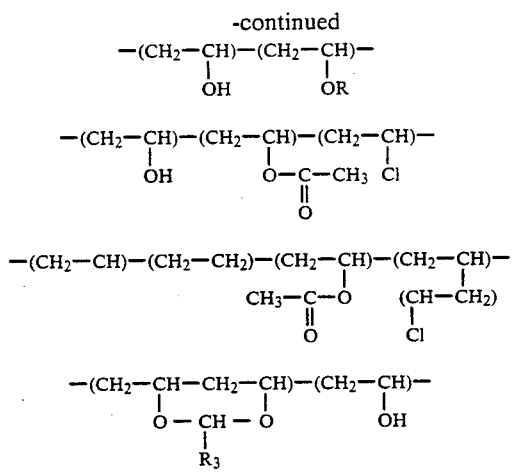

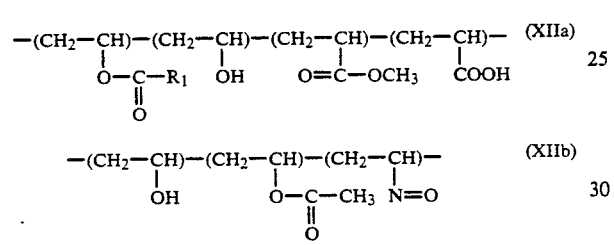

wherein $R_3$ is H or a saturated or unsaturated $C_1$–$C_{21}$ hydrocarbon, preferably H, —$CH_3$, —$C_2H_5$ or —$C_3H_7$ Preferred copolymers of component (b-1) are those which can be described as containing vinyl alcohol (II) units together with vinyl ether (III) and/or vinyl ester (IV) units. Such copolymer types correspond to compounds of the formulas (VII) to (XI) from which compounds of the formulas (VII), (VIII) and (IX) are preferred.

These preferred copolymers of component (b-1) are copolymers as obtained by polymerization of a vinyl ester with one or more monomers selected from the group consisting of ethylene and vinyl esters, with subsequent hydrolysis of at least some of the vinyl ester groups.

Such preferred copolymers of component (b-1) are e.g. polyvinylalcohol-co-vinyl-acetate; ethylene/vinyl alcohol/vinyl acetate copolymers; ethylene/vinyl chloride/vinyl alcohol/vinyl acetate graft copolymers; vinyl alcohol/vinyl acetate/vinyl chloride copolymers; vinyl alcohol/vinyl acetate/vinyl chloride/diacryl amide copolymers; vinyl alcohol/vinyl butyral copolymers; vinyl alcohol/vinyl acetate/ vinyl pyrrolidone copolymers; vinyl alcohol/ styrene copolymers. Combinations or mixtures of these copolymers are included within the scope of component (b-1).

Second Embodiment (b-2)

Component (b-2) is preferably a synthetic polymer, preferably a copolymer containing carboxylate groups as well as other units such as are obtained by copolymerization of acrylic acid, methacrylic acid, crotonic acid, maleic acid, itaconic acid, e.g. in their acid or carboxylate form, with monomers such as ethylene, vinyl chloride, vinyl esters such as vinyl acetate, vinyl ethers, acrylic acid esters, acrylonitrile, methacrylic acid esters, maleic acid esters, acryl amide, omega-octadecene, vinyl-butyl ether, vinyl pyrrolidone and other known monomers. Such copolymers and their derivatives are known.

If a carboxyl group-containing monomer is used for preparing the polymer, then at least a part of the carboxyl groups must be neutralized with a cation as defined above. Such copolymers as well as methods for their production are known. Preferably component b-2 substantially does not contain free acid groups.

Component (b-2) may have a general formula wherein the number of repeating units varies for each individual type of copolymer and is known per se as, e.g., described in "Encyclopaedia of Polymer Science and Technology, Interscience Publ. Vol. 14, 1971". These copolymers may be exemplified by the following general formulae incorporating the mer units described above. The units within the brackets represent the individual mer units within each copolymer. These units may be combined in any known fashion, including random or block copolymerization. The molecular weight of the copolymer may be within known ranges.

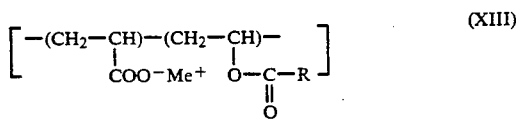

wherein R is a saturated or unsaturated $C_1$–$C_{21}$-hydrocarbon, preferably methyl, ethyl, propyl or butyl;

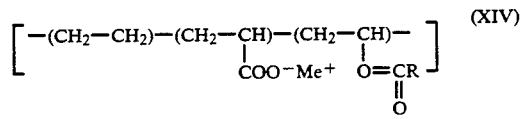

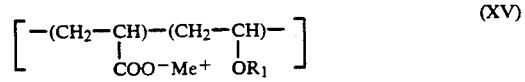

wherein $R_1$ is alkyl ($C_1$–$C_4$), preferably methyl.

Preferred copolymers of the component (b-2) containing carboxylate groups are those which can be described as being derived from acrylic acid, methacrylic acid, crotonic acid, maleic acid, itaconic acid, methylacrylate, methylmethacrylate, acrylamide, acrylonitrile and/or methylvinylether.

More preferred polymers of the compound (b-2) are those that can be described as being derived from acrylic acid, methacrylic acid, maleic acid, methacrylate, ethyl acrylate and/or methylvinylether. Such copolymers may be also copolymerized with ethylene, propylene, or styrene, which are not considered as a "functional group" within the scope of this invention.

Such preferred copolymer types correspond to compounds of the formulas (XIII) to (XV).

Such copolymers are, e.g., polyacrylic acid-co-vinylacetate; ethylene/acrylic acid/vinyl acetate copolymers; ethylene/vinyl chloride/acrylic acid/vinyl acetate graft copolymers; acrylic acid/ vinyl acetate/ vinyl chloride copolymers; acrylic acid/vinyl methylether copolymers; vinyl acetate/ acrylic acid/ acrylic acid methylester copolymer; vinyl acetate/ crotonic acid copolymers; vinyl acetate/ maleic acid copolymers; methacrylic acid/ vinyl acetate/ vinyl pyrrolidone copolymers; acrylic acid/ acrylonitrile copolymer; ethylene/ propylene / acrylic acid copolymer; and styrene/ acrylic acid copolymer, wherein a part or all of the acid groups are present in their carboxylate form.

The amount of carboxyl and carboxylate containing moieties within a copolymer will depend on the type of copolymer. Said amount will generally be from 5 mol % to 50 mol %, preferably from 8 mol % to 40 mol %, and most preferably from 10 mol % to 30 mol %.

The degree of neutralization of the carboxyl groups to form carboxylate groups is preferably from 30% to 100% and more preferably from 40% to 90%.

Third Embodiment (b-3)

The polymer of the component (b-3) is preferably a synthetic polymer, as obtained by the polymerization of monomers containing tertiary amino groups and/or salts thereof and/or quarternary amino groups such as poly(2-vinyl pyridine); poly(4-vinyl pyridine); polyvinyl carbazole, 1-vinyl imidazole and/or salts thereof and/or their quaternized derivatives as well as with other polymers as are obtained by copolymerization of such amines with other monomers such as acrylonitrile, butylmethacrylate, styrene and other known monomers. Although such copolymers and their derivatives are known, care must be taken in the case of salts, such as the salts with HCl or $H_2SO_4$, to avoid undesired secondary or alternative reactions. These limitations are known to those skilled in the art.

The expression amine salts includes the salts formed with an inorganic or organic acid, e.g. salts with inorganic or organic acids such as HCl, $H_2SO_4$, and acetic acid. The expressions "quaternized derivative" and "quaternary ammonium groups" mean quaternized derivatives of tertiary amines, e.g. quaternized with an alkyl halide such as methyl chloride.

Such obtained repeating units in the polymer of component (b-3) can be exemplified by the following formula:

R is $-NR_1R_2$; $-N^{\oplus}R_1R_2R_3A^{\ominus}$, wherein $R_1$ and $R_2$ together represent a pyridine residue; a carbazyl residue; an imidazolyl residue.

$R_3$ is H or alkyl ($C_1-C_{21}$), $A^{\ominus}$ is an anion.

The polymers of component (b-3) may have a general formula wherein the number of repeating units varies for each individual type of copolymer and is known per se as e.g. described in "Encyclopaedia of Polymer Science and Technology, Interscience Publ. Vol. 14, 1971." These copolymers may be described by the following general formulas incorporating the mer units described above. The units within the brackets represent the individual mer units within each copolymer. These units may be combined in any known fashion, including random or block copolymerization. The molecular weight of the copolymer may be within known ranges.

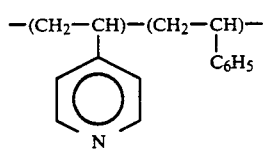

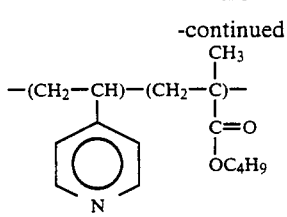

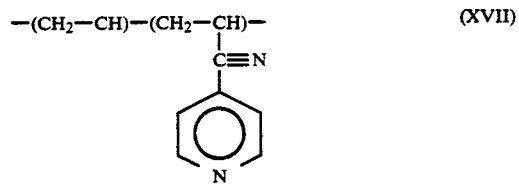

Preferred polymers of the compound (b-3) are those derived from 2-vinyl-pyridine; 4-vinyl pyridine and vinyl carbazole.

Preferred copolymers of the component (b-3) are those which can be described as being derived from 4-vinyl pyridine (I, R=pyridine residue), acrylonitrile (II), butyl methacrylate (III), styrene (IV). Such copolymer types correspond to compounds of the formulas (II) to (IV) which are preferred.

Polysaccharides are known and described e.g. in Encyclopaedia of Polymer Science and Engineering (2nd edition) 1987.

Polysaccharides are naturally occurring carbohydrate polymers in which monosaccharide units are linked directly through glycosidic linkages. Such polymers are found in the plant, animal and microbial kingdoms.

Preferred polysaccharides used in this invention are the different celluloses, the different starches and the known hemi-celluloses, especially celluloses and starches, respectively, and their derivatives. Most preferred are the starch derivatives. It should be understood that these starches may be the same as or different from the starting materials of component (a).

Fourth Embodiment (b-4)

The polymer of the component (b-4) is preferably an alkoxylated polysaccharide, which contains hydroxy alkyl groups and which further may contain other functional groups, e.g. alkyl ether groups, and/or alkyl ester groups. Said hydroxy alkyl groups are preferably hydroxy ethyl and/or hydroxy propyl groups.

In the following, the degree of substitution (DS) is defined as the average number of hydroxyl groups in the anhydroglucose unit that are substituted in a particular product. In the case of starch or cellulose for instance, the DS value may range from 0 to 3.0. This value however, is preferably within the range of about 0.05 to about 2.5 and preferably within the range of about 0.1 to about 1.5.

The molar substitution (MS) is defined as the total number of moles of a reagent such as ethylene or propylene oxide which becomes attached to the polysaccharide.

The average length of the pendant chain (n) is given by the ratio MS/DS. Examples of component (b-4) are the following compounds:

1. hydroxyethyl cellulose
   (DS: 0.2–1.5; MS: 0.3–2.5)
2. hydroxypropyl cellulose
   (DS: 0.2–1.5; MS: 0.3–4.0)
3. hydroxyethyl hydroxypropyl cellulose (DS: 0.2-1.5 for hydroxyethyl and hydroxypropyl with MS of 0.3-2.5 for hydroxyethyl and MS of 0.3-4.0 for hydroxypropyl)
4. hydroxypropyl methyl cellulose
   (DS: 0.2-1.5 for hydroxyethyl and MS: 0.3-4.0; DS 0.1-2.5 for methyl)
5. hydroxyethyl methyl cellulose
   (DS: 0.2-1.5 for hydroxyethyl and MS: 0.3-2.5; DS 0.1-2.5 for methyl)
6. hydroxybutyl methyl cellulose
   (DS: 0.1-1.0 for hydroxybutyl and MS: 0.3-1.0; DS 0.1-2.5 for methyl)
7. ethylhydroxyethyl cellulose
   (DS: 0.1-2.5 for ethyl and DS: 0.2-1.5 for hydroxyethyl with MS: 0.3-2.5)
8. dihydroxypropyl cellulose
   (DS: 0.2-1.5 for hydroxyethyl and MS: 0.3-2.5; DS 0.1-2.5 for methyl)
9. methyl cellulose
   (DS: 0.1-2.5)
10. ethyl cellulose
    (DS: 0.1-2.5)
11. methylethyl cellulose
    (DS: 0.1-2.5 for methyl and ethyl)
12. benzyl cellulose
    (DS: 0.1-2.0)
13. hydroxypropyl starch acetate
    (MS of 3-6 hydroxypropyl groups and a DS of 1.0-2.5 acetate groups)
14. hydroxypropyl starch laurate
    (MS: 0.66; DS: 1.2-3.0)
15. hydroxyethyl starch acetate
    (MS of 0.66 and a DS of 1.2-3)
16. hydroxyethyl starch laurate
    (MS: 0.66; DS: 1.2-3.0)
17. hydroxyethyl starch
    (DS: 0.05-1.5; MS: 5-10)
18. hydroxypropyl starch
    (DS: 0.05-1.5; MS: 5-10)
19. hydroxyethyl alginate
    (DS 0.1-1.0; MS: 2-3)
20. hydroxyethyl guar gum
    (DS: 0.1-1.0; MS: 2-3)
21. hydroxypropyl guar gum
    (DS: 0.1-1.0; MS: 2-3)
22. hydroxyethyl locust bean gum
    (DS: 0.1-1.0; MS: 2-3)
23. hydroxypropyl locust bean gum
    (DS: 0.1-1.0; MS: 2-3)
24. methyl tamarind gum
    (DS: 0.1-1.5)
25. ethyl tamarind gum
    (DS:0.05-1.5)
26. hydroxyethyl tamarind gum
    (DS: 0.1-1.0; MS: 1-4)
27. hydroxypropyl tamarind gum
    (DS: 0.1-1.0; MS: 1-3)
28. methyl xanthan gum
    (DS: 0.1-1.5)
29. ethyl xanthan gum
    (DS: 0.1-1.0; MS: 1-3)
30. hydroxyethyl xanthan gum
    (DS: 0.1-1.0; MS: 1-3)
31. hydroxypropyl xanthan gum
    (DS: 0.1-1.2; MS: 1-3)
32. methyl pullulan
    (DS: 0.1-2.0)
33. ethyl pullulan
    (DS: 0.1-2.5)
34. hydroxyethyl pullulan
    (DS: 0.1-1.0; MS: 1-3)
35. hydroxypropyl pullulan
    (DS: 0.1-1.2; MS: 1-4)
36. methyl xylan
    (DS: 0.1-2.5)
37. ethyl xylan
    (DS: 0.1-2.5)
38. hydroxyethyl xylan
    (DS: 0.1-1.5; MS: 0.5-2)
39. hydroxypropyl xylan
    (DS: 0.1-1.5; MS: 0.5-3)

The preferred components b-4) are compounds No. 1, 2, 3, 4, 5, 6, 7, 13, 15, 17, 18, 19, 20, 21, 22, 23, 34, 36, 39 taken from the above list.

The most preferred components b-4) are compounds No. 1, 2, 3, 4, 5, 6, 7, 13, 15, 17, 18, and 19 taken from the above list.

Method for the Alkylation and Alkoxylation of Polysaccharides

The alkylated and alkoxylated ethers of polysaccharides are produced by known methods such as nucleophilic substitution under alkaline conditions of the hydroxyl groups of the polysaccharides with one or more of the following alkylating agents: alkyl halides, arylalkyl halides and epoxides.

With an epoxide e.g. ethylene oxide, propylene oxide, one obtains an hydroxyethyl or hydroxypropyl ether respectively.

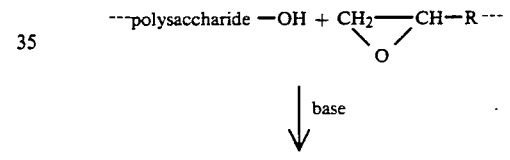

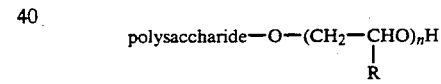

With the alkyl halide, primarily the chloride such as methyl chloride, ethyl chloride etc., one obtains the methyl or ethyl ether.

With the aryl-alkyl halide, such as benzyl chloride, one obtains a benzyl ether.

The alkyl halide, aryl-alkyl halide and epoxide can be combined together to give a mixed ether derivative. For instance, methyl chloride and propylene oxide may be added in mixture to the alkaline polysaccharide to lead to a methylhydroxypropyl ether.

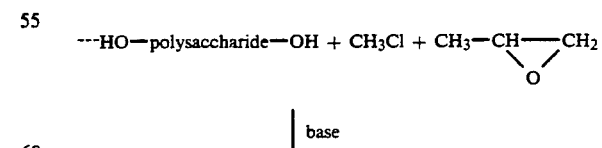

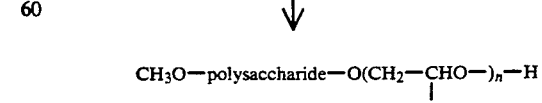

These methods and compounds are known per se.

When using the epoxide as reagent, several molecules of the epoxide may also react with each other so that a polyalkoxy chain results. The number (n) of units present in the chain can be determined from the degree of substitution (DS) and the molar substitution (MS). The average length of the pendant chain (n) is given by the ratio MS/DS.

Fifth Embodiment (b-5)

The compounds of component (b-5) are selected from the group consisting of copolymers of vinyl pyrrolidone.

Copolymers of vinyl pyrrolidone are known and described in Encyclopaedia of Polymer Science and Technology, Interscience Publ., 1971, Vol. 14, p. 242-243.

Preferred are copolymers of vinyl pyrrolidone with one or more monomers selected from the group of vinyl esters, vinyl alcohol, allyl alcohol, ethylene, propylene, butylene, isoprene, butadiene, styrene, vinyl ethers, and dimethylaminoethyl methacrylate.

Preferred are copolymers of vinyl pyrrolidone with a monomer selected from the group consisting of vinyl esters, vinyl alcohol, styrene and dimethylaminoethyl methacrylate.

These copolymers have a molar content of vinyl pyrrolidone between 5% to 95% and a molar content of the other monomer or monomers of between 95% to 5%. Preferred is a molar content of vinyl pyrrolidone between 10% and 30%. Preferred are copolymers of N-vinyl pyrrolidone.

Preferred are further the poly(N-vinyl pyrrolidone-vinyl ester) copolymers and from these the poly(N-vinyl pyrrolidone-vinyl acetate) copolymers.

The preferred molar ratios of vinyl pyrrolidone units to the units of the other monomer or monomers are within the ranges 90:10; 70:30; 30:70 or 10:90.

The N-vinyl pyrrolidone units have the formula

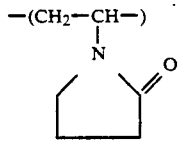

(XX)

and the vinyl ester units correspond to the formula

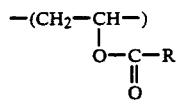

(XXI)

wherein

R is preferably —$CH_3$, —$C_2H_5$, —$C_3H_7$, most preferably —$CH_3$.

Sixth Embodiment (b-6)

The compounds of component (b-6) are selected from the group consisting of cationically modified polysaccharides.

Polysaccharides and cationically modified polysaccharides are known and are described e.g. in Encyclopaedia of Polymer Science and Technology, 2nd edition 1987, or O. B. Wurzburg, Modified Starches: Properties and Uses, CRC Press, Inc., Boca Raton, Fla, p. 113ff.

Polysaccharides are defined as naturally occurring carbohydrate polymers in which monosaccharide units are linked directly through glycosidic linkages. Polysaccharides originate from the plant-, animal- and microbial kingdoms. The preferred polysaccharides are the different starches, celluloses, hemicelluloses, xylanes, gums, alginates, pectins and pullulans. The most preferred are starch and cellulose.

Cationically modified polysaccharides are chemically modified polysaccharides in which a part of all of the functional hydroxyl groups of the polysaccharide have been substituted by residues containing cationic groups. Cationically modified polysaccharides are obtained by the chemical reaction of a polysaccharide with compounds containing amino, imino, ammonium, sulfonium or phosphonium groups, all of which can carry a positive charge. Preferred cationically modified polysaccharides within the scope of the present invention are those carrying a tertiary amino group or a quaternary ammonium group.

Preferred are cellulose and starch derivatives in the form of tertiary aminoalkyl ethers as obtained by reaction with, 2-dialkylaminoethyl chloride, preferably 2-diethylaminoethyl chloride; and 2,3-(epoxypropyl) trimethylammonium chloride.

For example, a starch reacted with 2-diethylaminoethyl chloride will under conventional reaction conditions, yield a starch derivative of the formula starch —O—$CH_2$—$CH_2$—$N(CH_2CH_3)_2$ or its salt, e.g. the HCl salt; and a starch reacted with 2,3-(epoxypropyl) trimethylammonium chloride will yield a starch derivative of the formula starch —O—$CH_2$—CH(OH)—$CH_2N(CH_2CH_3)_2$ or its salt, e.g. its HCl salt.

Most preferred are polysaccharide derivatives in the form of quaternary ammonium ethers as obtained by reacting the polysaccharide, preferably cellulose or starch, with a reagent containing a trialkyl ammonium group, e.g. by reaction with 2,3-epoxypropyltrimethyl ammonium chloride. This, e.g. for starch, will yield a substitution of the formula

starch —O—$CH_2CH(OH)CH_2$—N $(CH_3)_3$ Cl.

It is possible to co-substitute such polysaccharides containing said tertiary aminoalkyl ether group and/or said quaternary ammonium ether groups with further substituents. Such co-substituted compounds are within the scope of the present invention.

Example of such further substituents are hydroxyalkyl, preferably hydroxyethyl or hydroxylpropyl and/or carboxyalkyl preferably carboxymethyl and/or alkyl ether preferably methyl ether or ethyl ether.

The number of hydroxyl groups per anhydroglucose unit which are substituted by a residue containing a functional group is called the "degree of substitution" (D.S.). The maximum value is 3.0. The term "functional group" as used herein includes the cationic groups as well as the groups which are optionally added such as hydroxy alkyl and/or carboxy alkyl and/or alkyl ether.

For the present invention the degree of substitution is preferably from about 0.01 to about 2.5 and more preferably from about 0.01 to about 1.5. Most preferred is a value from about 0.01 to about 0.50.

Preferred are polysaccharides which are substituted by a dialkylaminoalkyl group, a salt or a quaternized derivative thereof. Preferred are the quaternized derivatives thereof.

Examples of substituents, which may be substituting the polysaccharides, preferably starch or cellulose, as mentioned above, are given in Table (b-6)-A. The degree of substitution is as given above.

TABLE (b-6)-A

| No. | substituent |
|---|---|
| 1 | dimethyl amino ethyl |
| 2 | diethyl amino ethyl |
| 3 | 2-hydroxy-3-pyridinium chloride propyl |
| 4 | 2-hydroxy-3-alpha-picolinium chloride propyl |
| 5 | 2-hydroxy-3-trimethyl ammonium chloride propyl |
| 6 | trimethyl ammonium chloride ethyl |
| 7 | 3-trimethyl ammonium chloride propyl |
| 8 | dimethyl-imino carbamate ammonium chloride |
| 9 | diethyl-imino carbamate ammonium chloride |

These substituents may be attached to any of the mentioned polysaccharides, preferably to starch or cellulose.

Most preferred are the quarternary ammonium salts as shown in Table (b-6)-1 under the Nos. 5, 6 and 7.

The quaternary salts given need not necessarily be the hydrochloride. Any other anion known like the sulfate or acetate will be suitable.

Seventh Embodiment (b-7)

The compounds of component (b-7) are selected from the group consisting of anionically modified polysaccharides.

Polysaccharides and anionically modified polysaccharides are known and are described e.g. in Encyclopaedia of Polymer Science and Technology, 2nd Edition, 1987.

Anionically modified polysaccharides are chemically modified polysaccharides in which a part or all of the functional hydroxyl groups of the polysaccharide have been substituted by other groups which contain anionic functional groups.

Such anionic functional groups are known and are preferably selected from the group consisting of phosphate, phosphonate, sulfate, sulfonate or carboxylate groups in form of their free acids or as salts thereof. Such salt is preferably an alkali metal salt or an organic base salt. Such acid groups may be partially esterified.

It is possible to co-substitute such polysaccharides containing said anionic groups with further substituents. Such co-substituted compounds are within the scope of the present invention.

An example of such further substituents are hydroxyalkyl, preferably hydroxyethyl or hydroxylpropyl and/or alkyl ether preferably methyl ether or ethyl ether, preferred are alkyl ethers.

The average number of hydroxyl groups per anhydroglucose unit which are substituted by a residue containing an anionic group is called the "degree of substitution" (DS). The maximum value is 3.0.

For the present invention the degree of substitution is preferably from about 0.01 to about 2.9 and more preferably from about 0.01 to about 2.5. Most preferred is a value from about 0.05 to about 1.0.

Preferred are polysaccharides which are substituted by phosphate groups, sulfate groups or carboxyl groups in the form of free acids or salts thereof. Preferred are polysaccharides substituted by phosphate groups or carboxyl groups in the form of their free acids or salts thereof.

Such substituents are herein below exemplified as starch derivatives and stand generally for polysaccharide derivatives as follows:

Monostarch phosphates

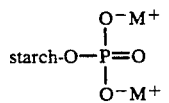

with $M^+ = H^+$, an alkali metal cation, $NH_4^+$, an organic cation, such as pyridinium, trimethyl ammonium, and triethyl ammonium, and
D.S = 0.01-2.0.

Distarch phosphates (XXII)

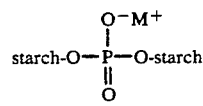

with $M^+ = H^+$, an alkali metal cation, $NH_4^+$, an organic cation such as pyridinium, trimethyl ammonium, and triethyl ammonium,
D.S. = 0.01-1.0.

Monostarch alkanephosphonates (XXIII)

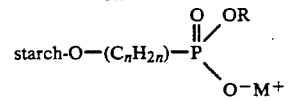

$R = H^+$, $CH_3$, $C_2H_5$, $C_3H_7$ or $M^+$
$M = H^+$, an alkali metal ion, $NH_4^+$, an organic cation such as pyridinium, trimethyl ammonium, triethyl ammonium,
n = 2-5, and
D.S. = 0.01-2.0.

Monostarch sulfates (XXIV)

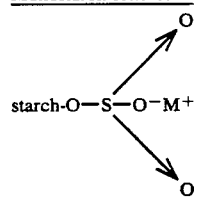

with $M^+ = H^+$, alkali metal cation, $NH_4^+$, organic cation such as pyridinium, trimethyl ammonium, and triethyl ammonium and
D.S. = 0.02-2.0.

Carboxyalkyl starch (XXV)

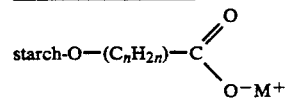

$M^+ = H^+$, an alkali metal ion, $NH_4^+$, an organic cation such as pyridinium, trimethyl ammonium, triethyl ammonium, and
n = 1-5, and
D.S. = 0.01-2.0.

starch dicarboxyalkyl hemi-esters

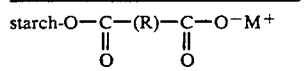
(XXVI)

R=—($C_nH_{2n}$) or —CH=CH—,
n=2-5,
$M^+$=$H^+$, an alkali metal ion, $NH_4^+$, an organic cation such as pyridinium, trimethyl ammonium, and triethyl ammonium, and
D.S=0.01-1.5.

Monostarch sulfosuccinate hemi-ester

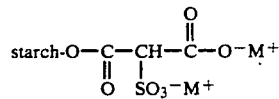
(XXVII)

with $M^+$=$H^+$, an alkali metal cation, $NH_4^+$, an organic cation such as pyridinium, trimethyl ammonium, and triethyl ammonium, and
D.S.=0.001-1.0.

The Examples given above stand, as mentioned, generally for polysaccharide derivatives. Preferred derivatives are those from celluloses and from starch. Preferred further are those containing carboxyl groups, e.g. carboxymethyl cellulose or carboxylmethyl starch with different degrees of substitution.

Preferred are the groups in their salt form.

Eighth Embodiment (b-8)

The copolymer of the component (b-8) is preferably a synthetic copolymer containing vinyl alcohol units as well as aliphatic units as are obtained by copolymerization of vinyl esters, preferably vinyl acetate with monomers preferably ethylene, propylene, isobutylene, and/or styrene with subsequent hydrolysis of the vinyl ester group. Such copolymers and their derivatives are known.

Copolymers thus obtained may have a general formula wherein the number of repeating units varies for each individual type of copolymer and is known per se as e.g. described in "Encyclopaedia of Polymer Science and Technology, Interscience Publ. Vol. 14, 1971".

Preferred copolymers of component (b-8) are those containing vinyl alcohol units and aliphatic chain units as obtained by copolymerization with ethylene and/or propylene, preferably with ethylene.

Such polymers are e.g. ethylene/vinyl alcohol copolymers (EVAL), propylene/vinyl alcohol copolymers.

Preferred are the ethylene/vinyl alcohol copolymers. The molar ratio of vinyl alcohol units to alkylene is preferably from about 10:90 to about 90:10. Preferred is a ratio of about 50:50 to about 85:15 and most preferred about 60:40 to 81:19.

A further embodiment of the present invention are those compounds of component (b-8) as named hereinbefore which further contain about 5 to about 20% of polystyrene units calculated to the total weight of the polymer.

Ninth Embodiment (b-9)

The compounds of component (b-9) are selected from the group consisting of polysaccharide graft copolymers and graft copolymers of polysaccharide derivatives.

Polysaccharides and polysaccharide graft copolymers as well as graft copolymers of polysaccharide derivatives are known and are described e.g. in Encyclopaedia of Polymer Science and Engineering, John Wiley & Sons, Volume 3, 1986. Polysaccharides are defined as naturally occuring carbohydrate polymers in which monosaccharide units are linked directly through glycosidic linkages. Polysaccharides are originate from plant-, animal- and microbial kingdoms. The preferred polysaccharides are the different starches, celluloses, hemicelluloses, xylanes, gums, alginates, pectins and pullulans. The most preferred are starch and cellulose.

Polysaccharide derivatives are e.g. polysaccharide ethers, alkoxylated polysaccharides, such as methyl cellulose, hydroxymethyl cellulose, hydroxyethyl cellulose, hydroxypropyl cellulose, or the analogous known derivatives from starch.

A polysaccharide graft copolymer is a polysaccharide covalently linked to a polymer so that separation by solvent extraction cannot be achieved without first degrading the polysaccharide e.g. by hydrolytic or oxidative degradation. The same is to be said analogously for graft copolymers of polysaccharide derivatives.

Graft copolymerization results from the formation of an active site at a point on the polysaccharide molecule or its derivative other than its end, and exposure to a polymerizable monomer.

In this sense, a polysaccharide or its derivative can be graft copolymerized with different polymerizable monomers, which can react with active hydrogen atoms or hydroxyl groups. Such monomers may, preferably, be selected from the group consisting of unsaturated monomers, lactones, alkylimines and lactams.

Preferred compounds, their weight percent graft, the average number of grafted monomeric units (n) and the average molecular weight of grafted claims ($M_w$) are given in Table (b-8)-A.

TABLE (b-8)-A

| No. | Polysaccharide | grafted monomer | weight % graft | n | $M_w$ |
|---|---|---|---|---|---|
| 1 | starch | styrene | 40 | 6.8 | 710 |
| 2 | starch | isoprene | 25 | 5.8 | 400 |
| 3 | starch | acrylonitrile | 49 | 9.2 | 500 |
| 4 | starch | methyl methacrylate | 50 | 13.6 | 1,360 |
| 5 | starch | methyl acrylate | 42 | 9.8 | 845 |
| 6 | starch | methyl acrylate/ butyl/acrylate | 50 | 6.25 | 700 |
| 7 | starch | acrylic acid | 45 | 9.2 | 450 |
| 8 | starch | acrylamide | 52 | 9.2 | 500 |
| 9 | starch | beta-propiolactone | 40 | 1.4 | 100 |
| 10 | starch | ethylenimine | 42 | 1.7 | 75 |
| 11 | starch | propylenimine | 35 | 1.2 | 70 |
| 12 | starch | caprolactam | 30 | 0.4 | 50 |
| 13 | starch | alkylammonium acrylate | 40 | 2.6 | 600 |
| 14 | starch | methyl vinyl ether | 40 | 10.3 | 600 |
| 15 | starch | acrylamide/ Na acrylate | 60 | 9.2 | 500 |
| 16 | amylose | butyl acrylate | 50 | 4.7 | 600 |
| 17 | amylose | butyl acrylate/ acrylonitrile | 40 | 3.0 | 550 |
| 18 | amylose | ethyl acrylate | 45 | 6.5 | 650 |
| 19 | amylose | ethyl acrylate/ acrylonitrile | 45 | 8.1 | 625 |
| 20 | dextrin | acrylamide | 48 | 9.0 | 490 |
| 21 | dextrin | acrylonitrile | 47 | 8.3 | 450 |
| 22 | carboxyl cellulose | styrene | 50 | 6.25 | 650 |
| 23 | carboxyl | butadiene | 40 | 4.6 | 250 |

TABLE (b-8)-A-continued

| No. | Polysaccharide | grafted monomer | weight % graft | n | $M_w$ |
|---|---|---|---|---|---|
| | cellulose | | | | |
| 24 | carboxyl cellulose | butadiene/ styrene | 42 | 4.0 | 320 |
| 25 | alginate | acrylamide | 45 | 2.8 | 200 |
| 26 | alginate | acrylonitrile | 42 | 8.3 | 450 |
| 27 | alginate | styrene | 48 | 5.0 | 520 |
| 28 | alginate | butadiene | 40 | 5.7 | 310 |
| 29 | alginate | methyl methacrylate | 43 | 3.4 | 340 |
| 30 | cellulose | styrene | 27.8 | 5.4 | 560 |
| 31 | cellulose | acrylonitrile | 27.0 | 7.7 | 420 |
| 32 | cellulose | styrene/ acrylonitrile | 26.0 | 5.7 | 450 |
| 33 | cellulose | acrylamide | 17.0 | 4.4 | 320 |
| 34 | cellulose | acrylic acid | 15.0 | 4.2 | 300 |
| 35 | cellulose | methylmethacrylate | 28.9 | 2.5 | 250 |
| 36 | cellulose | methyl acrylate | 36.0 | 3.2 | 280 |
| 37 | cellulose | ethyl acrylate | 34.0 | 3.1 | 310 |
| 38 | cellulose | butyl acrylate | 29.4 | 2.3 | 300 |
| 39 | cellulose | isobutyl acrylate | 29.6 | 1.7 | 220 |
| 40 | cellulose | butadiene | 25.0 | 3.5 | 190 |
| 41 | cellulose | butadiene/ styrene | 24.0 | 2.6 | 210 |
| 42 | cellulose | isoprene | 20.0 | 2.6 | 180 |
| 43 | cellulose | methacrylamide | 25.0 | 2.2 | 190 |
| 44 | cellulose | vinyl acetate | 22.0 | 2.7 | 230 |
| 45 | cellulose | vinyl chloride | 20.0 | 3.12 | 195 |
| 46 | cellulose | ethylene | 16.0 | 3.6 | 100 |
| 47 | ethyl cellulose | methacrylic acid | 35 | 3.8 | 325 |
| 48 | ethyl cellulose | methylmethacrylate | 32 | 3.0 | 300 |
| 49 | ethyl cellulose | styrene | 29 | 2.4 | 250 |
| 50 | ethyl cellulose | vinyl acetate | 30.5 | 2.3 | 200 |
| 51 | hydroxyethylcellulose | butyl acrylate | 35 | 2.2 | 280 |
| 52 | hydroxyethylcellulose | butyl acrylate/ acrylonitrile | 40 | 2.2 | 200 |
| 53 | hydroxyethylcellulose | ethyl acrylate | 41 | 1.9 | 190 |
| 54 | hydroxyethylcellulose | ethyl acrylate/ acrylonitrile | 45 | 2.7 | 210 |
| 55 | methyl cellulose | acrylonitrile | 40 | 4.6 | 250 |
| 56 | cellulose acetate | acrylamide | 20 | 2.8 | 200 |
| 57 | cellulose acetate | acrylonitrile | 25 | 3.5 | 190 |
| 58 | cellulose acetate | methyl acrylate | 22 | 2.6 | 220 |
| 59 | cellulose acetate | ethyl acrylate | 24 | 2.3 | 230 |
| 60 | cellulose acetate | methyl methacrylate | 20 | 2.2 | 220 |
| 61 | cellulose | vinyl acetate | 20 | 2.3 | 200 |

Preferred graft copolymers are those made from cellulose or starch. More preferred are those which are grafted with a monomer or with monomers selected from the group consisting of styrene; butadiene; isoprene; acrylonitrile; alkylacrylate, preferably methylacrylate; alkylmethacrylate, preferably methylmethacrylate; acrylic acid; methacrylic acid; alkyl vinyl ether, preferably methyl vinyl ether; and acrylamide.

Most preferred are those which are grafted with a monomer or with monomers selected from the group consisting of isoprene; acrylonitrile; methylacrylate; methyl methacrylate; acrylic acid; methyl vinyl ether and acrylamide.

The alkylammonium acrylates mentioned under No. 13 of Table (b-9)-1 correspond to the formula $$CH_2=CH-CO_2-(CH_2)_x-NR_3^+A^-$$ (XXVIII)

wherein
x=2, 3 or 4, preferably 2 or 3,
R=methyl or ethyl, preferably methyl
A=an anion, preferably chloride or acetate, preferably acetate.

Preferred graft polymerization includes also the monomers selected from the group of beta propiolactone, ethyleneimine, trimethyleneimine and caprolactam.

Preferred from Table (b-8)-1 are the compounds Nos. 1, 3, 5, 7, 9, 10, 11, 12, 13, 14, 17, 20, 21, 22, 25, 26, 29, 30, 31, 33, 34, 36, 43, 44, 45, 46, 49, 50, 55, 57, 61.

Most preferred from Table (b-8)-1 are the compounds Nos. 1, 3, 4, 5, 6, 9, 10, 12, 14, 16, 21, 22, 25, 30, 44, 46, 61.

Tenth Embodiment (b-10)

The compounds of component (b-10) are selected from the group consisting of polyalkyleneimines and polyalkyleneimine copolymers.

Polyalkyleneimines are those polyamines which are derived from cyclic amine precursors. Such precursors are secondary or tertiary amines or amides Polyalkyleneimines are known and described, e.g. in Encyclopaedia of Polymer Science and Engineering, John Wiley & Sons, Volume 1, pages 680 ff (1987).

Polyamines of component (b-10) can be derived from unsubstituted or substituted ethyleneimines (aziridines)

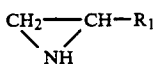 (XXIX)

yielding a polymer of the formula $$-(CH_2-\underset{|}{\overset{R_1}{C}}H-NH)-$$ (XXX)

wherein
$R_1$ is H or $CH_3$; preferably H;

as a linear polymer, generally with an average molecular weight ($M_w$) of about 25,000 to about 430,000, or as a branched polymer with an average molecular weight of about 300 to about 100,000.

Further useful polyimines can be derived from N-substituted ethyleneimines as follows:

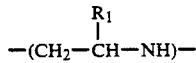 (XXXI)

wherein $R_1$ is methyl or hydrogen, preferably hydrogen and wherein R has the meaning as given in Table (b-10)-A.

TABLE (b-10)-A

| No. | monomer | molecular weight of the polymer ($M_w$) |
|---|---|---|
| 1a | 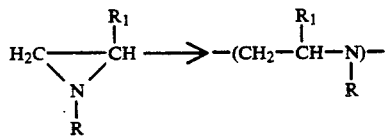 | 25,000–430,000 (linear) |
| 1b | " | 300–100,000 |

TABLE (b-10)-A-continued

| No. | monomer | | molecular weight of the polymer ($M_w$) (branched) |
|---|---|---|---|
| 2 | $CH_2—CH_2$ NR | $R = —CH_2—CH_2OH$ | ca. 2,000 |
| 3 | " | $R = —CH_2—CH_2—CN$ | ca. 2,000 |
| 4 | " | $R = —COCH_3$ | ca. 24,000–40,000 |
| 5 | " | $R = —COC_2H_5$ | ca. 24,000–40,000 |
| 6 | $CH_2—CH_2$ \| \| $CH_2—N—R$ | $R = H$ | ca. 300–100,000 |
| 7 | " | $R = CH_3$ | ca. 2,000 |
| 8 | " | $R = —CH_2CH_2—CO_2C_2H_5$ | ca. 2,500 |

In principle such polyimines having free reactive NH-groups can be submitted to different reaction, such as acylation or arylation.

Such polyimines are also known per se. They can be used as a component (b-10) according to this invention.

The different alkyleneimines monomers can be copolymerized with each other. Also numerous grafted copolymers are known. Such compounds can also be used as a component (b-10) according to this invention.

Preferred as component (b-10) are polyalkyleneimines as derived from at least one compound selected from the group consisting of alkyleneimine, N-substituted alkyleneimine and 2-methyl-ethyleneimine.

More preferred as component (b-10) are polyalkyleneimines as derived from at least one compound selected from the group consisting of ethyleneimine, N-acetyl-ethyleneimine (containing the $=N—CO—CH_3$ group) and N-propionyl-ethyleneimine (containing the $=N—CO—C_2H_5$ group).

Eleventh Embodiment (b-11)

The compounds of component (b-11) are selected from the group consisting of styrene sulfonic acid polymers, styrene sulfonic acid copolymers and salts thereof.

Poly(styrene sulfonic acid) compounds, styrene sulfonic acid copolymers, both with different degrees of sulfonation, their corresponding sulfonates (salts) as well as the method for their production are known and described, e.g. in Encyclopaedia of Polymer and Engineering, John Wiley & Sons, 1987.

Poly(styrene sulfonic acid), i.e. styrene sulfonic acid polymers useful according to this invention have a molecular weight generally from about 2000 to about 1,500,000, preferably from about 4000 to about 1,200,000.

Styrene sulfonic acid copolymers are known and can be described as copolymers of different unsaturated monomers with styrene sulfonic acid, for example their sulfonates.

As a special interest within the scope of this invention are block copolymers of sulfonated styrene with unsaturated monomers such as ethylene, propylene, butylene, isobutylene, butadiene, isoprene, and/or styrene.

Preferred salts thereof, including the corresponding sulfonates are their salts with metal ions or the ammonium ion, preferably an alkali metal ion, magnesium or zinc or $NH_4^+$, preferably sodium, potassium or zinc, preferably the sodium salt.

Preferred are polystyrene sulfonic acids and polystyrene sulfonate sodium salts preferably with an average molecular weight of 10,000 to 400,000. The degree of sulfonation is between about 5% and about 100%, preferably between about 10% and about 50%.

Twelfth Embodiment (b-12)

The component (b-12) is a compound selected from the group consisting of polymers and copolymers which contain carboxylic groups in the form of their salts as further defined hereinbelow.

Polymers and copolymers thus obtained are known per se and may have a general formula wherein the number of repeating units varies for each individual type of polymer resp. copolymer as e.g. described in "Encyclopaedia of Polymer Science and Technology, Interscience Publ. Vol. 14, 1971".

Such polymers in their salt form are obtained by polymerization of e.g. acrylic acid, methacrylic acid, crotonic acid, maleic acid, maleic acid anhydride, itaconic acid, itaconic acid anhydride or a mixture of such acids and subsequent salt formation of a part or of all the carboxyl groups.

The polymers and copolymers of component (b-12) do not contain further functional groups. The term "functional group" as used herein includes all known polar groups that may be bound to the polymer chain such as, for example, hydroxyl alkoxy, carboxylalkyl, alkyl carboxy, halo, pyrrolidono, acetal and the like.

Copolymers of component (b-12) are further those wherein said acids have been copolymerized with one or more unsaturated monomers containing no functional groups. The term "unsaturated monomers containing no functional group" includes for example alkenes such ethylene, isobutylene, proypylene, etc. It also includes styrene, as the benzene nucleus but this is not considered to be a functional group within the scope of this invention.

Copolymers in their salt form useful as component (b-12) therefore contain carboxyl groups in their salt form as well as other units as are obtained by copolymerization of acrylic acid, methacrylic acid, crotonic acid, maleic acid, itaconic acid, with monomers such as ethylene, butylene isobutylene, propylene, isoprene, butadiene and/or styrene or other known monomers of this class with subsequent salt formation. Such copolymers are known.

Preferred is a copolymer of said acids With ethylene, e.g. the ethylene-acrylic-acid copolymer in the form of its salt or an ethylene-methacrylic acid copolymer in the form of its salt.

The polymers and copolymers of the present invention contain carboxylate groups of the formula:

—COOM wherein M is a monovalent or polyvalent cation, the ammonium cation ($NH_4^+$) or an organic base cation.

When M is a metal cation, it is preferably an alkali cation, preferably sodium or lithium or a divalent ion such as magnesium or zinc or as an organic base cation preferably one of the formula

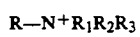
$R—N^+R_1R_2R_3$     (XXXII)

wherein

R is alkyl ($C_1$-$C_{18}$), or alkylene carrying further $N^+ R_1 R_2 R_3$ residues;

$R_1$, $R_2$, $R_3$, independent of each other, are hydrogen, or an alkyl($C_1$-$C_4$).

Said organic base cation can also be a positively charged pyridine residue, carbazyl residue or p-aminophenyl residue.

Preferably M is sodium or zinc wherein the polymer contains also free carboxyl groups.

Such obtained repeating units in the polymer carrying carboxylate groups can be exemplified by the following formulas:

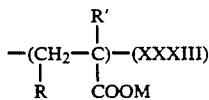

where
R is H, $CH_3$, —COOH or —COOM
R' is H, $CH_3$ or —$CH_2$—COOH or —$CH_2$—COOM
M is as defined above.

Preferred copolymers are those containing repeating units as exemplified in the formulas (XXXIV) and (XXXV).

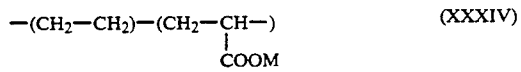

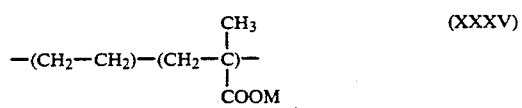

The amount of carboxyl and carboxylate containing monomeric moiety within a copolymer will depend on the type of copolymer. Said amount will generally be between 3 mol % and 40 mole %, preferably between 3.5 mol % and 30 mol % and most preferably between 3.5 mol % and 20 mol % calculated to the total amount of monomeric moieties within the molecule.

The degree of neutralization of the carboxyl groups to form the carboxylates is preferably from 30% to 100%. More preferred is a degree of neutralization of 40% to 90%.

As mentioned above, the polymer composition comprising the components (a) and (b), including (b-1), (b-2), (b-3), (b-4), (b-5), (b-6), (b-7), (b-8), (b-9), (b-10), (b-11), (b-12) and mixtures thereof, optionally contains one or more substantially water-insoluble hydrophobic polymers (component (c)), as well as further additives.

As previously mentioned, the present invention also contemplates the combination of component (a) and (c) without the requirement of component (b). Examples of substantially water-insoluble hydrophobic thermoplastic materials useful as component (c) in this embodiment are polyolefins, such as polyethylene (PE), polyisobutylenes, polypropylenes, vinylpolymers such as poly(vinyl chloride) (PVC); poly(vinyl acetates), polystyrenes; polyacrylonitriles (PAN); polyvinylcarbazols (PVK); substantially water-insoluble poly(acrylic acid) esters or poly(methacrylic acid) esters: polyacetals (POM): polycondensates such as polyamides (PA), thermoplastic polyesters, polycarbonates poly(aklylene terephthalates); polyarylethers; thermoplastic polyimides; but also poly(hydroxy butyrate) (PHB) and high molar-mass, essentially water-insoluble poly(alkylene oxides) such as polymers of ethylene oxide and propylene oxide as well as their copolymers are included.

Further included are substantially water-insoluble thermoplastic copolymers of the different kinds known such as ethylene/vinyl acetate-copolymers (EVA) ethylene/vinyl alcohol-copolymers (EVAL); ethylene/acrylic acid-copolymers (EAA); ethylene/ethyl acrylate-copolymers (EEA); ethylene/methyl acrylate-copolymers (EMA); acrylonitrile/butadiene/styrene-copolymers (ABS); styrene/acrylonitrile-copolymers (SAN); as well as their mixtures.

Thirteenth Embodiment (c)

Preferred among these component (c) materials of the thirteenth embodiment are those with a set processing temperature preferably within the range of 95° C. to 210° C., preferably within the range of 95° C. to 190° C. Even more preferred are those polymers containing polar groups such as ether, acid or ester groups. Such polymers include e.g. copolymers of ethylene, propylene or isobutylene such as ethylene/vinyl acetate-copolymers (EVA), ethylene/vinyl alcohol-copolymers, ethylene/acrylic acid-copolymers (EAA), ethylene/ethyl acrylate-copolymers (EEA), ethylene/methacrylate copolymers (EMA), styrene/acrylonitrile-copolymers (SAN); polyacetals (POM) and their mixtures as mentioned above.

The component (c) as used in any of the present compositions is a substantially water-insoluble polymer or a mixture of such substantially water-insoluble polymers. Component (c) is preferably present in an amount effective to enhance the physical properties of articles made from the composition of the invention (which amount is sometimes referred to herein as an "effective amount" of component (c)), for example increase of dimensional stability of final products made therefrom or adjusting the degree of biodegradability.

As used herein a "substantially water-insoluble thermoplastic polymer" is a polymer which preferably absorbs less than 10% of water, more preferably less than 5% per 100 grams of the polymer at room temperature and most preferably less than 2% per 100 grams of the polymer at room temperature.

Examples of substantially water-insoluble thermoplastic materials are polyolefins, such as polyethylene (PE), polyisobutylenes, polypropylenes; vinyl polymers such as poly(vinyl chloride) (PVC); poly(vinyl acetates); polystyrenes; polyacrylonitriles (PAN); polyvinyl carbazoles (PVK); substantially water-insoluble polyacrylates or polymethacrylates such as poly(acrylic acid) esters and poly(methacrylic acid) esters; polyacetals (POM); thermoplastic polycondensates such as polyamides (PA), polyesters, polyurethanes, polycarbonates, poly(alkylene terephthalates); polyarylethers and thermoplastic polyimides; poly(hydroxy butyrate)(PHB) and high molar-mass, substantially water-insoluble or crystallizable poly(alkylene oxides) such as polymers or copolymers of ethylene oxide and propylene oxide as well as their copolymers.

Further included are substantially water-insoluble thermoplastic copolymers known such as alkylene/vinyl ester-copolymers preferably ethylene/vinyl acetate-copolymers (EVA); ethylene/vinyl alcohol-copolymers (EVAL); alkylene/acrylates or methacrylate copolymers preferably ethylene/acrylic acid copolymers (EAA); ethylene/ethyl acrylate-copolymers (EEA); ethylene/methyl acrylate-copolymers (EMA); acrylonitrile-butadiene-styrene copolymers (ABS-copolymers); styrene/acrylonitrile-copolymers (SAN);

alkylene/maleic anhydride copolymers preferably ethylene/maleic anhydride copolymers; acrylic acid esters/acrylonitrile copolymers; acrylamide/acrylonitrile copolymers; block copolymers of amide-ethers, block copolymers of amide-esters; block copolymers of urethane-ethers, block copolymers of urethane-esters; as well as mixtures thereof.

Preferred from these are those which undergo melt formation at a set processing temperature within the range of about 95° C. to about 260° C., preferably within the range of about 95° C. to about 220° C. more preferably within the range of about 95° C. to about 210° C. and most preferably within the range of about 95° C. to about 190° C.

Also preferred are those polymers containing polar groups such as ester, ether, acid, amide, or urethane groups. Such polymers include e.g. copolymers of ethylene, propylene or isobutylene with vinyl compounds or acrylates such as, ethylene/vinyl acetate copolymers (EVA), ethylene/vinyl alcohol-copolymers (EVAL), ethylene/acrylic acid-copolymers (EAA), ethylene/ethyl acrylate-copolymers (EEA), ethylene/-methacrylate-copolymers (EMA), styrene/acrylonitrile- copolymers (SAN); block copolymers of amide-ethers, block copolymers of amide-esters; block copolymers of urethane TM ethers, block copolymers of urethane-esters; as well as mixtures thereof.

Certain copolymers useful as a component (c) are exemplified hereinbelow schematically by the following general formulas. The units within brackets represent the individual component mer units within each copolymer. These units may be combined in any known fashion, including random or block copolymerization, and the molecular weight of the polymer may be within known ranges.

These copolymers are preferred for use with component b-1 and b-3. Where R is preferably methyl, ethyl, propyl, butyl, or octadecyl, more preferably methyl, ethyl, propyl, or butyl and most preferably methyl.

$$-(CH_2-CH_2)-(CH_2-CH)- \atop | \atop O=C-OR \qquad (XXXVI)$$

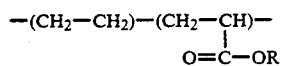

(XXXVII)

R$_2$ is H or CH$_3$
R$_4$ is H, —CH$_3$ or —CH$_2$, —CH$_3$

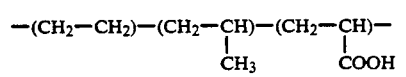

(XXXVIII)

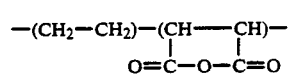

(XXXIX)

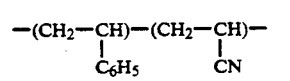

(XL)

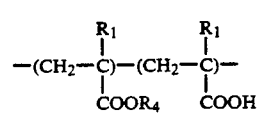

(XLI)

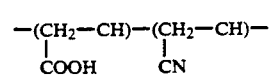

(XLII)

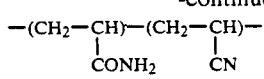

(XLIII)

Most preferred for component (c) for use with component (b-2) are those polymers containing one type of functional group which is the same type of functional group as that of component (b-2) which is not carboxyl.

Preferred for selection as component (c) for use with component (b-4) are those polymers containing polar groups such as ether, acid, ester, amide, or urethane groups. Such polymers include e.g. copolymers of ethylene, propylene or isobutylene with vinyl compounds or acrylates such as ethylene/vinyl acetate-copolymers (EVA), ethylene/vinyl alcohol-copolymers (EVAL), ethylene/acrylic acid-copolymers (EAA), ethylene/ethyl acrylate-copolymers (EEA), ethylene/methacrylate-copolymers (EMA), styrene/acrylonitrile-copolymers (SAN); polyacetals; block copolymers of amide-ethers, amide-esters; block copolymers of urethane-ethers, urethane-esters; as well as their mixtures.

Most preferred for use with component (b-4) are those polymers containing polar groups and most preferably those which contain active hydrogen atoms, ester groups and/or ether groups and/or urethane groups.

Such substantially water-insoluble thermoplastic polymers may be added in any desired amount as described herein.

Acid groups such as carboxyl groups and hydroxyl groups such as hydroxymethyl, hydroxypropyl or vinyl alcohol groups may react together prior or during processing. It is therefore a precaution that carboxyl groups and hydroxyl groups which may react together to the disadvantage of the blend system are absent, especially with component (b-7). However, this does not necessarily always happen and such useful combinations, which for the person skilled in the art are a matter of system optimization, are included within the scope of the present invention.

Such polymers may be used in any known form. Their molecular weight is also generally known in the art. It is also possible to use such polymers of relatively low molecular weight (oligomers). The choice of a particular molecular weight range is a matter of optimization and routine experimentation known to the one skilled in the art.

In the composition according to this invention, the two components (a) and (b) or the three components (a), (b) and (c) always add up to 100% and the values of the components given in percent hereinbelow refer to the sum of 100%.

The ratio of destructurized starch to component (b) and optionally to the sum of components (b) and (c) can be 1:99 to 99:1. It is however preferred that the destructurized starch contributes noticeably to the properties of the final material. Therefore, it is preferred that the destructurized starch is present in an amount of at least about 20%, more preferably about 50% and most preferably in the range of about 70% to about 99% by weight of the entire composition. That is, component (b) is and optionally the sum of the components (b) and (c) are present in amounts of about 80% or less, more preferably less than or equal to about 50% and most preferably in the range of about 30% to about 1% by weight of the entire composition.

The ratio of destructurized starch to component (b-1) and optionally to the sum of components (b-1) and (c) can be 1:99 to 99:1. It is however, preferred that the destructurized starch contributes noticeably to the properties of the final material. Therefore, it is preferred that the destructurized starch is present in an amount of at least about 20%, more preferably about 50% and most preferably in the range of about 70% to about 99% by weight of the entire composition. That is, component (b-1) and optionally the sum of the components (b-1) and (c) are present in amounts of about 80% or less, more preferably less than or equal to about 50% and most preferably in the range of about 30% to about 1% by weight of the entire composition.

The ratio of destructurized starch to component (b-2) and optionally to the sum of the components (b-2) and (c) can be 1:99 to 99:1. It is however, preferred that the destructurized starch contributes noticeably to the properties of the final material. Therefore, it is preferred that the destructurized starch is present in an amount of at least about 20%, more preferably about 50% and most preferably in the range of about 70% to about 99% by weight of the entire composition. That is, component (b-2) and optionally the sum of the components (b-2) and (c) are present in amounts of about 80% or less, more preferably less than or equal to about 50% and most preferably in the range of about 30% to about 1% by weight of the entire composition.

The ratio of destructurized starch to component (b-5) or to the sum of the components (b-5) and (c) can be 1:99 to 99:1. It is however preferred that the destructurized starch contributes noticeably to the properties of the final material. Therefore, it is preferred that the destructurized starch is present in an amount of at least 20%, more preferably 50% and most preferably in the range of 60% to 90% by weight of the entire composition. That is, the sum of the components (b-5) and (c) are present in amounts of about 80% or less, more preferably less than or equal to 50% and most preferably in the range of 40% to 10% by weight of the entire composition.

The ratio of destructurized starch to component (b-7) and optionally to the sum of components (b-7) and (c) can be 1:99 to 99:1. It is however, preferred that the destructurized starch contributes noticeably to the properties of the final material. Therefore, it is preferred that the destructurized starch is present in an amount of at least 20%, more preferably 50% and most preferably in the range of 70% to 99% by weight of the entire composition. That is, component (b-7) and optionally the sum of the components (b-7) and (c) are present in amounts of about 80% or less, more preferably less than or equal to 50% and most preferably in the range of 30% to 1% by weight of the entire composition.

The ratio of destructurized starch to component (b-8) and optionally to the sum of components (b-8) and (c) can be 1:99 to 99:1. It is however, preferred that the destructurized starch contributes noticeably to the properties of the final material. Therefore, it is preferred that the destructurized starch is present in an amount of at least about 10%, more preferably about 50% and most preferably in the range of about 60% to about 90% by weight of the entire composition. That is, component (b-8) and optionally the sum of the components (b-8) and (c) are present in amounts of about 90% or less, more preferably less than or equal to about 50% and most preferably in the range of about 40% to about 10% by weight of the entire composition.

The ratio of destructurized starch to component (b-9) may vary preferably from about 99:1 to 70:30, preferably from about 98:2 to about 80:20. Most preferred is a ratio from about 95:5 to about 90:10.

The ratio of destructurized starch to the sum of the components (b-9) and (c) can be 1:99 to 99:1. It is however, preferred that the destructurized starch contributes noticeably to the properties of the final material. Therefore, it is preferred that the destructurized starch is present in an amount of at least about 20%, more preferably about 50% and most preferably in the range of about 60% to about 95% by weight of the entire composition. That is, the sum of the components (b-9) and (c) are present in amounts of about 80% or less, more preferably less than or equal to about 50% and most preferably in the range of about 40% to about 5% by weight of the entire composition.

The ratio of destructurized starch to component (b-10) and optionally to the sum of components (b-10) and (c) can be 1:99 to 99:1. It is however preferred that the destructurized starch contributes noticeably to the properties of the final material. Therefore, it is preferred that the destructurized starch is present in an amount of at least 20%, more preferably 60% and most preferably in the range of about 70% to 90% by weight of the entire composition. That is, component (b-10), and optionally the sum of the components (b-10) and (c) are present in amounts of about 80% or less, more preferably less than or equal to about 40% and most preferably in the range of about 30% to about 10% by weight of the entire composition.

The ratio of the destructurized starch to the component (b-10) preferably varies from about 99:1 to about 60:40 preferably from about 98:2 to about 70:30. Most preferred is a ratio from about 90:10 to about 80:20.

The preferred ratio of destructurized starch to component (b-11) differs slightly from the other embodiments which the ratio may vary from about 99:1 to 70:30 preferably it is from about 98:2 to about 80:20. Most preferred is a ratio from about 95:5 to about 90:10.

The ratio of destructurized starch to the sum of components (b-11) and (c) can be 1:99 to 99:1. It is however, preferred that the destructurized starch contributes noticeably to the properties of the final material. Therefore, it is preferred that the destructurized starch is present in an amount of at least about 20%, more preferably about 50% and most preferably in the range of about 60% to about 95% by weight of the entire composition. That is, the sum of the components (b-11) and (c) are present in amounts of about 80% or less, more preferably less than or equal to about 50% and most preferably in the range of about 40% to about 5% by weight of the entire composition.

The ratio of destructurized starch to component (b-12) is preferably from about 10:90 to about 99:1, preferably from about 30:70 to about 95:5. Most preferred is a ratio from about 50:50 to about 90:10.

The ratio of destructurized starch to the sum of components (b-12) and (c) can be 1:99 to 99:1. It is however, preferred that the destructurized starch contributes noticeably to the properties of the final material. Therefore, it is preferred that the destructurized starch is present in an amount of at least 20%, more preferably about 40% and most preferably in the range of about 60% to about 90% by weight of the entire composition. That is, the sum of the components (b) and (c) are present in amounts of about 80% or less, more preferably less than or equal to about 60% and most preferably in the range of about 40% to about 10% by weight of the entire composition.

In the thirteenth embodiment, the ratio of the water-containing destructurized starch to component (c) can be 0.1:99.9 to 99.9:0.1. It is however preferred that the destructurized starch contributes noticeably to the properties of the final material. Therefore, it is preferred that the destructurized starch is present in an amount of at least 50% and more preferably in the range of 70% to 99.5% by weight of the entire composition, i.e. the synthetic polymer is present in a concentration of less than 50% and more preferably in a concentration in the range of 30% to 0.5% by weight of the entire composition.

A mixture of 0.5 to 15% by weight of the synthetic polymer (component (c)) and 99.5 to 85% of the water containing destructurized starch shows already a significant improvement in the properties of the obtained materials. For certain applications a ratio of the synthetic polymer to the starch/water component of 0.5–5% to 99.5–95% is preferred and especially a ratio of 0.5–2% to 99.5–98% by weight.

Component (b) is a relatively polar material. When it functions in the present compositions in combination with component (c), it is able to mix more readily with a more polar component (c) than with a less polar one. Accordingly, with components (c) that are more polar, relatively less of component (b) will be required than with less components (c) that are less polar. The skilled worker will be able to select appropriate ratios of components (b) and (c) to obtain a substantially homogenous melt composition.

Compositions comprising 1 to 15% by weight of component (b) or the sum of the components (b) and (c) and 99 to 85% of destructurized starch show a significant improvement in the properties of the obtained materials. For certain applications the preferred ratio of component (b) or the sum of components (b) and (c) to the destructurized starch component is about 1 to about 10% to about 99 to about 90% by weight of the total composition. If the destructurized starch contains water, the percentage of this destructurized starch component present is meant include the weight of water.

The starch may be mixed prior to destructurization with additives as named hereinbelow to yield a free flowing powder useful for continuous processing or may be destructurized and granulated before it is mixed with components (b) or (b) and (c) or (c) alone or the other optionally added components. Thus, the starch may be partially or wholly destructurized prior to being mixed with other components or additives, and in the former case further destructurized during additional processing. The other components to be added are preferably granulated to a granular size equal to that of the granulated destructurized starch.

However, it is possible to process native starch or pre-extruded and/or destructurized granulated or powdered starch together with powdered or granulated additives and/or the polymeric material in any desired mixture or sequence.

Thus, it is preferred that components (a), (b) and (c) as well as other conventional additives be mixed in a standard mixer. This mixture can then be passed through an extruder to produce granulates or pellets as one form of shaped articles which are also useful as starting material for processing into other articles. However, it is possible to avoid granulating and to process the obtained melt directly using down-stream equipment to produce films, blown films including, sheets, profiles, pipes, tubes, foams or other shaped articles. The sheets can be used for thermoforming.

It is preferred that fillers, lubricants and/or plasticizers be added to the starch before destructurization. However the addition of coloring agents as well as of the components (b), (c) and additives other than the aforementioned can be added before, during or after destructurization.

The substantially destructurized starch/water component or granules have a water content in the range of about 10 to about 22% by weight of the starch/water component, preferably about 10 to 20%, more preferably about 12 to about 19% and most preferably about 14 to about 18% by weight of the starch/water component.

The water content described above refers to the percentage of water relative to the weight of the starch/water component within the total composition and not to the weight of the total composition itself, which would include also the weight of any added substantially water-insoluble thermoplastic polymer.

In order to destructurize the starch and/or to form a melt of the new polymeric composition according to this invention, it is suitably heated in a screw and barrel of an extruder for a time long enough to effectuate destructurization and melt formation. The temperature is preferably within the range of 105° C. to 240° C., more preferably within the range of 130° C. to 190° C. depending on the type of starch used. For this destructurization and melt formation, the composition is heated in a closed volume. A closed volume can be a closed vessel or the volume created by the sealing action of the unmolten feed material as happens in the screw and barrel of injection molding or extrusion equipment. In this sense the screw and barrel of an injection molding machine or an extruder is to be understood as being a closed vessel. Pressures created in a closed vessel correspond to the vapor pressure of water at the temperature used but of course additional pressure may be applied and/or generated as normally occurs in a screw and barrel. The preferred applied and/or generated pressures are in the range of pressures which occur in extrusion and are known per se, e.g. from 5 to $150 \times 10^5$ N/m$^2$ preferably from 5 to $75 \times 10^5$ N/m$^2$ and most preferably from 5 to $50 \times 10^5$ N/m$^2$. If the thus-obtained composition is comprised only of destructurized starch, it may be granulated and ready to be mixed with the further components according to a chosen mixing and processing procedure to obtain the granular mixture of the destructurized starch/polymer starting material to be fed to the screw barrel.

However, the obtained melt in the screw and barrel may be injection molded directly into a suitable mold, i.e. directly further processed to a final product if all necessary components are already present.

Within the screw, the granular mixture obtained as described above is heated to a temperature which is generally within the range of about 80° C. to about 240° C., preferably within the range of about 120° C. to about 220° C. and most preferably within the range of about 130° C. to about 190° C. Preferably, such mixture is heated to a sufficiently high temperature and for a time long enough until the endothermic transition analysis (DSC) indicates that the specific relatively narrow peak just prior to the endotherm characteristic of oxidative and thermal degradation of starch has disappeared.

The minimum pressures under which the melts are formed correspond to the water vapor pressures produced at said temperatures. The process is carried out in a closed volume as explained above, i.e. in the range of the pressures which occur in extrusion or molding processes and known per se, e.g. from zero to $150 \times 10^5$ $N/m^2$ preferably from zero to $75 \times 10^5$ $N/m^2$ and most preferably from zero to $50 \times 10^5$ $N/m^2$.

When forming a shaped article by extrusion, the pressures are preferably as mentioned above. If the melt according to this invention is, e.g., injection molded, the normal range of injection pressures used in injection molding is applied, e.g. from $300 \times 10^5$ $N/m^2$ to $3000 \times 10^5$ $N/m^2$ and preferably from $700 \times 10^5$ to $2200 \times 10^5$ $N/m^2$.

Accordingly, the present invention provides a thermoplastic destructurized-starch substantially homogenous melt formed by the process comprising:

1) providing a mixture comprising starch and at least one polymer which contains at least two different types of functional groups, one of said types being hydroxyl groups (component (b-1)); and 2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one polymer which contains at least two different types of functional groups, one of said types being hydroxyl groups (component (b-1));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The present invention provides a thermoplastic destructurized-starch substantially homogenous melt formed by the process comprising:

1) providing a mixture comprising starch and at least one polymer which does not contain hydroxyl groups and is selected from the group consisting of polymers which contain at least two types of functional groups bound to the same molecule, one type of these groups being carboxylate groups (component (b-2)); and 2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one polymer which does not contain hydroxyl groups and is selected from the group consisting of polymers which contain at least two types of functional groups bound to the same molecule, one type of these groups being carboxylate groups (component (b-2));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention also provides a thermoplastic destructurized-starch substantially homogenous melt formed by the process comprising:

1) providing a mixture comprising starch and at least one polymer selected from the group consisting of polymers which contain tertiary amino groups and/or salts thereof and/or quaternary ammonium groups (component (b-3)); and 2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one polymer selected from the group consisting of polymers which contain tertiary amino groups and/or salts thereof and/or quaternary ammonium groups (component (b-3));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The present invention provides a thermoplastic destructurized-starch substantially homogenous melt formed by the process comprising:

1) providing a mixture comprising starch and at least one polymer selected from the group of polysaccharides which have been chemically modified to contain added hydroxyalkyl groups and/or contain alkyl ether groups, and/or contain ester groups (component (b-4)); and 2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one polymer selected from the group of polysaccharides which have been chemically modified to contain added hydroxyalkyl groups and/or contain alkyl ether groups, and/or contain ester groups (component (b-4));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention provides a thermoplastic destructurized-starch substantially homogenous melt formed by the process comprising:

1) providing a mixture comprising starch and at least one compound selected from the group consisting of copolymers of vinyl pyrrolidone (component (b-5));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group consisting of copolymers of vinyl pyrrolidone (component (b-5));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The present invention also provides a thermoplastic destructurized-starch substantially homogenous melt formed by the process comprising:

1) providing a mixture comprising starch and at least one compound selected from the group consisting of cationically modified polysaccharides (component (b-6));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group consisting of cationically modified polysaccharides (component (b-6));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention also provides a thermoplastic destructurized-starch substantially homogenous melt formed by the process comprising:

1) providing a mixture comprising starch and at least one compound selected from the group consisting of anionically modified polysaccharides (component (b-7));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group consisting of anionically modified polysaccharides (component (b-7));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

Accordingly, the present invention provides a thermoplastic destructurized-starch substantially homogenous melt formed by the process comprising:

1) providing a mixture comprising starch and at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group (component (b-8));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group; said polymer being present in an amount effective to enhance the physical properties of said articles (which amount is sometimes referred to herein as an "effective amount" of component (b-8));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention also provides a thermoplastic destructurized-starch substantially homogenous melt formed by the process comprising:

1) providing a mixture comprising starch and at least one compound selected from the group consisting of polysaccharide graft copolymers and graft copolymers of polysaccharide derivatives (component (b-9));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group consisting of polysaccharide graft copolymers and graft copolymers of polysaccharide derivatives (component (b-9));

2) heating said mixture in a closed volume under sufficient temperature and pressure for a time long enough to effect destructurization of said starch and form a substantially homogenous melt;

3) shaping said melt into an article; and 4) allowing said shaped article to cool to a substantially dimensionally stable thermoplastic product.

The invention provides a thermoplastic destructurized-starch substantially homogenous melt formed by the process comprising:

1) providing a mixture comprising starch and at least one compound selected from the group consisting of polyalkyleneimine polymers and polyalkyleneimine copolymers (component (b-10));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group consisting of polyalkyleneimine polymers and polyalkyleneimine copolymers (component (b-10));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention provides a thermoplastic destructurized-starch substantially homogenous melt formed by the process comprising:

1) providing a mixture comprising starch and at least one compound selected from the group consisting of styrene sulfonic acid polymers, styrene sulfonic acid copolymers, and salts thereof (component (b-11));

2) heating said mixture in a closed volume under sufficient temperature and pressure for a time long enough to effectuate destructurization of said starch and form said melt.

The present invention also provides a thermoplastic destructurized-starch product having substantial dimensional stability formed by the process comprising:

1) providing a mixture comprising starch and at least one compound selected from the group consisting of styrene sulfonic acid polymers, styrene sulfonic acid copolymers, and salts thereof (component (b-11));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The invention provides a thermoplastic destructurized-starch substantially homogenous melt formed by the process comprising:

1) providing a mixture comprising starch and at least one compound selected from the group of polymers and copolymers which contain carboxylic groups which partially or wholly are present in the form of their salts and wherein said polymers or copolymers do not contain further functional groups (component (b-12));

2) heating said mixture in a closed volume under sufficient temperature and pressure for a time long enough to effectuate destructurization of said starch and formation of said melt.

The present invention also provides a thermoplastic destructurized-starch product having substantial dimensional stability formed by the process comprising:

1) providing a mixture comprising starch and at least one compound selected from the group of polymers and copolymers which contain carboxylic groups which partially or wholly are present in the form of their salts and wherein said polymers or copolymers do not contain further functional groups (component (b-12));

2) heating said mixture in a closed volume under sufficient temperature and pressure for a time long enough to effectuate destructurization of said starch and form a substantially homogenous melt;

3) shaping said melt into an article; and 4) allowing said shaped article to cool to a substantially dimensionally stable thermoplastic product.

The mixture provided in step 1) of any or the above-described processes may additionally contain component (c) and additives as described herein.

The present invention also provides a method of producing a polymeric material comprising:

1) providing a mixture comprising starch and a substantially water-insoluble synthetic thermoplastic polymer (component (c));

2) heating said mixture in a closed volume under sufficient temperature and pressure for a time long enough to effectuate destructurization of said starch and form a substantially homogenous melt.

The present invention further provides the additional steps of:

3) shaping said melt into an article;

4) allowing said shaped article to cool to a substantially dimensionally stable thermoplastic product.

The present invention also contemplates the addition of component (c) (and in the case of other embodiments, component (b)) during the heating, as well as before heating.

Various hydrophilic polymers may be used as additives. These include water-soluble and water-swellable polymers. As such it includes animal gelatin, vegetable gelatins; proteins· such as sunflower protein, soybean proteins, cotton seed proteins, peanut proteins, rape seed proteins, blood proteins, egg proteins, acrylated proteins; water-soluble polysaccharides; alkyl celluloses, hydroxyalkyl celluloses and hydroxyalkylalkyl celluloses, such as methyl cellulose, hydroxymethyl cellulose, hydroxyethyl cellulose, hydroxypropyl cellulose, hydroxyethylmethyl cellulose, hydroxypropylmethyl cellulose, hydroxybutylmethyl cellulose, cellulose esters and hydroxyalkyl cellulose esters such as cellulose acetylphthalate (CAP), hydroxypropylmethyl cellulose (HPMCP); analogous known polymers made from starch; carboxyalkylcelluloses and their esters carboxyalkylalkylcelluloses, carboxymethyl celluloses and their alkalimetal salts; water-soluble or water-swellable synthetic polymers such as: polyacrylic acids and polyacrylic acid esters, polymethacrylic acids and their salts and polymethacrylic acid esters, polyvinyl alcohols, polyvinyl acetatephthalates (PVAP), poly(vinyl acetates), polyvinyl pyrrolidone, polycrotonic acids; polyitaconic acid, polymaleic acid; suitable are also phthalated gelatin, gelatin succinate, cross-linked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Preferred are synthetic polymers, most preferably, are polyacrylic acid esters, polymethacrylic acids, polymethacrylic acid esters, polyvinyl alcohols and polyvinyl pyrrolidone.

Such hydrophilic polymers may optionally be added up to about 50% based on the starch/water component, preferably up to about 30% and most preferably between about 5% and about 20% based on the starch/water component. If any hydrophilic polymer is added, its mass should be considered along with the starch in determining the appropriate amount of water in the composition.

Other useful additives include, without limitation, adjuvants, fillers, lubricants, mold release agents, plasticizers, foaming agents, stabilizers, coloring agents, pigments, extenders, chemical modifiers, flow accelerators, flavorings, fragrances and mixtures thereof.

Examples of fillers are inorganic fillers, such as the oxides of magnesium, aluminum, silicon, titanium, and the like, preferably in a concentration in the range of about 0.02 to about 3% by weight, and more preferably about 0.20 to about 1% based on the total weight of all the components.

Examples of lubricants are stearates of aluminum, calcium, magnesium and tin as well as talc, silicones, and the like, which may be present in concentrations of about 0.02 to about 5%, preferably at about 0.1 to about 3% based upon the weight of the total composition.

Examples of plasticizers include low molecular poly(alkylene oxides), such as poly(ethylene glycols), poly(propylene glycols), poly(ethylene-propylene glycols); organic plasticizers of low molar masses, such as glycerol, pentaerythritol, glycerol monoacetate, diacetate or triacetate; propylene glycol, sorbitol, xylitol, mannitol, sodium diethylsulfosuccinate, and the like, added in concentrations ranging from about 0.5 to about 15%, preferably ranging from about 0.5 to about 5% based on the total weight of all the components. Examples of coloring agents include known azo dyes, organic or inorganic pigments, or coloring agents of natural origin. Inorganic pigments are preferred, such as the oxides of iron or titanium. These oxides, known per se, may be added in concentrations ranging from about 0.001 to about 10%, preferably about 0.5 to about 3%, based on the weight of all the components.

There may further be added compounds to improve the flow properties of the starch material such as animal or vegetable fats, preferably in their hydrogenated form, especially those which are solid at room temperature. These fats have preferably a melting point of 50° C. or higher. Preferred are triglycerides of $C_{12}$-, $C_{14}$-, $C_{16}$-, and $C_{18}$- fatty acids.

These fats can be added alone without adding extenders or plasticizers.

These fats can advantageously be added alone or together with monoglycerides and/or diglycerides or phosphatides, especially lecithin. The mono- and diglycerides are preferably derived from the types of fats described above, i.e. from $C_{12}$-, $C_{14}$-, $C_{16}$-, and $C_{18}$- fatty acids.

The total amount of fats, monoglycerides, diglycerides and/or lecithins used are up to about 5% and preferably within the range of about 0.5 to about 2% by weight of the total weight of starch and any added hydrophilic polymer.

The materials may further contain stabilizers, such as antioxidants, e.g. thiobisphenols, alkyldienbisphenols secondary aromatic amines; light stabilizers such as UV-absorbers and UV-quenchers; hydroperoxide decomposers; free-radical scavengers; and stabilizers against microorganisms.

The compositions of the invention form thermoplastic melts on heating in a closed volume, i.e. under conditions of controlled water-content and pressure. Such melts can be processed just like conventional thermoplastic materials, using, for example, conventional apparatus for injection molding, blow molding, extrusion and coextrusion (rod, pipe and film extrusion), compression molding and foaming, to produce desired articles. The articles include bottles, sheets, films, packaging materials, pipes, rods, laminated films, sacks, bags, pharmaceutical capsules, granules, powders or foams.

For example, these compositions may be used to prepare low density packaging materials (e.g. foams) by any known methods. Conventional blowing agents may be utilized if desired or, for certain compositions, the water itself may act as the blowing agent. Open cell and closed cell foams may be produced as desired by varying the composition and processing conditions. These foams produced from the present compositions will demonstrate improved properties (e.g., dimensional stability, moisture resistance, etc.) when compared with foams made of starch without incorporation of the components (b) and (c) according to this invention.

These compositions may be used as carrier materials for active substances, and may be mixed with active ingredients, such as pharmaceuticals and/or agriculturally active compounds such as insecticides or pesticides for subsequent release applications of these ingredients. The resulting extruded materials can be granulated or worked to fine powders.

The following examples serve to provide further appreciation of the invention but are not meant in any way to restrict the effective scope of the invention. All percentages throughout the specification and claims are by weight of the total composition unless otherwise indicated.

Example (b-1)-1

(a) 5000 g of potato starch containing 14.87% water were placed in a high speed mixer and 485 g of water were added under stirring. To the above mixture of starch and water, 425 g of polyvinyl alcohol-co-vinyl acetate, (component (b-1)) containing 11%–13% of the monomeric units as vinyl acetate and 87%–89% of the monomeric units as vinyl alcohol sold as Airvol 540S by Air Products, Allentown, Pa.; and 42 g of polyethylene-co-vinyl acetate (component (c)) containing 80% of the monomeric units as ethylene and 20% of the monomeric units as vinyl acetate sold as Escorene UL02020 by Exxon, New York, N.Y.; 42.5 g of hydrogenated fat (lubricant/release agent) sold as Boeson VP by Boehringer Ingelheim; 21.25 g of a melt flow accelerator (lecithin) sold as Metarin P by Lucas Meyer and 21.25 g of titanium dioxide (pigment and solid mixture flow accelerator) were added under stirring. The water content of the final mixture was 19.98%.

(b) 5000 g of the mixture prepared under (a) were fed through a hopper into a Leistritz Single Screw Lab Extruder LSM 30 having a temperature profile of 55° C./ 145° C./ 165° C./ 165° C. The screw speed was 50 rpm. The output of extrudate was 124 g/min.

The extrudate was cut into granulates and stored for further processing.

(c) For further processing the granulates were conditioned to a water content of 17% by adding water under stirring in a conventional mixer. The obtained material was then fed through a hopper to a Kloeckner-Ferromatic FM 60 injection-molding machine, for the production of tensile test pieces. The temperature profile was 90° C./ 155° C./ 155° C./ 155° C., the screw speed: 180 rpm, the shot weight 8.2 g, the residence time 450 sec., the injection pressure 1800 bar, the back pressure 30 bar.

All tensile test pieces were conditioned in a climatic cabinet at 50% R.H. for five days as an arbitrary standard condition.

The test pieces were of standard DIN design (DIN No. 53455).

(d) The conditioned tensile test pieces were then tested for their stress/strain behavior on an Instron tensile test apparatus, each test with 4 pieces.

The samples were measured at room temperature using an extension rate of 10 mm per minute. Results are presented in Table 1 and compared with those obtained with tensile test pieces obtained from the same starch processed in a similar way but in absence of components (b) and (c). It can be seen from the results that the Young's modulus of the ternary blend is decreased from 1.56 to 1.29 showing a softening of the injection molded blend material compared to similar tensile test pieces produced from unblended starch.

The break stress goes from 32.72 MPa to 37.22 MPa indicating an increase of the strength of the blend. The break strain (elongation at break) going from 15.82% to 33.33% and break energy from 194.30 kJ/m$^2$ to 415.75 kJ/m$^2$ showing a considerable increase in the toughness of the blend material over the unblended one.

TABLE (b-1)-1

|  | Break Strain (%) | Break Energy (kJ/m$^2$) |
|---|---|---|
| starch (unblended starch) | 15.82 | 194.3 |
| ternary blend (b-1)-1 | 33.33 | 415.75 |

Of course different blend compositions show different values for the physical parameters indicated. To obtain the best values is a matter of optimization by varying the concentration of the different components, which is no problem to the expert in the art.

Example (b-1)-1 is repeated with the following blends as per the Examples (b-1)-2 to 10 whereby analogous results as given in Table (b-1)-1 obtained.

Example (b-1)-2

Example (b-1)-1 is repeated except that the ratio of the components is varied as given in Table (b-1)-2. For comparison perspective, Example (b-1)-1 is shown as Blend No. 1.

TABLE (b-1)-2

| Blend No. | starch: component (b + c) (weight ratio) | component (b): component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness as judged by resistance to breaking upon bending increases from blend 9 to blend 2 in concert with the combined increase in vinyl alcohol content. While the resistance to softening in humid atmosphere is improved in all cases relative to unmodified starch, the resistance of blends 1,4,5 and 6 are particularly good. These results illustrate the unexpected combinations as benefits in performance.

Example (b-1)-3

Example (b-1)-1 is repeated by replacing component (b) (polyvinyl alcohol-co-vinyl acetate) by poly(hydroxyethyl methacrylate) (HEMA). Component (c) (polyethylene-co-vinyl acetate) is replaced by polymethyl methacrylate. The resulting injection molded polymer is tougher and more resistant to humid than unmodified starch polymer.

Example (b-1)-4

Example (b-1)-1 is repeated by replacing component (b) (polyvinyl alcohol-co-vinyl acetate) by poly(hydroxyethyl methacrylate) (HEMA). Polyethylene-co-vinyl acetate (86% ethylene, 14% vinyl acetate) is used as component (c). The resulting injection molded polymer is tougher and more resistant to humid air than unmodified starch polymer.

Example (b-1)-5

Example (b-1)-1 is repeated by increasing component (b) to 850 g and replacing component (c) by 85 g of polystyrene. The resulting injection molded polymer is tougher and more resistant to humid air than unmodified starch polymer.

Example (b-1)-6

Example (b-1)-1 is repeated by increasing component (b) to 1700 g and replacing component (c) by 42 g of polyvinyl chloride-co-vinyl acetate (91% vinyl chloride—9% vinyl acetate). The resulting injection molded polymer is tougher and more resistant to humid air than unmodified starch polymer.

Example (b-1)-7

Example (b-1)-1 is repeated by replacing component (b) with polyvinyl alcohol-co-vinyl butyral (40% vinyl alcohol, 60% vinyl butyral). Component (c) is replaced by 42 g polyvinyl butyral. The resulting injection molded polymer is tougher and more resistant to humid air than unmodified starch polymer.

Example (b-1)-8

Example (b-1)-1 is repeated by increasing component (b) to 3400 g and replacing component (c) by 38 g polypropylene. The resulting injection molded polymer is tougher and more resistant to humid air than unmodified starch polymer.

Example (b-1)-9

(a) 9500 g of potato starch containing 15.1% water were placed in a high speed mixer and 425 g of polyvinyl alcohol-co-vinyl acetate (component (b)) sold as Airvol 540S by Air Products and containing 11–13% of the monomeric units as vinyl acetate and 87–89% of the monomeric units as vinyl alcohol. 80.75 g of hydrogenated fat (lubricant release agent) sold as Boeson VP by Boehringer Ingelheim, 40.37 g of a melt flow accelerator (lecithin) sold as Metarin P by Lucas Meyer were added under stirring. The water content of the final mixture was 14.43%.

(b) 10,000 g of the mixture prepared under (a) were fed through a hopper into a Werner & Pfleiderer corotating twin screw extruder (model Continua 37).

The temperature profile of the four sections of the barrel was respectively 20° C./180° C./180° C./80° C.

Extrusion was carried out with a mixture output of 8 kg/hr (screw speed 200 rpm). Water was added at the inlet with a flow rate of 2 kgs/hr. The water content of the material during extrusion was therefore 31.5%. In the last section of the extruder, 80 mbar reduced pressure was applied to remove part of the water as water vapor.

The water content of the granulates was 17.15% as measured after they had equilibrated at room temperature.

(c) The granulates of the pre-blended mixture as obtained under (b) (H₂O content: 17.5%) were fed through a hopper to an Arburg 329-210-750 injection molding machine for the production of tensile test pieces. The temperature profile of the barrel was: 90° C./165° C./165° C./165° C.

The shot weight was 8 g, the residence time 450 sec., the injection pressure 2082 bar, the back pressure 80 bar, the screw speed 180 rpm.

The tensile test pieces thus produced were conditioned in a climatic cabinet at 50% R.H. for five days as an arbitrary standard condition.

The test pieces were of standard DIN design (DIN No. 53455).

(d) The conditioned tensile test pieces were then tested for their stress/strain behavior on a Zwick tensile test apparatus.

The samples were measured at room temperature using an extension rate of 10 mm per minute. Results are presented in Table (b-1)-3 and compared with those obtained with tensile test pieces obtained from the same starch processed in a similar way but in absence of components (b) and (c).

ture. They were brought to a water content of 17% by spraying water under stirring in a conventional mixer.

(c) The granulates of the pre-blended mixture as obtained under (b) (H₂O content: 17%) were fed through a hopper to an Arburg 329-210-750 injection molding machine for the production of tensile test pieces. The temperature profile of the barrel was: 90° C./ 185° C./185° C./185° C.

The shot weight was 7.9 g, the residence time 450 sec., the injection pressure 2200 bar, the back pressure 80 bar, the screw speed 180 rpm.

The tensile test pieces thus produced were conditioned in a climatic cabinet at 50% R.H. for five days as an arbitrary standard condition to equilibrate them at a water content of about 14%.

The test pieces were of standard DIN design (DIN No. 53455).

(d) The conditioned tensile test pieces were then tested for their stress/strain behaviour on a Zwick tensile test apparatus as given in Example (b-1)-9.

Example (b-1)-11

(a) 8900 g of potato starch containing 15.1% water were placed in a high speed mixer and 765 g of polyvinyl alcohol-co-vinyl acetate (component (b)) sold as Airvol 540S by Air Products (containing 11-13 mole % vinyl acetate and 87-89 mole % vinyl alcohol). 85 g polyethylene-co-vinyl acetate (component (c)) containing 20 mole % vinyl acetate and 80 mole % ethylene) sold as Escorene U102020 by Exxon; 85 g polyethylene (component (c)) sold as Lupolen 2410T by BASF. 75.65

TABLE (b-1)-3

|  | unblended starch | Example Nos. (b-1)- | | | | | | | | |
| --- | --- | --- | --- | --- | --- | --- | --- | --- | --- | --- |
|  |  | 9 | 10 | 11 | 12 | 13 | 14 | 15 | 16 | 17 |
| break strain % | 22 | 38.5 | 56 | 26 | 33 | 37 | 27 | 43 | 55 | 43 |
| break energy KJ/m² | 325 | 506 | 900 | 338 | 444 | 520 | 315 | 499 | 687 | 500 |

Example (b-1)-10

(a) 8000 g of potato starch containing 15% water were placed in a high speed mixer and 2720 g of polyvinyl alcohol-co-vinyl acetate (component (b)) sold as Airvol 540S by Air Products and containing 11-13% of the monomeric units as vinyl acetate and 87-89% of the monomeric units as vinyl alcohol; 68 g of hydrogenated fat (lubricant release agent) sold as Boeson VP by Boehringer Ingelheim, 34 g of a melt flow accelerator (lecithin) sold as Metarin P by Lucas Meyer were added under stirring. The water content of the final mixture was 15.6%.

(b) 10,000 g of the mixture prepared under (a) were fed through a hopper into a Werner & Pfleiderer co-rotating twin screw extruder (model Continua 37).

The temperature profile of the four sections of the barrel was respectively 20° C./50° C./100° C./50° C.

Extrusion was carried out with a mixture output of 8 kg/hr (screw speed 200 rpm). Water was added at the inlet with a flow rate of 1 kg/hr. The water content of the material during extrusion was therefore 25%. In the last section of the extruder, 22 mbar reduced pressure was applied to remove part of the water as water vapor.

The water content of the granulates was 14.8% as measured after they had equilibrated at room temperag of hydrogenated fat (lubricant/release agent) Boeson VP and 37.82 g of a melt flow accelerator (lecithin/-Metarin P) were added under stirring. The water content of the final mixture was 13.5%.

(b) 9000 g of the mixture prepared under (a) were fed through a hopper into the same twin-screw co-rotating extruder described in Example (b-1)-9. The extrusion of the mixture was carried out with the same temperature profile: 20° C./180° C./180° C./80° C. The other parameters of the extrusion experiment were the following:
material output: 9 kg/hr
screw speed: 200 rpm
water added: 2 kg/hr
reduced pressure (last section): 300 mbar
water-content during extrusion: 29.2%

The water content of the granulates was 17.12% as measured after they had equilibrated at room temperature.

(c) The granulates obtained under (b) were processed using the same injection molding machine described in (c) of Example (b-1)-9. The temperature profile of the barrel was 90° C./165° C./165° C./165° C. The other processing parameters were:
shot weight: 8 g
residence time: 450 sec.
injection pressure: 1825 bar back pressure: 80 bar
screw speed: 180 rpm The tensile test pieces thus produced were conditioned and tested on a Zwick tensile test apparatus as described in (d) of Example (b-1)-9.

Results are presented in Table (b-1)-3.

Example (b-1)-12

(a) 8900 g of potato starch containing 15.5% water were placed in a high speed mixer and 765 g of polyvinyl alcohol-co-vinyl acetate (component (b)) containing 11%. 14 mole % vinyl alcohol and 87–89 mole % vinyl acetate; 170 g of polyamide-block-polyether (component c) sold as Pebax MA-4011 by Atochem; 75.65 g of hydrogenated fat (lubricant/ release agent) Boeson VP; 37.82 g of a melt flow accelerator (lecithin) Metarin P were added under stirring. The water content of the final mixture was 13.4%.

(b) 9000 g of the mixture prepared under (a) were fed through a hopper into the same twin-screw co-rotating extruder described in Example (b-1)-9.

The extrusion of the mixture was carried out with the following processing parameters:
temperature profile: 20° C./220° C./220° C./80° C.
material output: 8 kg/hr
screw speed: 200 rpm
water added: 2 kg/hr
reduced pressure (last section): 150 mbar
water content during extrusion: 29.14%

The water content of the granulates was 17.20% after they had equilibrated at room temperature.

(c) The granulates of (b) were processed using the same injection molding machine of Example (b-1)-9. The processing parameters were the following:
temperature profile: 90° C./165° C./165° C./165° C.
shot weight: 8 g
residence time; 450 sec
injection molding: 2220 bar
back pressure; 80 bar
screw speed: 180 rpm The tensile test pieces thus produced were conditioned and tested on a Zwick tensile test apparatus described in (d) of Example (b-1)-9.

Results are presented in Table (b-1)-3.

Example (b-1)-13

(a) 8900 g of potato starch containing 15.1% water were placed in a high speed mixer and 765 g of polyvinyl alcohol-co-vinyl acetate (component (b)) Airvol 540S and containing 11–13 mole % of vinyl alcohol and 87–89 mole % vinyl acetate; 170 g of a thermoplastic elastomer polyurethane block polyether (component (c)) sold as Pellethane 2103-80-AE by Dow Chemical Company, Midland, Mich.; 75.65 g of hydrogenated fat (lubricant/release agent) Boeson VP; 37.82 g of a melt flow accelerator (lecithin) Metarin P were added under stirring. The water content of the final mixture was 13.5%.

(b) 9000 g of the mixture prepared under (a) were fed through a hopper into the same twin-screw co-rotating extruder described in Example (b-1)-9.

The extrusion of the mixture was carried out with the following processing temperature:
temperature profile: 20° C./220° C./220° C./80° C.
material output: 8 kg/hr
screw speed: 200 rpm
water added: 2 kg/hr
reduced pressure (last section): 80 mbar
water content during extrusion: 29.2%

The water content of the granulates was 16.9% after they had equilibrated at room temperature.

(c) The granulates obtained under (b) were processed using the same injection molding machine described in (c) of Example (b-1)-9. The processing parameters were the following:
temperature profile: 90° C./165° C./165° C./165° C.
weight: 8 g
residence time; 450 sec
injection molding: 2220 bar
back pressure; 80 bar
screw speed: 180 rpm The tensile test pieces thus produced were conditioned and tested on a Zwick tensile test apparatus described in (d) of Example (b-1)-9.

Results are presented in Table (b-1)-3.

Example (b-1)-14

(a) 8000 g of potato starch containing 15.1% water were placed in a high speed mixer and 340 g of polyvinyl alcohol-co-vinyl acetate, Airvol 540S (component (b)) containing 11–13 mole % of vinyl alcohol and 87–89 mole % vinyl acetate; 680 g of polyamide block polyether thermoplastic elastomer polyurethane (component (c) sold as Pebax MA-4011 by Atochem; 680 g of polyurethane-block-polyether thermoplastic elastomer (component (c)) sold as Pellethane 2103-80-AE by Dow Chemical Company; 68 g of hydrogenated fat (lubricant/release agent) Boeson VP; 34 g of a melt flow accelerator (lecithin) Metarin P were added under stirring. The water content of the final mixture was 12.3%.

(b) 9000 g of the mixture prepared under (a) were fed through a hopper into the same twin-screw co-rotating extruder described in Example (b-1)-9.

The extrusion of the mixture was carried out with the following processing parameters:
temperature profile: 20° C./220° C./220° C./80° C.
material output: 8 kg/hr
screw speed: 200 rpm
water added: 2.1 kg/hr
reduced pressure (last section): 600 mbar
water content during extrusion: 27.7%

The water content of the granulates was 16.8% after they had equilibrated at room temperature.

(c) The granulates obtained under (b) were processed using the same injection molding machine described in (c) of Example (b-1)-9. The processing parameters were the following:
temperature profile: 90° C./165° C./165° C./165° C.
shot weight: 8 g
residence time; 450 sec
injection molding: 1650 bar
back pressure; 80 bar
screw speed: 180 rpm The tensile test pieces thus produced were conditioned and tested on a Zwick tensile test apparatus described in (d) of Example (b-1)-9.

Results are presented in Table (b-1)-3.

Example (b-1)-15

Example (b-1)-14 was repeated with the differences that (i) potato starch was decreased to 5000 g, (ii) polyvinyl alcohol-co-vinyl acetate (Airvol 540S) was increased to 1770 g, (iii) polyamide (Pebax-4011) was decreased to 531 g and (iv) the polyurethane (Pellethane 2103-80-AE) was decreased to 531 g.

Results are given in Table (b-1)-3.

Example (b-1)-16

(a) 7000 g of potato starch containing 15.0% water were placed in a high speed mixer and 1700 g of polyvinyl alcohol-co-vinyl acetate (component (b)) Airvol 540S (component (b)) containing 11-13 mole % of vinyl acetate and 87-89 mole % vinyl alcohol (Airvol 540S); 425 g of a thermoplastic elastomer polyamide-block-polyether Pebax Ma-4011 of Atochem; 425 g of thermoplastic elastomer polyurethane-block-polyether Pellethane 2103-80-AE by Dow Chemical Company; 59.5 g of hydrogenated fat (lubricant/release agent) Boeson VP; 29.75 g of a melt flow accelerator (lecithin) Metarin P were added under stirring. The water content of the final mixture was 11%.

(b) 9000 g of the mixture prepared under (a) were fed through a hopper into the same twin-screw co-rotating extruder described in Example (b-1)-9.

The extrusion of the mixture was carried out with the following processing parameters:
temperature profile: 20° C./220° C./220° C./80° C.
material output: 8 kg/hr
screw speed: 200 rpm
water added: 2.1 kg/hr
reduced pressure (last section): 600 mbar
water content during extrusion: 26.8%

The water content of the granulates was 16.8% after they had equilibrated at room temperature.

(c) The granulates obtained under (b) were processed using the same injection molding machine described in (c) of Example (b-1)-9. The processing parameters were the following:
temperature profile: 90° C./165° C./165° C./165° C.
shot weight: 8 g
residence time; 450 sec
injection molding: 2280 bar
back pressure; 80 bar
screw speed: 180 rpm.

The tensile test pieces thus produced were conditioned and tested on a Zwick tensile test apparatus described in (d) of Example (b-1)-9.

Results are presented in Table (b-1)-3.

Example (b-1)-17

(a) 5000 g of potato starch containing 15.0% water were placed in a high speed mixer and 708 g of polyvinyl alcohol-co-vinyl acetate, Airvol 540S (component (b)) containing 11-13 mole % of vinyl alcohol and 87-89 mole % vinyl acetate (Airvol 540S); 2125 g of a polyethylene-co-vinyl alcohol EVAL EP-L-101 (component (c)) containing 73 mole % vinyl alcohol and 27 mole % ethylene; 42.5 g of hydrogenated fat (lubricant-/release agent) Boeson VP; 21.3 g of a melt flow accelerator (lecithin) Metarin P were added under stirring. The water content of the final mixture was 9.8%.

(b) 9000 g of the mixture prepared under (a) were fed through a hopper into the same twin-screw co-rotating extruder described in Example (b-1)-9.

The extrusion of the mixture was carried out with the following processing parameters:
temperature profile: 20° C./80° C./220° C./180° C.
material output: 8 kg/hr
screw speed: 200 rpm
water added: 2.1 kg/hr
reduced pressure (last section): 33 mbar
water content during extrusion: 28.7%

The granulates were brought to a water content of 17% by spraying water under stirring in a conventional mixer.

(c) The granulates obtained under (b) were processed using the same injection molding machine described in (c) of Example (b-1)-9. The processing parameters were the following:
temperature profile: 90° C./175° C./175° C./175° C.
shot weight: 7.6 g
residence time; 450 sec
injection molding: 2020 bar
back pressure; 80 bar
screw speed: 180 rpm The tensile test pieces thus produced were conditioned and tested on a Zwick tensile test apparatus described in (d) of Example (b-1)-9.

Results are given in Table (b-1)-3.

EXAMPLE (b-1)-18

Example (b-1)-1 (Sections (a) and (b)) is repeated except that the water content is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-1)-19

During each of the injection molding operations in Examples (b-1)-2-14 an experiment is performed to demonstrate the utility of making foams. The molten material was obtained as described in Example (b-1)-1, Sections a), b) and c) in each case was extruded into the open atmosphere (Section c) instead of being injection molded into a closed mold. In every case the material is converted into a foamed extrudate useful for loose-fill in packaging applications.

Example (b-1)-20

The granulates from Example (b-1)-1 are mixed with polystyrene in the proposition of 30 to 70 parts by weight and are treated according to Example (b-1)-18. The resulting foamed extrudate contains a very fine and uniform structure suitable for a variety of uses including structural foam.

Example (b-2)-1

(a) 5000 g of potato starch containing 14.87% water are placed in a high speed mixer and 485 g of water are added under stirring. To the above mixture of starch and water, 425 g of crotonic acid-co-vinyl acetate, sodium salt (component (b)) containing 13% of the monomeric units as vinyl acetate and 87% of the monomeric units as crotonic acid of which 90% are in form of sodium salt and 42 g of polyethylene-co-vinyl acetate (component (c)) containing 80% of the monomeric units as ethylene and 20% of the monomeric units as vinyl acetate (sold as Escorene UL02020 by Exxon); 42.5 g of hydrogenated fat (lubricant/release agent) sold as Boeson VP by Boehringer Ingelheim; 21.25 g of a melt flow accelerator (lecithin) and 21.25 g of titanium dioxide (pigment and solid mixture flow accelerator) are added under stirring. The water content of the final mixture is 20%.

(b) 5000 g of the mixture prepared under (a) are fed through a hopper into a Leistritz Single Screen Lab Extruder LSM 30 having a temperature profile of 55°

C./145° C./165° C./165° C. with an output of extrudate of 100 g/min.

The extrudate is cut into granulates and the water content is determined to be 13.10%. The granulates are then brought back to a water content of 17% by spraying of water under stirring in a conventional mixer.

(c) The granulates of the pre-blended mixture as obtained under (b) are fed through a hopper to an injection-molding machine Kloeckner-Ferromatic FM 60, for the production of tensile test pieces. The processing conditions are the following: temperature profile: 90° C./155° C./155° C./155° C., shot weight: 8.2 g, residence time: 450 sec., injection pressure: 1800 bar, back pressure: 30 bar.

All the tensile test pieces are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on an Instron tensile test apparatus, each test with 4 pieces.

The samples are measured at room temperature using an extension rate of 10 mm per minute. Results are presented in Table (b-2)-1 and compared with those obtained with tensile test pieces obtained from the same starch processed in a similar way but in absence of components (b) and (c).

The break strain (elongation at break) going from 15.82% to 31.20% and break energy from 194.30 kJ/m$^2$ to 395.25 kJ/m$^2$ showing a considerable increase in the toughness of the blend material over the unblended one.

Of course, blend compositions show different values for the physical parameters indicated. To obtain the best values is a matter of optimization by varying the concentration of the different components, which is no problem to the expert in the art.

TABLE (b-2)-1

| | Break Strain (%) | Break Energy (kJ/m$^2$) |
|---|---|---|
| starch (unblended starch) | 15.82 | 194.3 |
| ternary blend (b-2)-1 | 31.20 | 395.25 |

Example (b-2)-1 is repeated with the following blends as per the Examples (b-2)-2 to 6 whereby analoguous results as given in Table (b-2)-1 are obtained.

Example (b-2)-2

Example (b-2)-2 is repeated except that the ratio of the components is varied as given in Table 2. For comparison perspective, Example 1 is shown as Blend No. 1.

TABLE (b-2)-2

| Blend No. | starch: component (b) + (c) (weight ratio) | component (b): component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness as judged by resistance to breaking upon bending increases from blend 9 to blend 2 in concert with the combined increase in crotonic acid-co-vinyl acetate and sodium salt content. While the resistance to softening in humid atmosphere is improved in all cases relative to unmodified starch, the resistance of blends 1,4,5 and 6 are particularly good. These results illustrate the unexpected combinations as benefits in performance.

Example (b-2)-3

Example (b-2)-1 is repeated by using 800 g of the same sodium salt of polyvinylcrotonic acid-co-vinyl acetate, (component (b)) instead of 425 g and 250 g of the same polyethylene-co-vinyl acetate (component (c)).

The resulting injection molded polymer is tougher and more resistant to humid air than unblended starch polymer.

Example (b-2)-4

Example (b-2)-1 is repeated by using 1200 g of the same of sodium salt of polyvinylcrotonic acid/co-vinyl acetate, (component (b)) instead of 425 g and 500 g of the same polyethylene-co-vinyl acetate Escorene UL02020 (component c) instead of 42 g.

The resulting injection molded polymer is tougher and more resistant to humid air than unblended starch polymer.

Example (b-2)-5

Example (b-2)-1 is repeated but without polyethylene-co-vinyl acetate (component (c)).

The results obtained are shown in Table (b-2)-3.

TABLE (b-2)-3

| | Break Strain (%) | Break Energy (kJ/m$^2$) |
|---|---|---|
| starch (unblended starch) | 16.00 | 195.00 |
| binary blend (b-2)-1 | 26.00 | 350.00 |

These results show an increase of break strain and break energy (increase of strength and toughness of the binary blend).

In a further run, the content of the sodium salt of polyvinyl-crotonic acid-co-vinyl acetate binary blend is increased to 850 g and 2125 g respectively.

The physical-mechanical properties of the resulting injection molded polymers are superior to those of the unblended starch.

Example (b-2)-6

Example (b-2)-5 with the binary blend is repeated but by replacing the 425 g of the sodium salt of polycrotonic acid-co-vinyl acetate, (component (b)) by 850 g of polymethylmethacrylate-co-methacrylic acid, sodium salt having the following composition: 80% of the monomeric units as methylmethacrylate and 20% of the monomeric units as methacrylic acid of which 90% are in form of sodium salt. The results are shown in Table (b-2)-4.

The obtained injection molded test pieces show improved physical-mechanical properties as compared to those of unblended starch.

TABLE (b-2)-4

|  | Break Strain (%) | Break Energy (kJ/m$^2$) |
|---|---|---|
| starch (unblended starch) | 16.00 | 195.00 |
| binary blend (b-2)-6 | 35.00 | 400.00 |
| binary blend (b-2)-7 | 45.00 | 700.00 |

Example (b-2)-7

Example (b-2)-6 is repeated but 1700 g of the sodium salt of polymethyl methacrylate-co-methacrylic acid, (component (b)) is used instead of 850 g. The physical-mechanical properties of the obtained test pieces are shown on Table (b-2)-4. It can be seen that these properties compared to those of unblended starch are considerably better.

Example (b-2)-8

(a) 5000 g of potato starch containing 15.1% water are placed in a high speed mixer with 130 g of the sodium salt of polymethylmethacrylate-co-methacrylic acid, (component (b)) described in Example 6; 85 g of Nylon 12 (component (c)) Vestamid L-1700 Huels Chemie; 42.5 g of hydrogenated fat (lubricant release agent) Boeson VP, Boehringer Ingelheim, and 21.25 g of a melt flow accelerator (lecithin) sold as Metarin P by Lucas Meyer are added under stirring. The water content of the final mixture is 14.2%.

(b) 5000 g of the mixture prepared under (a) are fed through a hopper into a Werner & Pfleiderer co-rotating twin screw extruder (model Continua 37).

The temperature profile of the four sections of the barrel is 20° C./80° C./220° C./100° C., respectively.

Extrusion is carried out with a mixture output of 8 kg/hr (screw speed 200 rpm). Water is added at the inlet with a flow rate of 4.1 kgs/hr. The water content of the material during extrusion is therefore 31.5%. In the last section of the extruder 300 mbar reduced pressure is applied to remove part of the water as water vapor.

The water content of the granulates is 17.4% as measured after they have equilibrated at room temperature.

(c) The granulates of the pre-blended mixture as obtained under (b) (H$_2$O content: 17.4%) are fed through a hopper to an injection molding machine Arburg 329-210-750 for the production of tensile test pieces. The temperature profile of the barrel is: 90° C./155° C./155° C./155° C., respectively.

The shot weight is 8 g, the residence time 450 sec., the injection pressure 1833 bar, the back pressure 80 bar, the screw speed 180 rpm.

All the tensile test pieces were conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. The physical-mechanical properties of the corresponding injection molded test pieces are superior to those of the unblended starch.

Example (b-2)-9

(a) 2100 g of potato starch containing 15% water are placed in a high speed mixer and 765 g of the sodium salt of acrylamide-co-acrylic acid, (component (b)) containing 90 mole % acrylamide and 10 mole % acrylic acid is blended with 5950 g of thermoplastic polyamide elastomer (component (c)) sold as Pebax MA-4011 by Atochem. 17.85 g of hydrogenated fat (lubricant-/release agent) Boeson VP and 8.93 g of a melt flow accelerator (lecithin/Metarin P) are then added under stirring. The water content of the final mixture is 13.5%.

(b) 8000 g of the mixture prepared under (a) are fed through a hopper into the same twin-screw co-rotating extruder described in Example 8. The extrusion of the mixture is carried out with the same temperature profile: 20° C./80° C./240° C./80° C. The other parameters of the extrusion experiment are the following:
material output: 9 kg/hr
screw speed: 200 rpm
water added: 1.8 kg/hr
reduced pressure (last section): 500 mbar
water-content during extrusion: 28.6%

The water content of the granulates is 6.95% as measured after they had equilibrated at room temperature. The granulates are then remoistured to 17% H$_2$O.

(c) The granulates obtained under (b) are processed using the same injection molding machine described in (c) of Example (b2)-8. The temperature profile of the barrel is 90° C./155° C./155° C./155° C. The other processing parameters were:
shot weight: 6.6 g
residence time: 450 sec.
injection pressure: 550 bar
back pressure: 80 bar
screw speed: 180 rpm The tensile test pieces thus produced are conditioned and tested on a Zwick tensile test apparatus as described in (d) of Example (b-2)-8.

Results are presented in Table (b-2)-5.

TABLE (b-2)-5

|  | Break Strain (%) | Break Energy (kJ/m$^2$) |
|---|---|---|
| starch (unblended starch) | 22.00 | 325.00 |
| ternary blend (b-2)-9 | 200.00 | 850.00 |

Example (b-2)-10

Example (b-2)-8 is repeated replacing the 130 g of the sodium salt of polymethylmethacrylate-co-methacrylic acid, (component (b)) by 425 g of the sodium salt of polycrotonic acid-co-vinyl acetate, and the 85 g of Nylon 12 Vestamid L-1700 is replaced by 85 g of a thermoplastic polyamide elastomer PEBAX MA-4011 by Atochem (component (c)).

The physical-mechanical properties of the corresponding injection molded test pieces are superior to those of the unblended starch.

Example (b-2)-11

Example (b-2)-10 is repeated using 210 g of the sodium salt of polycrotonic acid-co-vinyl acetate (component (b)) instead of 425 g. To this polymer, 425 g of thermoplastic polyamide elastomer PEBAX MA-4011 (component (c)) by Atochem and 425 g of thermoplastic polyurethane elastomer sold as Pellethane 2103-80-AE (component (c)), Dow Chemical Co. are added in Section a).

The physical-mechanical properties of the corresponding injection molded test pieces are superior to those of the unblended starch.

Example (b-2)-12

Example (b-2)-11 is repeated including the addition of 42.5 g of polyethylene sold as Lupolen 2410 T BASF (third component (c)) to the other components.

The physical-mechanical properties of the corresponding injection molded test pieces are superior to those of the unblended starch.

Example (b-22)-13

Example (b-2)-8 (Section a) is repeated. b) 5000 g of the mixture prepared under Section a) are fed through a hopper into a Werner-Pfleiderer co-rotating twin screw extruder (model Continua 37) and the process is carried out in a similar way as the one described in Section (b) of Example (b-2)-8. Water added at the inlet is adjusted so that the water content of the material is 21% by weight. The cutter is removed from the die face and a continuous extrudate is obtained which is foamed as a result of the excess water evaporation. The foam is chopped into 30–40 mm lengths and is useful as a loose-fill, packaging insulation material.

Example (b-2)-14

During each of the injection molding operations in Examples (b-2)-1 through (b-2)-12, an experiment is performed to demonstrate the utility of making foams. The molten material which is obtained and described in Example (b-2)-1, and in Example (b-2)-8, Sections a), b) and c) in each case is extruded into the open atmosphere (Section c) instead of being injected and molded into a closed mold. In every case the material is converted into a foamed extrudate useful for loose-fill in packaging applications.

Example (b-2)-15

The granulates from Example (b-2)-1 are mixed with polystyrene in the proportion of 30 to 70 parts by weight and are treated according to Example (b-2)-13 (Section b) The resulting foamed extrudate contains a very fine and uniform cell structure suitable for a variety of uses including structural foam.

Example (b-3)-1

(a) 9000 g of potato starch containing 15.1% water were placed in a high speed mixer and 850 g of poly-4-vinyl pyridine, 76.5 g of hydrogenated fat (a lubricant release agent, (Boeson VP) Boehringer Ingelheim), and 38.2 g of a melt flow accelerator (lecithin) Metarin P by Lucas Meyer were added under stirring. The water content of the final mixture was 13.6%.

(b) 10,000 g of the mixture prepared under (a) above were fed through a hopper into a Werner & Pfleiderer co-rotating twin screw extruder (model Continua 37).

The temperature profile of the four sections of the barrel was 20° C./180° C./180° C./80° C., respectively.

Extrusion was carried out with a mixture output of 8 kg/hr (screw speed 200 rpm). Water was added at the inlet with a flow rate of 2 kgs/hr. The water content of the material during extrusion was therefore 28.1%. In the last section of the extruder 80 mbar reduced pressure was applied to remove part of the water as water vapor. The extrudate going out from the nozzle was cut into granulates using a rotating knife.

The water content of the granulates was 16.8% as measured after they had equilibrated at room temperature.

(c) The granulates of the pre-blended mixture as obtained under (b) were fed through a hopper to an Arburg 329-210-750 injection molding machine for the production of tensile test pieces. The temperature profile of the barrel was: 90° C./175° C./175° C./175° C./.

The shot weight was 8 g, the residence time 450 sec., the injection pressure 1870 bar, the back pressure 80 bar, and the screw speed 180 rpm.

The tensile test pieces thus produced were conditioned in a climatic cabinet at 50% R.H. for five days as an arbitrary standard condition.

The test pieces were of standard DIN design (DIN No. 53455).

(d) The conditioned tensile test pieces were then tested for their stress/strain behavior on a Zwick tensile test apparatus.

The samples were measured at room temperature using an extension rate of 10 mm per minute. Results are presented in Table (b-3)-1 and compared with those obtained with tensile test pieces obtained from the same starch processed in a similar way but in absence of component (b).

TABLE (b-3)-1

|  | unblended starch | Example No. 1 |
|---|---|---|
| break strain % | 21 | 31.2 |
| break energy KJ/m$^3$ | 8800 | 11934 |

Example (b-3)-2

Example (b-3)-1 was repeated except that component (b) poly-4-vinyl pyridine is increased to 1700 g. The resulting injection molded polymer was tougher and more resistant to humid air than unblended starch polymer similar to the values shown in Table (b-3)-1.

Example (b-3)-3

Example (b-3)-1 was repeated except that 425 g of Pebax MA-4011 polyamide-block-polyether Atochem (component (c)) and 425 g of a thermoplastic elastomer polyurethane block polyether (component (c)) Pellethane 2103-80-AE, (Dow Chemical Company) were added. The resulting injection molded polymer was tougher and more resistant to humid air than unblended starch polymer similar to the values shown in Table (b-3)-1.

Example (b-3)-4

Example (b-3)-1 was repeated with the change that the following polymers as component (c) were added:

a) 1000 g of polyethylene-co-vinyl alcohol (EP-L-101, component (c)) containing 73 mol % vinyl alcohol and 27 mol % ethylene.

b) 800 g of polyethylene-co-vinyl acetate containing 80 mol % of ethylene and 20 mol % of vinyl acetate (Escorene UL 02020; Exxon).

The resulting injection molded polymer is tougher and more resistant to humid air than the unblended starch polymer similar to the values given in Table (b-3)-1.

Example (b-3)-5

Example (b-3)-1, steps (a) and (b) are repeated with the exception that the water content of the granulate is increased to 22%.

(c) The granulates of the pre-blended mixture as obtained under (b) are mixed with 10000 g of polystyrene and fed through a hopper to an Arburg 329-210-750, injection molding machine wherefrom the melt is injected into the open air. The temperature profile of the barrel was 90° C./175° C./175° C./175° C.

A foamed extrudate is obtained which is useful for loose-fill in packaging applications.

The materials of Examples (b-3)-1 through (b-3)-4 can also be foamed as described in this Example without the addition of additional polymer using the method as described hereinabove under step c).

Example (b-4)-1

(a) 5000 g of potato starch containing 15.10% water are placed in a high speed mixer and 477.6 g of water are added under stirring. To the above mixture of starch and water, 425 g of hydroxypropyl cellulose (DS=1.0; MS=3.0), (component (b)) Klucel EF; Aqualon Company and 42 g of Hostaform 52021C polyoxymethylene (POM) (component (c)) Hoechst; 42.5 g of Boeson VP hydrogenated fat (lubricant/release agent) Boehringer Ingelheim; 21.25 g of Metarin P melt flow accelerator (lecithin) Lucas Meyer and 21.25 g of titanium dioxide (pigment and solid mixture flow accelerator) are added under stirring. The water content of the final mixture is 19.98%.

(b) 5000 g of the mixture prepared under (a) are fed through a hopper into a Leistritz Single Screw Lab Extruder LSM 30 having a temperature profile of 55° C./145° C./165° C./165° C. The output of extrudate was 100 g/min.

The extrudate is cut into granulates and the water content is determined to be 13.10%. The granulates are then brought back to a water content of 17% by spraying of water under stirring in a conventional mixer.

(c) The granulates of the pre-blended mixture as obtained under (b) are fed through a hopper to an Kloeckner-Ferromatic FM 60 injection molding machine for the production of tensile test pieces. The temperature profile is 90° C./155° C./155° C./155° C., the shot weight 8.0 g, the residence time 450 sec., the injection pressure 1600 bar, the back pressure 30 bar.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on an Instron tensile test apparatus, each test with 4 pieces.

The samples are measured at room temperature using an extension rate of 10 mm per minute. Results are presented in Table 1 and compared with those obtained with tensile test pieces obtained from the same starched processed in a similar way but in absence of components (b) and (c). It can be seen from the results that the break strain (elongation at break) is going from 15.82% to 32.40% and break energy from 194.30 kJ/m$^2$ to 410.25 kJ/m$^2$ showing a considerable increase in the toughness of the blend material over the unblended one.

TABLE (b-4)-1

|  | Break Strain % | Break Energy (kJ/m$^2$) |
|---|---|---|
| starch (unblended starch) | 15.82 | 194.3 |
| ternary blend (b-4)-1 | 32.40 | 410.25 |

Also, the values for the dimensional stability of the test pieces in humid air are much superior compared to those obtained for non-blended destructurized starch.

Of course, different blend compositions show different values for the physical parameters indicated. The best values are achieved by optimization by varying the concentration of the different components, as is known by one skilled in the art.

Example (b-4)-1 is repeated with the following blends as per the Examples (b-4)-2 to 6 whereby analogous results as given in Table (b-4)-1 as well as good results for the dimensional stability were obtained.

Example (b-4)-2

Example (b-4)-1 is repeated except that the ratio of the components is varied as given in Table (b-4)-2. For comparison perspective, Example (b-4)-1 is shown as Blend No. 1.

TABLE (b-4)-2

| Blend No. | starch: components(b) + (c) (weight ratio) | component (b): component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness, as judged by resistance to breaking upon bending, increases from blend 9 to blend 2 in concert with the combined increase in hydroxy propyl cellulose content. While the resistance to softening in humid atmosphere is improved in all cases relative to unmodified starch, the resistance of blends 1,4,5 and 6 are particularly good. These results illustrate the unexpected combinations as benefits in performance.

Example (b-4)-3

Example (b-4)-1 is repeated by replacing component (b) with hydroxypropyl-methyl cellulose (DS=1.0 for hydroxypropyl group, MS=2.0; DS=0.5 for the methyl group). Component (c) is replaced by ethylene-acrylic acid copolymer (80% ethylene and 20% acrylic acid).

The resulting injection molded polymer is tougher and more resistant to humid air than unmodified starch polymer.

Example (b-4)-4

Example (b-4)-1 is repeated by replacing component (b) with methyl cellulose (DS=0.5). Component (c) is replaced by ethylene-vinyl alcohol copolymer (38% ethylene, 62% vinyl alcohol) EVAL EP-F-101; Kuraray. The resulting injection molded polymer blend is tougher and more resistant to humid air than unblended starch.

Example (b-4)-5

Example (b-4)-1 is repeated except that component (b) is replaced with hydroxypropyl starch acetate (DS=1.0 for acetate; DS=0.5 for the hydroxypropyl group with MS=3.0). Component (c) is replaced by Escorene UL 02020 ethylene-vinyl acetate copolymer (80% ethylene, 20% vinyl acetate) Exxon. The resulting injection molded polymer blend is tougher and more resistant to humid air than unblended starch.

Example (b-4)-6

Example (b-4)-1 is repeated except that the hydroxyethyl starch (DS=0.8; MS=5) content of component (b) is increased. Component (c) is replaced by vinyl alcohol-vinyl acetate copolymer (87%–89% vinyl alcohol; 11%–13% vinyl acetate) Airvol 540 S by Air Products.

The resulting injection molded polymer blend is tougher and more resistant to humid air than unmodified starch.

Example (b-4)-7

(a) 9000 g of potato starch containing 15.1% water are placed in a high speed mixer together with 850 g of Natrosol hydroxyethyl cellulose (DS=1.5; MS=2.5) (component (b)) Aqualon Company. 76.5 g of Boeson VP hydrogenated fat (lubricant release agent) Boehringer Ingelheim, 38.25 g of a melt flow accelerator (Metarin P lecithin), Lucas Meyer are added under stirring. The water content of the final mixture is 14.19%.

(b) 10,000 g of the mixture prepared under (a) are fed through a hopper into a Werner & Pfleiderer co-rotating twin screw extruder (model Continua 37).

The temperature profile of the four sections of the barrel is 20° C./180° C./180° C./80° C., respectively. Extrusion is carried out with a mixture output of 8 kg/hr (screw speed 200 rpm). Water was added at the inlet with a flow rate of 2.1 kgs/hr. The water content of the material during extrusion is therefore 32%. In the last section of the extruder 300 mbar reduced pressure is applied to remove part of the water as water vapor.

The water content of the granulates is 17.4% as measured equilibration at room temperature.

(c) The granulates of the pre-blended mixture ($H_2O$ content: 17.4%) as obtained under (b) are fed through a hopper to an Arburg 329-210-750 injection molding machine for the production of tensile test pieces. The temperature profile of the barrel is: 90° C./165° C./165° C./165° C.

The shot weight is 8 g, the residence time 450 sec., the injection pressure 1616 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. Results are presented in Table (b-4)-3 and compared with those obtained with tensile test pieces obtained from the same starch processed in a similar way but in absence of components (b) and (c).

TABLE (b-4)-3

| | unblended starch | Example Nos. | | |
|---|---|---|---|---|
| | | 7 | 8 | 9 |
| break strain % | 22 | 32 | 31 | 486 |
| break energy $KJ/m^2$ | 325 | 435 | 421 | 1937 |

Example (b-4)-8

(a) Example (b-4)-7 is repeated using 255 g of Natrosol hydroxyethyl cellulose (DS=1.5; MS=2.5); Aqualon Company instead of 850 g and 170 g Grilamid L-20-GN Nylon 12 (component (c)); Ems-Chemie. The weight of the other materials of Section a) of Example 7 is the same. The water content of the final mixture is 14.1%.

(b) The extrusion is carried out as in Section b) of Example (b-4)-7 but the temperature profile of the barrel is respectively 20° C./80° C./220° C./130° C. The other processing characteristics are the following:

mixture output: 8.4 kg/hr
screw speed: 200 rpm
water addition: 4.1 kg/hr
reduced pressure: 450 mbar
water content of granulates: 16.35%

(c) The injection molding of the granulates after they have been remoistured to 17% $H_2O$ is carried out with the same equipment as in Example 7. The processing conditions are the following:

temperature profile: 90° C./165° C./165° C./165° C.
shot weight: 8 g
residence time: 450 sec.
injection pressure: 1650 bar
back pressure: 80 bar
screw speed: 180 rpm The tensile test pieces obtained are conditioned at 50% R.H. for 5 days and then their stress-strain behavior on a Zwick tensile test apparatus is determined. Results are presented on Table (b-4)-3.

Example (b-4)-9

(a) 2100 g of potato starch containing 15.1% water are placed in a high speed mixer and 765 g of Klucel EF hydroxypropyl cellulose (component (b)) Aqualon Company. 5950 g of thermoplastic polyurethane elastomer (component c)) sold as Pellethane 2103-80-AE by Dow Chemical Co. 17.85 g of Boeson VP hydrogenated fat (lubricant/release agent) and 8.9 g of a melt flow accelerator (lecithin/Metarin P) are added under stirring. The water content of the final mixture is 7.85%.

(b) 8000 g of the mixture prepared under (a) were fed through a hopper into the same twin-screw co-rotating extruder described in Example 6. The extrusion of the mixture was carried out with the following temperature profile: 20° C./80° C./120° C./100° C. The other parameters of the extrusion experiment were the following:

material output: 8.8 kg/hr
screw speed: 200 rpm
water added: 1.8 kg/hr
reduced pressure (last section): 800 mbar
water-content during extrusion: 23.5%

The water content of the granulates was 2% as measured after they had equilibrated at room temperature.

(c) The granulates obtained under (b) were processed using the same injection molding machine described in (c) of Example (b-4)-6. The temperature profile of the barrel is 90° C./175° C./175° C./175° C. The other processing parameters were:

shot weight: 6.5 g
residence time: 450 sec.
injection pressure; 1830 bar
back pressure: 80 bar
screw speed: 180 rpm The tensile test pieces thus produced are conditioned at 50% R.H. and tested on a Zwick tensile test apparatus as described in (d) of Example (b-4)-7.

Results are presented in Table (b-4)-3.

Example (b-4)-10

(a) 4800 g of potato starch containing 15% water are placed in a high speed mixer and 765 g of Klucel EF hydroxypropyl cellulose (component (b)) Aqualon Company; 3400 g of Pellethane 2103-80-AE thermoplastic polyurethane elastomer (component (c)) Dow Chemical Co; 255 g of polyethylene sold as Lupolen 2410 by BASF; 40.8 g of Boeson VP hydrogenated fat (lubricant/release agent) and 20.3 g of a melt flow accelerator (lecithin/Metarin P) are added under stirring. The water content of the final mixture is 7.8%. The mixture is further processed as in Sections b) and c) of Example (b-4)-7. The resulting injection molded polymer blend is tougher and more resistant to humid air than unblended starch.

Example (b-4)-11

Example (b-4)-7 (Section a) is repeated. b) 5000 g of the mixture prepared under Section a) are fed through a hopper into a Werner-Pfleiderer co-rotating twin screw extruder (model Continua 37) and processing carried out in a similar way as the one described in Section b) of Example (b-4)-7. Water added at the inlet is adjusted so that the water content of the material is 21% by weight. The cutter is removed from the die face and a continuous extrudate is obtained which is foamed as a result of the excess water evaporation. The foam is chopped into 30-40 mm lengths and is useful as a loose-fill, packaging insulation material.

Example (b-4)-12

During each of the injection molding operations in Examples (b-4)-1 through (b-4)-10, an experiment is performed to demonstrate the utility of making foams. The molten material which is obtained as described in Example 1 or 7, Sections a), b) and c) in each case is extruded into the open atmosphere (Section c) instead of being injection molded into a closed mold. In every case, the material is converted into a foamed extrudate useful for loose-fill in packaging applications.

Example (b-4)-13

The granulates from Example (b-4)-1 are mixed with polystyrene in the proportion of 30 to 70 parts by weight and are treated according to Example (b-4)-11 (Section b). The resulting foamed extrudate contains a very fine and uniform cell structure suitable for a variety of uses including structural foam.

Example (b-5)-1

(a) 10,000 g of potato starch containing 15.1% water are placed in a high speed mixer and 85 g of polyvinyl pyrrolidone (component (c)) sold as Type K 30 by Bayer; 85 g of Boeson VP hydrogenated fat (lubricant release agent); Boehringer Ingelheim; and 42.5 g of a melt flow accelerator (Metarin P lecithin) Lucas Meyer are added under stirring. The water content of the final mixture is 14.7%.

(b) 10,000 g of the mixture prepared under (a) are fed through a hopper into a Werner & Pfleiderer co-rotating twin screw extruder (model Continua 37).

The temperature profile of the four sections of the barrel are 20° C./150° C./150° C./80° C., respectively.

Simultaneously, using a dosing unit, poly(N-vinyl pyrrolidone-co-vinyl acetate) (component b) sold as Kollidon VA-64 by Bayer containing 54 mole % of vinyl pyrrolidone and 46 mole % of vinyl acetate, are added at a rate of 2 kgs/hr.

Extrusion is carried out with a mixture output of 8 kg/hr (screw speed 200 rpm). Water is added at the inlet with a flow rate of 2 kgs/hr. The water content of the material during extrusion is 28%. In the last section of the extruder 120 mbar reduced pressure is applied to remove part of the water as water vapour.

The water content of the granulates is 17.15% as measured after they have equilibrated at room temperature.

(c) The granulates of the pre-blended mixture as obtained under (b) (H$_2$O content: 17.15%) are fed through a hopper to an Arburg 329-210-750 injection molding machine for the production of tensile test pieces. The temperature profile of the barrel is: 90° C./155° C./155° C./155° C.

The shot weight is 7.7 g, the residence time 450 sec., the injection pressure 800 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. Results are presented in Table (b-5)-1 and compared with those obtained with tensile test pieces obtained from the same starch processed in a similar way but in absence of components b) and c).

TABLE (b-5)-1

| | unblended starch | Example Nos. | | | | | |
|---|---|---|---|---|---|---|---|
| | | 1 | 3 | 4 | 5 | 6 | 7 |
| break strain % | 22 | 32 | 25 | 32 | 146 | 29 | 31 |
| break energy KJ/m² | 325 | 450 | 350 | 430 | 540 | 480 | 430 |

Example (b-5)-2

Example (b-5)-1 is repeated except that the ratio of the components is varied as given in Table (b-5)-2. For comparative purposes Example (b-5)-1 is shown as Blend No. 1.

TABLE (b-5)-2

| Blend No. | starch: component (b) + (c) (weight ratio) | component (b-5): component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness as judged by resistance to breaking upon bending increases from blend 9 to blend 2 in concert with the combined increase in polyvinyl pyrrolidone-co-vinyl acetate content. While the resistance to softening in humid atmosphere is improved in all cases relative to unmodified starch, the resistance of blends 1,4,5 and 6 are particularly good. These results illustrate the unexpected combinations as benefits in performance.

Example (b-5)-3

(a) 9000 g of potato starch containing 15% water are placed in a high speed mixer and 255 g of Kollidon VA-64 poly-N-vinyl pyrrolidone-co-vinyl acetate (component (b)), Bayer, containing 54% of the monomeric units as vinyl pyrrolidone and 46% of the monomeric units as vinyl acetate, 340 g of ethylene-vinyl acetate copolymer (component (c)) containing 80 mole % of ethylene and 20 mole % of Escorene UL02020 vinyl acetate, Exxon; 255 g of Vestamid L-1700 Nylon 12, Huels Chemie; 76.5 g of Boeson VP hydrogenated fat (lubricant release agent), Boehringer Ingelheim, and 38 g of a melt flow accelerator (Metarin P lecithin), Lucas Meyer are added under stirring. The water content of the final mixture is 15.6%.

(b) 10,000 g of the mixture prepared under (a) were fed through a hopper into a Werner & Pfleiderer co-rotating twin screw extruder (model Continua 37).

The temperature profile of the four sections of the barrel is 20° C./80° C./230° C./150° C., respectively.

Extrusion is carried out with a mixture output of 8.2 kg/hr (screw speed 200 rpm). Water is added at the inlet with a flow rate of 2.9 kg/hr. The water content of the material during extrusion is 38%. In the last section of the extruder, 600 mbar reduced pressure is applied to remove part of the water as water vapor.

The water content of the granulates is 9.35% as measured after they have equilibrated at room temperature. They are brought to a water content of 17% by spraying water under stirring in a conventional mixer.

(c) The granulates of the pre-blended mixture as obtained under (b) (H₂O content: 17%) are fed through a hopper to an Arburg 329-210-750 injection molding machine for the production of tensile test pieces. The temperature profile of the barrel is: 90° C./165° C./165° C./165° C.

The shot weight is 7.8 g, the residence time 450 sec., the injection pressure 1380 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-5)-1. Results are presented in Table (b-5)-1..

Example (b-5)-4

(a) 8000 g of potato starch containing 15.1% water are placed in a high speed mixer and 425 g of Kollidon VA-64 pyrrolidone-co-vinyl acetate (component (b)), Bayer (containing 46 mole % vinyl acetate and 54 mole % vinyl pyrrolidone). 1275 g polyethylene-co-vinyl alcohol (component (c)) containing 73 mole % vinyl alcohol and 27 mole % ethylene Eval-EP-L-101 Kuraray), 68 g of Boeson VP hydrogenated fat (lubricant-/release agent) and 34 g of a melt flow accelerator (lecithin/Metarin P) are added under stirring. The water content of the final mixture is 12.3%.

(b) 9000 g of the mixture prepared under (a) are fed through a hopper into the same twin-screw co-rotating extruder described in Example (b-5)-1. The extrusion of the mixture is carried out with the following temperature profile: 20° C./80° C./190° C./150° C. The other parameters of the extrusion experiment are the following:

material output: 10 kg/hr
screw speed: 200 rpm
water added: 3.2 kg/hr
reduced pressure (last section): 300 mbar
water-content during extrusion: 39%

The water content of the granulates is 16.8% as measured after they have equilibrated at room temperature.

(c) The granulates obtained under (b) are processed using the same injection molding machine described in (c) of Example (b-5)-1. The temperature profile of the barrel is 90° C./165° C./165° C./165° C. The other processing parameters were:

shot weight: 7.8 g
residence time: 450 sec.
injection pressure; 1650 bar
back pressure: 80 bar
screw speed: 180 rpm The tensile test pieces thus produced are conditioned and tested on a Zwick tensile test apparatus as described in (d) of Example (b-5)-1.

Results are presented in Table (b-5)-1.

Example (b-5)-5

(a) 2000 g of potato starch containing 15.2% water are placed in a high speed mixer and 1275 g of polyvinyl pyrrolidone-co-vinyl acetate (component (b)) containing 54 mole % vinyl pyrrolidone and 46 mole % vinyl acetate, sold as Kollidon VA-64 by Bayer; 1275 g of Escorene UL02020 polyethylene-co-vinyl acetate (component (c)) sold as by Exxon and containing 80 mole % ethylene and 20 mole % vinyl acetate; 4250 g of a thermoplastic polyurethane elastomer sold as Pellethane 2103-80-AEF by Dow Chemical Co.; 17 g of hydrogenated fat (lubricant/release agent) Boeson VP; 8.5 g of a melt flow accelerator (lecithin) Metarin P are added under stirring. The water content of the final mixture is 3.5%.

8000 g of the mixture prepared under (a) are fed through a hopper into the same twin-screw co-rotating extruder described in Example (b-5)-1.

The extrusion of the mixture is carried out with the following processing parameters:
- temperature profile: 20° C./80° C./240° C./180° C.
- material input: 8 kg/hr
- screw speed: 200 rpm
- water added: 1.8 kg/hr
- reduced pressure (last section): 300 mbar
- water content during extrusion: 21.2%

The water content of the granulates is 17.20% after remoisturing and equilibration at room temperature.

(c) The granulates of (b) are processed using the same injection molding machine of Example (b-5)-1. The processing parameters are the following:
- temperature profile: 90° C./175° C./175° C./175° C.
- shot weight: 6.5 g
- residence time; 450 sec
- injection molding: 1925 bar
- back pressure; 80 bar
- screw speed: 180 rpm The tensile test pieces thus produced are conditioned and tested on a Zwick tensile test apparatus described in (d) of Example (b-5)-1.

Results are presented in Table (b-5)-2.

Example (b-5)-6

(a) 8000 g of potato starch containing 15.1% water are placed in a high speed mixer and 2592 g of polyvinyl pyrrolidone-co-vinyl acetate (component (b)) containing 54 mole % of vinyl pyrrolidone and 46 mole % vinyl acetate; 64.8 g of hydrogenated fat (lubricant/release agent) Boeson VP; 32.4 g of a melt flow accelerator (lecithin) Metarin P are added under stirring. The water content of the final mixture is 11.3%.

(b) 9000 g of the mixture prepared under (a) are fed through a hopper into the same twin-screw co-rotating extruder described in Example (b-5)-1.

The extrusion of the mixture is carried out with the following processing temperature:
- temperature profile: 20° C./80° C./100° C./80° C.
- material output: 7.6 kg/hr
- screw speed: 200 rpm
- water added: 1 kg/hr
- reduced pressure (last section): 28 mbar
- water content during extrusion: 21.2%

The water content of the granulates is 16.9% after they have been re-hydrated and equilibrated at room temperature.

(c) The granulates obtained under (b) are processed using the same injection molding machine described in (c) of Example (b-5)-1. The processing parameters are the following:
- temperature profile: 90° C./165° C./165° C./165° C.
- shot weight: 7.7 g
- residence time; 450 sec
- injection molding: 1830 bar
- back pressure; 80 bar
- screw speed: 180 rpm The tensile test pieces thus produced are conditioned and tested on a Zwick tensile test apparatus described in (d) of Example (b-5)-1.

Results are presented in Table (b-5)-2.

Example (b-5)-7

(a) 8000 g of potato starch containing 15.1% water are placed in a high speed mixer and 1296 g of polyvinyl pyrrolidone-co-vinyl acetate, (component (b)) containing 54 mole % of vinyl pyrrolidone and 46 mole % vinyl acetate; 324 g of polyamide block polyether thermoplastic elastomer (component (c)) sold as Pebax MA-4011 by Atochem; 324 g of polyurethane-block-polyether thermoplastic elastomer (component (c)) sold as Pellethane 2103-80-AE by Dow Chemical Company; 64.8 g of hydrogenated fat (lubricant/release agent) Boeson VP; 32.4 g of a melt flow accelerator (lecithin) Metarin P are added under stirring. The water content of the final mixture is 11.9%.

(b) 9000 g of the mixture prepared under (a) are fed through a hopper into the same twin-screw co-rotating extruder described in Example (b-5)-1.

The extrusion of the mixture is carried out with the following processing parameters:
- temperature profile: 20° C./80° C./180° C./140° C.
- material output: 8.8 kg/hr
- screw speed: 200 rpm
- water added: 1.8 kg/hr
- reduced pressure (last section): 33 mbar
- water content during extrusion: 28.1%

The water content of the granulates are 16.8% after they have been re-hydrated and equilibrated at room temperature.

(c) The granulates obtained under (b) are processed using the same injection molding machine described in (c) of Example (b-5)-1. The processing parameters are the following:
- temperature profile: 90° C./165° C./165° C./165° C.
- shot weight: 7.7 g
- residence time; 450 sec
- injection molding: 1470 bar
- back pressure; 80 bar
- screw speed: 180 rpm The tensile test pieces thus produced are conditioned and tested on a Zwick tensile test apparatus described in (d) of Example (b-5)-1.

Results are presented in Table (b-5)-2.

Example (b-5)-8

Example (b-5)-6 is repeated with the exception that the mixture prepared under section (a) contains in addition to the other components, 85 g of polyethylene sold as Lupolen 2410 T by BASF, used as component (c). The resulting injection molded polymer blend is tougher and more resistant to humid air than unblended starch.

Example (b-5)-9

(a) 10,000 g of potato starch containing 15.2% $H_2O$ are placed in a high speed mixer and 85 g of polyvinyl alcohol-co-vinyl acetate (component (c)) containing 87–89 mole % of vinyl alcohol units and 11–13 mole % of vinyl acetate units sold as Airvol 5405 by Air Products are added under stirring and then 85 g of hydrogenated fat (lubricant, release agent), 42.5 g of a melt flow accelerator (lecithin) and 42.5 g of titanium dioxide (pigment and solid mixture flow accelerator) are added under stirring. The water content of the final mixture is 14.8%.

(b) This part is conducted in an identical way as part (b) of Example (b-5)-1, but using as component (b) poly(N-vinyl pyrrolidone-vinyl acetate, 54:46) type Kollidon VA-64 sold by Bayer and added at 2 kg/hr by means of a separate dosing unit.

The resulting injection molded polymer blend is tougher and more resistant to humid air than unblended starch.

Example (b-5)-10

(a) 8000 g of potato starch containing 15% water are placed in a high speed mixer and 255 g of poly-(N-vinyl pyrrolidone-co-vinyl acetate) (component (b)) sold as Kollidon VA-64 by Bayer and containing 44 mole % as vinyl acetate and 54 mole % as vinyl pyrrolidone; 340 g of ethylene vinyl acetate copolymer (component (c)) containing 80 mole % of ethylene and 20 mole % of vinyl acetate sold as Escorene UL02020 by Exxon; 68 g of hydrogenated fat (lubricant release agent) sold as Boeson VP by Boehringer Ingelheim, 34 g of a melt flow accelerator (lecithin) sold as Metarin P by Lucas Meyer are added under stirring. The water content of the final mixture is 13.8%.

(b) 8000 g of the mixture prepared under (a) are fed through a hopper into a Werner & Pfleiderer co-rotating twin screw extruder (model Continua 37). The temperature profile of the four sections of the barrel is 20° C./80° C./230° C./150° C., respectively.

Extrusion is carried out with a mixture output of 8.2 kg/hr (screw speed 200 rpm). Water is added at the inlet with a flow rate of 2.9 kg/hr. The water content of the material during extrusion is therefore 37%. In the last section of the extruder 600 mbar reduced pressure is applied to remove part of the water as water vapor.

The water content of the granulates is 9.5% as measured after they have equilibrated at room temperature. They are brought to a water content of 17% by spraying water under stirring in a conventional mixer.

(c) The granulates of the pre-blended mixture as obtained under (b) ($H_2O$ content: 17%) are fed through a hopper to an Arburg 329-210-750 injection molding machine for the production of tensile test pieces. The temperature profile of the barrel is: 90° C./ 155° C./155° C./155° C.

The shot weight is 7.8 g, the residence time 450 sec., the injection pressure 1800 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-5)-1.

The resulting injection molded polymer blend is tougher and more resistant to humid air than unblended starch.

Example (b-5)-11

Example (b-5)-1 (Sections a) and b)) is repeated except that the water content of the potato starch is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-5)-12

During each of the injection molding operations in Examples (b-5)-1 through (b-5)-10, an experiment is performed to demonstrate the utility of making foams. The molten material is obtained as described in Example (b-5)-1, Sections a), b) and c) in each case is extruded into the open atmosphere (Section c) instead of being injection molded into a closed mold. In every case the material is converted into a foamed extrudate useful for loose-fill in packaging applications.

Example (b-5)-13

The granulates from Example (b-5)-1 are mixed with polystyrene in the proportion of 30 to 70 parts by weight and are treated according to Example (b-5)-12. The resulting foamed extrudate contains a very fine and uniform cell structure suitable for a variety of uses including structural foam.

Example (b-6)-1

(a) 5000 g of potato starch containing 16.0% water were placed in a high speed mixer and 451 g of water were added under stirring. To the above mixture of starch and water, 42 g of 2-hydroxy-3-trimethyl ammonium chloride propyl starch ether (DS=0.05) (component (b)); 425 g of polyethylene-co-vinyl alcohol (component (c)) containing 71 mole % of vinyl alcohol and 29 mole % of ethylene sold as Clarene L-4 by Solvay; 42.5 g of hydrogenated fat (lubricant/release agent) sold as Boeson VP by Boehringer Ingelheim; 21.25 g of a melt flow accelerator (lecithin) sold as Metarin P by Lucas Meyer and 21.25 g of titanium dioxide (pigment and solid mixture flow accelerator) were added under stirring. The water content of the final mixture was 20.8%.

(b) 5000 g of the mixture prepared under (a) were fed through a hopper into a Leistritz Single Screw Lab Extruder LSM 30 having a temperature profile of 55° C./145° C./165° C./165° C. The screw speed was 50 rpm. The output of extrudate was 110 g/min.

The extrudate was cut into granulates and stored for further processing.

(c) For further processing, the granulates were conditioned to a water content of 17% by adding water under stirring in a conventional mixer. The obtained material was then fed through a hopper to a Kloeckner-Ferromatic FM 60 injection-molding machine, for the production of tensile test pieces. The temperature profile was 90° C./155° C./155° C./155° C., the screw speed: 180 rpm, the shot weight 8.8 g, the residence time 450 sec., the injection pressure 1450 bar, the back pressure 30 bar.

All tensile test pieces were conditioned in a climatic cabinet at 50% R.H. for five days as an arbitrary standard condition.

The test pieces were of standard DIN design (DIN No. 53455).

(d) The conditioned tensile test pieces were then tested for their stress/strain behavior on an Instron tensile test apparatus, each test with 4 pieces.

The samples were measured at room temperature using an extension rate of 10 mm per minute. Results were presented in Table (b-6)-1 and compared with those obtained with tensile test pieces obtained from the same starch processed in a similar way but in absence of components (b) and (c). It can be seen from the results that the break strain (elongation at break) went from 15.82% to 42% and break energy from 194.3 kJ/m² to 485 kJ/m² showing a considerable increase in the toughness of the blend material over the unblended one.

TABLE (b-6)-1

|  | Break Strain % | Break Energy (kJ/m²) |
|---|---|---|
| starch (unblended starch) | 15.82 | 194.3 |
| ternary blend (b-6)-1 | 33.33 | 415.75 |

Of course, different blend compositions show different values for the physical parameters indicated. To obtain the best values is a matter of optimization by varying the concentration of the different components, a procedure known to one skilled in the art.

Example (b-6)-1 is repeated with the following blends as per the Examples (b-6)-2 through (b-6)-9 whereby analogous results as given in Table (b-6)-1 are obtained.

Example (b-6)-2

Example (b-6)-1 was repeated by replacing component (c) by poly(vinyl alcohol-co-vinyl acetate) containing 87-89 mole % vinyl alcohol and 11-13 mole % vinyl acetate and sold as Airvol 540S by Air Products. The ratio of the components is varied as given in Table (b-6)-2.

TABLE (b-6)-2

| Blend No. | starch: component (b) + (c) (weight ratio) | component (b): component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers were tougher and more resistant to humid air than the unmodified starch polymer. The toughness as judged by resistance to breaking upon bending increases from blend 9 to blend 2 in concert with the combined increase in cationic starch content. While the resistance to softening in humid atmosphere is improved in all cases relative to unmodified starch, the resistance of blends 1,4,5 and 6 are particularly good. These results illustrate the unexpected combinations as benefits in performance.

Example (b-6)-3

(a) 9500 g of potato starch containing 15.1% water were placed in a high speed mixer and 425 g of quaternized ammonium cationic starch (DS=0.07) sold as Posamyl E7 by Avebe; 80.75 g of hydrogenated fat (lubricant release agent) sold as Boeson VP by Boehringer Ingelheim and 40.37 g of a melt flow accelerator (lecithin) sold as Metarin P by Lucas Meyer were added under stirring. The water content of the final mixture was 14.4%.

(b) 10,000 g of the mixture prepared under (a) were fed through a hopper into a Werner & Pfleiderer co-rotating twin screw extruder (model Continua 37). The temperature profile of the four sections of the barrel was 20° C./180° C./180° C./80° C., respectively.

Extrusion was carried out with a mixture output of 8.8 kg/hr (screw speed 200 rpm). Water was added at the inlet with a flow rate of 1.9 kg/hr. In the last section of the extruder 300 mbar reduced pressure was applied to remove part of the water as water vapor.

The water content of the granulates was 17.15% as measured after they were re-hydrated and had equilibrated at room temperature.

(c) The granulates of the pre-blended mixture as obtained under (b) (H₂O content: 17.5%) were fed through a hopper to an Arburg 329-210-750 injection molding machine for the production of tensile test pieces. The temperature profile of the barrel was: 90° C./175° C./175° C./175° C.

The shot weight was 8 g, the residence time 450 sec., the injection pressure 1210 bar, the back pressure 80 bar, and the screw speed 180 rpm.

The tensile test pieces thus produced were conditioned in a climatic cabinet at 50% R.H. for five days as an arbitrary standard condition.

The test pieces were of standard DIN design (DIN No. 53455).

(d) The conditioned tensile test pieces were then tested for their stress/strain behavior on a Zwick tensile test apparatus.

The samples are measured at room temperature using an extension rate of 10 mm per minute. Results were presented in Table (b-6)-3 and compared with those of tensile test pieces obtained from the same starch processed in a similar way but in absence of components (b) and (c).

TABLE (b-6)-3

|  | unblended starch | Example Nos. | | | | |
|---|---|---|---|---|---|---|
|  |  | 3 | 4 | 5 | 6 | 7 |
| break strain % | 22 | 36 | 34 | 30 | 25 | 35 |
| break energy KJ/m² | 325 | 495 | 460 | 400 | 350 | 450 |

Example (b-6)-4

(a) 8900 g of potato starch containing 15% water were placed in a high speed mixer and 765 g of quaternized ammonium cationic starch (DS=0.07) sold as Posamyl E-7 by Avebe (component (b)); 85 g of polyethylene-co-vinyl acetate (component (c)) containing 80 mole % of ethylene and 20 mole % of vinyl acetetate sold as Escorene UL02020 by Exxon; 85 g of polyethylene Lupolen 2410T of BASF; 80 g of hydrogenated fat (lubricant release agent) sold as Boeson VP by Boehringer Ingelheim, and 40 g of a melt flow accelerator (lecithin) sold as Metarin P by Lucas Meyer are added under stirring. The water content of the final mixture was 13.4%.

(b) 10,000 g of the mixture prepared under (a) were fed through a hopper into a Werner & Pfleiderer co-rotating twin screw extruder (model Continua 37).

The temperature profile of the four sections of the barrel were 20° C./180° C./180° C./80° C., respectively.

Extrusion was carried out with a mixture output of 8.1 kg/hr (screw speed 200 rpm). Water was added at the inlet with a flow rate of 2.1 kg/hr. The water content of the material during extrusion was therefore 31.4%. In the last section of the extruder 200 mbar reduced pressure was applied to remove part of the water as water vapor.

The water content of the granulates was 16.8% as measured after they had equilibrated at room temperature.

(c) The granulates of the pre-blended mixture as obtained under (b) ($H_2O$ content: 16.8%) were fed through a hopper to an Arburg 329-210-750 injection molding machine for the production of tensile test pieces. The temperature profile of the barrel was: 90° C./175° C./175° C./175° C.

The shot weight is 8.0 g, the residence time 450 sec., the injection pressure 1430 bar, the back pressure 80 bar, the screw speed 180 rpm.

The tensile test pieces thus produced were conditioned in a climatic cabinet at 50% R.H. for five days as an arbitrary standard condition.

The test pieces were of standard DIN design (DIN No. 53455).

(d) The conditioned tensile test pieces were then tested for their stress/strain behaviour on a Zwick tensile test apparatus as described in Example (b-6)-3.

Results are presented in Table (b-6)-3.

Example (b-6)-5

(a) 8900 g of potato starch containing 15.1% water were placed in a high speed mixer and 765 g of quaternized ammonium cationic starch (DS=0.07) (component b) sold as Posamyl E7 by Avebe; 170 g of thermoplastic polyamide elastomer Pebax-MA-4011 sold by Atochem; 75.65 g of Boeson VP hydrogenated fat (lubricant/release agent) and 37.82 g of a melt flow accelerator (lecithin/Metarin P) were added under stirring. The water content of the final mixture was 12.1%.

(b) 9000 g of the mixture prepared under (a) were fed through a hopper into the same twin-screw co-rotating extruder described in Example (b-6)-3. The extrusion of the mixture was carried out with the following temperature profile: 20° C./220° C./220° C./80° C. The other parameters of the extrusion experiment were as follows:
material output: 8.4 kg/hr
screw speed: 200 rpm
water added: 2.1 kg/hr
reduced pressure (last section): 600 mbar
water-content during extrusion: 30.4%

The water content of the granulates was 17.3% as measured after they had equilibrated at room temperature.

(c) The granulates obtained under (b) are processed using the same injection molding machine described in (c) of Example (b-6)-3. The temperature profile of the barrel is 90° C./165° C./165° C./165° C. The other processing parameters were:
shot weight: 8 g
residence time: 450 sec.
injection pressure; 1830 bar
back pressure: 80 bar
screw speed: 180 rpm The tensile test pieces thus produced were conditioned and tested on a Zwick tensile test apparatus as described in (d) of Example (b-6)-3.

Results are presented in Table (b-6)-3.

Example (b-6)-6

(a) 8000 g of potato starch containing 14.9% water were placed in a high speed mixer and 340 g of quaternized ammonium cationic starch (DS=0.07) sold as Posamyl E7 by Avebe; 680 g of thermoplastic polyurethane elastomer (component (c)) sold as Pellethane 2103-80-AE by the Dow Chemical Company; 680 g of polyamide-block-polyether (component (c)) sold as Pebax MA-4011 by Atochem; 68 g of hydrogenated fat (lubricant/release agent) Boeson VP; and 34 g of a melt flow accelerator (lecithin) Metarin P were added under stirring. The water content of the final mixture was 13.1%.

(b) 9000 g of the mixture prepared under (a) were fed through a hopper into the same twin-screw co-rotating extruder described in Example (b-6)-3.

The extrusion of the mixture is carried out with the following processing parameters:
temperature profile: 20° C, 220° C./220° C./80° C.
material output: 8.4 kg/hr
screw speed: 200 rpm
water added: 2.1 kg/hr
reduced pressure (last section): 150 mbar
water content during extrusion: 31.2%

The water content of the granulates was 16.8% after they had been re-hydrated and equilibrated at room temperature.

(c) The granulates of (b) were processed using the same injection molding machine of Example (b-6)-3. The processing parameters were the following:
temperature profile: 90° C./165° C./165° C./165° C.
shot weight: 7.8 g
residence time; 450 sec
injection molding: 1650 bar
back pressure; 80 bar
screw speed: 180 rpm The tensile test pieces thus produced were conditioned and tested on a Zwick tensile test apparatus described in (d) of Example (b-6)-3.

Results are presented in Table (b-6)-3.

Example (b-6)-7

(a) 7000 g of potato starch containing 15.1% water were placed in a high speed mixer and 1700 g of quaternized ammonium cationic starch (DS=0.07) (component (b)) sold as Posamyl E7 by Avebe; 425 g of a thermoplastic polyamide elastomer sold as Pebax MA-4011 by Atochem; 425 g of a thermoplastic elastomer polyurethane block polyether (component (c)) sold as Pellethane 2103-80-AE by Dow Chemical Company; 59.5 g of Boeson VP hydrogenated fat (lubricant/release agent); and 29.8 g of a melt flow accelerator (lecithin) Metarin P are added under stirring. The water content of the final mixture was 10.9%.

(b) 9000 g of the mixture prepared under (a) were fed through a hopper into the same twin-screw co-rotating extruder described in Example (b-6)-3.

The extrusion of the mixture was carried out with the following processing temperature:
temperature profile: 20° C./220° C./220° C./80° C.
material output: 8.4 kg/hr
screw speed: 200 rpm
water added: 2.1 kg/hr
reduced pressure (last section): 600 mbar
water content during extrusion: 27.8%

The water content of the granulates was 17.3% after they had equilibrated at room temperature.

(c) The granulates obtained under (b) were processed using the same injection molding machine described in (c) of Example (b-6)-3. The processing parameters were the following:
temperature profile: 90° C./175° C./175° C./175° C.
shot weight: 8 g
residence time; 450 sec
injection molding: 1650 bar
back pressure; 80 bar
screw speed: 180 rpm

Example (b-6)-8

Example (b-6)-5 was repeated by replacing component (b) with diethylaminoethyl starch (DS=0.1) and component (c) by polyvinylpyrrolidone K30 sold by Bayer. The resulting injection molded polymer was tougher and more resistant to humidity than unmodified starch polymer.

Example (b-6)-9

Example (b-6)-5 was repeated by replacing component (b) with 3-triethyl ammonium acetate propyl starch ether (DS=0.05). Polyvinyl alcohol-co-vinyl acetate (87-89 mole % vinyl alcohol; 11-13 mole % vinyl acetate (Airvol 540S of Air Products)) is used as component (c). The resulting injection molded polymer was tougher and more resistant to humid air than unmodified starch polymer.

Example (b-6)-10

Example (b-6)-1 (Sections a) and b)) was repeated except that the water content was adjusted to 22%, and the cutter was removed from the die face. A continuous extrudate was obtained which was foamed as a result of the excess water evaporation. The foam was chopped into 30-40 mm lengths and was useful as a loose-fill, packaging insulation material.

Example (b-6)-11

During each of the injection molding operations in Examples (b-6)-1-9 an experiment was performed to demonstrate the utility of making foams. The molten material was obtained as described in Example (b-6)-1 or (b-6)-3, Sections a), b) and c) in each case is extruded into the open atmosphere (Section c) instead of being injection molded into a closed mold. In every case the material was converted into a foamed extrudate useful for loose-fill in packaging applications.

Example (b-6)-12

The granulates from Example (b-6)-1 or (b-6)-3 were mixed with polystyrene in the proportion of 30 to 70 parts by weight and were treated according to the procedure set forth in Example (b-6)-11. The resulting foamed extrudate contains a very fine and uniform cell structure suitable for a variety of uses including structural foam.

Example (b-7)-1

(a) 4000 g of potato starch containing 15.1% water are placed in a high speed mixer and 1700 g of cellulose monophosphate, sodium salt, D.S.: 0.23 (component (b)) sold by Fluka, 3400 g of polyethylene-co-vinyl acetate (component (c)) containing 80 mole % ethylene and 20 mole % vinyl acetate (Escorene UL02020 of Exxon); 34 g of hydrogenated fat (lubricant release agent) sold as Boeson VP by Boehringer Ingelheim, 17 g of a melt flow accelerator (lecithin) sold as Metarin P by Lucas Meyer are added under stirring. The water content of the final mixture is 6.6%.

(b) 8000 g of the mixture prepared under (a) are fed through a hopper into a Werner & Pfleiderer co-rotating twin screw extruder (model Continua 37).

The temperature profile of the four sections of the barrel is 20° C./50° C./100° C./80° C., respectively.

Extrusion is carried out with a mixture output of 8.4 kg/hr (screw speed 200 rpm). Water is added at the inlet with a flow rate of 1.4 kg/hr. The water content of the material during extrusion is therefore 20.5%. In the last section of the extruder 200 mbar reduced pressure is applied to remove part of the water as water vapor.

The water content of the granulates is 10.2% as measured after they have equilibrated at room temperature. They are re-hydrated at 17% $H_2O$ by spraying water under stirring in a conventional mixer.

(c) The granulates of the pre-blended mixture as obtained under (b) ($H_2O$ content: 17%) are fed through a hopper to an injection molding machine Arburg 329-210-750 for the production of tensile test pieces. The temperature profile of the barrel is: 90° C./165° C./165° C./165° C.

The shot weight is 7 g, the residence time 450 sec., the injection pressure 1280 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. Results are presented in Table (b-7)-1 and compared with those of the tensile test pieces obtained from the same starch processed in a similar way but in absence of components (b) and (c).

TABLE (b-7)-1

|  | unblended starch | Example Nos. (b-7) | | | | | |
|---|---|---|---|---|---|---|---|
|  |  | 1 | 3 | 4 | 5 | 6 | 7 |
| break strain % | 22 | 26 | 30 | 68 | 530 | 34 | 30 |
| break energy KJ/m$^2$ | 325 | 350 | 420 | 750 | 1800 | 445 | 395 |

Of course different blend compositions show different values for the physical parameters indicated. To obtain the best values is a matter of optimization by varying the concentration of the different components, which is known to one skilled in the art.

Example (b-7)-1 is repeated with the following blends as per the Examples (b-7)-2 through (b-7)-8 whereby analogous results as given in Table (b-7)-1 are obtained.

Example (b-7)-2

Example (b-7)-1 is repeated except that the ratio of the components is varied as given in Table (b-7)-2. For comparison perspective, Example (b-7)-1 is shown as Blend No. 1.

TABLE (b-7)-2

| Blend No. | starch: component (b) + (c) (weight ratio) | component (b-7): component (c) (weight ratio) |
| --- | --- | --- |
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness as judged by resistance to breaking upon bending increases from blend 9 to blend 2 in concert with the combined increase in cellulose phosphate content. While the resistance to softening in humid atmosphere is improved in all cases relative to unmodified starch, the resistance of blends 1,4,5 and 6 are particularly good. These results illustrate the unexpected combinations as benefits in performance.

Example (b-7)-3

(a) 8900 g of potato starch containing 15% water are placed in a high speed mixer and 765 g of carboxymethyl starch (component (b)) sold as Retabond AC-1 by Avebe; 85 g of polyethylene-co-vinyl alcohol (component (c)) containing 68 mole % vinyl alcohol and 32 mole % ethylene (Eval EP-F-101 of Kuraray); 85 g of polymethylacrylate sold as Degalan G-6 by Degussa; 75.6 g of hydrogenated fat (lubricant release agent) sold as Boeson VP by Boehringer Ingelheim, and 38 g of a melt flow accelerator (lecithin) sold as Metarin P by Lucas Meyer are added under stirring. The water content of the final mixture is 13.4%.

(b) 9000 g of the mixture prepared under (a) are fed through a hopper into a Werner & Pfleiderer co-rotating twin screw extruder (model Continua 37).

The temperature profile of the four sections of the barrel is 20° C./80° C./200° C./140° C., respectively.

Extrusion is carried out with a mixture output of 8.4 kg/hr (screw speed 200 rpm). Water is added at the inlet with a flow rate of 3.2 kg/hr. The water content of the material during extrusion is therefore 33%. In the last section of the extruder 450 mbar reduced pressure is applied to remove part of the water as water vapor.

The water content of the granulates is 17.2% as measured after they have equilibrated at room temperature.

(c) The granulates of the pre-blended mixture as obtained under (b) (H₂O content: 17.2%) are fed through a hopper to an injection molding machine Arburg 329-210-750 for the production of tensile test pieces. The temperature profile of the barrel is: 90° C./175° C./175° C./175° C.

The shot weight is 8.0 g, the residence time 450 sec., the injection pressure 1920 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-7)-1.

Results are presented in Table (b-7)-1.

Example (b-7)-4

(a) 5000 g of potato starch containing 15.1% water are placed in a high speed mixer and 1275 g of carboxymethyl starch (component (b)) sold as Retabond AC-1 by Avebe; 2975 g of polyethylene-co-vinyl alcohol (component (c)) containing 68 mole % vinyl alcohol and 32 mole % ethylene) sold as Eval EP-F-101 by Kuraray. 42.5 g of Boeson VP hydrogenated fat (lubricant/release agent) and 21.25 g of a melt flow accelerator (lecithin/Metarin P) are added under stirring. The water content of the final mixture is 8.1%.

(b) 9000 g of the mixture prepared under (a) are fed through a hopper into the same twin-screw co-rotating extruder described in Example (b-7)-1. The extrusion of the mixture is carried out with the following temperature profile: 20° C./80° C/200° C./120° C. The other parameters of the extrusion experiment are the following:

material output: 9.6 kg/hr
screw speed: 200 rpm
water added: 2.5 kg/hr
reduced pressure (last section): 50 mbar
water-content during extrusion: 28.1%

The water content of the granulates is 9.6% as measured after they have equilibrated at room temperature. They are brought to a water content of 17% by spraying water under stirring in a conventional mixer.

(c) The granulates obtained under (b) are processed using the same injection molding machine described in (c) of Example (b-7)-1. The temperature profile of the barrel is 90° C./175° C./175° C./175° C. The other processing parameters are:

shot weight: 7.5 g
residence time: 450 sec.
injection pressure; 1925 bar
back pressure: 80 bar
screw speed: 180 rpm The tensile test pieces thus produced are conditioned and tested on a Zwick tensile test apparatus as described in (d) of Example (b-7)-1.

Results are presented in Table (b-7)-1.

Example (b-7)-5

(a) 2100 g of potato starch containing 15.3% water are placed in a high speed mixer and 765 g of starch phosphate (component (b)) sold as Retamyl A.P by Avebe; 5950 g of polyamide-block-polyether (component (c)) sold as Pebax MA-4011 by Atochem; 17.9 g of Boeson VP hydrogenated fat (lubricant/ release agent); and 9 g of a melt flow accelerator (lecithin) Metarin P are added under stirring. The water content of the final mixture is 3.6%.

(b) 8000 g of the mixture prepared under (a) are fed through a hopper into the same twin-screw co-rotating extruder described in Example (b-7)-1.

The extrusion of the mixture is carried out with the following processing parameters:
- temperature profile: 20° C./80° C./220° C./180° C.
- material output: 8 kg/hr
- screw speed: 200 rpm
- water added: 1 kg/hr
- reduced pressure (last section): 800 mbar
- water content during extrusion: 29.14%

The water content of the granulates is 5.3% after they have equilibrated at room temperature. They are brought to a water content of 17% by spraying water under stirring in a conventional mixer.

(c) The granulates of (b) are processed using the same injection molding machine of Example 1. The processing parameters are the following:
- temperature profile: 90° C./165° C./165° C./165° C.
- shot weight: 6.7 g
- residence time; 450 sec
- injection molding: 1210 bar
- back pressure; 80 bar
- screw speed: 180 rpm The tensile test pieces thus produced are conditioned and tested on a Zwick tensile test apparatus described in (d) of Example (b-7)-1.

Results are presented in Table (b-7)-1.

Example (b-7)-6

(a) 8000 g of potato starch containing 15.1% water are placed in a high speed mixer and 340 g of starch phosphate sold as Retamyl AP by Avebe (component (b)); 680 g of thermoplastic polyamide elastomer sold as Pebax-MA 4011 by Atochem; 680 g of a thermoplastic elastomer polyurethane block polyether (component (c)) sold as Pellethane 2103-80-AE by Dow Chemical Company; 68 g of Boeson VP hydrogenated fat (lubricant/release agent); and 34 g of a melt flow accelerator (lecithin) Metarin P are added under stirring. The water content of the final mixture is 12.3%.

(b) 9000 g of the mixture prepared under (a) are fed through a hopper into the same twin-screw co-rotating extruder described in Example (b-7)-1.

The extrusion of the mixture is carried out with the following processing temperature:
- temperature profile: 20° C./220° C./220° C./80° C.
- material output: 8.4 kg/hr
- screw speed: 200 rpm
- water added: 2.1 kg/hr
- reduced pressure (last section): 80 mbar
- water content during extrusion: 28.9%

The water content of the granulates is 16.9% after they have equilibrated at room temperature.

(c) The granulates obtained under (b) are processed using the same injection molding machine described in (c) of Example (b-7)-1. The processing parameters are the following:
- temperature profile: 90° C./175° C./175° C./175° C.
- shot weight: 7.8 g
- residence time; 450 sec
- injection molding: 2100 bar
- back pressure; 80 bar
- screw speed: 180 rpm The tensile test pieces thus produced are conditioned and tested on a Zwick tensile test apparatus described in (d) of Example (b-7)-1.

Results are presented in Table (b-7)-1.

Example (b-7)-7

(a) 7000 g of potato starch containing 15.1% water are placed in a high speed mixer and 1700 g of starch phosphate (component (b)), sold as Retamyl AP by Avebe; 425 g of polyamide block polyether thermoplastic elastomer polyurethane (component (c)) sold as Pebax MA-4011 by Atochem; 425 g of polyurethane-block-polyether thermoplastic elastomer (component (c)) sold as Pellethane 2103-80-AE by Dow Chemical Company; 60 g of Boeson VPhydrogenated fat (lubricant/release agent); and 30 g of a melt flow accelerator (lecithin) Metarin P are added under stirring. The water content of the final mixture is 13.2%.

(b) 9000 g of the mixture prepared under (a) are fed through a hopper into the same twin-screw co-rotating extruder described in Example (b-7)-1.

The extrusion of the mixture is carried out with the following processing parameters:
- temperature profile: 20° C./220° C./220° C./80° C.
- material output: 8.4 kg/hr
- screw speed: 200 rpm
- water added: 2.1 kg/hr
- reduced pressure (last section): 600 mbar
- water content during extrusion: 29.6%

The water content of the granulates is 17.3% after they have equilibrated at room temperature.

(c) The granulates obtained under (b) are processed using the same injection molding machine described in (c) of Example (b-7)-1. The processing parameters are the following:
- temperature profile: 90° C./165° C./165° C./165° C.
- shot weight: 8 g
- residence time; 450 sec
- injection molding: 1760 bar
- back pressure; 80 bar
- screw speed: 180 rpm The tensile test pieces thus produced are conditioned and tested on a Zwick tensile test apparatus described in (d) of Example (b-7)-1.

Results are presented in Table (b-7)-1.

Example (b-7)-8

Example (b-7)-1 is repeated by replacing component (c) with poly(vinyl alcohol-co-vinyl acetate) containing 87-89 mole % of vinyl alcohol and 11-13 mole % of vinyl acetate, sold as Airvol 540 S by Air Products.

The resulting injection molded polymer blend is tougher and more resistant to humid air than unblended starch.

Example (b-7)-9

Example (b-7)-1 (Sections a) and b)) is repeated except that the water content is adjusted to 22%, and the cutter is removed from the die face. A continuous extrudate is obtained which is foamed as a result of the excess water evaporation. The foam is chopped into 30-40 mm lengths and is useful as a loose-fill, packaging insulation material.

Example (b-7)-10

During each of the injection molding operations in Examples (b-7)-1 through (b-7)-8 an experiment is performed to demonstrate the utility of making foams. The molten material is obtained as described in Example (b-7)-1. Sections a), b) and c) in each case is extruded into the open atmosphere (Section (c)) instead of being injection molded into a closed mold. In every case the material is converted into a foamed extrudate useful for loose-fill in packaging applications.

Example (b-7)-11

The granulates from Example (b-7)-1 are mixed with polystyrene in the proportion of 30 to 70 parts by weight and are treated according to Example (b-7)-10. The resulting foamed extrudate contains a very fine and uniform cell structure suitable for a variety of uses including structural foam.

Example (b-8)-1

(a) 9500 g of potato starch containing 15.1% water are placed in a high speed mixer and 3226 g of polyethylene-co-vinyl alcohol (component (b)) containing 73 mole % of vinyl alcohol and 27 mole % of ethylene sold as EVAL-L-101 by Kuraray; 80.75 g of Boeson VP hydrogenated fat (lubricant release agent) by Boehringer Ingelheim, and 40.37 g of a melt flow accelerator (lecithin) sold as Metarin P by Lucas Meyer are added under stirring. The water content of the final mixture is 11.2%.

(b) 10,000 g of the mixture prepared under (a) are fed through a hopper into a Leistritz co-rotating twin screw extruder (model LSM 34 GL).

The temperature profile of the main sections of the barrel is 25° C./90° C./180° C./200° C./160° C./120° C./130° C., respectively.

Extrusion is carried out with a mixture output of 8.8 kg/hr (screw speed 200 rpm). Water is added at the inlet with a flow rate of 2.5 kg/hr. The water content of the material during extrusion is therefore 29%. In the last section of the extruder 200 mbar reduced pressure is applied to remove part of the water as water vapor. The water content of the granulates is 8.5% as measured after they have equilibrated at room temperature. They are brought to a water content of 17% by spraying water under stirring in a conventional mixer.

(c) The granulates of the pre-blended mixture as obtained under (b) (H$_2$O content: 17%) are fed through a hopper to an injection molding machine Kloeckner-Ferromatic FM 60 for the production of tensile test pieces. The temperature profile of the barrel is: 90° C./165° C./165° C./165° C.

The shot weight is 8 g, the residence time 450 sec., the injection pressure 800 bar, the back pressure 30 bar, the screw speed 180 rpm.

The tensile test pieces thus produced are conditioned in a climatic cabinet at 50% R.H. for five days as an arbitrary standard condition.

The test pieces are of standard ISO design (ISO No. R527).

(d) The conditioned tensile test pieces are then tested for their stress/strain behavior on a Zwick tensile test apparatus.

The samples are measured at room temperature using the extrusion rate of 10 mm per minute. Results are presented in Table (b-8)-1 and compared with those of the tensile test pieces obtained from the same starch processed in a similar way but in absence of component (b).

TABLE (b-8)-1

|  | unblended starch | Example Nos. (b-8)- | | | | |
| --- | --- | --- | --- | --- | --- | --- |
|  |  | 1 | 3 | 4 | 5 | 6 |
| break strain % | 22 | 30 | 17 | 13 | 5 | 4 |

TABLE (b-8)-1-continued

|  | unblended starch | Example Nos. (b-8)- | | | | |
| --- | --- | --- | --- | --- | --- | --- |
|  |  | 1 | 3 | 4 | 5 | 6 |
| break energy KJ/m$^2$ | 325 | 520 | 290 | 215 | 73 | 52 |

Example (b-8)-2

Example (b-8)-1 is repeated except that the ratio of the components is varied as given in Table (b-8)-2. For comparison perspective, Example (b-8)-1 is shown as Blend No. 1.

TABLE (b-8)-2

| Blend No. | starch: component (b) + (c) (weight ratio) | component (b-8)-: component (c) (weight ratio) |
| --- | --- | --- |
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unmodified starch polymer. The toughness as judged by resistance to breaking upon bending increases from blend 9 to blend 2 in concert with the combined increase in ethylene-vinyl alcohol content. While the resistance to softening in humid atmosphere is improved in all cases relative to unmodified starch, the resistance of blends 1,4,5 and 6 are particularly good. These results illustrate the unexpected combinations as benefits in performance.

Example (b-8)-3

Example (b-8)-1 is repeated by replacing component (b) (EVAL-L-101) with polyethylene-co-vinyl alcohol Clarene L-4 of Solvay containing 71 mole % of vinyl alcohol and 29 mole % of ethylene. The break strain and break energy of the resulting injection molded blend are shown in Table (b-8)-1. It can be seen that a lower vinyl alcohol content as compared to EVAL-L-101, leads to a decrease in the tensile properties, even lower than those of starch without component (b).

Example (b-8)-4

Example (b-8)-1 is repeated by replacing component (b) (EVAL-L-101) with polyethylene-co-vinyl alcohol EVAL-F-101 of Kuraray containing 68 mole % of vinyl alcohol and 32 mole % of ethylene. The break strain and break energy of the resulting injection molded blend are shown in Table (b-8)-1. It can be seen that a lower vinyl alcohol content as compared to EVAL-L-101, leads to a decrease in the tensile properties, even lower than those of starch without component (b).

Example (b-8)-5

Example (b-8)-1 is repeated by replacing component (b) (EVAL-L-101) with polyethylene-co-vinyl alcohol EVAL-K-102 of Kuraray containing 62 mole % of vinyl alcohol and 38 mole % of ethylene. The break strain and break energy of the resulting injection molded blend are shown in Table (b-8)-1. It can be seen that a lower vinyl alcohol content as compared to EVAL-L-101, leads to a decrease in the tensile properties, even lower than those of starch without component (b).

Example (b-8)-6

Example (b-8)-1 is repeated by replacing component b) (EVAL-L-101) with polyethylene-co-vinyl alcohol EVAL-E-105 of Kuraray containing 56 mole % of vinyl alcohol and 44 mole % of ethylene. The break strain and break energy of the resulting injection molded blend are shown in Table (b-8)-1. It can be seen that a lower vinyl alcohol content as compared to EVAL-L-101, leads to a decrease in the tensile properties, even lower than those of starch without component (b).

Example (b-8)-7

(a) 5000 g of potato starch containing 15% water are placed in a high speed mixer and 4250 g of polyethylene-co-vinyl alcohol (component (b)) sold as EVAL-L-101 by Kuraray and containing 73 mole % of vinyl alcohol and 27 mole % of ethylene; 42.5 g of Boeson VP hydrogenated fat (lubricant release agent) by Boehringer Ingelheim, and 21.25 g of a melt flow accelerator (lecithin) sold as Metarin P by Lucas Meyer are added under stirring. The water content of the final mixture is 8.1%.

(b) 9000 g of the mixture prepared under (a) are fed through a hopper into a Werner & Pfleiderer co-rotating twin screw extruder (model Continua 37).

The temperature profile of the four sections of the barrel is 20° C./80° C./190° C./150° C., respectively.

Extrusion is carried out with a mixture output of 8.8 kg/hr (screw speed 200 rpm). Water is added at the inlet with a flow rate of 2.5 kg/hr. The water content of the material during extrusion is therefore 30%. In the last section of the extruder 35 mbar reduced pressure is applied to remove part of the water as water vapor.

The water content of the granulates is 8.5% as measured after they have equilibrated at room temperature. They are brought to a water content of 17% by spraying water under stirring in a conventional mixer.

(c) The granulates of the pre-blended mixture as obtained under (b) (H$_2$O content: 17%) are fed through a hopper to an Arburg 329-210-750 injection molding machine for the production of tensile test pieces. The temperature profile of the barrel is: 90° C./175° C./175° C./175° C.

The shot weight is 7.3 g, the residence time 450 sec., the injection pressure 1650 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-8)-1. Results are presented in Table (b-8)-3.

TABLE (b-8)-3

|  | unblended starch | Example Nos. (b-8)- | | |
| --- | --- | --- | --- | --- |
|  |  | 7 | 8 | 9 |
| Break Strain | 22 | 150 | 25 | 370 |
| (%) Break Energy (KJ/m$^2$) | 325 | 1560 | 350 | 1830 |

Example (b-8)-8

(a) 9500 g of potato starch containing 15.1% water are placed in a high speed mixer and 255 g of polyethylene-co-vinyl alcohol (component (b)) sold as EVAL-F-101 by Kuraray (containing 68 mole % vinyl alcohol and 32 mole % ethylene). 170 g of Nylon 12 (component c)) sold as Vestamid L-1700 by Huels Chemie; 51 g of Boeson VP hydrogenated fat (lubricant/release agent) and 25.5 g of a melt flow accelerator (lecithin/Metarin P) are added under stirring. The water content of the final mixture is 14%.

(b) 9000 g of the mixture prepared under (a) are fed through a hopper into the same twin-screw co-rotating extruder described in Example (b-8)-7. The extrusion of the mixture is carried out with the following temperature profile: 20° C./80° C./170° C./80° C. The other parameters of the extrusion experiment are the following:
material output: 9.1 kg/hr
screw speed: 200 rpm
water added: 1.4 kg/hr
reduced pressure (last section): 30 mbar
water-content during extrusion: 26.8%

The water content of the granulates is 14.5% as measured after they have equilibrated at room temperature. They are brought to a water content of 17% H$_2$O by spraying water under stirring in a conventional mixer.

The granulates obtained under (b) are processed using the same injection molding machine described in (c) of Example (b-8)-7. The temperature profile of the barrel is 90° C./155° C./155° C./155° C. The other processing parameters are:
shot weight: 8 g
residence time: 450 sec.
injection pressure; 2200 bar
back pressure: 80 bar
screw speed: 180 rpm The tensile test pieces thus produced are conditioned and tested on a Zwick tensile test apparatus as described in (d) of Example (b-8)-1.

Results are presented in Table (b-8)-3.

Example (b-8)-9

(a) 2000 g of potato starch containing 15.2% water are placed in a high speed mixer and 850% of polyethylene-co-vinyl alcohol (component (b)) (EVAL-L-101 of Kuraray) containing 73 mole % vinyl alcohol and 27 mole % ethylene; 5950 g of polyamide-block-polyether (component (c) sold as Pebax MA-4011 by Atochem; 17 g of Boeson VP hydrogenated fat (lubricant/release agent); and 8.5 g of a melt flow accelerator (lecithin) Metarin P are added under stirring. The water content of the final mixture is 3.4%.

(b) 8000 g of the mixture prepared under (a) are fed through a hopper into the same twin-screw co-rotating extruder described in Example (b-8)-7.

The extrusion of the mixture is carried out with the following processing parameters:

temperature profile: 20° C./80° C./220° C./180° C.
material output: 8.8 kg/hr
screw speed: 200 rpm
water added: 1.8 kg/hr
reduced pressure (last section): 33 mbar
water content during extrusion: 21.1%

The water content of the granulates is 8.5% after they have equilibrated at room temperature. They are brought back to a water content of 17% $H_2O$ by spraying water under stirring in a conventional mixer.

(c) The granulates of (b) are processed using the same injection molding machine of Example (b-8)-7. The processing parameters are the following:
temperature profile: 90° C./165° C./165° C./165° C.
shot weight: 6.6 g
residence time; 450 sec
injection molding: 1100 bar
back pressure; 80 bar
screw speed: 180 rpm The tensile test pieces thus produced are conditioned and tested on a Zwick tensile test apparatus described in (d) of Example (b-8)-1.

Results are presented in Table (b-8)-3.

Example (b-8)-10

Example (b-8)-9 is repeated by replacing component (c) with a thermoplastic polyurethane elastomer sold as Pellethane 2103-80-AEF by Dow Chemical Company. The resulting injection molded polymer is tougher than unblended starch polymer.

Example (b-8)-11

Example (b-8)-7 is repeated but in addition to EVAL-L-101 (component (b)), 170 g of polyethylene Lupolen 2410 T of BASF are added to the starch. The resulting injection molded polymer has stress-strain properties similar to the material obtained in Example (b-8)-7 i.e. it is considerably tougher than the unblended starch polymer.

Example (b-8)-12

Example (b-8)-8 is repeated with the exception that component (c) is replaced by polyethylene-co-vinyl acetate (80 mole % ethylene, 20 mole % vinyl acetate), Escorene UL 02020 sold by Exxon.

The ratio of the components is varied as given in Table (b-8)-4.

TABLE (b-8)-4

| Blend No. | starch: component (b) + (c) (weight ratio) | component (b): component (c) (weight ratio) |
| --- | --- | --- |
| 2 | 50:50 | 1:10 |
| 3 | 60:40 | 1:20 |
| 4 | 70:30 | 1:50 |
| 5 | 80:20 | 1:99 |
| 6 | 90:10 | 10:1 |
| 7 | 94:6 | 20:1 |
| 8 | 98:2 | 50:1 |
| 9 | 99:1 | 100:1 |

The resulting injection molded polymers are tougher than the unblended starch polymers.

Example (b-8)-13

Example (b-8)-1 (Sections a) and b)) is repeated except that the water content is adjusted to 22%, and the cutter is removed from the die face. A continuous extrudate is obtained which is foamed as a result of the excess water evaporation. The foam is chopped into 30-40 mm lengths and is useful as a loose-fill, packaging insulation material.

Example (b-8)-14

During each of the injection molding operations in Examples (b-8)-2 through (b-8)-12 an experiment is performed to demonstrate the utility of making foams. The molten material is obtained as described in Example (b-8)-1 or 7, Sections a), b) and c) in each case is extruded into the open atmosphere (Section (c) instead of being injection molded into a closed mold. In every case the material is converted into a foamed extrudate useful for loose-fill in packaging applications.

Example (b-8)-15

The granulates from Example (b-8)-1 or (b-8)-7 are mixed with polystyrene in the proposition of 30 to 70 parts by weight and are treated according to Example (b-8)-14. The resulting foamed extrudate contains a very fine and uniform cell structure suitable for a variety of uses including structural foam.

Example (b-9)-1

(a) 5000 g of potato starch containing 14.5% water are placed in a high speed mixer and 500 g of water are added under stirring. To the above mixture of starch and water, 42 g of starch-g-polystyrene containing 20% grafted polystyrene having an average $M_w$ of 350,000 (component (b)) 425 g of polystyrene polystyrol 144C (component (c)) sold by BASF; 42.5 g of Boeson VP hydrogenated fat (lubricant/release agent) by Boehringer Ingelheim; 21.25 g of a melt flow accelerator (lecithin) sold as Metarin P by Lucas Meyer and 21.25 g of titanium dioxide (pigment and solid mixture flow accelerator) are added under stirring. The water content of the final mixture is 20.2%.

(b) 5000 g of the mixture prepared under (a) are fed through a hopper into a Leistritz Single Screw Lab Extruder LSM 30 having a temperature profile of 55° C./145° C./165° C./165° C. The screw speed is 50 rpm. The output of extrudate is 105 g/min.

The extrudate is cut into granulates and stored for further processing.

(c) For further processing the granulates are conditioned to a water content of 17% by adding water under stirring in a conventional mixer. The obtained material is then fed through a hopper to a Kloeckner-Ferromatic FM 60 injection-molding machine, for the production of tensile test pieces. The temperature profile is 90° C./155° C./155° C./155° C., the screw speed: 180 rpm, the shot weight 8.4 g, the residence time 450 sec., the injection pressure 1200 bar, the back pressure 30 bar.

All tensile test pieces are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on an Instron tensile test apparatus, each test with 4 pieces.

The samples are measured at room temperature using an extension rate of 10 mm per minute. Results are presented in Table (b-9)-1 and compared with those obtained with tensile test pieces obtained from the same starch processed in a similar way but in absence of components b) and c) (Example (b-9)-1). It can be seen from the results that the break strain (elongation at break) is going from 15.82% to 45% and break energy from 194.30 kJ/m² to 510 kJ/m² showing a considerable increase in the toughness of the blend material over the unblended one.

TABLE (b-9)-1

|  | Break Strain (%) | Break Energy (kJ/m²) |
|---|---|---|
| starch (unblended starch) | 15.82 | 194.3 |
| ternary blend (b-9)-1 | 45 | 510 |

Of course different blend compositions show different values for the physical parameters indicated. To obtain the best values is a matter of optimization by varying the concentration of the different components, which is a procedure known to one skilled in the art.

Example (b-9)-1 is repeated with the following blends as per the Examples (b-9)-2 through (b-9)-10 whereby analogous results as given in Table (b-9)-1 are obtained.

Example (b-9)-2

Example (b-9)-1 is repeated by replacing component (b) by starch-g-poly(methyl acrylate) containing 42% grafted poly(methyl acrylate) having an average $M_w$ of 845,000, and by replacing component (c) with poly(methyl methacrylate) Degalan G-6 of Degussa. The ratio of the components is varied as given in Table (b-9)-2.

TABLE (b-9)-2

| Blend No. | starch: component (b) + (c) (weight ratio) | component(b-9)-: component (c) (weight ratio) |
|---|---|---|
| 2 | 50:50 | 100:1 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher more resistant to humid air than the unmodified starch polymer. The toughness as judged by resistance to breaking upon bending increases from blend (b-9)-9 to blend 2 in concert with the combined increase in starch-g-poly(methyl acrylate) content. While the resistance to softening in humid atmosphere is improved in all cases relative to unblended starch, the resistance of blends 1,4,5 and 6 are particularly good. These results illustrate the unexpected combinations as benefits in performance.

Example (b-9)-3

Example (b-9)-1 is repeated except that component (b) (starch-g-polystyrene) is replaced with starch-g-poly(methyl acrylate) containing 42% grafted poly(methyl acrylate) having an average $M_w$ of 845,000. Component (c) (polystyrene) is replaced by the thermoplastic polyurethane elastomer Pellethane 2103-80-AEF sold by the Dow Chemical Company. The resulting injection molded polymer is tougher and more resistant to humid air than unblended starch polymer.

Example (b-9)-4

Example (b-9)-1 is repeated except that component (b) (starch-g-polystyrene) is replaced with starch-g-poly(methyl methacrylate) containing 20% of grafted poly(methyl methacrylate). The thermoplastic polyamide elastomer Pebax MA-4011 sold by Atochem is used as component (c).

The resulting injection molded polymer is tougher and more resistant to humid air than unblended starch polymer.

Example (b-9)-5

Example (b-9)-1 is repeated except that component (b) is replaced by starch-g-poly(methyl methacrylate) containing 20% of grafted poly(methyl methacrylate) and replacing component (c) by 212 g of the thermoplastic polyurethane elastomer Pellethane 2103-80-AEF and 212 g of the thermoplastic polyamide elastomer Pebax MA-4011. The resulting injection molded polymer is tougher and more resistant to humid air than unblended starch polymer.

Example (b-9)-6

Example (b-9)-1 is repeated; replacing component (b) by starch-g-poly(methyl methacrylate) containing 20% of grafted poly(methyl methacrylate) and replacing component (c) by Nylon 12 Vestamid L-1700 sold by Huels Chemie. The resulting injection molded polymer is tougher and more resistant to humid air than unblended starch polymer.

Example (b-9)-7

Example (b-9)-1 is repeated except that component (b) is replaced with starch-g-poly(methyl methacrylate) having 20% grafted poly(methyl methacrylate). Component (c) is replaced by poly(methyl methacrylate) Degalan G-6 sold by Degussa. The resulting injection molded polymer is tougher and more resistant to humid air than unblended starch polymer.

Example (b-9)-8

Example (b-9)-1 is repeated except that component (b) is replaced with starch-g-poly(methyl methacrylate) containing 20% of grafted poly(methyl methacrylate) and replacing component (c) by polyethylene Lupolen 2410T of BASF. The resulting injection molded polymer is tougher and more resistant to humid air than unblended starch polymer.

Example (b-9)-9

Example (b-9)-1 (Sections a) and b)) is repeated except that the water content is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-9)-10

During each of the injection molding operations in Examples (b-9)-2 through (b-9)-8 an experiment is performed to demonstrate the utility of making foams. The molten material is obtained as described in Example 1, Sections a), b) and c) in each case is extruded into the open atmosphere (Section c) instead of being injection molded into a closed mold. In every case the material is converted into a foamed extrudate useful for loose-fill in packaging applications.

Example (b-9)-11

The granulates from Example (b-9)-1 are mixed with polystyrene in the proportion of 30 to 70 parts by weight and are treated according to Example (b-9)-10. The resulting foamed extrudate contains a very fine and uniform cell structure suitable for a variety of uses including structural foam.

Example (b-10)-1

(a) 9500 g of potato starch containing 15.1% water are placed in a high speed mixer and 850 g of a 50% aqueous solution of polyethyleneimine (component b) sold as Polymin P by BASF; 80.75 g of Boeson VP hydrogenated fat (lubricant release agent) by Boehringer Ingelheim, and 40.37 g of a melt flow accelerator (lecithin) sold as Metarin P by Lucas Meyer are added under stirring. The water content of the final mixture was 14.8%.

(b) 10,000 g of the mixture prepared under (a) are fed through a hopper into a Werner & Pfleiderer co-rotating twin screw extruder (model Continua 37).

The temperature profile of the four sections of the barrel is 20° C./180° C./180° C./80° C., respectively.

Extrusion is carried out with a mixture output of 8.4 kg/hr (screw speed 200 rpm). Water is added at the inlet with a flow rate of 2.1 kgs/hr. The water content of the material during extrusion is therefore 32.5%. In the last section of the extruder 400 mbar reduced pressure is applied to remove part of the water as water vapor.

The water content of the granulates is 17.4% as measured after they have equilibrated at room temperature.

(c) The granulates of the pre-blended mixture as obtained under (b) ($H_2O$ content: 17.4%) are fed through a hopper to an Arburg 329-210-750 injection molding machine for the production of tensile test pieces. The temperature profile of the barrel is: 90° C./165° C./165° C./165° C.

The shot weight is 8 g, the residence time 450 sec., the injection pressure 1470 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behaviour on a Zwick tensile test apparatus.

The samples are measured at room temperature using an extension rate of 10 mm per minute. Results are presented in Table (b-10)-1 and compared with those of the tensile test pieces obtained from the same starch processed in a similar way but in absence of components (b) and (c).

TABLE (b-10)-1

|  | unblended starch | Example Nos. (b-10)- | | | | | |
|---|---|---|---|---|---|---|---|
|  |  | 1 | 3 | 4 | 6 | 7 | 8 |
| break strain % | 22 | 30 | 30 | 26 | 33 | 29 | 55 |
| break energy kJ/m² | 325 | 390 | 490 | 350 | 444 | 410 | 850 |

Example (b-10)-2

Example (b-10)-1 is repeated except that the ratio of the components is varied as given in Table (b-10)-2. For comparison perspective, Example (b-10)-1 is shown as Blend No. 1.

TABLE (b-10)-2

| Blend No. | starch: component (b) + (c) (weight ratio) | component(b-10)-: component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:9.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unblended starch polymer. The toughness as judged by resistance to breaking upon bending increases from blend 9 to blend 2 in concert with the combined increase in polyethyleneimine content. While the resistance to softening in humid atmosphere is improved in all cases relative to unblended starch, the resistance of blends 1,4,5 and 6 are particularly good. These results illustrate the unexpected combinations as benefits in performance.

Example (b-10)-3

(a) 8900 g of potato starch containing 15% water are placed in a high speed mixer and 170 g of a 50% aqueous solution of polyethyleneimine (component b) sold as Polyxin P by BASF; 85 g of polyethylene-co-acrylic acid (component (c)) sold as Primacor 5980 by the Dow Chemical Company containing 80% by weight ethylene and 20% by weight acrylic acid; 765 g of polyethylene (component (c)) sold as Lupolen 2410T by BASF; 75.6 g of Boeson VP hydrogenated fat (lubricant release agent) by Boehringer Ingelheim, and 37.8 g of a melt flow accelerator (lecithin) sold as Metarin P by Lucas Meyer are added under stirring. The water content of the final mixture is 13.6%.

(b) 10,000 g of the mixture prepared under (a) are fed through a hopper into a Werner & Pfleiderer co-rotating twin screw extruder (model Continua 37).

The temperature profile of the four sections of the barrel is 20° C./180° C./180° C./80° C., respectively.

Extrusion is carried out with a mixture output of 8.4 kg/hr (screw speed 200 rpm). Water is added at the inlet with a flow rate of 2.1 kg/hr. The water content of the material during extrusion is therefore 31.5%. In the last section of the extruder 100 mbar reduced pressure is applied to remove part of the water as water vapor.

The water content of the granulates is 13.9% as measured after they have equilibrated at room temperature. They are brought to a water content of 17% by spraying water under stirring in a conventional mixer.

(c) The granulates of the pre-blended mixture as obtained under (b) ($H_2O$ content: 17%) are fed through a hopper to an Arburg 329-210-750 injection molding machine for the production of tensile test pieces. The temperature profile of the barrel is: 90° C./165° C./165° C./ 165° C.

The shot weight is 7.7 g, the residence time 450 sec., the injection pressure 2200 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior or: a Zwick tensile test apparatus as shown in Example (b-10)-1. Results are presented in Table (b-10)-1.

Example (b-10)-4

(a) 8000 g of potato starch containing 15.1% water are placed in a high speed mixer and 680 g of a 50% aqueous solution of polyethyleneimine (component (b)) sold as Polymin P by BASF; 680 g of thermoplastic polyamide elastomer (component (c)) PEBAX MA-4011 sold by Atochem; 680 g of thermoplastic polyurethane (component (c)) Pellethane 2103-80-AEF sold by the Dow Chemical Company, 68 g of Boeson VP hydrogenated fat (lubricant/release agent) and 37.82 g of a melt flow accelerator (lecithin/ Metarin P) are added under stirring. The water content of the final mixture is 12.4%.

(b) 9000 g of the mixture prepared under (a) are fed through a hopper into the same twin-screw co-rotating extruder described in Example (b-10)-1. The extrusion of the mixture is carried out with the following temperature profile: 20° C./50° C./190° C./150° C. The other parameters of the extrusion experiment are the following:

material output: 7.4 kg/hr
screw speed: 200 rpm
water added: 0.5 kg/hr
reduced pressure (last section) 800 mbar
water-content during extrusion: 17.6%

The water content of the granulates is 3% as measured after they have equilibrated at room temperature. They are brought to a water content of 17% by spraying water under stirring in a conventional mixer.

(c) The granulates obtained under (b) are processed using the same injection molding machine described in (c) of Example (b-10)-1. The temperature profile of the barrel is 90° C./175° C./175° C./175° C. The other processing parameters are:

shot weight: 7.7 g
residence time: 450 sec.
injection pressure: 1900 bar
back pressure: 80 bar
screw speed: 180 rpm The tensile test pieces thus produced are conditioned and tested on a Zwick tensile test apparatus as described in (d) of Example (b-10)-1.

Results are presented in Table (b-10)-1.

Example (b-10)-5

Example (b-10)-1 is repeated by replacing component (b) by poly N-hydroxyethyl ethylenimine) of $M_w$ 60,000–80,000 (in 31% aqueous solution) sold Ltd. In addition ethylene vinyl alcohol copolymer (component (c)) (27 mole % ethylene, 73 mole % vinyl alcohol) sold as EVAL-L-101 by Kuraray, is added to the mixture. The ratio of the components is varied as given in Table (b-10)-3.

TABLE (b-10)-3

| Blend No. | starch: component (b) + (c) (weight ratio) | component(b-10)- component (c) (weight ratio) |
|---|---|---|
| 12 | 50:50 | 1:10 |
| 13 | 60:40 | 1:20 |
| 14 | 70:30 | 1:50 |
| 15 | 80:20 | 1:99 |
| 16 | 90:10 | 10:1 |
| 17 | 94:6 | 20:1 |
| 18 | 98:2 | 50:1 |
| 19 | 99:1 | 100:1 |

The resulting injection molded polymers are tougher and more resistant to humid air than the unblended starch polymer.

Example (b-10)-6

(a) 8900 g of potato starch containing 15% water are placed in a high speed mixer and 510 g of a 50% aqueous solution of polyethyleneimine (component (b)) sold as Polymin P by BASF, 85 g of polyethylene-co-acrylic acid (component (c)) containing 80% by weight ethylene and 20% by weight of acrylic acid sold as Primacor 5980 by the Dow Chemical Company; 425 g of polystyrene (component (c)) Polystyrol 144-C sold by BASF; 75.65 g of hydrogenated fat (lubricant/ release agent) Boeson VP; 37.82 g of a melt flow accelerator (lecithin) Metarin P are added under stirring. The water content of the final mixture is 15.8%.

(b) 9000 g of the mixture prepared under (a) are fed through a hopper into the same twin-screw co-rotating extruder described in Example (b-10)-1.

The extrusion of the mixture is carried out with the following processing parameters:

temperature profile: 20° C./200° C./200° C./ 80° C.
material output: 8.4 kg/hr
screw speed: 200 rpm
water added: 2.1 kg/hr
reduced pressure (last section): 100 mbar
water content during extrusion: 33.3%

The water content of the granulates is 13.9% after they have equilibrated at room temperature. They are then brought to a water content of 17% by spraying water under stirring in a conventional mixer.

(c) The granulates of (b) are processed using the same injection molding machine of Example (b-10)-1. The processing parameters are the following:

temperature profile: 90° C./165° C./165° C./ 165° C.
shot weight: 7.8 g
residence time: 450 sec
injection molding: 2220 bar
back pressure: 80 bar
screw speed: 180 rpm The tensile test pieces thus produced are conditioned and tested on a Zwick tensile test apparatus described in (d) of Example (b-10)-1.

Results are presented in Table (b-10)-1.

Example (b-10)-7

(a) 8800 g of potato starch containing 15.1% water are placed in a high speed mixer and 680 g of a 50% aqueous solution of polyethyleneimine (component (b)) sold as Polymin P by BASF; 1360 g of a thermoplastic elastomer polyurethane block polyether (component (c)) sold as Pellethane 2103-80-AE by Dow Chemical Company; 75 g of hydrogenated fat (lubricant/ release agent) Boeson VP; 38 g of a melt flow accelerator (lecithin) Metarin P are added under stirring. The water content of the final mixture is 15.2%.

(b) 9000 g of the mixture prepared under (a) are fed through a hopper into the same twin-screw co-rotating extruder described in Example (b-10)-1.

The extrusion of the mixture is carried out with the following processing conditions:
- temperature profile: 20° C./50° C./190° C./ 150° C.
- material output: 8 kg/hr
- screw speed: 200 rpm
- water added: 0.5 kg/hr
- reduced pressure (last section): 600 mbar
- water content during extrusion: 20.2%

The water content of the granulates is 5% after they have equilibrated at room temperature. They are brought to a water content of 17% by spraying water under stirring in a conventional mixer.

(c) The granulates obtained under (b) are processed using the same injection molding machine described in (c) of Example (b-10)-1. The processing parameters are the following:
- temperature profile: 90° C./175° C./175° C./ 175° C.
- shot weight: 7.8 g
- residence time: 450 sec
- injection molding: 1800 bar
- back pressure: 80 bar
- screw speed: 180 rpm The tensile test pieces thus produced are conditioned and tested on a Zwick tensile test apparatus described in (d) of Example (b-10)-1.

Results are presented in Table (b-10)-1.

Example (b-10)-8

(a) 8000 g of potato starch containing 15.1% water are placed in a high speed mixer and 680 g of a 50% aqueous solution of polyethyleneimine (Polymin P) (component b); 680 g of polyamide block polyether thermoplastic elastomer (component c) sold as Pebax MA-4011 by Atochem; 68 g of hydrogenated fat (lubricant/ release agent) Boeson VP; 34 g of a melt flow accelerator (lecithin) Metarin P are added under stirring. The water content of the final mixture is 16.3%.

(b) 9000 g of the mixture prepared under (a) are fed through a hopper into the same twin-screw co-rotating extruder described in Example (b-10)-1.

The extrusion of the mixture is carried out with the following processing parameters:
- temperature profile: 20° C./200° C./200° C./ 150° C.
- material output: 7.8 kg/hr
- screw speed: 200 rpm
- water added: 0.5 kg/hr
- reduced pressure (last section): 800 mbar
- water content during extrusion: 21.2%

The water content of the granulates was 3% after they have equilibrated at room temperature. They are then brought back to a water content of 17% $H_2O$ by spraying water under stirring in a conventional mixer.

(c) The granulates obtained under (b) are processed using the same injection molding machine described in (c) of Example (b-10)-1. The processing parameters are the following:
- temperature profile: 175° C.
- shot weight: 7.8 g
- residence time: 450 sec
- injection molding: 1850 bar
- back pressure: 80 bar
- screw speed: 180 rpm The tensile test pieces thus produced are conditioned and tested on a Zwick tensile test apparatus described in (d) of Example (b-10)-1.

Results are presented in Table (b-10)-1.

Example (b-10)-9

Example (b-10)-1 (Sections (a) and (b)) is repeated except that the water content is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-10)-10

During each of the injection molding operations in Examples (b-10)-2 through (b-10)-8 an experiment is performed to demonstrate the utility of making foams. The molten material is obtained as described in Example (b-1-)-1, Sections (a), (b) and (c) in each case is extruded into the open atmosphere (Section (c)) instead of being injection molded into a closed mold. In every case the material is converted into a foamed extrudate useful for loose-fill in packaging applications.

Example (b-10)-11

The granulates from Example (b-10)-1 are mixed with polystyrene in the proportion of 30 to 70 parts by weight and are treated according to Example (b-10)-10. The resulting foamed extrudate contains a very fine and uniform cell structure suitable for a variety of uses including structural foam.

Example (b-11)-1

(a) 9500 g of potato starch containing 15.1% water are placed in a high speed mixer and 425 g of the sodium salt of poly(styrene sulfonic acid) (component (b)) having a $M_w$ of 70,000 and sold by Monomer-Polymer and Dajac Laboratories Inc; 80.75 g of hydrogenated fat (lubricant release agent) sold as Boeson VP by Boehringer Ingelheim, 40.37 g of a melt flow accelerator (lecithin) sold as Metarin P by Lucas Meyer are added under stirring. The water content of the final mixture is 14.43%.

(b) 10,000 g of the mixture prepared under (a) are fed through a hopper into a Werner & Pfleiderer co-rotating twin screw extruder (model Continua 37).

The temperature profile of the four sections of the barrel is respectively 20° C./180° C./180° C./80° C.

Extrusion is carried out with a mixture output of 8.4 kg/hr (screw speed 200 rpm). Water is added at the inlet with a flow rate of 2.1 kg/hr. The water content of the material during extrusion is therefore 32.2%. In the last section of the extruder 300 mbar reduced pressure is applied to remove part of the water as water vapor.

The water content of the granulates is 17.15% as measured after they have equilibrated at room temperature.

(c) The granulates of the pre-blended mixture as obtained under (b) ($H_2O$ content: 17.5%) are fed through a hopper to an injection molding machine Arburg 329-210-750 for the production of tensile test pieces. The temperature profile of the barrel is: 90° C./ 165° C./155° C./165° C.

The shot weight is 8 g, the residence time 450 sec., the injection pressure 1760 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. Results are presented in Table (b-11)-1 and compared with those of the tensile test pieces obtained from the same starch processed in a similar way but in absence of components b) and c).

TABLE (b-11)-1

| | unblended starch | Example Nos. (b-11)- | | | | | | | |
|---|---|---|---|---|---|---|---|---|---|
| | | 1 | 3 | 4 | 5 | 6 | 7 | 8 | 9 |
| break strain % | 22 | 30 | 28 | 360 | 35 | 32 | 33 | 28 | 33 |
| break energy kJ/m² | 325 | 420 | 385 | 1200 | 375 | 395 | 460 | 630 | 750 |

Example (b-11)-2

Example (b-11)-1 is repeated except that the ratio of the components is varied as given in Table (b-11)-2. For comparison perspective, Example (b-11)-1 is shown as Blend No. 1.

TABLE (b-11)-2

| Blend No. | starch: component (b) + (c) (weight ratio) | component(b-11) component (c) (weight ratio) |
|---|---|---|
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unblended starch polymer. The toughness as judged by resistance to breaking upon bending increases from blend 9 to blend 2 in concert with the combined increase in the content of the sodium salt of poly(styrene sulfonic acid. While the resistance to softening in humid atmosphere is improved in all cases relative to unblended starch, the resistance of blends 1,4,5 and 6 are particularly good. These results illustrate the unexpected combinations as benefits in performance.

Example (b-11)-3

(a) 8900 g of potato starch containing 15% water are placed in a high speed mixer and 765 g of poly(styrene sulfonic acid, sodium salt) (component (b)) having a $M_w$ of 70,000 and sold by Monomer-polymer and Dajac Laboratories Inc.; 170 g of polystyrene (component (c)) sold as Polystyrol 144-C by BASF, 340 g of polyethylene (component (c)) Lupolen 2410T of BASF; 80 g of hydrogenated fat (lubricant release agent) sold as Boeson VF by Boehringer Ingelheim, 40 g of a melt flow accelerator (lecithin) sold as Metarin P by Lucas Meyer are added under stirring. The water content of the final mixture is 13%.

(b) 10,000 g of the mixture prepared under (a) are fed through a hopper into a Werner & Pfleiderer co-rotating twin screw extruder (model Continua 37).

The temperature profile of the four sections of the barrel is respectively 20° C./180° C./180° C./80° C. Extrusion is carried out with a mixture output of 8 kg/hr (screw speed 200 rpm). Water is added at the inlet with a flow rate of 2.1 kg/hr. The water content of the material during extrusion is therefore 32.7%. In the last section of the extruder 500 mbar reduced pressure is applied to remove part of the water as water vapor.

The water content of the granulates is 17.2% as measured after they have equilibrated at room temperature.

(c) The granulates of the pre-blended mixture as obtained under (b) ($H_2O$ content: 17%) are fed through a hopper to an injection molding machine Arburg 329-210-750 for the production of tensile test pieces. The temperature profile of the barrel is: 90° C./165° C./165° C./ 165° C..

The shot weight is 7.9 g, the residence time 450 sec., the injection pressure 1650 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-11)-1.

The results are presented in Table (b-11)-1.

Example (b-11)-4

(a) 2100 g of potato starch containing 15.1% water are placed in a high speed mixer and 765 g of poly(styrene, sulfonic acid, sodium salt) (component (b)) having a $M_w$ of 70,000 and sold by Monomer-Polymer and Dajac Laboratories Inc., (component (c)) 4250 g of thermoplastic polyamide elastomer Pebax MA-4011 of Atochem, 1700 g of thermoplastic polyurethane elastomer (component (c)) Pellethane 2103-80-AEF of the Dow Chemical Company; 18 g of hydrogenated fat (lubricant/release agent) Boeson VP and 9 g of a melt flow accelerator (lecithin/Metarin P) are added under stirring. The water content of the final mixture is 3.6%.

(b) 8000 g of the mixture prepared under (a) are fed through a hopper into the same twin-screw co-rotating extruder described in Example (b-11)-1. The extrusion of the mixture is carried out with the following temperature profile 20° C./80° C./190° C./ 150° C. The other parameters of the extrusion experiment are the following:

material output: 7.4 kg/hr
screw speed: 200 rpm water added: 2 kg/hr
reduced pressure (last section) 800 mbar
water-content during extrusion: 22.9%

The water content of the granulates is 2% as measured after they have equilibrated at room temperature. They are brought to a water content of 17% by spraying water under stirring in a standard mixer.

(c) The granulates obtained under (b) are processed using the same injection molding machine described in (c) of Example (b-11)-1 The temperature profile of the barrel is 90° C./175° C./175° C./175° C. The other processing parameters are:
shot weight: 6.8 g
residence time: 450 sec.
injection pressure: 2200 bar
back pressure: 80 bar
screw speed: 180 rpm The tensile test pieces thus produced are conditioned and tested on a Zwick tensile test apparatus as described in (d) of Example (b-11)-1.

Results are presented in Table (b-11)-1.

Example (b-11)-5

(a) 8000 g of potato starch containing 15% water are placed in a high speed mixer and 340 g of poly(styrene sulfonic acid, sodium salt) (component (b)) having a $M_w$ of 70,000 and sold by Monomer-Polymer and Dajac Laboratories Inc., 680 g of thermoplastic polyamide-block-polyether elastomer (component (c)) sold as Pebax MA-4011 by Atochem, 680 g of thermoplastic polyurethane elastomer (component (c)) sold as Pellethane 2103-80-AEF by the Dow Chemical Company; 72 g of hydrogenated fat (lubricant/ release agent) Boeson VP; 36 g of a melt flow accelerator (lecithin) Metarin P are added under stirring. The water content of the final mixture is 12.2%.

(b) 9000 g of the mixture prepared under (a) are fed through a hopper into the same twin-screw co-rotating extruder described in Example (b-11)-1.

The extrusion of the mixture is carried out with the following processing parameters:
temperature profile: 20° C./220° C./220° C./ 80° C.
material output: 7 kg/hr
screw speed: 200 rpm
water added: 2.1 kg/hr
reduced pressure (last section): 200 mbar
water content during extrusion: 28.7%

The water content of the granulates is 17.1% after they have equilibrated at room temperature.

(c) The granulates of (b) are processed using the same injection molding machine of Example (b-11)-1. The processing parameters are the following:
temperature profile: 90° C./165° C./165° C.
shot weight: 7.8 g
residence time: 450 sec
injection molding: 1650 bar
back pressure: 80 bar
screw speed: 180 rpm The tensile test pieces thus produced are conditioned and tested on a Zwick tensile test apparatus described in (d) of Example (b-11)-1.

Results are presented in Table (b-11)-1.

Example (b-11)-6

(a) 7000 g of potato starch containing 15.1% water are placed in a high speed mixer and 1700 g of poly(styrene sulfonic acid, sodium salt) (component (b)) having a $M_w$ of 70,000 and sold by Monomer-Polymer and Dajac Laboratories Inc.; 425 g of a thermoplastic polyamide elastomer (component (c)) sold as Pebax MA-4011 by Atochem; 424 g of a thermoplastic elastomer polyurethane block polyether (component (c)) sold as Pellethane 2103-80-AE by Dow Chemical Company; 60 g of hydrogenated fat (lubricant/ release agent) Boeson VP; 30 g of a melt flow accelerator (lecithin) Metarin P are added under stirring. The water content of the final mixture is 12.3%.

(b) 9000 g of the mixture prepared under (a) are fed through a hopper into the same twin-screw co-rotating extruder described in Example (b-11)-1.

The extrusion of the mixture is carried out with the following processing temperature:
temperature profile: 20° C./ 220° C/ 220° C/ 80° C.
material output: 8 1 kg/hr
screw speed: 200 rpm
water added: 2.1 kg/hr
reduced pressure (last section): 600 mbar
water content during extrusion: 30.5%

The water content of the granulates is 17.3% after they have equilibrated at room temperature.

(c) The granulates obtained under (b) are processed using the same injection molding machine described in (c) of Example (b-11)-1. The processing parameters are the temperature profile: 90° C./175° C./175° C./ 175° C.

shot weight: 8 g
residence time: 450 sec
injection molding: 1670 bar
back pressure: 80 bar
screw speed: 180 rpm The tensile test pieces thus produced are conditioned and a Zwick tensile test apparatus described in (d) of Example (b-11)-1.

Results are presented in Table (b-11)-1.

Example (b-11)-7

(a) 8900 g of potato starch containing 15.1% water are placed in a high speed mixer and 765 g of poly(styrene sulfonic acid, sodium salt) (component (b)) having a $M_w$ of 70,000 and sold by Monomer-Polymer and Dajac Laboratories Inc.; 170 g of high impact polystyrene (component (c) sold as Polystyrol SB-432-B by BASF; 3400 g of polyethylene Lupolen 2410 T (component (c)) sold by BASF; 80 g of hydrogenated fat (lubricant/ release agent) Boeson VP; 40 g of a melt flow accelerator (lecithin) Metarin P are added under stirring. The water content of the final mixture is 13.8%.

(b) 9000 g of the mixture prepared under (a) are fed through a hopper into the same twin-screw co-rotating extruder described in Example (b-11)-1.

The extrusion of the mixture is carried out with the following processing parameters:
temperature profile: 20° C./80° C./160° C./ 100° C.
material output: 10 kg/hr
screw speed: 200 rpm
water added: 2.1 kg/hr
reduced pressure (last section): 35 mbar
water content during extrusion: 27.7%

The water content of the granulates is 13.5% after they have equilibrated at room temperature. They are brought to a water content of 17% by spraying water under stirring in a standard mixer.

(c) The granulates obtained under (b) are processed using the same injection molding machine described in (c) of Example (b-11)-1. The processing parameters were the following:

temperature profile: 90° C./175° C./175° C./ 175° C.
shot weight: 7.9 g
residence time: 450 sec
injection molding: 1830 bar
back pressure: 80 bar
screw speed: 180 rpm The tensile test pieces thus produced are conditioned and tested on a Zwick tensile test apparatus described in (d) of Example (b-11)-1.

Results are presented in Table (b-11)-1.

Example (b-11)-8

(a) 7000 g of potato starch containing 15.0% water are placed in a high speed mixer and 30 g of poly(styrene sulfonic acid, sodium salt) (component b) of $M_w$ of 70,000 from Monomer-Polymer and Dajac Laboratories Inc.; 300 g of polystyrene Polystyrol 144-C from BASF; 59.5 g of hydrogenated fat (lubricant/ release agent) Boeson VP; 29.75 g of a melt flow accelerator (lecithin) Metarin P are added under stirring. The water content of the final mixture is 14.2%.

(b) 7000 g of the mixture prepared under (a) are fed through a hopper into a Leistritz twin-screw co-rotating extruder (Model LSM 34 GL).

The extrusion of the mixture is carried out with the following processing parameters:
temperature profile: 25° C./90° C./150° C./ 170° C./180° C./ 120° C./120° C.
material output: 14 kg/hr
screw speed: 80 rpm
water added: 3.1 kg/hr
reduced pressure (last section): none
water content during extrusion: 31.8%

The water content of the granulates is 17% after they have equilibrated at room temperature.

(c) The granulates obtained under (b) are processed using a Kloeckner-Ferromatic FM 60 injection molding machine. The processing parameters are the following:
temperature profile: 90° C./165° C./165° C./ 165° C.
shot weight: 21 g
residence time: 450 sec
injection molding: 725 bar
back pressure: 80 bar
screw speed: 180 rpm
test pieces thus produced of standard ISO design: ISO R 527 are conditioned and tested on a Zwick tensile test apparatus described in (d) of Example (b-11)-1.

Results are presented in Table (b-11)-1.

Example (b-11)-9

(a) 10,000 g of potato starch containing 15.0% water are placed in a high speed mixer and 85 g of poly(styrene sulfonic acid, sodium salt) (component (b) of a $M_w$ of 70,0000 from Monomer-Polymer and Dajac Laboratories Inc.; 850 g of Polystyrene Polystyrol 144 C from BASF (component (c)); 85 g of hydrogenated fat (lubricant/ release agent) Boeson VP; 42.5 g of a melt flow accelerator (lecithin) Metarin P are added under stirring. The water content of the final mixture is 13.6%.

(b) 9000 g of the mixture prepared under (a) are fed through a hopper into the same twin-screw co-rotating extruder described in Example (b-11)-8.

The extrusion of the mixture is carried out with the following processing parameters:
temperature profile: 25° C./90° C./150° C./ 170° C./180° C./ 120° C./120° .C
material output: 13.2 kg/hr
screw speed: 80 rpm
water added: 3.1 kg/hr
reduced pressure (last section): 100 mbar
water content during extrusion: 39.2%

The granulates are brought to a water content of 17% by spraying water under stirring in a conventional mixer. (c) The granulates obtained under (b) are processed using the same injection molding machine described in (c) of Example (b-11)-8. The processing parameters are the following:
temperature profile: 90° C./155° C./155° C./ 155° C.
shot weight: 21.2 g
residence time: 450 sec
injection molding: 1600 bar
back pressure: 80 bar
screw speed: 180 rpm The tensile test pieces thus produced standard ISO design: ISO R 527 are conditioned and tested on a Zwick tensile test apparatus described in (d) of Example (b-11)-1.

Results are given in Table (b-11)-1.

Example (b-11)-10

Example (b-11)-9 is repeated, replacing component (b) (poly(styrene sulfonic acid, sodium salt) by the sodium salt of a sulfonated diblock-copolymer made of polystyrene (block A), and polyethylene-co-propylene (block B). The sulfonation is carried out on the polystyrene block of Kraton G 1701 a commercial product sold by Shell in which block A contains 37% by weight of styrene units and block B contains 63% by weight of ethylene-propylene units. The sulfonation is made using acetyl sulfate as reagent which is prepared by stirring a mixture of 9.8 g concentrated sulfuric acid, 10.2 g acetic anhydride and 200 ml of dichloromethane for 30 minutes at room temperature.

This mixture is then added slowly to a solution of 30 g Kraton G 1701 in 300 ml CH2Cl2 The color of the reaction mixture changes from red to dark brown after about 30 minutes during which time the polymer precipitates. The mixture is stirred another 4 hours to complete the reaction. Then 500 ml of water are added, the mixture is transferred to a separatory funnel and the organic solvent is removed. The aqueous phase which contains the polymer is neutralized with a 50% NaOH-solution. The solid is collected by vacuum filtration, thoroughly washed with deionized water and dried over P2O5 30.6 g are obtained (yield: 82%). The material is characterized by its infra-red spectrum which shows a strong characteristic sulfonate band at 1200 $cm^{-1}$ and a medium characteristic sulfonate band at 1050 $cm^{-1}$.

The resulting injection-molded polymer is tougher and more resistant to humid air than unblended starch polymer.

Example (b-11)-11

Example (b-11)-1 (Sections a) and b)) is repeated except that the water content is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-11)-12

During each of the injection molding operations in Examples (b-11)-2 through (b-11)-10 an experiment is performed to demonstrate the utility of making foams.

The molten material is obtained as described in Example (b-11)-1, Sections (a), (b) and (c) in each case is extruded into the open atmosphere (Section c) instead of being injection molded into a closed mold. In every case the material is converted into a foamed extrudate useful for loose-fill in packaging applications.

presented in Table (b-12)-1 and compared with those of the tensile test pieces obtained from the same starch processed in a similar way but in absence of components (b) and (c).

TABLE (b-12)-1

|  | unbl. starch | Example Nos. (b-12)- | | | | | | | | | | |
| --- | --- | --- | --- | --- | --- | --- | --- | --- | --- | --- | --- | --- |
|  |  | 1 | 3 | 4 | 5 | 6 | 7 | 8 | 9 | 10 | 11 | 12 |
| break strain % | 22 | 27 | 29 | 57 | 62 | 63 | 28 | 24 | 69 | 250 | 48 | 80 |
| break energy kJ/m² | 325 | 365 | 340 | 410 | 315 | 330 | 380 | 310 | 485 | 900 | 575 | 490 |

Example (b-11)-13

The granulates from Example (b-11)-1 are mixed with polystyrene in the proportion of 30 to 70 parts by weight and are treated according to Example (b-11)-12. The resulting foamed extrudate contains a very fine and uniform cell structure suitable for a variety of uses including structural foam.

Example (b-12)-1

(a) 9500 g of potato starch containing 15.1% water are placed in a high speed mixer and 425 g of polyethylene-co-methacrylic acid, sodium salt (component (b)) containing 90% by weight of ethylene and 10% by weight of methacrylic acid sold as Surlyn 8528 by Du Pont; 80.75 g of hydrogenated fat (lubricant release agent) sold as Boeson VP by Boehringer Ingelheim, 40.37 g of a melt flow accelerator (lecithin) sold as Metarin P by Lucas Meyer are added under stirring. The water content of the final mixture is 14.3%.

(b) 10,000 g of the mixture prepared under (a) are fed through a hopper into a Werner & Pfleiderer co-rotating twin screw extruder (model Continua 37).

The temperature profile of the four sections of the barrel is respectively 20° C./180° C./180° C./80° C. Extrusion is carried out with a mixture output of 8 kg/hr (screw speed 200 rpm). Water is added at the inlet with a flow rate of 2.1 kg/hr. The water content of the material during extrusion is therefore 32%. In the last section of the extruder 500 mbar reduced pressure is applied to remove part of the water as water vapor.

The water content of the granulates is 16.9% as measured after they have equilibrated at room temperature.

(c) The granulates of the pre-blended mixture as obtained under (b) ($H_2O$ content 16.9) are fed through a hopper to an injection molding machine Arburg 329-210-750 for the production of tensile test pieces. The temperature profile of the barrel is: 90° C./ 175° C./175° C./175° C.

The shot weight is 7.9 g, the residence time 450 sec., the injection pressure 2090 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus.

The samples are measured at room temperature using an extension rate of 10 mm per minute. Results are

Example (b-12)-2

Example (b-12)-1 is repeated except that the ratio of the components is varied as given in Table (b-12-)-2. For comparison perspective, Example (b-12)-1 is shown as Blend No. 1.

TABLE (b-12)-2

| Blend No. | starch: component (b) + (c) (weight ratio) | component(b-12) component (c) (weight ratio) |
| --- | --- | --- |
| 2 | 50:50 | 100:0 |
| 3 | 60:40 | 99:1 |
| 4 | 70:30 | 50:1 |
| 5 | 80:20 | 20:1 |
| 1 | 91.5:8.5 | 10:1 |
| 6 | 90:10 | 1:1 |
| 7 | 94:6 | 1:10 |
| 8 | 98:2 | 1:50 |
| 9 | 99:1 | 1:99 |

The resulting injection molded polymers are tougher and more resistant to humid air than the unblended starch polymer. The toughness as judged by resistance to breaking upon bending increases from blend 9 to blend 2 in concert with the combined increase in polyethylene-co-methacrylic acid, sodium salt (Surlyn 8528) content. While the resistance to softening in humid atmosphere is improved in all cases relative to unblended starch, the resistance of blends 1,4,5 and 6 are particularly good. These results illustrate the unexpected combinations as benefits in performance.

Example (b-12)-3

(a) 8900 g of potato starch containing 15% water are placed in a high speed mixer and 765 g of polyethylene-co-methacrylic acid, sodium salt (component (b)) containing 90% by weight of ethylene and 10% by weight of methacrylic acid sold as Surlyn 8528 by Du Pont; 85 g of polyethylene-co-vinyl acetate (component (c)) containing 80 mole % ethylene and 20 mole % vinyl acetate, sold as Escorene UL 02020 by Exxon; 85 g of polyethylene (component (c)) Lupolen 2410T sold by BASF; 75.7 g of hydrogenated fat (lubricant release agent) sold as Boeson VP by Boehringer Ingelheim, 37.8 g of a melt flow accelerator (lecithin) sold as Metarin P by Lucas Meyer are added under stirring. The water content of the final mixture is 13%.

(b) 10,000 g of the mixture prepared under (a) are fed through a hopper into a Werner & Pfleiderer co-rotating twin screw extruder (model Continua 37).

The temperature profile of the four sections of the barrel is respectively 20° C./180° C./180° C./80° C.

Extrusion is carried out with a mixture output of 8.7 kg/hr (screw speed 200 rpm). Water is added at the inlet with a flow rate of 2.1 kg/hr. The water content of the material during extrusion is therefore 31%. In the last section of the extruder 400 mbar reduced pressure is applied to remove part of the water as water vapor.

The water content of the granulates is 16.9% as measured after they have equilibrated at room temperature.

(c) The granulates of the pre-blended mixture as obtained under (b) ($H_2O$ content: 16.9%) are fed through a hopper to an injection molding machine Arburg 329-210-750 for the production of tensile test pieces. The temperature profile of the barrel is 90° C./ 165° C./165° C./ 165° C..

The shot weight is 7.6 g, the residence time 450 sec., the injection pressure 2100 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-12)-1. Results are presented in Table (b-12)-1.

Example (b-12)-4

(a) 5000 g of potato starch containing 15% water are placed in a high speed mixer and 4250 g of polyethylene-co-methacrylic acid, sodium salt (component (b)) containing 90% by weight of ethylene and 10% by weight of methacrylic acid sold as Surlyn 8528 by Du Pont; 42.5 g of hydrogenated fat (lubricant/release agent) Boeson VP and 21.3 g of a melt flow accelerator (lecithin/Metarin P) are added under stirring. The water content of the final mixture is 7.4%.

(b) 9000 g of the mixture prepared under (a) are fed through a hopper into the same twin-screw co-rotating extruder described in Example 1. The extrusion of the mixture is carried out with the following temperature profile 20° C./220° C./220° C./80° C. The other parameters of the extrusion experiment are the following:
material output: 8 kg/hr
screw speed: 200 rpm
water added: 2.1 kg/hr
reduced pressure (last section) 70 mbar
water-content during extrusion: 26.7%

The water content of the granulates is 17.1% as measured after they have equilibrated at room temperature.

(c) The granulates obtained under (b) are processed using the same injection molding machine described in (c) of Example 1. The temperature profile of the barrel is 90° C./175° C./175° C./175° C. The other processing parameters were:
shot weight: 6.4 g
residence time: 450 sec.
injection pressure: 1100 bar
back pressure: 80 bar
screw speed: 180 rpm The tensile test pieces thus produced are conditioned and tested on a Zwick tensile test apparatus as described in (d) of Example (b-12)-1.

Results are presented in Table (b-12)-1.

Example (b-12)-5

(a) 4000 g of potato starch containing 15.2% water are placed in a high speed mixer and 1700 g of polyethylene-co-methacrylic acid, sodium salt (component (b)) containing 90% by weight of ethylene and 10% by weight of methacrylic acid sold as Surlyn 8528 by Du Pont; 2550 g of polyethylene-co-vinyl acetate (component (c)) containing 80 mole % ethylene and 20 mole % vinyl acetate sold as Escorene UL02020 by Exxon; 850 g of polyethylene (component (c)) sold as Lupolen 2410T by BASF. 34 g of hydrogenated fat (lubricant/release agent) Boeson VP; 17 g of a melt flow accelerator (lecithin) Metarin P are added under stirring. The water content of the final mixture is 5.3%.

(b) 8000 g of the mixture prepared under (a) are fed through a hopper into the same twin-screw co-rotating extruder described in Example (b-12)-1.

The extrusion of the mixture is carried out with the following processing parameters:
temperature profile: 20° C./180° C./180° C./ 80° C.
material output: 8.4 kg/hr
screw speed: 200 rpm
water added: 2.1 kg/hr
reduced pressure (last section): 450 mbar
water content during extrusion: 25%

The water content of the granulates is 13.9% after they have equilibrated at room temperature. They are then brought to a water content of 17% by spraying water under stirring in a standard mixer.

(c) The granulates of (b) are processed using the same injection molding machine of Example (b-12)-1. The processing parameters are the following:
temperature profile: 90° C./175° C./175° C./ 175° C.
shot weight: 6 g
residence time: 450 sec
injection molding: 825 bar
back pressure: 80 bar
screw speed: 180 rpm The tensile test pieces thus produced are conditioned and tested o: a Zwick tensile test apparatus described in (d) of Example (b-12)-1.

Results are presented in Table (b-12)-1.

Example (b-12)-6

(a) 4000 g of potato starch containing 15.1% water are placed in a high speed mixer and 5100 g of polyethylene-co-methacrylic acid, sodium salt (component (b)) containing 90% by weight of ethylene and 10% by weight of methacrylic acid, sold as Surlyn 8528 by Du Pont; 34 g of hydrogenated fat (lubricant/ release agent) Boeson VP; 17 g of a melt flow accelerator (lecithin) Metarin P are added under stirring. The water content of the final mixture is 5%.

(b) 9000 g of the mixture prepared under (a) are fed through a hopper into the same twin-screw co-rotating extruder described in Example (b-12)-1.

The extrusion of the mixture is carried out with the following processing parameters:
temperature profile: 20° C./180° C./180° C./ 80° C.
material output: 8.3 kg/hr
screw speed: 200 rpm
water added: 2.5 kg/hr
reduced pressure (last section): 300 mbar
water content during extrusion: 27.6%

The water content of the granulates is 16.4% after they have equilibrated at room temperature.

The granulates obtained under (b) are processed using the same injection molding machine described in (c) of Example (b-12)-1. The processing parameters are the following:
temperature profile: 90° C./175° C./175° C./ 175° C.
shot weight: 6 g
residence time: 450 sec injection molding: 1100 bar
back pressure: 80 bar
screw speed: 180 rpm The tensile test pieces thus produced are conditioned and tested on a Zwick tensile test apparatus described in (d) of Example (b-12)-1.

Example (b-12)-7

(a) 9000 g of potato starch containing 15.1% water are placed in a high speed mixer and 850 g of polyethylene-co-methacrylic acid, sodium salt (component (b)) containing 85% by weight of ethylene and 15% by weight of methacrylic acid, sold as Surlyn 8940 by Du Pont; 76.5 g of hydrogenated fat (lubricant/ release agent) Boeson VP; 38.3 g of a melt flow accelerator (lecithin) Metarin P are added under stirring. The water content of the final mixture is 12.9%.

(b) 9000 g of the mixture prepared under (a) are fed through a hopper into the same twin-screw co-rotating extruder described in Example (b-12)-1.

The extrusion of the mixture is carried out with the following processing parameters:
temperature profile: 20° C./80° C./80° C./ 80° C.
material output: 8.6 kg/hr
screw speed: 200 rpm
water added: 2.1 kg/hr
(last section): 30 mbar
water content during extrusion: 31%

The water content of the granulates is 15.6% after they have equilibrated at room temperature. They are then brought to a water content of 17% by spraying water under stirring in a standard mixer.

(c) The granulates obtained under (b) are processed using the same injection molding machine described in (c) of Example (b-12)-1. The processing parameters are the following:
temperature profile: 90° C./165° C./165° C./ 165° C.
shot Weight: 7.9 g
residence time: 450 sec
injection molding: 2020 bar
back pressure: 80 bar
screw speed: 180 rpm The tensile test pieces thus produced are conditioned and tested on a Zwick tensile test apparatus described in (d) of Example (b-12)-1.

Results are presented in Table (b-12)-1.

Example (b-12)-8

(a) 8900 g of potato starch containing 15.0% water are placed in a high speed mixer and 765 g of polyethylene-co-methacrylic acid, sodium salt (component (b)) containing 85% by weight of ethylene and 15% of methacrylic acid sold as Surlyn 8920 by Du Pont; 85 g of polyvinyl alcohol-co-vinyl acetate (component (c)) containing 11-13 mole % of vinyl acetate and 87-89 mole % of vinyl alcohol, sold as Airvol 540S by Air Products; 85 g of polymethyl(methacrylate) (component (c)) sold as Degalan G-6 by Degussa; 75.7 g of hydrogenated fat (lubricant/ release agent) Boeson VP; 37.8 g of a melt flow accelerator (lecithin) Metarin P are added under stirring. The water content of the final mixture is 13.3%.

(b) 9000 g of the mixture prepared under (a) are fed through a hopper into the same twin-screw co-rotating extruder described in Example (b-12)-1.

The extrusion of the mixture is carried out with the following processing parameters:
temperature profile: 20° C./80° C./180° C./ 150° C.
material output: 9.3 kg/hr
screw speed: 200 rpm
water added: 4.1 kg/hr
reduced pressure (last section): 40 mbar
water content during extrusion: 42.7%

The water content of the granulates is 13.5% after they have equilibrated at room temperature.

(c) The granulates obtained under (b) are processed using the same injection molding machine described in (c) of Example (b-12)-1. The processing parameters are the temperature profile: 90° C./175° C./175° C./ 175° C.
shot weight: 7.8 g
residence time: 450 sec
injection molding: 1830 bar
back pressure: 80 bar
screw speed: 180 rpm The tensile test pieces thus produced are conditioned and tested on a Zwick tensile test apparatus described in (d) of Example (b-12)-1.

Results are presented in Table (b-12)-1.

Example (b-12)-9

(a) 3000 g of potato starch containing 15.0% water are placed in a high speed mixer and 5950 g of polyethylene-co-methacrylic acid sodium salt (component (b)) containing 85% by weight of ethylene and 15% by weight of methacrylic acid, sold as Surlyn 8940 by Du Pont; 25.5 g of hydrogenated fat (lubricant/ release agent) Boeson VP; 12.8 g of a melt flow accelerator (lecithin) Metarin P are added under stirring. The water content of the final mixture is 8.4%.

(b) 9000 g of the mixture prepared under (a) are fed through a hopper into the same twin-screw co-rotating extruder described in Example (b-12)-1.

The extrusion of the mixture is carried out with the following processing parameters:
temperature profile: 20° C./80° C./100° C./ 80° C.
material output: 7.9 kg/hr
screw speed: 200 rpm
water added: 1.1 kg/hr
reduced pressure (last section): 25 mbar
water content during extrusion: 19.5%

The granulates having a water content of 15.8% are brought to a water content of 17% by spraying water under stirring in a conventional mixer.

(c) The granulates obtained under (b) are processed using the same injection molding machine described in (c) of Example (b-12)-1. The processing parameters are the following:
temperature profile: 90° C./165° C./165° C./ 165° C.
shot weight: 6 g
residence time: 450 sec
injection molding: 1100 bar
back pressure: 80 bar
screw speed: 180 rpm The tensile test pieces thus produced are conditioned and tested on a Zwick tensile test apparatus described in (d) of Example (b-12)-1.

Results are given in Table (b-12)-1.

Example (b-12)-10

(a) 2100 g of potato starch containing 15% water are placed in a high speed mixer and 765 g of polyethylene-co-acrylic acid, sodium salt (component (b)) containing 80% by weight of ethylene and 20% by weight of acrylic acid, prepared by neutralizing fluxed polyethylene-co-acrylic acid Primacor 5980 of the Dow Chemical Company with a sodium hydroxide solution; 5950 g of a thermoplastic polyamide elastomer sold as Pebax Ma-4011 by Atochem; 18 g of hydrogenated fat (lubricant release agent) sold as Boeson VP by Boehringer Ingelheim, 9 g of a melt flow accelerator (lecithin) sold as Metarin P by Lucas Meyer are added under stirring. The water content of the final mixture is 6.5%.

(b) 8000 g of the mixture prepared under (a) are fed through a hopper into a Werner & Pfleiderer co-rotating twin screw extruder (model Continua 37).

The temperature profile of the four sections of the barrel is respectively 20° C./80° C./240° C./180° C.

Extrusion is carried out with a mixture output of 8 kg/hr (screw speed 200 rpm). Water is added at the inlet with a flow rate of 1.8 kg/hr. The water content of the material during extrusion is therefore 23.3%. In the last section of the extruder 500 mbar reduced pressure is applied to remove part of the water as water vapor.

The water content of the granulates is 7% as measured after they have equilibrated at room temperature. They are brought to a water content of 17% by spraying water under stirring in a conventional mixer.

(c) The granulates of the pre-blended mixture as obtained under (b) ($H_2O$ content: 17%) are fed through a hopper to an injection molding machine Arburg 329-210-750 for the production of tensile test pieces. The temperature profile of the barrel is: 90° C./165° C./165° C./ 165° C..

The shot weight is 6.7 g, the residence time 450 sec., the injection pressure 460 bar, the back pressure 80 bar, the screw speed 180 rpm.

The tensile test pieces thus produced are conditioned in a climatic cabinet at 50% R.H. for five days as an arbitrary standard condition.

The test pieces are of standard DIN design (DIN No. 53455).

(d) The conditioned tensile test pieces are then tested for their stress/strain behavior on a Zwick tensile test apparatus as given in Example (b-12)-1.

Results are presented in Table (b-12)-1.

Example (b-12)-11

(a) 8900 g of potato starch containing 15.1% Water are placed in a high speed mixer and 3022 g of polyethylene-co-methacrylic acid, sodium salt (component (b)) sold as Surlyn 8660 and sold by Du Pont (containing 90% by weight of ethylene and 10% by weight of methacrylic acid); 75.65 g of hydrogenated fat (lubricant-/release agent) Boeson VP and 37.82 g of a melt flow accelerator (lecithin/Metarin P) are added under stirring. The water content of the final mixture is 11.2%.

(b) 9000 g of the mixture prepared under (a) are fed through a hopper into a Leistritz twin-screw co-rotating extruder (model LSM 34GL). The extrusion of the mixture is carried out with the following temperature profile: 25° C./90° C./150° C./120° C./95° C./ 90° C. The other parameters of the extrusion experiment are the following:
 material output: 11.5 kg/hr
 screw speed: 120 rpm
 reduced pressure (last section) 200 mbar
 water-content during extrusion: 39.2%

The water content of the granulates is 17.3% as measured after they have equilibrated at room temperature.

(c) The granulates obtained under (b) are processed using an injection molding machine Kloeckner Ferromatic FM 60. The temperature profile of the barrel is 90° C./ 155° C./155° C./155° C. The other processing parameters are
 shot weight: 20 g
 residence time: 450 sec.
 injection pressure: 767 bar
 back pressure: 80 bar
 screw speed: 180 rpm The tensile test pieces are of standard ISO design (ISO No R527). They are conditioned and tested on a Zwick tensile test apparatus as described in (d) of Example (b-12)-1.

Results are presented in Table (b-12)-1.

Example (b-12)-12

(a) 8900 g of potato starch containing 15% water are placed in a high speed mixer and 6044 g of polyethylene-co-methacrylic acid, sodium salt (component b)) containing 90% by weight of ethylene and 10% by weight of methacrylic acid (sold as Surlyn 8660 by Du Pont); 75.65 g of hydrogenated fat (lubricant/ release agent) Boeson VP; 37.82 g of a melt flow accelerator (lecithin) Metarin P are added under stirring. The water content of the final mixture was 8.9%.

(b) 9000 g of the mixture prepared under (a) are fed through a hopper into the same twin-screw co-rotating extruder described in Example (b-12)-11.

The extrusion of the mixture is carried out with the following processing parameters:
 temperature profile: 25° C./90° C./150° C./ 170° C./120° C./95° C./ 90° C.
 material output: 11.5 kg/hr
 screw speed: 120 rpm
 water added: 4.6 kg/hr;
 reduced pressure (last section): 200 mbar
 water content during extrusion: 37.6%

The water content of the granulates is 17.4% after they have equilibrated at room temperature.

(c) The granulates of (b) are processed using the same injection molding machine of Example (b-12)-11. The processing parameters are the following:
 temperature profile: 90° C./155° C./155° C./ 155° C.
 shot weight: 20 g
 residence time: 450 sec
 injection molding: 441 bar
 back pressure 80 bar
 screw speed: 180 rpm The tensile test pieces thus produced (ISO Design R527) are conditioned and tested on a Zwick tensile test apparatus described in (d) of Example (b-12)-1. Results are presented in Table (b-12)-1.

Example (b-12)-13

Example (b-12)-11 is repeated by adding to the mixture of section a) 302 g of polyethylene Lupolen 2410T of BASF. The resulting injection molded polymer is tougher than unblended starch polymer as judged by resistance to breaking upon bending.

Example (b-12)-14

(a) 8900 g of potato starch containing 15.1% Water are placed in a high speed mixer and 510 g of polyethyene-co-acrylic acid, sodium salt, (component (b)) containing 80% by weight of ethylene and 20% by weight of acrylic acid prepared by neutralizing fluxed polyethylene-co-acrylic acid Primacor 5980 of the Dow Chemical Company with a sodium hydroxyde solution; 510 g of Nylon 12 (component (c)) sold as Vestamid L-1700 by Huels Chemie; 75.65 g of hydrogenated fat (lubricant/ release agent) Boeson VP; 37.82 g of a melt flow accelerator (lecithin) Metarin P are added under stirring. The water content of the final mixture is 13.4%.

(b) 9000 g of the mixture prepared under (a) are fed through a hopper into the same twin-screw co-rotating extruder described in Example (b-12)-1.

The extrusion of the mixture is carried out with the following processing temperature:
temperature profile: 20° C./80° C./190° C./ 190° C.
material output: 9.1 kg/hr
screw speed: 200 rpm
water added: 2.9 kg/hr
reduced pressure (last section): 40 mbar
water content during extrusion: 37.6%

The water content of the granulates is 9.9% after they have equilibrated at room temperature. They are brought to a water content of 17% by spraying water in a standard mixer.

(c) The granulates obtained under (b) are processed using the same injection molding machine described in (c) of Example (b-12)-1. The processing parameters are the following:
temperature profile: 90° C./175° C./175° C./ 175° C.
shot weight: 8 g
residence time: 450 sec
injection molding: 2220 bar
back pressure: 80 bar
screw speed: 180 rpm The corresponding injection molded polymers blend is tougher than the unblended starch polymer, as judged by resistance to breaking upon bending.

Example (b-12)-15

(a) 8000 g of potato starch containing 15.1% water are placed in a high speed mixer and 765 g of polyvethylene-co-acrylic acid, sodium salt (component (b)) prepared by neutralizing fluxed Primacor 5980 (80% by weight ethylene and 20% by weight acrylic acid) with a sodium hydroxide solution; 425 g of polyvinyl alcohol-co-vinyl acetate (87–89 mole % vinyl alcohol, 11–13 mole % vinyl acetate) (component (c)) sold as Airvol 540S by Air Products; 425 g of poly(methyl methacrylate) (component (c)) sold as Degalan G-6 by Degussa; 68 g of hydrogenated fat (lubricant/ release agent) Boeson VP; 34 g of a melt flow accelerator (lecithin) Metarin P are added under stirring. The water content of the final mixture is 12.4%.

(b) 9000 g of the mixture prepared under (a) are fed through a hopper into the same twin-screw co-rotating extruder described in Example (b-12)-1.

The extrusion of the mixture is carried out with the processing parameters:
temperature profile: 20° C./80° C./180° C./ 150° C.
material output: 9.3 kg/hr
screw speed: 200 rpm
water added:: 4.1 kg/hr
reduced pressure (last section): 40 mbar
water content during extrusion: 42.1%

The water content of the granulates is 13.5% after they have equilibrated at room temperature. They are brought to a water content of 17% by spraying water in a standard mixer.

The granulates obtained under (b) are processed using the same injection molding machine described in (c) of Example (b-12)-1. The processing parameters are the following:

temperature profile: 90° C./175° C./175° C./ 175° C.
shot weight: 7.8 g
residence time: 450 sec
injection molding: 1850 bar
back pressure 80 bar
screw speed: 180 rpm The corresponding injection molded polymer blend is tougher than the unblended starch polymer, as judged by resistance to breaking upon bending.

Example (b-12)-16

Example (b-12)-13 is repeated, replacing polyethylene (component (c)) Lupolen 2410T by 425 g of polystyrene Polystyrol 144-C sold by BASF.

The corresponding injection molded polymer blend is tougher than the unblended starch polymer, as judged by resistance to breaking upon bending.

Example (b-12)-17

Example (b-12)-10 is repeated with the difference that (i) potato starch (H$_2$O content: 15%) is increased to 8000 g, (ii) the thermoplastic polyamide elastomer (component (c)) Pebax Ma-4011 is replaced by 1360 g of thermoplastic polyurethane elastomer Pellethane 2103-80-Ae of the Dow Chemical Company.

The corresponding injection molded polymer blend is tougher than the unblended starch polymer, as judged by resistance to breaking upon bending.

Example (b-12)-18

Example (b-12)-1 (Sections a) and b)) is repeated except that the water content is adjusted to 22%, and the cutter is removed from the die face. A continuous extrudate is obtained which is foamed as a result of the excess water evaporation. The foam is chopped into 30–40 mm lengths and is useful as a loose-fill, packaging insulation material.

Example (b-12)-19

During each of the injection molding operations in Examples (b-12)-2 through (b-12)-17 an experiment is performed to demonstrate the utility of making foams. The molten material is obtained as described in Example (b-12)-1, Sections a), b) and c) in each case is extruded into the open atmosphere (Section c) instead of being injection molded into a closed mold. In every case the material is converted into a foamed extrudate useful for loose-fill in packaging applications.

Example (b-12)-20

The granulates from Example (b-12)-1 are mixed with polystyrene in the proportion of 30 to 70 parts by weight and are treated according to Example (b-12)-19. The resulting foamed extrudate contains a very fine and uniform cell structure suitable for a variety of uses including structural foam.

Example (c-1)-1

(a) Preparation of destructurized starch granulates.

Natural potato starch, a lubricant/release agent (hydrogenated fat) and a melt flow accelerator (lecithin) and titanium dioxide were mixed together in the relative proportions in a powder mixer for 10 minutes so that a composition consisting of 80.6 parts of natural potato starch, one part of the hydrogenated triglyceride of the fatty acid $C_{18}$:$C_{16}$:$C_{14}$ in a ratio of 65:31:4 weight percent, 0.7 parts lecithin, 0.7 parts of titanium dioxide and 17 parts water in the form of a freely flowing powder is obtained. This material was then fed to the hopper of an extruder. In the screw barrel the powder was melted. The temperature within the barrel was measured to be 175° C., the average total residence time was 12 minutes (approximately 10 minutes heating time, approximately 2 minutes in molten state) and the pressure generated was equal to the vapor pressure of the moisture present in the volume of the extruder barrel. The melt was then extruded, and cut into granulates of an average diameter of 2 to 3 mm. The material was hard, white with a fine foamed structure. The water content was 12%, as water was allowed to escape when the melt left the extruder nozzle.

The obtained granulated material was then conditioned to a water content of 17%.

(b) Preparation of destructurized starch granules of acid-washed potato starch.

600 g of native potato starch were suspended in 700 cm$^3$ of 0.2 M HCl and stirred for 10 minutes. The suspension was filtered and the starch washed on the filter three times with 200 cm$^3$ portions of 0.2 M HCl. The starch was again suspended in 500 cm$^3$ 0.2 M HCl, stirred again for 10 minutes, filtered, washed three times with 200 cm$^3$ portions of 0.2 M HCl.

After the treatment with HCl, the excess of acid was removed by washing on a filter with demineralized (deionized) water in the following way: the starch was washed twice with 200 cm$^3$ portions of deionized water and then suspended in 500 cm of deionized water. This washing procedure with deionized water (to remove excess acid) was repeated twice to get the starch free of HCl. This was controlled by adding silver nitrate to the washing water. When there was no more silver chloride precipitating in the washing water, the Washing was completed. The washed starch was pressed on the filter and dried in a conditioning room (25° C., 40% RH) until it equilibrated at about 17.0% H$_2$O.

Analyses have been carried out before and after the acid washing of starch for mono- and divalent ions and results obtained showed that the Ca$^{+2}$-ions bridging the phosphate groups were essentially removed.

(c) Injection molding of a mixture of destructurized starch and synthetic polymer.

The granulates as obtained under (a) and the granules as obtained under (b) above were mixed with a synthetic polymer in the weight ratios as specified in Table (c-1)-1 below and injection molded to produce test pieces suitable for measuring their dimensional stability. The test pieces were injection molded using a Kloeckner FM60 injection molding machine at an injection molding temperature at the end of the barrel of 165° C. at a cycle time of about 15 seconds. The injection molding pressure was about 1600 bars and the back pressure about 75 bars.

(d) Testing and testing conditions

The test pieces were placed (laid on a screen) in a climatic cabinet in which a high relative humidity (near 100% R.H.) was maintained using a 1% aqueous sulfuric acid solution at room temperature. For each blend material 3 test pieces were used to obtain average figures relating to dimensional stability.

The test pieces obtained from the mold, were cut to a length of about 87–90 mm, which is close to the optimal length which can be measured on a NIKON profile projector V12.

After cutting the length, the samples were initially equilibrated to 14% H$_2$O content, placed on the NIKON V12 and their widths and lengths were measured.

The samples were then placed in the climatic cabinet and exposed to a high relative humidity at room temperature. Reference samples of unblended starch were placed under the same conditions. The dimensions were measured on each of the 3 pieces and recorded after 1, 2 and 3 days.

The lengths measured are given in Table (c-1)-1.

In width, slight expansions of up to 4% with 1% polymer content and less than 4% with 5% polymer, were generally observed.

The FIGS. 1, 2, 3 and 4 illustrate the results obtained according to this Example for storing three days under the indicated conditions.

FIGS. 1.1 to 1.4 show comparative test results for untreated starch, blended starch containing 1% of polyethylene and 5% of polyethylene when stored three days according to Example (c-1)-1(d)FIG.

FIGS. 2.1 to 2.4 show comparative test results for untreated starch, blended starch containing 1% of polyacetal and 5% of polyacetal when stored three days according to Example (c-1)-1(d).

FIGS. 3.1 to 3.4 show comparative test results for untreated starch, blended starch containing 1% of EAA (ethylene/acrylic acid-copolymer) and 5% of EAA (ethylene/acrylic acid-copolymer) when stored three days according to Example (c-1)-1(d).

FIGS. 4.1 to 4.4 show comparative test results for untreated starch, blended starch containing 1% of EVA (ethylene/vinyl acetate-copolymer) and 5% of EVA (ethylene/vinyl acetate-copolymer) when stored three days according to Example (c-1)-1(d).

TABLE (c-1)-1

| No. | polymer added | % by weight of polymer added | dimensional deformation, change in % after 1 day | 2 days | 3 days |
|---|---|---|---|---|---|
| 1. | none, | comparative example | −40 | −50.1 | −54 |
| 2. | polyethylene | 0.5 | −15 | −20 | −25 |
| 3. | " | 1.0 | −13 | −14 | −17 |
| 4. | " | 5.0 | +1.3 | +0.2 | −1.8 |
| 5. | polystyrene | 1.0 | +1.05 | −0.5 | −6.7 |
| 6. | " | 5.0 | +0.45 | −0.3 | −0.8 |
| 7. | polyacetal | 0.1 | ±1 | −4.0 | −10 |
| 8. | " | 1.0 | +1.5 | +0.4 | −6.2 |
| 9. | " | 5.0 | +0.7 | +0.1 | −0.6 |
| 10. | " | 10.0 | ±0.1 | ±0.1 | ±0.1 |
| 11. | " | 20.0 | ±0.1 | ±0.1 | ±0.1 |
| 12. | EAA* | 0.5 | −0.2 | −7.0 | −18.0 |
| 13. | " | 1.0 | +0.07 | −4.0 | −11.0 |
| 14. | " | 5.0 | +0.6 | −1.4 | −5.0 |
| 15. | " | 10.0 | +0.1 | −0.1 | −0.4 |
| 16. | EVA** | 0.5 | −0.5 | −5.0 | −17.1 |
| 17. | " | 1.0 | +0.3 | −0.5 | −7.0 |
| 18. | " | 5.0 | +0.2 | −1.2 | −4.8 |
| 19. | " | 20.0 | −0.1 | −0.1 | −2.0 |

*EAA = ethylene/acrylic acid—copolymer (9% acrylic acid comonomer)
**EVA = ethylene/vinyl acetate—copolymer (10% vinyl acetate comonomer)

Example (c-1)-2

The granulates obtained according to Example (c-1)-1(a) and the granules obtained according to Example (c-1)-1(b) were each mixed with polyethylene, polystyrene, polyacetal, ethylene/acrylic/acid-copolymers (9% acrylic acid-comonomer) and ethylene/vinyl acetate-copolymer (10% vinyl acetate-comonomer) each time in ratio of 25%, 50%, 75% and 90% by weight of polymer added. Dimensional changes were nominal after exposure to humid air according to Example (c-1)-1(d).

The invention being thus described, it will be obvious that the same may be varied in many ways. Such variations are not to be regarded as a departure from the spirit and scope of the invention and all such modifications are intended to be included within the scope of the following claims:

We claim:

1. A composition of matter capable of being formed into articles having substantial dimensional stability comprising:
   (a) destructurized starch; and
   (b) at least one substantially water-insoluble thermoplastic polymer.

2. The composition of claim 1, wherein the thermoplastic polymer is selected from the group consisting of polyolefines, vinylpolymers, polyacetals (POM), polycondensates, thermoplastic polyesters, polycarbonates, poly(alkylene therephthalates), polyarylethers, thermoplastic polymides, polyhydroxybutyrate (PHB), high molecular weight essentially water-insoluble polyalkylene oxides and copolymers and mixtures thereof.

3. The composition of claim 2, wherein the thermoplastic polymer is selected from the group consisting of polyethylene (PE), polyisobutylenes, polypropylenes, poly(vinyl chloride) (PVC), poly (vinyl acetates), polyvinylalcohols, polystyrenes, polyacrylonitriles (PAN), polyvinylcarbazols (PVK), polyamides (PA), essentially water-insoluble poly (acrylic acid esters) and essentially water-insoluble poly (methacrylic acid esters) and their copolymers and mixtures thereof.

4. The composition of claim 2, wherein the thermoplastic polymer is selected from the group consisting of ethylene/vinyl acetate-copolymers (EVA), ethylene/-vinyl alcohol-copolymers (EVAL), ethylene/acrylic acid-copolymers (EAA), ethylene/ethyl acrylate-copolymers (EEA), ethylene/methyl acrylate-copolymers (EMA), ABS-copolymers, styrene/acrylonitrile-copolymers (SAN), polyacetals and mixtures thereof.

5. The composition of claims 1, 2, 3 or 4 wherein the ratio of destructurized starch to synthetic polymer is 0.1:99.9 to 99.9:0.1, and wherein the starch is present in an amount of at least 50% by weight of the entire composition.

6. The composition of claims 1, 2, 3, or 4, wherein the ratio of the synthetic polymer to the starch/water component is about 0.5–5% to about 99.5–95% by weight.

7. The composition of claim 5 wherein said starch is selected from the group consisting of chemically essentially non-modified starch being carbohydrates of natural, vegetable origin composed mainly of amylose, amylopectin and mixtures thereof, physically modified starch, starch with a modified acid value (pH), starch in which the divalent ions bridging the phosphate groups have been eliminated and the eliminated ions have been replaced partially or wholly by the same or different mono- or polyvalent ions, pre-extruded starches, chemically modified starches, biologically modified starches and mixtures thereof.

8. The composition of claim 7 wherein said composition is heated in a closed volume for a time sufficient to effect destructurization and at a temperature within the range of about 105° C. to about 190° C.

9. The composition of claim 8, wherein pressure is applied in the range of from about zero to about $150 \times 10^5$ N/m².

10. The composition of claim 9, wherein the starch has a water content in the range of about 10 to about 20% by weight of the starch/water component.

11. The composition of claim 1, wherein the starch/synthetic polymer mixture contains a material selected from the group consisting of extenders, fillers, lubricants, plasticizers, coloring agents and mixtures thereof.

12. The composition of claim 11, characterized in that there is added at least one extended within the range of up to about 50% based on the weight of all components.

13. The composition of claim 12, characterized in that there is added at least one inorganic filler in a concentration of about 0.02 to about 3%.

14. The composition of claim 11, wherein there is added a plasticizer within the range of about 0.5 to about 15%.

15. The composition of claim 14, wherein a coloring agent is added in a concentration of about 0.001 to about 10%.

16. The composition of claim 14, wherein the sum of the plasticizer and water content does not exceed 25%.

17. The composition of claims 1 or 16, further comprising at least one active ingredient selected from the group consisting of pharmaceuticals, agriculturally active compounds and combinations and mixtures thereof.

18. The composition of claim 1 in the form of a melt blend.

19. The composition of claim 1 cooled to obtain a solid.

20. A thermoplastic destructurized starch product having substantial dimensional stability formed by the process comprising:
   1) providing a mixture of destructurized starch and at least one substantially water-insoluble thermoplastic polymer;
   2) heating said mixture in a closed volume under sufficient temperature and pressure for a time long enough to effect destructurization of said starch and form a substantially homogenous melt;
   3) shaping said melt into an article; and
   4) allowing said shaped article to cool to a substantially dimensionally stable thermoplastic product.

21. The product of claim 20, wherein the substantially water-insoluble thermoplastic polymer is selected from the group consisting of polyolefines, vinylpolymers, polyacetals (POM), polycondensates, thermoplastic polyesters, polycarbonates, poly (alkylene therephthalates), polyarylethers, thermoplastic polyamides, polyhydroxybutyrate (PHB), high molecular weight essentially water-insoluble polyalkylene oxides and copolymers and mixtures thereof.

22. The product of claim 21, wherein the thermoplastic polymer is selected from the group consisting of polyethylene (PE), polyisobutylenes, polypropylenes, poly (vinyl chloride) (PVC), poly (vinyl acetates), polyvinylalcohols, polystyrenes, polyacrylonitriles (PAN), polyvinylcarbazols (PVK), polyamides (PA), essentially water-insoluble poly (acrylic acid esters) and essentially water-insoluble poly (methacrylic acid esters) and copolymers and mixtures thereof.

23. The product of claim 21, wherein the thermoplastic polymer is selected from the group consisting of ethylene/vinyl acetate-copolymers (EVA), ethylene/-vinyl alcohol-copolymers (EVAL), ethylene/acrylic acid-copolymers (EAA), ethylene/ethyl acrylate-copolymers (EEA), ethylene/methyl acrylate-copolymers (EMA), ABS-copolymers, styrene/a- crylonitrile-copolymers (SAN), polyacetals and mixtures thereof.

24. The product of claim 20 wherein there is added a plasticizer in the range of about 0.5 to about 15% by weight.

25. The product of claim 20, wherein said shaping process is selected from the group consisting of injection molding, blow molding, extrusion, coextrusion, compression molding, vacuum forming and thermoforming.

26. The product of claim 20 wherein said articles have been shaped as bottles, sheets, films, packaging materials, pipes, rods, laminates, sacks, bags, pharmaceutical capsules, granules or powders.

27. A thermoplastic substantially destructurized homogeneous melt formed by the process comprising:
1) providing a mixture of starch and at least one substantially water-insoluble synthetic thermoplastic polymer;
2) heating said mixture in a closed volume under sufficient temperature and pressure for a time sufficient to substantially destructurize said starch and form said melt.

28. A carrier for pharmaceutically or agriculturally active ingredients made from a homogenous thermoplastic melt comprising destructurized starch and a substantially water-insoluble thermoplastic polymer.

29. A composition of matter capable of being formed into an article having substantial dimensional stability comprising:
(a) destructurized starch, and
(b) at least one polymer containing at least two different types of functional groups, one of said functional groups being a hydroxyl group, wherein said polymer is present in an amount sufficient to modify in a desired manner at least one of the properties of: toughness; resistance to deformation in humid atmosphere; and compatibility with a substantially water-insoluble thermoplastic polymer.

30. The composition of claim 29, wherein component (b) comprises vinyl alcohol.

31. The composition of claim 30, wherein component (b) comprises a poly(vinyl ester) having partially hydrolyzed ester groups.

32. The composition of claim 30, wherein component (b) comprises a copolymer comprising vinyl alcohol and at least one monomer selected rom the group consisting of ethylene, vinyl chloride, vinyl ethers, acrylonitrile, acryl amide, omega-octadecene, vinyl butyl ether, vinyl-octadecyl ether, vinyl pyrrolidone and mixtures and combinations thereof.

33. The composition of claim 32, wherein component (b) is selected from the group consisting of poly(vinyl alcohol-co-vinylacetate), ethylene/vinyl alcohol/vinyl acetate copolymers, ethylene/vinyl chloride/vinyl alcoholvinyl acetate graft copolymers, vinyl alcohol/vinyl acetate/vinyl chloride copolymers, vinyl alcohol/vinyl acetate/vinyl chloride/diacryl amide copolymers, vinyl alcohol/vinyl butyral copolymers, vinyl alcohol/vinyl acetate/vinyl pyrrolidone copolymers, and mixtures or combinations thereof.

34. The composition of claim 32, wherein component (b) comprises a copolymer obtained by copolymerization of a vinyl ester with at least one monomer selected from the group consisting of ethylene, vinyl ethers and mixtures and combinations thereof, with subsequent partial or complete hydrolysis of the vinyl ester.

35. The composition of claim 29, wherein component (b) is a polymer or a copolymer obtained from polymerizing or copolymerizing monomers of the formula:

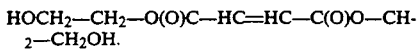

wherein
$R_2$ is hydrogen or methyl,
X does not form a vinyl alcohol and is an organic moiety with up to 8 carbon atoms substituted by 1 to 3 hydroxyl groups or 1 to 2 carboxylate groups or mixtures or combinations thereof, or an ester derivative of maleic acid or fumaric acid.

36. The composition of claim 35, wherein component (b) comprises a polymer or copolymer of at least one compound selected from the group consisting of compounds of the formula $CH_2=C(R_2)X_1$, wherein $X_1$ is $-CH_2OH$, $-O-CH_2-CH_2-OH$, $-C(O)OCH_2-CH_2OH$, $-C_6H_4-O-CH_2-CH_2OH$, or mixtures or combinations thereof and cis or trans compounds of the formula $HOCH_2-CH_2-O(O)C-HC=HC-C(O)O-CH_2-CH_2OH$.

37. The composition of claim 35, wherein component (b) comprises a copolymer of a monomer of a compound of formula $CH_2=C(R_2)X$ or a derivative of maleic or fumaric acid copolymerized with one or more vinyl esters, ethylene, vinyl chloride, vinyl esters, acrylonitrile, methacrylic acid esters, maleic acid esters, acrylamide, omega-octadecene, vinyl butyl ether, vinyl-octadecyl ether, vinyl pyrrolidone and mixtures and combinations thereof.

38. The composition of claim 37, wherein the weight percent of the hydroxyl moiety (—OH) is from 4.5 to 35 weight percent of component (b).

39. The composition of claim 29, wherein the weight percent ratio of destructurized starch to component (b) is about 1:99 to about 99:1.

40. The composition of claim 39, wherein destructurized starch comprises between about 50 percent and about 99 percent by weight of the total composition.

41. The composition of claim 29, wherein the destructurized starch has a water content of about 5 percent to about 40 percent by weight of the total starch content.

42. The composition of claim 29, wherein the destructurized starch has a water content of about 10 percent to about 22 percent by weight of the total starch content.

43. A composition of matter capable of being formed into an article having substantial dimensional stability comprising:
(a) destructurized starch, and
(b) at least one polymer containing at least two different types of functional groups, one of said functional groups being a hydroxyl group, and
(c) at least one substantially water-insoluble thermoplastic polymer that does not fall within the definition of component (b),
wherein (b) and (c) are present in a combined amount sufficient to effectuate dimensional stability and enhance at least one desired physical property of said article.

44. The composition of claim 43, wherein component (c) is selected from the group consisting of polyolefins, vinyl polymers, polystyrenes, polyacrylonitriles, poly(- vinyl carbazols), polyacrylates, polymethacrylates, polyacetals, thermoplastic polycondensates, polyarylethers, thermoplastic polyimides, high molar-mass substantially water-insoluble or crystallizable poly(alkylene oxides), and combinations and mixtures thereof.

45. The composition of claim 44, wherein component (c) is selected from the group consisting of polyethylenes, polypropylenes, polyisobutylenes, ethylene oxide polymers, propylene oxide polymers, polystyrenes and combinations and mixtures thereof.

46. The composition of claim 44, wherein component (c) is selected from the group consisting of poly(vinyl chlorides), poly(vinyl acetate), polyamides, thermoplastic polyesters, thermoplastic polyurethanes, polycarbonates, poly(alkylene terephthalates) and combinations and mixtures thereof.

47. The composition of claim 43, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers and combinations and mixtures thereof.

48. The composition of claim 47, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers and combinations and mixtures thereof.

49. The composition of claim 47, wherein components (b) and (c) comprise about 1 percent to about 99 percent by weight of the total composition.

50. The composition of claim 40, wherein components (b) and (c) comprise about 20 percent to about 80 percent by weight of the total composition.

51. The composition of claim 50, wherein components (b) and (c) comprise about 1 percent to about 30 percent by weight of the total composition.

52. The composition of claim 29, further comprising at least one material selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

53. The composition of claim 29, further comprising an agriculturally active compound.

54. The composition of claim 29, in the form of a melt blend.

55. The composition of claim 29, in the form of a cooled, solidified blend.

56. The composition of claim 29, in particulate, granulated or pelletized form.

57. A thermoplastic destructurized-starch product having substantial dimensional stability formed by a process comprising the steps of:
1) providing a mixture comprising starch and at least one polymer that contains at least two different types of functional groups, one of said types being hydroxyl groups (component b));

2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

58. The product of claim 57, wherein component (b) comprises vinyl alcohol units.

59. The product of claim 58, wherein component (b) is a partially hydrolyzed poly(vinyl ester).

60. The product of claim 58, wherein component (b) is a copolymer comprising vinyl alcohol and monomeric units obtained by polymerization of vinyl esters with at least one monomer selected from the group consisting of ethylene, vinyl chloride, vinyl ethers, acrylonitrile, acryl amide, omega-octadecene, vinyl butyl ether, vinyl-octadecyl ether, vinyl pyrrolidone and combinations and mixtures thereof with subsequent hydrolysis of at least some of the vinyl-ester groups.

61. The product of claim 60 wherein component (b) is selected from the group consisting of poly(vinyl alcohol-co-vinyl acetate), ethylene/vinyl alcohol/vinyl acetate copolymers, ethylene/vinyl chloride/vinyl alcohol/vinyl acetate graft copolymers, vinyl alcohol/vinyl acetate/vinyl chloride copolymers, vinyl alcohol/vinyl acetate/vinyl chloride/diacryl amide copolymers, vinyl alcohol/vinyl butyral copolymers, vinyl alcohol/vinyl acetate/vinyl pyrrolidone copolymers, and mixtures and combinations thereof.

62. The product of claim 60, wherein component (b) is a copolymer obtained by polymerization of a vinyl ester with at least one monomer selected from the group consisting of ethylene and vinyl ethers, with subsequent hydrolysis of at least some of the vinyl ester groups.

63. The product of claim 57, wherein component (b) is a polymer or a copolymer obtained from polymerizing or copolymerizing monomers of the formula:

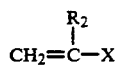

wherein
R$_2$ is hydrogen or methyl,
X does not form a vinyl alcohol and is an organic moiety with up to 8 carbon atoms substituted by 1 to 3 hydroxyl groups or containing 1 or 2 carboxylate groups or both, or of an ester derivative of maleic acid or fumaric acid which optionally contain hydroxyl groups.

64. The product of claim 63, wherein component (b) is a polymer or a copolymer of at least one compound of the formula CH$_2$=C(R$_2$)X$_1$, wherein X$_1$ is —CH$_2$OH, —O—CH$_2$—CH$_2$—OH, —C(O)OCH$_2$—CH$_2$OH or —C$_6$H$_4$—O—CH$_2$—CH$_2$OH, or a compound of the formula

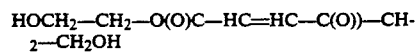

(cis or trans)

65. The product of claim 63, wherein the polymer of component (b) is a copolymer of (i) a compound of formula CH$_2$=C(R$_2$)X or derivatives of maleic or fumaric acid and (ii) at least one monomer selected from the group consisting of vinyl esters, ethylene, vinyl chloride, vinyl ethers, acrylic acid esters, acrylonitrile, methacrylic acid esters, maleic acid esters, acryl amide, omega-octadecene, vinyl butyl ether, vinyl-octadecyl ether, vinyl pyrrolidone and combinations and mixtures thereof.

66. The product of claim 65, wherein the hydroxyl moiety (—OH) comprises about 4.5 to about 35 weight percent of component (b).

67. The product of claim 57, wherein the weight percent ratio of destructurized starch to component (b) is about 1:99 to about 99:1.

68. The product of claim 57, wherein destructurization of the starch is carried out at a temperature above its melting point and glass transition temperature.

69. The product of claim 57, wherein the destructurization of the starch is carried out at a temperature of about 105° C. to about 240° C.

70. The product of claim 68, wherein the destructurization of the starch is carried out at a temperature of about 130° C. to about 190° C.

71. The product of claim 68, wherein the melt is formed at a pressure from the minimum pressure necessary to avoid formation of water vapor under the applied temperature to about $150 \times 10^5$ N/m$^2$.

72. The product of claim 71, wherein heat and pressure are maintained until the starch has undergone the specific narrow endothermic transition just prior to its endothermic change characteristic of oxidative and thermal degradation.

73. A thermoplastic destructurized-starch product having substantial dimensional stability formed by a process comprising the steps of:
  1) providing a mixture comprising: (a) starch; (b) at least one polymer that contains at least two different types of functional groups, one of said types being hydroxyl groups; and (c) at least one substantially water-insoluble thermoplastic polymer that does not fall within the definition of (b);
  2) heating said mixture in an closed volume under sufficient temperature and pressure for a time long enough to effect destructurization of said starch and form a substantially homogenous melt;
  3) shaping said melt into an article; and
  4) allowing said shaped article to cool to a substantially dimensionally stable thermoplastic product.

74. The product of claim 73, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, high molar-mass substantially water-insoluble or crystallizable poly(alkylene oxides), and combinations and mixtures thereof.

75. The product of claim 74, wherein said mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

76. The product of claim 57, in granulate form.

77. The product of claim 57, in pellet form.

78. The product of claim 57, in powder form.

79. The product of claim 57, further processed to form a shaped article selected from the group consisting of containers, bottles, pipes, rods, packaging material, sheets, foams, films, sacks, bags and pharmaceutical capsules.

80. The product of claim 78, further processed to form a shaped article selected from the group consisting of containers, bottles, pipes, rods, packaging material, sheets, foams, films, sacks, bags and pharmaceutical capsules.

81. The product of claim 57, wherein said mixture further comprises (c) a polymer selected from the group consisting of polyolefins, vinyl polymers, polystyrenes, polyacrylonitriles, poly(vinyl carbazols), polyacrylates, polymethacrylates, polyacetals, polycondensates, polyarylethers, thermoplastic polyimides, high molar-mass substantially water-insoluble or crystallizable poly(alkylene oxides), and combinations and mixtures thereof.

82. The product of claim 57, formed into an article by foaming, filming, compression molding, injection molding, blow molding, extruding, co-extruding, vacuum forming, thermoforming or combinations or mixtures thereof.

83. A thermoplastic destructurized-starch substantially homogenous melt formed by the process comprising:
  1) providing a mixture comprising (a) starch and (b) at least one polymer that contains at least two different types of functional groups, one of said types being hydroxyl groups; and
  2) heating said mixture in a closed volume under sufficient temperature and pressure for a time long enough to destructurize said starch and form said melt.

84. The melt of claim 83, wherein destructurization of the starch is carried out at a temperature above its melting point and glass transition temperature.

85. The melt of claim 84, wherein destructurization of the starch is carried out at a temperature from about 105° C. to about 240° C.

86. The melt of claim 85, wherein destructurization of the starch is carried out at a temperature from about 130° C. to about 190° C.

87. The melt of claim 86, formed at a pressure from the minimum pressure necessary to avoid formation of water vapor at the applied temperature to about $150 \times 10^5$ N/m$^2$.

88. The melt of claim 87, wherein said starch undergoes the specific narrow endothermic transition just prior to its endothermic change characteristic of oxidative and thermal degradation.

89. A thermoplastic destructurized-starch substantially homogenous melt formed by the process comprising:
  1) providing a mixture comprising: (a) starch; (b) at least one polymer containing at least two different types of functional groups, one of said functional groups being a hydroxyl group; and (c) at least one substantially water-insoluble thermoplastic polymer that does not fall within the definition of (b);
  2) heating said mixture in a closed volume under sufficient temperature and pressure for a time long enough to destructurize said starch and form said melt.

90. The melt of claim 89, wherein component (c) is selected from the group consisting of polyolefins, vinyl polymers, polystyrenes, polyacrylonitriles, poly(vinyl carbazols), polyacrylates, polymethacrylates, polyacetals, polycondensates, polyarylethers, thermoplastic polyimides, high molar-mass substantially water-insoluble or crystallizable poly(alkylene oxides), and combinations and mixtures thereof.

91. The melt of claim 90, wherein said mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

92. A composition of matter capable of being formed into an article having substantial dimensional stability comprising:
(a) destructurized starch, and
(b) at least one polymer that does not contain hydroxyl groups and is selected from the group consisting of polymers that contain at least two types of functional groups bound to the same molecule, one of said groups being a carboxylate group; wherein said polymer is present in an amount sufficient to modify in a desired manner at least one of the properties of: toughness, resistance to deformation in humid atmosphere; and compatibility with a substantially water-insoluble thermoplastic polymer.

93. The composition of claim 92, wherein component (b) further comprises alkoxy, carboxyalkyl, alkyl carboxy, halo or pyrrolidono groups or combinations or mixtures thereof.

94. The composition of claim 92, wherein component (b) is obtained by copolymerization of acrylic acid, methacrylic acid, crotonic acid, maleic acid or itaconic acid or combinations or mixtures thereof, with at least one comonomer selected from the group consisting of ethylene, vinyl chloride, vinyl esters, acrylic acid esters, acrylonitrile, methacrylic acid esters, maleic acid esters, acryl amide, vinylene carbonate, omega-octadecene, vinyl-butyl ether, vinyl pyrrolidone and combinations and mixtures thereof.

95. The composition of claim 92, wherein component (b) is a polymer derived from at least one monomer selected from the group consisting of: acrylic acid, methacrylic acid, crotonic acid, maleic acid, itaconic acid, methylacrylate, methylmethacrylate, acrylamide, acrylonitrile, methylvinyl ether and combinations and mixtures thereof.

96. The composition of claim 92, wherein component (b) comprises from about 5 mole percent to about 50 mole percent carboxyl and carboxylate containing moieties.

97. The composition of claim 92, wherein the degree of neutralization of the carboxyl groups is from about 30 percent to about 100 percent.

98. The composition of claim 92, wherein component (b) is selected from the group consisting of: polyacrylic acid-co-vinyl-acetate; ethylene/acrylic acid/vinyl acetate copolymers; ethylene/vinyl chloride/acrylic acid/-vinyl acetate graft copolymers; acylic acid/vinyl acetate/vinyl chloride copolymers; acrylic acid/vinylmethylether copolymers; vinyl acetate/ acrylic acid/acrylic acid methylester copolymer; vinyl acetate/crotonic acid copolymers; vinyl acetate/maleic acid copolymers; methacrylic acid/vinyl acetate/vinylpyrrolidone copolymers; ethylene/acrylic acid/methylacrylate copolymer; acrylic acid/acrylonitrile copolymer; ethylene/propylene/acrylic acid polymer; and styrene/acrylic acid copolymer, and combinations and mixtures thereof.

99. The composition of claim 92, wherein the weight percent ratio of destructurized starch to component (b) is from about 1:99 to about 99:1.

100. The composition of claim 99, wherein destructurized starch comprises about 50 percent to about 99 percent by weight of the total composition.

101. The composition of claim 92, wherein the destructurized starch comprises about 5 percent to about 40 percent water by weight.

102. The composition of claim 92, wherein the destructurized starch comprises about 10 percent to about 22 percent by weight water.

103. A composition of matter capable of being formed into an article having substantial dimensional stability comprising:
(a) destructurized starch, and
(b) at least one polymer that does not contain hydroxyl groups and is selected from the group consisting of polymers that contain at least two types of functional groups bound to the same molecule, one of said groups being a carboxylate group; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

104. The composition of claim 103, wherein component (c) is selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble and crystallizable poly(alkylene oxides) and combinations and mixtures thereof.

105. The composition of claim 104, wherein component (c) is selected from the group consisting of: polyethylenes, polypropylenes, polyisobutylenes, poly(vinyl chlorides), poly(vinyl acetate), polystyrene, polyamides, thermoplastic polyesters, thermoplastic polyurethanes, polycarbonates, poly(alkylene terephthalates) and combinations and mixtures thereof.

106. The composition of claim 103, wherein component (c) is selected from the group consisting of thermoplastic alkylene/vinyl ester-copolymers; ethylene/vinyl alcohol-copolymers; alkylene/acrylates or methacrylate copolymers; ABS-copolymers; styrene/acrylonitrile-copolymers; styrene-butadiene-copolymers, alkylene/maleic anhydride copolymers; partially hydrolyzed polyacrylates or polymethacrylates; partially hydrolyzed copolymers of acrylates and methacrylates; acrylic acid esters/acrylonitrile copolymers and hydrolysates thereof; acrylamide/acrylonitrile copolymers; and combinations and mixtures thereof.

107. The composition of claim 105, wherein component (c) is selected from the group consisting of ethylene/vinyl acetate-copolymers, ethylene/vinyl alcohol-copolymers, ethylene/acrylic acid-copolymers, ethylene/ethyl acrylate-copolymers, ethylene/methacrylate-copolymers, styrene/acrylonitrile-copolymers; block copolymers of urethane-ethers, urethane-esters; and mixtures and combinations thereof.

108. The composition of claim 104, wherein components (b) and (c) comprise about 1 percent to about 99 percent by weight of the total composition.

109. The composition of claim 103, wherein components (b) and (c) comprise about 20 percent to about 80 percent by weight of the total composition.

110. The composition of claim 109, wherein components (b) and (c) comprise about 1 percent to about 30 percent by weight of the total composition.

111. The composition of claim 92, further comprising at least one material selected from the group consisting of: adjuvants, fillers, lubricants, mold release agents, plasticizers, foaming agents, stabilizers, extenders, chemical modifiers, flow accelerators, coloring agents, pigments and combinations and mixtures thereof.

112. The composition of claim 92, further comprising an agriculturally active compound.

113. A melt blend comprising the composition of claim 92.

114. A cooled solidified blend comprising the composition of claim 92.

115. The composition of claim 92 in particular, granulated or pelletized form.

116. The composition of claim 103, further comprising an agriculturally active compound.

117. The composition of claim 103, in a form selected from the group consisting of: a melt blend, a cooled solidified blend, a plurality of particles, a plurality of granules and a plurality of pellets.

118. A thermoplastic destructurized-starch product having substantial dimensional stability formed by the process comprising the steps of:
1) providing a mixture comprising starch and at least one polymer that does not contain hydroxyl groups and is selected from the group consisting of polymers which contain at least two types of functional groups bound to the same molecule one type of these groups being carboxylate groups (component (b));
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

119. The product of claim 118, wherein component (b) further comprises at least one alkoxy, carboxylalkyl, alkyl carboxy, halo or pyrrolidono group.

120. The product of claim 118, wherein component (b) is obtained by copolymerization of acrylic acid, methacrylic acid, crotonic acid, maleic acid or itaconic acid, with at least one monomer selected from the group consisting of ethylene, vinyl chloride, vinyl esters, acrylic acid esters, acrylonitrile, methacrylic acid esters, maleic acid esters, acryl amide, vinylene carbonate, omega-octadecene, vinyl-butyl ether, vinyl pyrrolidone and combinations and mixtures thereof.

121. The product of claim 118, wherein component (b) is a polymer derived from at least one monomer selected from the group consisting of: acrylic acid, methacrylic acid, crotonic acid, maleic acid, itaconic acid, methylacrylate, methylmethacrylate, acrylamide, acrylonitrile, methylvinyl ether and combinations and mixtures thereof.

122. The product of claim 121, wherein the amount of carboxyl and carboxylate containing moieties within the copolymer is from about 5 mole percent to about 50 mole percent.

123. The product of claim 121, wherein the degree of neutralization of the carboxyl groups is from about 30 percent to about 100 percent.

124. The composition of claim 118, wherein component (b) is selected from the group consisting of: poly-acrylic acid-co-vinyl-acetate; ethylene/acrylic acid/vinyl acetate copolymers; ethylene/vinyl chloride/acrylic acid/vinyl acetate graft copolymers; acrylic acid/vinyl acetate/vinyl chloride copolymers; acrylic acid/vinyl methylether copolymers; vinyl acetate/acrylic acid-/acrylic acid methyl ester copolymer; vinyl acetate/-crotonic acid copolymers; vinyl acetate/maleic acid copolymers; methacrylic acid/ vinyl acetate/vinyl pyrrolidone copolymers; ethylene/ acrylic acid/methylacrylate copolymer; acrylic acid/ acrylonitrile copolymer; ethylene/propylene/acrylic acid copolymer; styrene/acrylic acid copolymer and mixtures and combinations thereof.

125. The product of claim 118, wherein the weight percent ratio of destructurized starch to component (b) is from about 1:99 to about 99:1.

126. The product of claim 118, wherein destructurization of the starch is carried out at a temperature above its melting point and glass transition temperature.

127. The product of claim 126, wherein the destructurization of the starch is carried out at a temperature from about 105° C. to about 240° C.

128. The product of claim 126, wherein the destructurization of the starch is carried out at a temperature from about 130° C. to about 190° C.

129. The product of claim 126, wherein the melt is formed at a pressure from the minimum pressure necessary to avoid formation of water vapor under the applied temperature to about $150 \times 10^5$ N/m².

130. The product of claim 129, wherein the heat and pressure are maintained until the starch has undergone the specific narrow endothermic transition just prior to its endothermic change characteristic of oxidative and thermal degradation.

131. A thermoplastic destructurized starch product having substantial dimensional stability formed by a process comprising the steps of:
1) providing a mixture comprising: (a) starch; (b) at least one polymer that does not contain hydroxyl groups and is selected from the group consisting of polymers that contain at least two types of functional groups and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

132. The product of claim 131, wherein component (c) is selected from the group consisting of polyolefins, vinyl polymers, polystyrenes, polyacrylonitriles, poly(-vinyl carbazols), polyacrylates, polymethacrylates, polyacetals, thermoplastic polycondensates, polyarylethers, thermoplastic polyimides, polyhydroxybutyrate, high molar-mass substantially water-insoluble and crystallizable poly(alkylene oxides) and combinations and mixtures thereof.

133. The product of claim 132, wherein said mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

134. The product of the claim 118, in granulate form.

135. The product of the claim 118, in pellet form.

136. The product of the claim 118, in powder form.

137. The product of claim 134, further processed to form a shaped article selected from the group consisting of containers, bottles, pipes, rods, packaging material, sheets, foams, films, sacks, bags and pharmaceutical capsules.

138. The product of claim 135, further processed to form a shaped article selected from the group consisting of containers, bottles, pipes, rods, packaging material, sheets, foams, films, sacks, bags and pharmaceutical capsules.

139. The product of claim 136, further processed to form a shaped article selected from the group consisting of containers, bottles, pipes, rods, packaging material, sheets, foams, films, sacks, bags and pharmaceutical capsules.

140. The product of claim 134, further comprising: (c) a polymer selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides), combinations and mixtures thereof.

141. The product of claim 135, further comprising: (c) a polymer selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides), combinations and mixtures thereof.

142. The product of claim 136, further comprising: (c) a polymer selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides), and combinations and mixtures thereof.

143. The shaped articles of claim 118, formed by foaming, filming, compression molding, injection molding, blow molding, extruding, co-extruding, vacuum forming, thermoforming or combinations thereof.

144. A thermoplastic destructurized-starch substantially homogenous melt formed by the process comprising the steps of:
1) providing a mixture comprising starch and at least one polymer that does not contain hydroxyl groups and is selected from the group consisting of polymers that contain at least two types of functional groups bound to the same molecule, one type of these groups being carboxylate groups (component (b));
2) heating said mixture in a closed volume under sufficient temperature and pressure for a time long enough to effect destructurization of said starch and form a substantially homogenous melt.

145. The melt of claim 144, wherein destructurization of the starch is carried out at a temperature above its melting point and glass transition temperature.

146. The melt of claim 145, wherein destructurization of the starch is carried out at a temperature from about 105° C. to about 240° C.

147. The melt of claim 146, wherein destructurization of the starch is carried out at a temperature from about 130° C. to about 190° C.

148. The melt of claim 147, wherein the melt is formed at a pressure from the minimum pressure necessary to avoid formation of water vapor under the applied temperature to about $150 \times 10^5$ N/m$^2$.

149. The melt of claim 148, wherein heat and pressure are maintained until the starch has undergone the specific narrow endothermic transition just prior to its endothermic change characteristic of oxidative and thermal degradation.

150. A thermoplastic destructurized-starch substantially homogenous melt formed by the process comprising:
1) providing a mixture comprising: (a) starch; (b) at least one polymer that does not contain hydroxyl groups and is selected from the group consisting of polymers that contain at least two types of functional groups bound to the same molecule, one type of the groups being carboxylate groups and (c) at least one substantially water-insoluble thermoplastic polymer that does not fall within the definition of (b); and
2) heating said mixture in a closed volume under sufficient temperature and pressure for a time long enough to destructurize said starch and form said melt.

151. The melt of claim 150, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides) and combinations and mixtures thereof.

152. The melt of claim 151, wherein the mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

153. A composition of matter capable of being formed into an article having substantial dimensional stability comprising:
(a) destructurized starch, and
(b) at least one polymer selected from the group consisting of polymers containing tertiary amino groups or salts thereof or quaternary ammonium groups; wherein said polymer is present in an amount sufficient to modify in a desired manner at least one of the properties of : toughness; resistance to deformation in humid atmosphere; and compatibility with a substantially water-insoluble thermoplastic polymer.

154. The composition of claim 153, wherein component (b) further comprises a functional group selected from the group consisting of : hydroxy, alkoxy, carboxy, carboxyalkyl, alkyl carboxy, halo, pyrrolidono and combinations and mixtures thereof; said groups being selected from those that will not react with the amino groups present and that will not degrade the starch.

155. The composition of the claim 153, wherein component (b) is obtained by the polymerization of at least one monomer containing at least one tertiary amino group or salt thereof or a quaternary ammonium group.

156. The composition of claim 153, wherein component (b) is obtained by the polymerization or copolymerization of at least one monomer selected from the group consisting of poly(2-vinyl pyridine), poly(4-vinyl pyridine), polyvinyl carbazole, 1-vinyl imidazole, salts thereof and quaternized derivatives and combinations and mixtures thereof.

157. The composition of claim 156, wherein component (b) is obtained by copolymerization of said monomer with a comonomer selected from the group consisting of acrylonitrile, butylmethacrylate and styrene.

158. The composition of claim 153, wherein the polymer of component (b) contains repeating units of the formula:

wherein
$R = NR_1R_2$; $-NR_1R_2R_3A$, wherein $R_1$ and $R_2$ together represent a pyridine residue; a carbazyl residue; or an imidazolyl residue,
$R_3$ is H or alkyl ($C_1$-$C_{21}$), and A is an anion.

159. The composition of claim 158, wherein component (b) is derived from a monomer selected from the group consisting of: 2-vinyl- pyridine; 4-vinyl pyridine; and vinyl carbazole.

160. The composition of claim 153, wherein the weight percent ratio of destructurized starch to component (b) is about 1:99 to about 99:1.

161. The composition of claim 160, wherein destructurized starch comprises from about 50 percent to about 99 percent by weight of the total composition.

162. The composition of claim 153, wherein the destructurized starch has a water content of about 5 percent to about 40 percent by weight.

163. The composition of claim 153, wherein the destructurized starch has a water content of about 10 percent to about 22 percent by weight.

164. A composition of matter capable of being formed into an article having substantial dimensional stability comprising:
(a) destructurized starch, and
(b) at least one polymer selected from the group consisting of polymers containing tertiary amino groups or salts thereof or quaternary ammonium groups; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

165. The composition of claim 164, wherein component (c) is elected from the group consisting of polyoelfins, vinyl. polymers, polystyrenes, polyacrylonitriles, polyacrylates, polymethacrylates, polyacetals, thermoplastic polycondensates, polyaraylethers, thermoplastic polyimides, high molar-mass substantially water-insoluble or crystallizable poly(alkylene oxides), and combinations and mixtures thereof.

166. The composition of claim 165, wherein component (c) is selected from the group consisting of polyethylenes, polypropylenes, polyisobutylenes, ethylene oxide polymers, propylene oxide polymers, polystyrenes and combinations and mixtures thereof.

167. The composition of claim 165, wherein component (c) is selected from the group consisting of poly(vinyl chlorides), poly(vinyl acetates), polyamides, thermoplastic polyesters, thermoplastic polyurethanes, polycarbonates, poly(alkylene terephthalates) and mixtures and combinations thereof.

168. The composition of claim 164, wherein component (c) is selected from the group consisting of alkylene/vinyl ester/copolymers, alkylene/acrylate or methacrylate copolymers, ABS copolymers; styrene/acrylonitrile copolymers, acrylic acid esters/acrylonitrile copolymers; acrylamide/acrylonitrile copolymers; block copolymers of amide-ethers, amide-esters; block copolymers of urethane-ethers, urethane-esters; and combinations and mixtures thereof.

169. The composition of claim 168, wherein component (c) is selected from the group consisting of ethylene/vinyl alcohol-copolymers, styrene/acrylonitrile copolymers; block copolymers of amide-ethers, amide-esters; block copolymers of urethane-ethers, urethane-esters; and combinations and mixtures thereof.

170. The composition of claim 164, wherein components (b) and (c) comprise from about 1 percent to about 99 percent by weight of said composition.

171. The composition of claim 170, wherein components (b) and (c) comprise about 20 percent to about 80 percent by weight of said composition.

172. The composition of claim 171, wherein components (b) and (c) comprise about 1 percent to about 30 percent by weight of said composition.

173. The composition of claim 153, further comprising at least one compound selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

174. The composition of claim 153, further containing an agriculturally active compound.

175. The composition of claim 153, in the form of a melt blend.

176. The composition of claim 153, in the form of a cooled solidified blend.

177. The composition of claim 153 in particulate, granulated or pelletized form.

178. The composition of claim 164, in the form of a melt blend or a cooled solidified blend.

179. The composition of claim 164, in particulate, granulated or pelletized form.

180. A thermoplastic destructurized-starch product having substantial dimensional stability formed by the process comprising the steps of:
1) providing a mixture comprising starch and at least one polymer selected from the group consisting of polymers containing tertiary amino groups or salts thereof or quaternary ammonium groups; said polymer being present in an amount effective to enhance at least one physical property of an article made from said mixture (component (b));
2) heating said mixture in a closed volume under sufficient temperature and pressure for a time long enough to effect destructurization of said starch and to form a substantially homogenous melt;
3) shaping said melt into an article; and
4) allowing said shaped article to cool to a substantially dimensionally stable thermoplastic product.

181. The product of claim 180, wherein component (b) further comprises a functional group selected from the group consisting of: hydroxy, alkoxy, carboxy, carboxyalkyl, alkyl carboxy, halo, pyrrolidono; said groups being selected from those that will not react with the amino groups present and that do not degrade the starch.

182. The product of claim 181, wherein component (b) is a polymer obtained by polymerization of at least one monomer containing a tertiary amino group or a salt thereof or a quaternary ammonium group.

183. The product of claim 181, wherein component (b) is obtained by the polymerization of copolymerization of a monomer selected from the group consisting of: poly(2-vinyl pyridine); poly(4-vinyl pyridine); polyvinyl carbazole, 1-vinyl imidazole, salts thereof, quaternized derivatives thereof and combinations and mixtures thereof.

184. The product of claim 183, wherein said monomer is copolymerized with a copolymer selected from the group consisting of: acrylonitrile, butylmethacylate and styrene.

185. The product of claim 183, wherein component (b) contains repeating units of the formula:

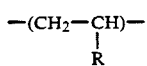

wherein
R is $NR_1R_2$; or $-NR_1R_2R_3A$, wherein $R_1$ and $R_2$ together represent a pyridine residue; a carbazyl residue; or an imidazolyl residue,
$R_3$ is H or alkyl ($C_1$-$C_{21}$), and A is an anion.

186. The product of claim 183, wherein component (b) comprises a monomer selected from the group consisting of: 2-vinyl pyridine; 4-vinyl pyridine; and vinyl carbazole.

187. The product of claim 180, wherein the weight percent ratio of destructurized starch to component (b) is from about 1:99 to about 99:1.

188. The product of claim 180, wherein destructurization of the starch is carried out at a temperature above its melting point and glass transition temperature.

189. The product of claim 180, wherein the destructurization of the starch is carried out at a temperature from about 105° C. to about 240° C.

190. The product of claim 188, wherein the destructurization of the starch is carried out at a temperature from about 130° C. to about 190° C.

191. The product of claim 188, wherein the melt is formed at a pressure from the minimum pressure necessary to avoid formation of water vapor under the applied temperature to about $150 \times 10^5$ N/m².

192. The product of claim 191, wherein the heat and pressure are maintained until the starch has undergone the specific narrow endothermic transition just prior to its endothermic change characteristic of oxidative and thermal degradation.

193. A thermoplastic destructurized starch product having substantial dimensional stability formed by a process comprising the steps of:
1) providing a mixture comprising: (a) starch; (b) at least one polymer selected from the group consisting of polymers containing tertiary amino groups or salts thereof or quaternary ammonium groups; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

194. The product of claim 188, wherein component (c) is selected from the group consisting of: polyolefins, vinyl polymers, polystyrenes, polyacrylonitriles, polyacrylates, polymethacrylates, polyacetals, thermoplastic polycondensates, polyarylethers, thermoplastic polyimides, high molar-mass substantially water-insoluble or crystallizable poly(alkylene oxides), and combinations and mixtures thereof.

195. The product of claim 193, wherein said mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

196. The product according to the claim 180, in the form of a granulate.

197. The product according to the claim 180, in the form of a pellet.

198. The product according to the claim 180, in the form of a powder.

199. The product of claim 195, in a form selected from the group consisting of: granules, pellets and powders.

200. The product of claim 180, in a form selected from the group consisting of: containers, bottles, pipes, rods, packaging material, sheets, foams, films, sacks, bags and pharmaceutical capsules.

201. The product of claim 180, wherein component (c) is selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, high molar-mass substantially water-insoluble or crystallizable poly(alkylene oxides), and combinations and mixtures thereof.

202. The product of claim 180, formed into an article by a method selected from the group consisting of: foaming, filming, compression molding, injection molding, blow molding, extruding, co-extruding, vacuum forming, thermoforming and combinations thereof.

203. A thermoplastic destructurized-starch substantially homogenous melt formed by a process comprising the steps of:
1) providing a mixture comprising starch and at least one polymer selected from the group consisting of polymers that contain tertiary amino groups, salts thereof and quaternary ammonium groups; said polymer being present in an amount effective to enhance at least one physical property of an article formed from said melt (component (b)), and
2) heating said mixture in a closed volume under sufficient temperature and pressure for a time long enough to destructurize said starch and to form said melt.

204. The melt of claim 203, wherein destructurization of the starch is carried out at a temperature above the melting point and glass transition temperature of said starch.

205. The melt of claim 203, wherein destructurization of the starch is carried out at a temperature from about 105° C. to about 240° C.

206. The melt of claim 205, wherein destructurization of the starch is carried out at a temperature from about 130° C. to about 190° C.

207. The melt of claim 206, wherein the melt is formed at a pressure from the minimum pressure necessary to avoid formation of water vapor under the applied temperature to about $150 \times 10^5$ N/m$^2$.

208. The melt of claim 207, wherein the heat and pressure are maintained until the starch has undergone the specific narrow endothermic transition just prior to its endothermic change characteristic of oxidative and thermal degradation.

209. A thermoplastic destructurized-starch substantially homogenous melt formed by the process comprising:
1) providing a mixture comprising: (a) starch; (b) at least one polymer selected from the group consisting of polymers that contain tertiary amino groups, salts thereof and quaternary ammonium groups; and (c) at least one substantially water-insoluble thermoplastic polymer that does not fall within the definition of (b);
2) heating said mixture in a closed volume under sufficient temperature and pressure for a time long enough to destructurize said starch and form said melt.

210. The melt of claim 209, wherein component (c) is selected from the group consisting of: polyolefins, vinyl polymers, polystyrenes, polyacrylonitriles, poly-acrylates, polymethacrylates, polyacetals, thermoplastic polycondensates, polyarylethers, thermoplastic polyimides, high molar-mass substantially water-insoluble or crystallizable poly(alkylene oxides) and combinations and mixtures thereof.

211. A composition of matter capable of being formed into an article having substantial dimensional stability comprising:
(a) destructurized starch, and
(b) at least one polymer selected from the group consisting of polysaccharides that have been modified to contain added hydroxylalkyl groups or alkyl ether groups, or ester groups; wherein said polymer is present in an amount sufficient to modify in a desired manner at least one of the properties of: toughness, resistance to deformation in humid atmosphere; and compatibility with a substantially water-insoluble thermoplastic polymer.

212. The composition of claim 211, wherein the modified polysaccharide is selected from the group consisting of: celluloses, starches and hemi-celluloses.

213. The composition of claim 211, wherein the polymer of component (b) is an alkoxylated polysaccharide that comprises hydroxy alkyl groups.

214. The composition of claim 213, wherein the alkoxylated polysaccharide further comprises an alkyl ether group or an alkyl ester group.

215. The composition of claim 213, wherein the alkoxylated polysaccharide further comprises a hydroxy ethyl group or a hydroxy propyl group.

216. The composition of claim 213, wherein the alkoxylated polysaccharide has a degree of substitution within the range from about 0.05 to about 2.5.

217. The composition of claim 213, wherein the alkoxylated polysaccharide has a degree of substitution within the range from about 0.1 to about 1.5.

218. The composition of claim 211, wherein the weight percent ratio of destructurized starch to component (b) is from about 1:99 to about 99:1.

219. The composition of claim 218, wherein destructurized starch comprises from about 50 percent to about 99 percent by weight of the total composition.

220. The composition of claim 211, wherein the destructurized starch has a water content from about 5 percent to about 40 percent by weight of the total starch content.

221. The composition of claim 211, wherein the destructurized starch has a water content from about 10 percent to about 22 percent by weight of the total starch content.

222. A composition of matter capable of being formed into an article having substantial dimensional stability comprising:
(a) destructurized starch, and
(b) at least one polymer selected from the group consisting of polysaccharides that have been modified to contain added hydroxyalkyl groups or alkyl ether groups, or ester groups; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

223. The composition of claim 222, wherein component (c) is selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

224. The composition of claim 223, wherein component (c) is selected from the group consisting of: polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

225. The composition of claim 222, wherein component (c) is selected from the group consisting of: alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

226. The composition of claim 225, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters, block copolymers of urethane-ethers, urethane-esters and combinations and mixtures thereof.

227. The composition of claim 222, wherein components (b) and (c) comprise from about 1 percent to about 99 percent by weight of the total composition.

228. The composition of claim 227, wherein components (b) and (c) comprise from about 20 percent to about 80 percent by weight of the total composition.

229. The composition of claim 228, wherein components (b) and (c) comprise from about 1 percent to about 30 percent by weight of the total composition.

230. The composition of claim 211, further comprising of at least one material selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

231. The composition of claim 211, further comprising an agriculturally active compound.

232. The composition of claim 211, in the form of a melt blend.

233. The composition of claim 211, in the form of a cooled solidified blend.

234. The composition of claim 211, in particulate, granulated or pelletized form.

235. The composition of claim 222, further comprising at least one material selected from the group consisting of: agriculturally active compounds, adjuvants, fillers, lubricants, mold release agents, plasticizers, foaming agents, stabilizers, extenders, chemical modifiers, flow accelerators, coloring agents, pigments and combinations and mixtures thereof.

236. The composition of claim 222, in a form selected from the group consisting of: melt blends, cooled solidified blends, particles, granules and powders.

237. A thermoplastic destructurized-starch product having substantial dimensional stability formed by a process comprising the steps of:
1) providing a mixture comprising starch and at least one polymer selected from the group of polysaccharides modified to contain added hydroxylkyl groups, alkyl ether groups, or contain ester groups or combinations and mixtures thereof.
2) heating said mixture in a closed volume under sufficient temperature and pressure for a time long enough to effectuate destructurization of said starch and form a substantially homogenous melt;
3) shaping said melt into an article; and
4) allowing said shaped article to cool to a substantially dimensionally stable thermoplastic product.

238. The product of claim 237, wherein the polysaccharide is selected from the group consisting of celluloses, starches and hemi-celluloses.

239. The product of claim 238, wherein the polysaccharide is selected from the group consisting of celluloses and starches.

240. The product of claim 239, wherein the polysaccharide is a starch.

241. The product of claim 237, wherein component (b) is an alkoxylated polysaccharide comprising at least one hydroxy alkyl group.

242. The product of claim 241, wherein the alkoxylated polysaccharide further comprises at least one alkyl ether group or at least one alkyl ester group or a combination thereof.

243. The product of claim 241, wherein the alkoxylated polysaccharide comprises a hydroxy ethyl group or a hydroxy propyl group or a combination thereof.

244. The product of claim 241, wherein the alkoxylated polysaccharide has a degree of substitution from about 0.05 to about 2.5.

245. The product of claim 241, wherein the alkoxylated polysaccharide has a degree of substitution from about 0.1 to about 1.5.

246. The product of claim 237, wherein the weight percent ratio of destructurized starch to component (b) is from about 1:99 to about 99:1.

247. The product of claim 237, wherein destructurization of the starch is carried out at a temperature above its melting point and glass transition temperature.

248. The product of claim 237, wherein the destructurization of the starch is carried out at a temperature from about 105° C. to about 240° C.

249. The product of claim 247, wherein the destructurization of the starch is carried out at a temperature from about 130° C. to about 190° C.

250. The product of claim 247, wherein the melt is formed at a pressure from the minimum pressure necessary to avoid formation of water vapor under the applied temperature to about $150 \times 10^5$ N/m².

251. The product of claim 250, wherein the heat and pressure are maintained until the starch has undergone the specific narrow endothermic transition just prior to its endothermic change characteristic of oxidative and thermal degradation.

252. A thermoplastic destructurized-starch product having substantial dimensional stability formed by a process comprising the steps of:
1) providing a mixture comprising: (a) starch; (b) at least one polymer selected from the group of polysaccharides modified to contain added hydroxyalkyl groups, alkyl ether groups, or contain ester groups or combinations and mixtures thereof; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

253. The product of claim 252, wherein component (c) is selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

254. The product of claim 252, wherein component (c) is selected from the group consisting of alkylene/vinyl ester/copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

255. The product of claim 237, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

256. The product of the claim 237, in the form of a granule.

257. The product of the claim 237, in the form of a pellet.

258. The product of the claim 237, in the form of a powder.

259. The product of claim 252, in granular, pellet or powder form.

260. The product of claim 259, further processed to form a shaped article selected from the group consisting of: containers, bottle, pipes, rods, packaging material, sheets, foams, films, sacks, bags, and pharmaceutical capsules.

261. The product of claim 256, further processed to form a shaped article selected from the group consisting of: containers, bottles, pipes, rods, packaging material, sheets, foams, films, sacks, bags and pharmaceutical capsules.

262. The product of claim 257, further processed to form a shaped article selected from the group consisting of: containers, bottles, pipes, rods, packaging material, sheets, foams, films, sacks, bags and pharmaceutical capsules.

263. The product of claim 258, further processed to form a shaped article selected from the group consisting of containers, bottles, pipes, rods, packaging material, sheets, foams, films, sacks, bags and pharmaceutical capsules.

264. The product of claim 252, wherein component (c) is selected from the group consisting of polyolefins, vinyl polymers, polystyrenes, polyacrylonitriles, poly(-vinyl carbazols), polyacrylates, polymethacrylates, polyacetals, polycondensates, polyarylethers, thermoplastic polyimides, substantially water-insoluble or crystallizable poly(alkylene oxides), and combinations and mixtures thereof.

265. The product of the claim 252, wherein component (c) is selected from the group consisting of: alkylene/vinyl ester copolymers, alkylene/acrylate and methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/ acrylonitrile copolymers, block copolymers of amide-ethers, amide-esters; block copolymers of urethane-ethers, urethane-esters and combinations and mixtures thereof.

266. The product of claim 260, wherein said processing comprises at least one step selected from: foaming, filming, compression molding, injection molding, blow molding, extruding, co-extruding, vacuum forming, thermoforming and combinations and mixtures thereof.

267. The product of claim 261, 262 or 263, wherein said processing comprises at least one step selected from foaming, filming, compression molding, injection molding, blow molding, extruding, co-extruding, vacuum forming, thermoforming and combinations and mixtures thereof.

268. A thermoplastic destructurized-starch substantially homogenous melt formed by a process comprising the steps of:
1) providing a mixture comprising starch and at least one polymer selected from the group consisting of: polysaccharides that have been chemically modified to contain added hydroxyalkyl groups or alkyl ether groups, or contain ester groups (component (b)); and
2) heating said mixture in a closed volume under sufficient temperature and pressure for a time long enough to destructurize said starch and form said melt.

269. The melt of claim 268, wherein destructurization of the starch is carried out in the presence of at least one compound selected from the group consisting of: stabilizers, extenders, coloring agents, pigments, chemical modifiers and combinations and mixtures thereof.

270. The melt of claim 268, wherein destructurization of the starch is carried out at a temperature from about 105° C. to about 240° C.

271. The melt of claim 270, wherein destructurization of the starch is carried out at a temperature from about 130° C. to about 190° C.

272. The melt of claim 271, wherein the melt is formed at a pressure from the minimum pressure necessary to avoid formation of water vapor under the applied temperature to about $150 \times 10^5$ N/m$^2$.

273. The melt of claim 272, wherein the heat and pressure are maintained until the starch has undergone the specific narrow endothermic transition just prior to its endothermic change characteristic of oxidative and thermal degradation.

274. A thermoplastic destructurized-starch substantially homogenous melt formed by the process comprising:
1) providing a mixture comprising: (a) starch; (b) at least one polymer selected from the group consisting of polysaccharides that have been chemically modified to contain added hydroxyalkyl groups or alkyl ether groups, or contain ester groups; and (c) at least one substantially water-insoluble thermoplastic polymer that does not fall within the definition of (b);
2) heating said mixture in a closed volume under sufficient temperature and pressures for a time long enough to destructurize said starch and form said melt.

275. The melt of claim 274, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides) and combinations and mixtures thereof.

276. The melt of claim 274, wherein component (c) is selected from the group consisting of: polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, substantially water-insoluble or crystallizable poly(alkylene oxides) and combinations and mixtures thereof.

277. The melt of claim 274, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide esters; block copolymers of urethane-ethers, urethane-esters and combinations and mixtures thereof.

278. The melt of claim 268, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

279. A composition of matter capable of being formed into an article having substantial dimensional stability comprising:
   (a) destructurized starch, and
   (b) at least one compound selected from the group consisting of copolymers of vinyl pyrrolidone; wherein said compound is present in an amount sufficient to modify in a desired manner at least one of the properties of: toughness; resistance to deformation in humid atmosphere; and compatibility with a substantially water-insoluble thermoplastic polymer.

280. The composition of claim 279, wherein component (b) is a copolymer of vinyl pyrrolidone with one or more monomers selected from the group of vinyl esters, vinyl alcohol, allyalcohol, ethylene, propylene, butylene, isoprene, butadiene, styrene, vinyl ethers, dimethylaminoethyl methacrylate and combinations and mixtures thereof.

281. The composition of claim 279, wherein component (b) is a copolymer of vinyl pyrrolidone with a monomer selected from the group consisting of vinyl esters, vinyl alcohol, styrene and dimethylaminoethyl methacrylate and combinations and mixtures thereof.

282. The composition of claim 279, wherein said copolymer has a molar content of vinyl pyrrolidone from about 5 percent to about 95 percent.

283. The composition of claim 279, wherein said copolymer has a molar content of vinyl pyrrolidone from about 10 percent to about 30 percent.

284. The composition of claim 279, wherein component (b) is a copolymer of N-vinyl pyrrolidone.

285. The composition of claim 284, wherein component (b) is a poly(N-vinyl pyrrolidone-vinyl ester) copolymer.

286. The composition of claim 284, wherein component (b) is poly(N-vinyl pyrrolidone-vinyl acetate) copolymer.

287. The composition of claim 279, wherein the weight percent ratio of destructurized starch to component (b) is from about 99:1 to about 99:1.

288. The composition of claim 287, wherein destructurized starch comprises from about 60 percent to about 90 percent of the total composition.

289. The composition of claim 279, wherein the destructurized starch has a water content from about 5 percent to about 40 percent by weight of the total starch content.

290. The composition of claim 279, wherein the destructurized starch has a water content from about 10 percent to about 22 percent by weight of the total starch content.

291. A composition of matter capable of being formed into an article having substantial dimensional stability comprising:
   (a) destructurized starch, and
   (b) at least one compound selected from the group consisting of copolymers of vinyl pyrrolidone; and
   (c) at least one substantially water-insoluble thermoplastic polymer that does not fall within the definition of component (b), wherein (b) and (c) are present in a combines amount sufficient to effectuate dimensional stability and enhance at least one desired physical property of said article.

292. The composition of claim 291, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

293. The composition of claim 292, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

294. The composition of claim 291, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

295. The composition of claim 294, wherein component (c) is selected from the group consisting of ethylene/vinyl acetate copolymers (EVA); ethylene/vinyl alcohol copolymers (EVAL), ethylene/acrylic acid copolymers (EAA), ethylene/ethylacrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

296. The composition of claim 291, wherein components (b) and (c) comprise from about 1 percent to about 99 percent by weight of the total composition.

297. The composition of claim 296, wherein components (b) and (c) comprise from about 20 percent to about 80 percent by weight of the total composition.

298. The composition of claim 297, wherein components (b) and (c) comprise from about 1 percent to about 30 percent by weight of the total composition.

299. The composition of claims 279 or 291, further comprising one or more materials selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

300. The composition of claim 279 or 291, further comprising an agriculturally active compound.

301. The composition of claim 279, in the form of a melt blend.

302. The composition of claim 279, in the form of a cooled solidified blend.

303. The composition of claim 279, in particulate, granulated or pelletized form.

304. The composition of claim 291, in a form selected from the group consisting of: melt blends, cooled solidified blends, particulates, powders, granules, pellets and combinations and mixtures thereof.

305. A thermoplastic destructurized-starch product having substantial dimensional stability formed by a process comprising the steps of:
1) providing a mixture comprising starch and at least one compound selected from the group consisting of copolymers of vinyl pyrrolidone (component (b)); said compound being present in an amount effective to enhance at least one physical property of an article made from said mixture;
2) heating said mixture in a closed volume under sufficient temperature and pressure for a time long enough to effectuate destructurization of said starch and form a substantially homogenous melt;
3) shaping said melt into an article; and
4) allowing said shaped article to cool to a substantially dimensionally stable thermoplastic product.

306. The product of claim 305, wherein component (b) is a copolymer of vinyl pyrrolidone with one or more monomers selected from the group consisting of: vinyl esters, vinyl alcohol, allyl alcohol, ethylene, propylene, butylene, isoprene, butadiene, styrene, vinyl ethers, dimethylaminoethyl methacrylate and combinations and mixtures thereof.

307. The product of claim 305, wherein component (b) is a copolymer of vinyl pyrrolidone with a monomer selected from the group consisting of vinyl esters, vinyl alcohol, styrene, dimethylaminoethyl methacrylate and combinations and mixtures thereof.

308. The product of claim 307, wherein said copolymer has a molar content of vinyl pyrrolidone from about 5 percent to about 95 percent.

309. The product to claim 305, wherein said copolymer has a molar content of vinyl pyrrolidone from about 10 percent to about 30 percent.

310. The product of claim 305, wherein component (b) is a copolymer of N-vinyl pyrrolidone.

311. The product of claim 305, wherein component (b) is a poly(N-vinyl pyrrolidone-vinyl ester) copolymer.

312. The product of claim 305, wherein component (b) is poly(N-vinyl pyrrolidone-vinyl acetate) copolymer.

313. The product of claim 305, wherein the weight percent ratio of destructurized starch to component (b) is from about 1:99 to about 99:1.

314. The product of claim 305, wherein destructurization of the starch is carried out at a temperature above its melting point and glass transition temperature.

315. The product of claim 305, wherein the destructurization of the starch is carried out at a temperature from about 105° C. to about 240° C.

316. The product of claim 314, wherein the destructurization of the starch is carried out at a temperature from about 130° C. to about 190° C.

317. The product of claim 314, wherein the melt is formed at a pressure from the minimum pressure necessary to avoid formation of water vapor under the applied temperature to about $150 \times 10^5$ N/m$^2$.

318. The product of claim 317, wherein the heat and pressure are maintained until the starch has undergone the specific narrow endothermic transition just prior to its endothermic change characteristic of oxidative and thermal degradation.

319. A thermoplastic destructurized-starch product having substantial dimensional stability formed by a process comprising the steps of:
1) providing a mixture comprising: (a) starch; (b) at least one compound selected from the group consisting of copolymers of vinyl pyrrolidone; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

320. The product of claim 319, wherein component (c) is selected from the group consisting of polyolefins, vinyl polymers, polystyrenes, polyacrylonitriles, polyacrylates. polymethacrylates, polyacetals, thermoplastic polycondensates, polyarylethers, thermoplastic polyimides, substantially water-insoluble or crystallizabel poly(alkylene oxides), and combinations and mixtures thereof.

321. The product of claim 319, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/ acrylonitrile copolymers and hydrolysates thereof, acrylamide/acrylonitrile copolymers, block copolymers of amideethers, amide-esters; block copolymers of urethanbeesters and combinations and mixtures thereof.

322. The product of claim 305, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

323. The product of the claim 305, in the form of a granulate.

324. The product of the claim 305, in the form of a pellet.

325. The product of the claim 305, in the form of a powder.

326. The product of claim 319, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

327. The product of claim 319, in powder, pelletized or granulate form.

328. The product of claim 327, further processed to form a shaped article selected from the group consisting of: containers, bottles, pipes, rods, packaging material, sheets, foams, films, sacks, bags, and pharmaceutical capsules.

329. The product of claim 323 or 324, further processed to form a shaped article selected from the group consisting of containers, bottles, pipes, rods, packaging material, sheets, foams, films, sacks, bags, and pharmaceutical capsules.

330. The product of claim 325, further melted and processed to form a shaped article selected from the group consisting of containers, bottles, pipes, rods, packaging material, sheets, foams films, sacks, bags and pharmaceutical capsules.

331. The product of claim 319, wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, substantially water-insoluble or crystallizable poly(alkylene oxides), and combinations and mixtures thereof.

332. The product of claim 319, wherein component (c) is selected from the group consisting of alkylene/vinyl ester/copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

333. The product of claim 328, wherein the further processing is selected from the group consisting of: foaming, filming, compression molding, injection molding, blow molding, extruding, co-extruding, vacuum forming, thermoforming and combinations thereof.

334. The product of claim 329, wherein the further processing is selected from the group consisting of: foaming, filming, compression molding, injection molding, blow molding, extruding, co-extruding, vacuum forming, thermoforming and combinations thereof.

335. The product of claim 360, wherein the further processing is selected form the group consisting of: foaming, filming, compression molding, injection molding, blow molding, extruding, co-extruding, vacuum forming, thermoforming and combinations thereof.

336. A thermoplastic destructurized-starch substantially homogenous melt formed by a process comprising the steps of:
1) providing a mixture comprising starch and at least one compound selected from the group consisting of copolymers of vinyl pyrrolidone; said compound being present in an amount effective to enhance at least one physical property of an article formed from said melt; and
2) heating said mixture in a closed volume under sufficient temperature and pressure for a time long enough to destructurize said starch and form said melt.

337. The melt of claim 336, wherein destructurization of the starch is carried out in the presence of one or more materials selected from the group consisting of adjuvants, fillers, lubricants, mold release agents, plasticizers, foaming agents, stabilizers, extenders, chemical modifiers, flow accelerators, coloring agents, pigments and mixtures thereof.

338. The melt of claim 336, wherein destructurization of the starch is carried out at a temperature from about 105° C. to about 240° C.

339. The melt of claim 336, wherein destructurization of the starch is carried out at a temperature from about 130° C. to about 190° C.

340. The melt of claim 339, wherein the melt is formed at a pressure from the minimum pressure necessary to avoid formation of water vapor under the applied temperature to about $150 \times 10^5$ N/m².

341. The melt of claim 340, wherein the heat and pressure are maintained until the starch has undergone the specific narrow endothermic transition just prior to its endothermic change characteristic of oxidative and thermal degradation.

342. A thermoplastic destructurized-starch substantially homogenous melt formed by the process comprising:
1) providing a mixture comprising: (a) starch; (b) at least one compound selected from the group consisting of copolymers of vinyl pyrrolidone; and (c) at least one substantially water-insoluble thermoplastic polymer that does not fall within the definition of (b);
2) heating said mixture in a closed volume under sufficient temperature and pressures for a time long enough to destructurize said starch and form said melt.

343. The melt of claim 342, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, polyhydroxybutyrates, high molar-mass essentially water-insoluble or crystallizable poly(alkylene oxides) and combinations and mixtures thereof.

344. The melt of claim 342, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

345. The melt of claim 336, further comprising at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

346. The melt of claim 342, further comprising at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

347. A composition of matter capable of being formed into an article having substantial dimensional stability comprising:
(a) destructurized starch, and
(b) at least one compound selected from the group consisting of cationically modified polysaccharides; wherein said polysaccharide is present in an amount sufficient to modify in a desired manner at least one of the properties of: toughness; resistance to deformation in humid atmosphere; and compatibility with a substantially water-insoluble thermoplastic polymer.

348. The composition of claim 347, wherein said cationically modified polysaccharide is selected from the group consisting of starches, celluloses, hemicelluloses, xylanes, gums, alginates, pectins and pullulans and combinations and mixtures thereof.

349. The composition of claim 348, wherein said cationically modified polysaccharide is selected from the group consisting of: starch and cellulose.

350. The composition of claim 347, wherein said cationically modified polysaccharide is obtained by chemical reaction of a polysaccharide with a compound containing an amino, imino, ammonium, sulfonium or phosphonium group.

351. The composition of claim 350, wherein the cationically modified polysaccharide comprises a tertiary amino group.

352. The composition according to claim 350, wherein the cationically modified polysaccharide comprises a quaternary ammonium group.

353. The composition of claim 350, wherein the cationically modified polysaccharide comprises a tertiary amino group obtained by chemical reaction with 2-dialkylaminoethyl chloride.

354. The composition of claim 350, wherein the cationically modified polysaccharide carries a quaternary ammonium group obtained by chemical reaction with 2,3-(epoxypropyl) trimethylammonium chloride.

355. The composition of claim 351 or 35, wherein the cationically modified polysaccharide is co-substituted by hydroxyalkyl, carboxyalkyl or alkylether groups.

356. The composition of claim 352, wherein the cationically modified polysacchardide is co-substituted by hydroxyalkyl, carboxyalkyl or alkylether groups.

357. The composition of claim 347, wherein the degree of substitution of the cationically modified polysaccharide is from about 0.01 to about 2.5.

358. The composition of claim 347, wherein the degree of substitution of the cationically modified polysaccharide is from about 0.01 to about 1.5.

359. The composition of claim 347, wherein the degree of substitution of the cationically modified polysaccharide is from about 0.01 to about 0.5.

360. The composition of claim 347, wherein the weight percent ratio of destructurized starch to component (b) is from about 1:99 to about 99:1.

361. The composition of claim 360, wherein destructurized starch is present in an amount from about 50 percent to about 99 percent by weight of the total composition.

362. The composition of claim 347, wherein the destructurized starch has a water content from about 5 percent to about 40 percent by weight of the total starch content.

363. The composition of claim 347, wherein the destructurized starch has a water content from about 10 percent to about 22 percent by weight of the total starch content.

364. A composition of matter capable of being formed into an article having substantial dimensional stability comprising:
(a) destructurized starch, and
(b) at least one compound selected from the group consisting of cationically modified polysaccharides; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

365. The composition of claim 364, wherein component (c) is selected from the group consisting of polyolefins, vinyl polymers, polystyrenes, polyacrylonitriles, poly(vinyl carbozols), polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

366. The composition of claim 365, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

367. The composition of claim 364, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and and combinations and mixtures thereof.

368. The composition of claim 367, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

369. The composition of claim 364, wherein components (b) and (c) comprise from about 1 percent to about 99 percent by weight of the total composition.

370. The composition of claim 369, wherein components (b) and (c) comprise from about 20 percent to about 80 percent by weight of the total composition.

371. The composition of claim 370, wherein components (b) and (c) comprise from about 1 percent to about 30 percent by weight of the total composition.

372. The composition of claims 347, further comprising at least one material selected from the group consisting of: adjuvants, fillers, lubricants, mold release agents, plasticizers, foaming agents, stabilizers, extenders, chemical modifiers, flow accelerators, coloring agents, pigments and combinations and mixtures thereof.

373. The composition of claim 347 or 364, further containing an agriculturally active compound.

374. The composition of claim 347 or 364, in the form of a melt blend.

375. The composition of claim 347 or 364, in the form of a cooled solidified blend.

376. The composition of claim 347 or 364, in particulate, granulated or pelletized form.

377. A thermoplastic destructurized-starch product having substantial dimensional stability formed by a process comprising the steps of:
1) providing a mixture comprising starch and at least one compound selected from the group consisting of cationically modified polysaccharides (component(b)),
2) heating said mixture in a closed volume under sufficient temperature and pressure for a time long enough to effectuate destructurization of said starch and form a substantially homogenous melt;
3) shaping said melt into an article; and
4) allowing said shaped article to cool to a substantially dimensionally stable thermoplastic product.

378. The product of claim 377, wherein the cationically modified polysaccharide is selected from the group consisting of starches, celluloses, hemicelluloses, xylanes, gums, alginates, pectins and pullulans and combinations and mixtures thereof.

379. The product of claim 377, wherein said cationically modified polysaccharide is selected from the group consisting of starch and cellulose.

380. The product of claim 377, wherein the cationically modified polysaccharide comprises a tertiary amino group.

381. The product to claim 377, wherein the cationically modified polysaccharide comprises a quaternary ammonium group.

382. The product of claim 377, wherein the cationically modified polysaccharide is co-substituted by at least one of the group consisting of: hydroxyalkyl, carboxyalkyl and alkylether groups.

383. The product of claim 377, wherein the degree of substitution of the cationically modified polysaccharide is from about 0.01 to about 2.5.

384. The product of claim 377, wherein the degree of substitution of the cationically modified polysaccharide is from about 0.01 to about 1.5.

385. The product of claim 377, wherein the weight percent ratio of destructurized starch to component (b) is from about 1:99 to about 99:1.

386. The product of claim 377, wherein destructurization of the starch is carried out at a temperature above its melting point and glass transition temperature.

387. The product of claim 377, wherein the destructurization of the starch is carried out at a temperature from about 105° C. to about 240° C.

388. The product of claim 386, wherein the destructurization of the starch is carried out at a temperature from about 130° C. to about 190° C.

389. The product of claim 386, wherein the melt is formed at a pressure from the minimum pressure necessary to avoid formation of water vapor under the applied temperature to about $150 \times 10^5$ N/m$^2$.

390. The product of claim 377, wherein the heat and pressure are maintained until the starch has undergone the specific narrow endothermic transition just prior to its endothermic change characteristic of oxidative and thermal degradation.

391. A thermoplastic destructurized-starch product having substantial dimensional stability formed by a process comprising the steps of:
1) providing a mixture comprising: (a) starch; (b) at least one compound selected from the group consisting of cationically modified polysaccharides; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

392. The product of claim 391, wherein component (c) is selected from the group consisting of: polyolefins, vinyl polymers, polystyrenes, polyacrylonitriles, poly(-vinyl carbazols), polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

393. The product of claim 391, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

394. The product of claim 377, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

395. The product of claim 371, in the form of a granulate.

396. The product of claim 377, in the form of a pellet.

397. The product of claim 377, in the form of a powder.

398. The product of claim 391, in a form selected from the group consisting of granules, powders and pellets.

399. The product of claim 391, further processed to form a shaped article selected from the group consisting of: containers, bottles, pipes, rods, packaging material, sheets, foams, films, sacks, bags and pharmaceutical capsules.

400. The product of claim 395, further processed to form a shaped article selected from the group consisting of: containers, bottles, pipes, rods, packaging material, sheets, foams, films, sacks, bags and pharmaceutical capsules.

401. The product of claim 396, further processed to form a shaped article selected from the group consisting of containers, bottles, pipes, rods, packaging material, sheets, foams, films, sacks, bags and pharmaceutical capsules.

402. The product of claim 397, further processed to form a shaped article selected from the group consisting of: containers, bottles, pipes, rods, packaging material, sheets, foams, films, sacks, bags and pharmaceutical capsules.

403. The product of claim 398, wherein component (c) is selected from the group consisting of polyolefins, vinyl polymers, polystyrenes, polyacrylonitriles, poly(-vinyl carbazols), polyacrylates, polymethacrylates, polyacetals, polycondensates, polyarylethers, thermoplastic polyimides, substantially water-insoluble or crystallizable poly(alkylene oxides), and combinations and mixtures thereof.

404. The product of the claim 398, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers urethane-ethers, urethane-esters and combinations and mixtures thereof.

405. The product of claim 399, wherein the further processing is selected from the group consisting of: foaming, filming, compression molding, injection molding, blow molding, extruding, co-extruding, vacuum forming, thermoforming and combinations thereof.

406. The product of claim 400, 401 or 402, wherein the further processing is selected from the group consisting of: foaming, filming, compression molding, injection molding, blow molding, extruding, co-extruding, vacuum forming, thermoforming and combinations thereof.

407. A thermoplastic destructurized-starch substantially homogenous melt formed by a process comprising the steps of:
1) providing a mixture comprising starch and at least one compound selected from the group consisting of cationically modified polysaccharides (component (b)); and
2) heating said mixture in a closed volume under sufficient temperature and pressure for a time long enough to destructurize said starch and form said melt.

408. The melt of claim 407, wherein destructurization of the starch is carried out in the presence of at least one material selected from the group consisting of: adjuvants, fillers, lubricants, mold release agents, plasticizers, foaming agents, stabilizers, extenders, chemical modifiers, flow accelerators, coloring agents, pigments and mixtures thereof.

409. The melt of claim 407, wherein destructurization of the starch is carried out at a temperature from about 105° C. to about 240° C.

410. The melt of claim 407, wherein destructurization of the starch is carried out at a temperature from about 130° C. to about 190° C.

411. The melt of claim 410, wherein the melt is formed at a pressure from the minimum pressure necessary to avoid formation of water vapor under the applied temperature to about $150 \times 10^5$ N/m².

412. The melt of claim 411, wherein the heat and pressure are maintained until the starch has undergone the specific narrow endothermic transition just prior to its endothermic change characteristic of oxidative and thermal degradation.

413. A thermoplastic destructurized-starch substantially homogenous melt formed by the process comprising:
1) providing a mixture comprising (a) starch; (b) at least one compound selected from the group consisting of cationically modified polysaccharides; and (c) at least one substantially water-insoluble thermoplastic polymer that does not fall within the definition of (b);
2) heating said mixture in a closed volume under sufficient temperature and pressure for a time long enough to destructurize said starch and form said melt.

414. The melt of claim 413 where component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrates, high molar-mass substantially water-insoluble or crystallizable poly(alkylene oxides) and combinations and mixtures thereof.

415. The melt of claim 413 wherein component (c) is selected from the group consisting of: alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

416. The melt of claim 413, wherein the mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

417. A composition of matter capable of being formed into an article having substantial dimensional stability comprising:
(a) destructurized starch, and
(b) at least one compound selected from the group consisting of anionically modified polysaccharides; said modified polysaccharide being present in an amount effective to enhance at least one physical property of said article.

418. The composition of claim 417, wherein said polysaccharide is selected from the group consisting of starches, celluloses, hemicelluloses, xylanes, gums, alginates, pectins, pullulans and combinations and mixtures thereof.

419. The composition of claim 418, wherein said anionically modified polysaccharide is selected from the group consisting of starch, cellulose and combinations and mixtures thereof.

420. The composition of the claim 417, wherein said polysaccharide comprises at least one phosphate group, sulfate group or carboxyl group in the form of its free acid or a salt thereof.

421. The composition of claim 420, wherein the polysaccharide comprises a sulfate group.

422. The composition of claim 420, wherein the polysaccharide comprises an ammonium salt, an alkali salt or an organic base salt of a sulfate group.

423. The composition of claim 420, wherein the polysaccharide comprises at least one carboxyl group.

424. The composition of claim 420, wherein the polysaccharide comprises an ammonium or alkali salt or organic base salt of a carboxyl group.

425. The composition of the claim 421, wherein the polysaccharide further comprises a hydroxyalkyl group or an alkylether group.

426. The composition of claim 417, wherein the degree of substitution of the polysaccharide is from about 0.01 to about 2.9.

427. The composition of claim 417, wherein the degree of substitution of the polysaccharide is from about 0.01 to about 2.5

428. The composition of claim 417, wherein the degree of substitution of the polysaccharide is from about 0.05 to about 1.5.

429. The composition of claim 417, wherein the weight percent ratio of destructurized starch to component (b) is from about 1:99 to about 99:1.

430. The composition of claim 429, wherein destructurized starch comprises from about 50 percent to about 99 percent of the total composition.

431. The composition of claim 417, wherein the destructurized starch has a water content of from about 5 percent to about 40 percent by weight of the total starch content.

432. The composition of claim 417, wherein the destructurized starch has a water content of from about 10 percent to about 22 percent by weight of the total starch content.

433. A composition of matter capable of being formed into an article having substantial dimensional stability comprising:
  (a) destructurized starch, and
  (b) at least one compound selected from the group consisting of anionically modified polysaccharides; and
  (c) at least one substantially water-insoluble thermoplastic polymer that does not fall within the definition of component (b), wherein (b) and (c) are present in a combined amount sufficient to effectuate dimensional stability and enhance at least one desired physical property of said article.

434. The composition of claim 433, wherein component (c) is selected from the group consisting of: polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

435. The composition of claim 434, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

436. The composition of claim 433, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

437. The composition of claim 436, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

438. The composition of claim 433 wherein components (b) and (c) comprise form about 1 percent to about 99 percent by weight of the total composition.

439. The composition of claim 438, wherein components (b) and (c) comprise from about 20 percent to about 80 percent by weight of the total composition.

440. The composition of claim 439 wherein components (b) and (c) comprise from about 1 percent to about 30 percent by weight of the total composition.

441. The composition of claim 417, further comprising at least one material selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

442. The composition of claim 433, further comprising at least one material selected from the group consisting of: adjuvants, fillers, lubricants, mold release agents, plasticizers, foaming agents, stabilizers, extenders, chemical modifiers, flow accelerators, coloring agents, pigments and combinations and mixtures thereof.

443. The composition of claim 417, further comprising an agriculturally active compound.

444. The composition of claim 417, in the form of a melt blend.

445. The composition of claim 417, in the form of a cooled solidified blend.

446. The composition of claim 417, in particulate, granulated, powdered or pelletized form.

447. The composition of claim 433, further comprising an agriculturally active compound.

448. The composition of claim 433, in the form of a melt blend.

449. The composition of claim 433, in the form of a cooled solidified blend.

450. The composition of claim 433, in particulate, granulated, pelletized or powdered form.

451. A thermoplastic destructurized-starch product having substantial dimensional stability formed by a process comprising the steps of:
  1) providing a mixture comprising starch and at least one compound selected from the group consisting of anionically modified polysaccharides in an amount sufficient to enhance at least one property of said product,
  2) heating said mixture in a closed volume under sufficient temperature and pressure for a time long enough to effectuate destructurization of said starch and form a substantially homogenous melt;
  3) shaping said melt into an article; and
  4) allowing said shaped article to cool to form a substantially dimensionally stable thermoplastic product.

452. The product of claim 451, wherein the polysaccharide is selected from the group consisting of starches, celluloses, hemicelluloses, xylanes, gums, alginates, pectins and pullulans and combinations and mixtures thereof.

453. The product of claim 451, wherein said polysaccharide is selected from the group consisting of: starch, cellulose and combinations and mixtures thereof.

454. The product of claim 451, wherein the polysaccharide further comprises at least one phosphate group, sulfate group or carboxyl group in the form of a free acid or a salt thereof.

455. The product of claim 451, wherein the polysaccharide further comprises at least one carboxyl group in the form of an ammonium or alkali salt or in the form of an organic base salt.

456. The product of claim 451, wherein the polysaccharide further comprises at least one hydroxyalkyl group or alkylether group.

457. The product of claim 451, wherein the degree of substitution of the polysaccharide is from about 0.01 to about 2.9.

458. The product of claim 451, wherein the degree of substitution of the anionically modified polysaccharide is from about 0.01 to about 2.5

459. The product of claim 451, wherein the weight percent ratio of destructurized starch to component (b) is from about 1:99 to about 99:1.

460. The product of claim 451, wherein destructurization of the starch is carried out at a temperature above its melting point and glass transition temperature.

461. The product of claim 451, wherein the destructurization of the starch is carried out at a temperature from about 105° C. to about 240° C.

462. The product of claim 461, wherein the destructurization of the starch is carried out at a temperature from about 130° C. to about 190° C.

463. The product of claim 460, wherein the melt is formed at a pressure from the minimum pressure necessary to avoid formation of water vapor under the applied temperature to about $150 \times 10^5$ N/m$^2$.

464. The product of claim 453, wherein the heat and pressure are maintained until the starch has undergone the specific narrow endothermic transition just prior to its endothermic change characteristic of oxidative and thermal degradation.

465. A thermoplastic destructurized-starch product having substantial dimensional stability formed by a process comprising the steps of:
1) providing a mixture comprising: (a) starch; (b) at least one compound selected from the group consisting of anionically modified polysaccharides; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

466. The product of claim 465 wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides) and combinations and mixtures thereof.

467. The product of claim 465, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

468. The product of claim 451, wherein said mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

469. The product of claim 451, in granular form.

470. The product of claim 451, in pelletized form.

471. The product of claim 451, in the form of a powder.

472. The product of claim 465, wherein said mixture further comprises at least one material selected from the group consisting of: adjuvants, lubricants, flow accelerators, mold release agents, plasticizers, foaming agents, stabilizers, extenders, coloring agents, pigments, chemical modifiers and combinations and mixtures thereof.

473. The product of claim 465, in granular, pelletized, or powdered form.

474. The product of claim 469, further processed to form a shaped article selected from the group consisting of containers, bottles pipes, rods packaging material, sheets, foams, films sacks, bags and pharmaceutical capsules.

475. The product of claim 470, further processed to form a shaped article selected from the group consisting of containers, bottles, pipes, rods, packaging material, sheets, foams, films, sacks, bags and pharmaceutical capsules.

476. The product of claim 471, further processed to form a shaped article selected from the group consisting of containers, bottles, pipes, rods, packaging material, sheets, foams, films, sacks, bags and pharmaceutical capsules.

477. The product of claim 473, wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, essentially water-insoluble or crystallizable poly(alkylene oxides) and combinations and mixtures thereof.

478. A product of claim 473, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

479. The product of claim 473 further processed to form a shaped article selected from the group consisting of: containers, bottles pipes, rods, packaging material, sheets, foams, films, sacks, bags, and pharmaceutical capsules.

480. The product of claim 474, wherein the further processing comprises foaming, filming, compression molding, injection molding, blow molding, extruding, co-extruding, vacuum-forming, thermo-forming and combinations thereof.

481. The product of claim 475, wherein the further processing comprises foaming, filming, compression molding, injection molding, blow molding, extruding, co-extruding, vacuum-forming, thermo-forming and combinations thereof.

482. The product of claim 476, wherein the further processing comprises foaming, filming, compression molding, injection molding, blow molding, extruding, co-extruding, vacuum-forming, thermo forming and combinations thereof.

483. The product of claim 479, wherein the further processing comprises foaming, filming, compression molding injection molding, blow molding, extruding, co-extruding, vacuum forming, thermo-forming and combinations thereof.

484. A thermoplastic destructurized-starch substantially homogenous melt formed by a process comprising the steps of:
1) providing a mixture comprising starch and at least one compound selected from the group consisting of anionically modified polysaccharides (component (b)); and
2) heating said mixture in a closed volume under sufficient temperature and pressure for a time long enough to destructurize said starch and form said melt.

485. The melt of claim 484, wherein destructurization of the starch is carried out in the presence of one or more materials selected from the group consisting of adjuvants, fillers, lubricants, mold release agents, plasticizers, foaming agents, stabilizers, extenders, chemical modifiers, flow accelerators, coloring agents, pigments and combinations and mixtures thereof.

486. The melt of claim 484, wherein destructurization of the starch is carried out at a temperature from about 105° C. to about 240° C.

487. The melt of claim 484, wherein destructurization of the starch is carried out at a temperature form about 130° C. to about 190° C.

488. The melt of claim 487, wherein the melt is formed at a pressure from the minimum pressure necessary to avoid formation of water vapor under the applied temperature to about $150 \times 10^5$ N/m².

489. The melt of claim 488, wherein the heat and pressure are maintained until the starch has undergone the specific narrow endothermic transition just prior to its endothermic change characteristic of oxidative and thermal degradation.

490. A thermoplastic destructurized-starch substantially homogenous melt formed by the process comprising:
1) providing a mixture comprising: (a) starch; (b) at least one compound selected from the group consisting of anionically modified polysaccharides; and (c) at least one substantially water-insoluble thermoplastic polymer that does not fall within the definition of (b);
2) heating said mixture in a closed volume under sufficient temperature and pressure for a time long enough to destructurize said starch and form said melt.

491. The melt of claim 384, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, thermoplastic polyimides, polyhydroxybutyrates, high molar-mass essentially water-insoluble or crystallizable poly(alkylene oxides) and combinations and mixtures thereof.

492. The melt of claim 484, wherein component (c) is selected from the group consisting of: alkylene/vinyl ester-copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

493. The melt of claim 484, wherein the mixture further comprises at least one material selected from the group consisting of adjuvants, lubricants, flow accelerators, mold release agents, plasticizers, foaming agents, stabilizers, extenders, coloring agents, pigments, chemical modifiers and combinations and mixtures thereof.

494. A composition of matter capable of being formed int an article having substantial dimensional stability comprising:
(a) destructurized starch, and
(b) at least one polymer selected from the group of copolymers containing vinyl alcohol units together with aliphatic chain units obtained by copolymerization of a vinyl ester with at least one unsaturated monomer containing no functional group, with subsequent hydrolysis of the vinyl ester; wherein said polymer is present in an amount sufficient to modify in a desired manner at least one of the properties of: toughness; resistance to deformation in humid atmosphere; and compatibility with a substantially water-insoluble thermoplastic polymer.

495. The composition of claim 494, wherein component (b) is obtained by copolymerization of vinyl acetate with at least one selected from the group consisting of: ethylene, propylene, isobutylene, and styrene, with subsequent hydrolysis of the vinyl ester group.

496. The composition of claim 495, wherein component (b) is obtained by copolymerization of vinyl acetate with ethylene or propylene, with subsequent hydrolysis of the vinyl ester group.

497. The composition of claim 496, wherein component (b) is a copolymer obtained by copolymerization of vinyl acetate with ethylene with subsequent hydrolysis of the vinyl ester group.

498. The composition of claim 496, wherein the molar ratio of vinyl alcohol units to alkylene units is from about 10:90 to about 90:10.

499. The composition of claim 496, wherein the molar ratio of vinyl alcohol units to alkylene units is from about 50:50 to about 85:15.

500. The composition of claim 496, wherein the molar ratio of vinyl alcohol units to alkylene units is from about 60:40 to about 81:19.

501. The composition of claim 496, wherein component (b) further comprises about 5 to 20 percent styrene units based on the total weight of the polymer.

502. The composition of claim 494, wherein the weight percent ratio of destructurized starch to component (b) is from about 1:99 to about 99:1.

503. The composition of claim 502, wherein destructurized starch comprises from about 50 percent to about 99 percent of the total composition.

504. The composition of claim 496, wherein the destructurized starch has a water content form about 5 percent to about 40 percent by weight of the total starch content.

505. The composition of claim 494, wherein the destructurized starch has a water content form about 10 percent to about 22 percent by weight of the total starch content.

506. A composition of matter capable of being formed into an article having substantial dimensional stability comprising:
(a) destructurized starch, and
(b) at least one polymer selected from the group of copolymers containing vinyl alcohol units together with aliphatic chain units obtained by copolymerization of a vinyl ester with at least one unsaturated monomer containing no functional group, (c) with subsequent hydrolysis of the vinyl ester group; and (c) at least one substantially water-insoluble thermoplastic polymer that does not fall within the definition of component (b), wherein (b) and (c) are present in a combined amount sufficient to effectuate dimensional stability and enhance at least one desired physical property of said article.

507. The composition of claim 506 wherein component (c) is selected from the group consisting of: polyolefins, vinyl polymers, polystyrenes, polyacrylonitriles, poly-acrylates, polymethacrylates, polyacetals, thermoplastic polycondensates, polyarylethers, thermoplastic polyimides, substantially water-insoluble or crystallizable poly(alkylene oxides), and combinations and mixtures thereof.

508. The composition of claim 507, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

509. The composition of claim 506, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

510. The composition of claim 509, wherein component (c) is selected from the group consisting of ethylene/vinyl acetate copolymers (EVA), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

511. The composition of claim 506, wherein components (b) and (c) comprise from about 1 percent to about 99 percent by weight of the total composition.

512. The composition of claim 511, wherein components (b) and (c) comprise form about 20 percent to about 80 percent by weight of the total composition.

513. The composition of claim 512, wherein components (b) and (c) comprise from about 1 percent to about 30 percent by weight of the total composition.

514. The composition of claim 494, further comprising at least one material selected from the group consisting of: adjuvants, fillers, lubricants, mold release agents, plasticizers, foaming agents, stabilizers, extenders, chemical modifiers, flow accelerators, coloring agents, pigments and combinations and mixtures thereof.

515. The composition of claim 494, further comprising an agriculturally active compound.

516. The composition of claim 494, in the form of a melt blend.

517. The composition of claim 494, in the form of a cooled solidified blend.

518. The composition of claim 494, in particulate, granulated or pelletized form.

519. The composition of claim 506, further comprising at least one material selected from the group consisting of: adjuvants, fillers, lubricants, mold release agents, plasticizers, foaming agents, stabilizers, extenders, chemical modifiers, flow accelerators, coloring agents, pigments and combinations and mixtures thereof.

520. The composition of claim 506, further comprising an agriculturally active compound.

521. The composition of claim 506, in the form of a melt blend or a cooled solidified blend.

522. The composition of claim 506, in particulate, granular or pelletized form.

523. A thermoplastic destructurized-starch product having substantial dimensional stability formed by a process comprising the steps of:

1) providing a mixture comprising a starch and at least one polymer selected from the group of copolymers containing vinyl alcohol units together with aliphatic chain units obtained by copolymerization of vinyl esters with at least one unsaturated monomer containing no functional group with subsequent hydrolysis of the vinyl ester group (component (b));

2) heating said mixture in a closed volume under sufficient temperature and pressure for a time long enough to effectuate destructurization of said starch and to form a substantially homogenous melt;

3) shaping said melt into an article; and 4) allowing said shaped article to cool to a substantially dimensionally stable thermoplastic product.

524. The product of claim 523, wherein component (b) is a copolymer obtained by copolymerization of vinyl acetate with ethylene, propylene, isobutylene, or styrene with subsequent hydrolysis of the vinyl ester group.

525. The product of claim 523, wherein component (b) is a copolymer obtained by copolymerization of vinyl acetate with ethylene or propylene with subsequent hydrolysis of the vinyl ester group.

526. The product of claim 523, wherein component (b) is a copolymer obtained by copolymerization of vinyl acetate with ethylene with subsequent hydrolysis of the vinyl ester group.

527. The product of claim 523, wherein the molar ratio of vinyl alcohol units to alkylene units is form about 50:50 to about 85:15.

528. The composition of claim 527, wherein component (b) further comprises from about 5 percent to about 20 percent polystyrene units based on the total weight of the polymer.

529. The product of claim 523, wherein the weight percent ratio of destructurized starch to component (b) is from about 1:99 to about 99:1.

530. The product of claim 523, wherein destructurization of the starch is carried out at a temperature above its melting point and glass transition temperature.

531. The product of claim 523, wherein the destructurization of the starch is carried out at a temperature from about 105° C. to about 240° C.

532. The product of claim 530, wherein destructurization of the starch is carried out at a temperature from about 130° C. to bout 190° C.

533. The product of claim 530, wherein the melt is formed at a pressure form the minimum pressure necessary to avoid formation of water vapor under the applied temperature to about 150×10⁵ N/m².

534. The product of claim 533, wherein the heat and pressure are maintained until the starch has undergone the specific narrow endothermic transition just prior to its endothermic change characteristic of oxidative and thermal degradation.

535. A thermoplastic destructurized-starch product having substantial dimensional stability formed by a process comprising the steps of:
1) providing a mixture comprising: (a) starch; (b) at least one polymer selected from the group of copolymers containing vinyl alcohol units together with alyphatic chain units obtained by copolymerization of a vinyl ester with at least one unsaturated monomer containing no functional group, with subsequent hydrolysis of the vinyl ester group; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

536. The product of claim 535, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

537. The product of claim 535, wherein component (c) is selected from the group consisting of alkylene/vinyl ester-copolymers, alkylene/acrylate or methacrylate copolymers, ABS copolymers, styrene/acrylonitrile copolymers, alkylene/.maleic anhydride copolymers, acrylic acid esters/acrylonitrile copolymers, acrylamide/acrylonitrile copolymers, block copolymers or amide-ethers, amide-esters; bloc copolymers of urethane-ethers, urethane-esters and combinations and mixtures thereof.

538. The product of claim 523, wherein said mixture further comprises at least one material selected from the group consisting of adjuvants, lubricants, flow accelerators, mold release agents, plasticizers, foaming gents, stabilizers, extenders, coloring agents, pigments, chemical modifiers and mixtures thereof.

539. The product of claim 523, in granulate form.

540. The product of claim 523, in pellet form.

541. The product of claim 523, in powder form.

542. The product of claim 535 wherein said mixture further comprises at least one material selected from the group consisting of: adjuvants, lubricants, flow accelerators, mold release agents, plasticizers, foaming agents, stabilizers, extenders, coloring agents, pigments chemical modifiers and mixtures thereof.

543. The product of claim 535, in granulate, pellet or powder form.

544. The product of claim 539, further processed to form a shaped article selected from the group consisting of: containers, bottles, pipes, rods, packaging material, sheets, foams, sacks, bags and pharmaceutical capsules.

545. The product of claim 540, further processed to form a shaped article selected from the group consisting of containers, bottles, pipes, rods, packaging material, sheets, foams, films, sacks, bags and pharmaceutical capsules.

546. The product of claim 541, further processed to form a shaped article selected from the group consisting of containers, bottles, pipes, rods, packaging material, sheets, foams, films, sacks, bags and pharmaceutical capsules.

547. The product of claim 542, further processed to form a shaped article selected from the group consisting of: containers, bottles, pipes, rods, packaging material, sheets, foams, films, sacks, bags, and pharmaceutical capsules.

548. The product of claim 543, wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, substantially water-insoluble or crystallizable poly(alkylene oxides), and combinations and mixtures thereof.

549. The product of claim 543, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

550. The product of claim 539, wherein the further processing comprises foaming, filming, compression molding, injection molding, blow molding, extruding, co-extruding, vacuum forming, thermo-forming and combinations thereof.

551. The product of claim 540, wherein the further processing comprises: foaming, filming, compression molding, injection molding, blow molding, extruding, co-extruding, vacuum-forming, thermo-forming and combinations thereof.

552. The product of claim 541, wherein the further processing comprises: foaming, filming, compression molding, injection molding, blow molding, extruding, co-extruding, vacuum-forming, thermo-forming and combinations thereof.

553. The product of claim 543, wherein the further processing comprises: foaming, filming, compression molding, injection molding, blow molding, extruding, co-extruding, vacuum-forming, thermo forming and combinations thereof.

554. A thermoplastic destructurized-starch substantially homogenous melt formed by a process comprising the steps of:
1) providing a mixture comprising starch and at least one polymer selected from the group of copolymers containing vinyl alcohol units together with aliphatic chain units obtained by copolymerization of vinyl esters with at least one unsaturated monomer containing no functional group with subsequent hydrolysis of the vinyl ester group; and
2) heating said mixture in a closed volume under sufficient temperature and pressure for a time long enough to destructurize said starch and form said melt.

555. The melt of claim 554, wherein destructurization of the starch is carried out in the presence of at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

556. The melt of claim 554, wherein destructurization of the starch is carried out at a temperature from about 105° C. to about 240° C.

557. The melt of claim 554, wherein destructurization of the starch is carried out at a temperature from about 130° C. to about 190° C.

558. The melt of claim 557, wherein the melt is formed at a pressure from the minimum pressure necessary to avoid formation of water vapor under the applied temperature to about $150 \times 10^5$ N/m$^2$.

559. The melt of claim 558, wherein the heat and pressure are maintained until the starch has undergone the specific narrow endothermic transition just prior to its endothermic change characteristic of oxidative and thermal degradation.

560. A thermoplastic destructurized-starch substantially homogenous melt formed by the process comprising:
1) providing a mixture comprising: (a) starch; (b) at least one polymer selected from the group of co-polymers containing vinyl alcohol units together with aliphatic chain units obtained by copolymerization of a vinyl ester with at least one unsaturated monomer containing no functional group, with subsequent hydrolysis of the vinyl ester group; and (c) at least one substantially water-insoluble thermoplastic polymer that does not fall within the definition of(b);
2) heating said mixture in a closed volume under sufficient temperature and pressure for a time long enough to destructurize said starch and form said melt.

561. The melt of claim 554, wherein component (c) is selected from the group consisting of polyolefins, vinyl polymers, polystyrenes, polyacrylonitriles, poly-acrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides) and combinations and mixtures thereof.

562. The melt of claim 554, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, acrylic acid esters/acrylonitrile copolymers, acrylamide/acrylonitrile copolymers, block copolymers of amide-ethers, amide-esters; block copolymers of urethane-ethers, urethane-esters and combinations and mixtures thereof.

563. The melt of claim 560, wherein the mixture additionally contains one or more materials selected from the group consisting of adjuvants, lubricants, flow accelerators, mold release agents, plasticizers, foaming agents, stabilizers, extenders, coloring agents, pigments, chemical modifiers and mixtures thereof.

564. A composition of matter capable of being formed into an article having substantial dimensional stability comprising:
(a) destructurized starch, and
(b) at least one compound selected from the group consisting of polysaccharide graft copolymers and graft copolymers of polysaccharide derivatives; wherein said polymer is present in an amount sufficient to modify in a desired manner at least one of the properties of: toughness; resistance to deformation in humid atmosphere; and compatibility with a substantially water-insoluble thermoplastic polymer.

565. The composition of claim 564, wherein component (b) is selected from the group consisting of: polysaccharides grafted with a monomer or with monomers selected from the group consisting of styrene; butadiene; isoprene; acrylonitrile; alkylacrylates; alkylmethacrylates; acrylic acid; methacrylic acid, alkyl vinyl ether, and acrylamide and combinations and mixtures thereof.

566. The composition of claim 564, wherein component (b) is selected from the group consisting of polysaccharides grafted with a monomer or with monomers selected from the group consisting of isoprene; acrylonitrile; methyl acrylate; methyl methacrylate; acrylic acid; methyl vinyl ether and acrylamide and combinations and mixtures thereof.

567. The composition of claim 564, wherein component (b) is selected from the group consisting of polysaccharides grafted with methyl acrylate or methyl methacrylate and combinations and mixtures thereof.

568. The composition of claim 564, wherein component (b) is selected from the group consisting of polysaccharides grafted with a monomer or with monomers selected from the group consisting of beta-propiolactone, ethyleneimine, propyleneimine and caprolactam and combinations and mixtures thereof.

569. The composition of claim 564, wherein component (b) is a graft copolymer of cellulose or starch.

570. The composition of claim 564, wherein the weight percent ratio of destructurized starch to component (b) is from about 1:99 to about 99:1.

571. The composition of claim 570, wherein destructurized starch comprises from about 60 percent to about 95 percent of the total composition.

572. The composition of claim 564, wherein the destructurized starch has a water content form about 5 percent to about 40 percent by weight of the total starch content.

573. The composition of claim 564, wherein the destructurized starch has a water content form about 10 percent to about 22 percent by weight of the total starch content.

574. A composition of matter capable of being formed into an article having substantial dimensional stability comprising:
(a) destructurized starch, and
(b) at least one compound selected from the group consisting of polysaccharide graft copolymers and graft copolymers of polysaccharide derivatives; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

575. The composition of claim 574, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

576. The composition of claim 574, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

577. The composition of claim 574, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

578. The composition of claim 577, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

579. The composition of claim 574, wherein components (b) and (c) comprise from about 1 percent to about 99 percent by weight of the total composition.

580. The composition of claim 579, wherein components (b) and (c) comprise from about 20 percent to about 80 percent by weight of the total composition.

581. The composition of claim 580, wherein components (b) and (c) comprise from about 1 percent to about 30 percent by weight of the total composition.

582. The composition of claim 564, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

583. The composition of claim 564, further comprising an agriculturally active compound.

584. The composition of claim 564, in the form of a melt blend.

585. The composition of claim 564, in the form of a cooled solidified blend.

586. The composition of claim 564, in particulate, granulated or pelletized form.

587. The composition of claim 574, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

588. The composition of claim 574, further comprising an agriculturally active compound.

589. The composition of claim 574, in the form of a melt blend or a cooled solidified blend.

590. The composition of claim 574, in particulate, granulated or pelletized form.

591. A thermoplastic destructurized-starch product having substantial dimensional stability formed by a process comprising the steps of:
1) providing a mixture comprising starch and at least one compound selected form the group consisting of polysaccharide graft copolymers and graft copolymers of polysaccharide derivatives (component (b)); said compound being present in an amount effective to enhance at least one physical properties of an article made from said mixture;
2) heating said mixture in a closed volume under sufficient temperature and pressure for a time long enough to effectuate destructurization of said starch and form a substantially homogenous melt;
3) shaping said melt into an article; and
4) allowing said shaped article to cool to form a substantially dimensionally stable thermoplastic product.

592. The product of claim 591, wherein component (b) is selected from the group consisting of polysaccharides grafted with a monomer or with monomers selected from the group consisting of styrene; butadiene; isoprene; acrylonitrile; alkylacrylates; alkylmethacrylates; acrylic acid; methacrylic acid, alkyl vinyl ether, acrylamide and combinations and mixtures thereof.

593. The product of claim 591, wherein component (b) is selected from the group consisting of polysaccharides grafted with a monomer or with monomers selected from the group consisting of isoprene; acrylonitrile; methyl acrylate; methyl methacrylate; acrylic acid; methyl vinyl ether and acrylamide and combinations and mixtures thereof.

594. The product of claim 593, wherein component (b) is selected from the group consisting of polysaccharides grafted with methyl acrylate or methyl methacrylate.

595. The product of claim 591, wherein component (b) is selected from the group consisting of polysaccharides grafted with a monomer or with monomers selected from the group consisting of beta-propiolactone, ethyleneimine, propyleneimine and caprolactam and combinations and mixtures thereof.

596. The product of claim 591, wherein component (b) is a grafted copolymer of cellulose or starch.

597. The product claim 591, wherein the weight percent ratio of destructurized starch to component (b) is from about 1:99 to about 99:1.

598. The product of claim 591, wherein destructurization of the starch is carried out at a temperature above its melting point and glass transition temperature.

599. The product of claim 591, wherein the destructurization of the starch is carried out at a temperature from about 105° C. to about 240° C.

600. The product of claim 599, wherein the destructurization of the starch is carried out at a temperature form about 130° C. to about 190° C.

601. The product of claim 591, wherein the melt is formed at a pressure from the minimum pressure necessary to avoid formation of water vapor under the applied temperature to about $150 \times 10^5$ N/m$^2$.

602. The product of claim 601, wherein the heat and pressure are maintained until the starch has undergone the specific narrow endothermic transition just prior to its endothermic change characteristic of oxidative and thermal degradation.

603. A thermoplastic destructurized-starch product having substantial dimensional stability formed by a process comprising the steps of:

1) providing a mixture comprising: (a) starch; (b) at least one compound selected from the group consisting of polysaccharide graft copolymers and graft copolymers of polysaccharide derivatives; and (c) at least one substantially water-insoluble thermoplastic polymer that does not fall within the definition of (b);

2) heating said mixture in a closed volume under sufficient temperature and pressure for a time long enough to effect destructurization of said starch and form a substantially homogenous melt;

3) shaping said melt into an article; and 4) allowing said shaped article to cool to a substantially dimensionally stable thermoplastic product.

604. The product of claim 603, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, essentially water-insoluble or crystallizable poly(alkylene oxides), and combinations and mixtures thereof.

605. The product of claim 603, wherein component (c) is selected form the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethaneesters and combinations and mixtures thereof.

606. The product of claim 591, wherein said mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

607. The product of claim 591, in granular form.

608. The product of claim 591, in pelletized form.

609. The product of claim 591, in powder form.

610. The product of claim 603, wherein said mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

611. The product of claim 603, in granular, pelletized or powdered form.

612. The product of claim 611, further processed to form a shaped article selected from the group consisting of: containers, bottles, pipes rods, packaging material, sheets forms, films, sacks, bags and pharmaceutical capsules.

613. The product of claim 607, further processed to form a shaped article selected from the group consisting of: containers, bottles, pipes, rods, packaging material, sheets foams, films, sacks, bags and pharmaceutical capsules.

614. The product of claim 608, further processed to form a shaped article selected from the group consisting of containers, bottles, pipes, rods, packaging material, sheets, foams, films, sacks, bags and pharmaceutical capsules.

615. The product of claim 609, further processed to form a shaped article selected from the group consisting of containers, bottles, pipes, rods, packaging material, sheets, foams, films, sacks, bags and pharmaceutical capsules.

616. The product of claim 611, wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, essentially water-insoluble or crystallizable poly(alkylene oxides), and combinations and mixtures thereof.

617. The product of claim 611, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

618. The product of claim 607, 608, 609 or 611, wherein the further processing comprises foaming, filming, compression molding, injection molding, blow molding, extruding, co-extruding, vacuum forming, thermo forming and combinations thereof.

619. A thermoplastic destructurized-starch substantially homogenous melt formed by a process comprising the steps of:

1) providing a mixture comprising starch and at least one compound selected from the group consisting of polysaccharide graft copolymers and graft copolymers of polysaccharide derivatives (component (b)); said compound being present in an amount effective to enhance at least one physical property of an article made from said mixture; and 2) heating said mixture in a closed volume under sufficient temperature and pressure for a time long enough to destructurize said starch and form said melt.

620. The melt of claim 619, wherein destructurization of the starch is carried out in the presence of at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

621. The melt of claim 619, wherein destructurization of the starch is carried out at a temperature from about 105° C. to about 240° C.

622. The melt of claim 619, wherein destructurization of the starch is carried out at a temperature from about 130° C. to about 190° C.

623. The melt of claim 619, wherein the melt is formed of a pressure from the minimum pressure necessary to avoid formation of water vapor under the applied temperature to about $150 \times 10^5$ N/m$^2$.

624. The melt of claim 623, wherein the heat and pressure are maintained until the starch has undergone the specific narrow endothermic transition just prior to its endothermic change characteristic of oxidative and thermal degradation.

625. A thermoplastic destructurized-starch substantially homogenous melt formed by the process comprising:
1) providing a mixture comprising: (a) starch; (b) at least one compound selected from the group consisting of polysaccharide graft copolymers and graft copolymers of polysaccharide derivatives; and (c) at least one substantially water-insoluble thermoplastic polymer that does not fall within the definition of (b);
2) heating said mixtures in a closed volume under sufficient temperature and pressure for a time long enough to destructurize said starch and form said melt.

626. The melt of claim 619, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, polyhydroxybutyrate, high molar-mass essentially water-insoluble or crystallizable poly(alkylene oxides) and combinations and mixtures thereof.

627. The melt of claim 619, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

628. The melt of claim 625, wherein the mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

629. A composition of matter capable of being formed into an article having substantial dimensional stability comprising:
(a) destructurized starch, and
(b) at least one compound selected from the group consisting of polyalkyleneimine polymers and polyalkyleneimine copolymers; said compound being present in an amount effective to enhance at least one physical property of said article; wherein said polymer is present in an mount sufficient to modify in a desired manner at least one of the properties of: toughness; resistance to deformation in humid atmosphere; and compatibility with a substantially water-insoluble thermoplastic polymer.

630. The composition of claim 629, wherein component (b) is derived from unsubstituted or substituted ethyleneimines.

631. The composition of claim 630, wherein component (b) is derived from ethyleneimines that correspond to the formula

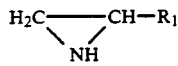

wherein
R₁ is hydrogen or methyl.

632. The composition of claim 631, wherein component (b) is a polyalkyleneimine derived from a compound selected from the group consisting of ethyleneimine, N-acetyl-ethyleneimine and N-propionyl-ethyleneimine.

633. The composition of claim 631, wherein component (b) is derived from ethyleneimine and has an average molecular weight from about 25,000 to about 430,000.

634. The composition of claim 629, wherein the weight percent ratio of destructurized starch to component (b) is from about 1:99 to about 99:1.

635. The composition of claim 634, wherein destructurized starch is present in an amount from about 60 percent to about 99 percent of the total composition.

636. The composition of claim 629, wherein the destructurized starch has a water content from about 5 percent to about 40 percent by weight of the total starch content.

637. The composition of claim 629, wherein the destructurized starch has a water content form about 10 percent to about 22 percent by weight of the total starch content.

638. A composition of matter capable of being formed into an article having substantial dimensional stability comprising:
(a) destructurized starch, and
(b) at least one compound selected from the group consisting of polyalkyleneimine polymers and polyalkyleneimine copolymers; and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

639. The composition of claim 638, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, substantially water-insoluble or crystallizable poly(alkylene oxides), and combination and mixtures thereof.

640. The composition of claim 639, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combination and mixtures thereof.

641. The composition of claim 638, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

642. The composition of claim 641, wherein component (c) is selected from the group consisting of ethylene/vinyl acetate copolymers a(EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; block copolymers of urethane-ethers, urethane-esters and combinations and mixtures thereof.

643. The composition of claim 638, wherein components (b) and (c) comprise from about 1 percent to about 99 percent by weight of the total composition.

644. The composition of claim 643, wherein components (b) and (c) comprise from about 10 percent to about 80 percent by weight of the total composition.

645. The composition of claim 644, wherein components (b) and (c) comprise from about 10 percent to about 40 percent by weight of the total composition.

646. The composition of claim 629, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

647. The composition of claim 629, further comprising an agriculturally active compound.

648. The composition of claim 629, in the form of a melt blend.

649. The composition of claim 629, in the form of a cooled solidified blend.

650. The composition of claim 629, in particulate, granulate or pelletized form.

651. The composition of claim 638, further comprising at least one material selected from the group consisting of adjuvants, filler, lubricants, mold release agents, plasticizers, forming agents, stabilizers, extenders, chemical modifiers, flow accelerators, coloring agents, pigments and mixtures thereof.

652. The composition of claim 638, further comprising an agriculturally active compound.

653. The composition of claim 638, in the form of a melt blend or a cooled solidified blend.

654. The composition of claim 638, in particulate, granulate or pelletized form.

655. A thermoplastic destructurized-starch product having substantial dimensional stability formed by a process comprising the steps of:
1) providing a mixture comprising starch and at least one compound selected from the group consisting of at least one compound selected from the group consisting of polyalkyleneimine polymers and polyalkyleneimine copolymers (component (b)); said compound being present in an amount effective to enhance at least one physical property of an article made from said mixture,
2) heating said mixture in a closed volume under sufficient temperature and pressure for a time long enough to effectuate destructurization of said starch and form a substantially homogenous melt;
3) shaping said melt into an article; and
4) allowing said shaped article to cool to a substantially dimensionally stable thermoplastic product.

656. The product of claim 655, wherein component (b) is derived from unsubstituted or substituted ethyleneimines.

657. The product of claim 655, wherein component (b) is derived from ethyleneimines which correspond to the formula

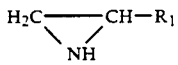

wherein
$R_1$ is hydrogen or methyl.

658. The product of claim 655, wherein component (b) is a polyalkyleneimine as derived from a compound selected from the group consisting of ethyleneimine, N-acetyl-ethyleneimine and N-propionyl-ethyleneimine.

659. The product of claim 655, wherein component (b) is derived from ethyleneimine and has an average molecular weight from about 25,000 to about 430,000.

660. The product of claim 655, wherein the weight percent ratio of destructurized starch to component (b) is from about 1:99 to about 99:1.

661. The product of claim 655, wherein destructurization of the starch is carried out at a temperature above its melting point and glass transition temperature.

662. The product of claim 655, wherein the destructurization of the starch is carried out at temperatures from about 105° C. to about 240° C.

663. The product of claim 661, wherein the destructurization of the starch is carried out at a temperature from about 130° C. to about 190° C.

664. The product of claim 661, wherein the melt is formed at a pressure from the minimum pressure necessary to avoid formation of water vapor under the applied temperature to about $150 \times 10^5$ N/m².

665. The product of claim 661, wherein the heat and pressure are maintained until the starch has undergone the specific narrow endothermic transition just prior to is endothermic change characteristic of oxidative and thermal degradation.

666. A thermoplastic destructurized-starch product having substantial dimensional stability formed by a process comprising the steps of:
1) providing a mixture comprising: (a) starch; (b) at least one compound selected from the group consisting of polyalkyleneimine polymers and polyalkyleneimine copolymers; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

667. The product of claim 666, wherein component (c) is selected form the group consisting of polyolefins, vinyl polymers, polystyrenes, polyacrylonitriles, poly(-vinyl carbazols), polyacrylates, polymethacrylates, polyacetals, thermoplastic polycondensates, polyarylethers, substantially water-insoluble or crystallizable poly(alkylene oxides), and combinations and mixtures thereof.

668. The product of claim 666, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

669. The product of claim 655, wherein said mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

670. The product of claim 655, in the form of a granulate.

671. The product of claim 655, in the form of a pellet.

672. The product of claim 655, in the form of a powder.

673. The product of claim 666, wherein said mixture further comprises at least one material selected from the group consisting of adjuvants, lubricants, flow accelerators, mold release agents, plasticizers, foaming agents, stabilizers, extenders, coloring agents, pigments and mixtures thereof.

674. The product of claim 666, in granulate, powder or pelletized form.

675. The product of claim 674, further processed to form a shaped article selected from the group consisting of containers, bottles, pipes, rods, packaging material, sheets, foams, films, sacks, bags and pharmaceutical capsules.

676. The product of claim 670, further processed to form a shaped article selected from the group consisting of containers, bottles, pipes, rods, packaging material, sheets, foams, films, sacks, bags and pharmaceutical capsules.

677. The product of claim 671, further processed to form a shaped article selected from the group consisting of containers, bottles, pipes, rods, packaging material, sheets, foams, films, sacks, bags and pharmaceutical capsules.

678. The product of claim 672, further processed to form a shaped article selected from the group consisting of containers, bottles, pipes, rods, packaging material, sheets, foams, films, sacks, bags and pharmaceutical capsules.

679. The product of claim 674, wherein component (c) is selected from the group consisting of polyolefins, vinyl polymers, polystyrenes, polyacrylonitriles, poly(vinyl carbazols), polyacrylates, polymethacrylates, polyacetals, polycondensates, polyarylethers, substantially water-insoluble or crystallizable poly(alkylene oxides), and combinations and mixtures thereof.

680. The product of the claim 674, wherein component (c) is selected from the group consisting of alkylene/vinyl ester copolymers; alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/ acrylonitrile copolymers and hydrolysates thereof, acrylamide/acrylonitrile copolymers, block copolymers of amide-ethers, amide-esters; block copolymers of urethane-ethers, urethane-esters and mixtures thereof.

681. The product of claim 670, wherein the further processing comprises foaming, filming, compression molding, injection molding, blow molding, extruding, co-extruding, vacuum-forming, thermo-forming and combinations thereof.

682. The product of claim 671, wherein the further processing comprises foaming, filming, compression molding, injection molding, blow molding, extruding, co-extruding, vacuum-forming, thermo-forming and combinations thereof.

683. The product of claim 672, wherein the further processing comprises foaming, filming, compression molding, injection molding, blow molding, extruding, co-extruding, vacuum-forming, thermo-forming and combinations thereof.

684. The product of claim 674 wherein the further processing comprises foaming, filming, compression molding, injection molding, blow molding, extruding, co-extruding, vacuum-forming, thermo-forming and combinations thereof.

685. A thermoplastic destructurized-starch substantially homogenous melt formed by a process comprising the steps of:
1) providing a mixture comprising starch and at least one compound selected from the group consisting of polyalkyleneimine polymers and polyalkyleneimine copolymers (component (b)); said compound being present in an amount effective to enhance at least one physical property of an article made from said mixture; and
2) heating said mixture in a closed volume under sufficient temperature and pressure for a time long enough to destructurize said starch and form said melt.

686. The melt of claim 685, wherein destructurization of the starch is carried out in the presence of at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

687. The melt of claim 685, wherein destructurization of the starch is carried out at a temperature from about 105° C. to about 240° C.

688. The melt of claim 685, wherein destructurization of the starch is carried out at a temperature form about 130° C. to about 190° C.

689. The melt of claim 688, wherein the melt is formed at a pressure from the minimum pressure necessary to avoid formation of water vapor under the applied temperature to about $150 \times 10^5$ N/m².

690. The melt of claim 689, wherein the heat and pressure are maintained until the starch has undergone the specific narrow endothermic transition just prior to its endothermic change characteristic of oxidative and thermal degradation.

691. A thermoplastic destructurized-starch substantially homogenous melt formed by the process comprising:
1) providing a mixture comprising: (a) starch; (b) at least one compound selected from the group consisting of polyalkyleneimine polymers and polyalkyleneimine copolymers; and (c) at least one substantially water-insoluble thermoplastic polymer that does not fall within the definition of (b);
2) heating said mixtures in a closed volume under sufficient temperature and pressure for a time long enough to destructurize said starch and form said melt.

692. The melt of claim 685, wherein component (c) is selected from the group consisting of polyolefins, vinyl polymers, polystyrenes, polyacrylonitriles, poly(vinyl carbazols), polyacrylates, polymethacrylates, polyacetals, thermoplastic polycondensates, polyarylethers, polyhydroxybutyrate, high molar-mass substantially water-insoluble or crystallizable poly(alkylene oxides) and combinations and mixtures thereof.

693. The melt of claim 685, wherein component (c) is selected from the group consisting of alkylene/vinyl ester-copolymers, alkylene/acrylate or methacrylate ester-copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

694. The melt of claim 685, wherein the mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

695. A composition of matter capable of being formed into an article having substantial dimensional stability comprising:
   (a) destructurized starch, and
   (b) at least one compound selected from the group consisting of styrene sulfonic acid polymers, styrene sulfonic acid copolymers, and salts thereof; said compound being present in an mount effective to enhance at least one physical property of said article wherein said polymer is present in an amount sufficient to modify in a desired manner at least one of the properties of: toughness; resistance to deformation in humid atmosphere; and compatability with a substantially water-insoluble thermoplastic polymer.

696. The composition of claim 695, wherein component (b) has a molecular weight from about 2,000 to about 1,500,000.

697. The composition of claim 695, wherein component (b) is a block copolymer of sulfonated styrene with an unsaturated monomer or a salt thereof.

698. The composition of claim 697, wherein said unsaturated monomer is selected from the group consisting of ethylene, butylene, isobutylene, propylene, butadiene, isoprene and styrene.

699. The composition of claim 695, wherein component (b) is a copolymer of sulfonated styrene and ethylene or a salt thereof.

700. The composition of claim 695, wherein component (b) is a copolymer of sulfonated styrene and butadiene or a salt thereof.

701. The composition of claim 695, wherein component (b) is a metal salt or ammonium salt.

702. The composition of claim 701, wherein said salt is a sodium, potassium, magnesium or zinc salt.

703. The composition of the claim 701, wherein said salt is a sodium or zinc salt.

704. The composition of claim 701, wherein the average molecular weight of component (b) is from about 10,000 to about 400,000.

705. The composition of claim 701, wherein the compound of component (b) has a degree of substitution from about 5 percent to about 100 percent.

706. The composition of claim 701, wherein the degree of substitution is from about 10 percent to about 50 percent.

707. The composition of claim 695, wherein the weight percent ratio of destructurized starch to component (b) is from about 1:99 to about 99:1.

708. The composition of claim 707, wherein destructurized starch comprises form about 60 percent to about 95 percent of the total composition.

709. The composition of claim 695, wherein the destructurized starch has a water content form about 5 percent to about 40 percent by weight of the total starch content.

710. The composition of claim 695, wherein the destructurized starch ha a water content from about 10 percent to about 22 percent by weight of the total starch content.

711. A composition of matter capable of being formed into an article having substantial dimensional stability comprising:
   (a) destructurized starch, and
   (b) at least one compound selected from the group consisting of styrene sulfonic acid polymer, styrene sulfonic acid copolymers, and salts thereof; and
   (c) at least one substantially water-insoluble thermoplastic polymer that does not fall within the definition of component (b), wherein (b) and (c) are present in a combined amount sufficient to effectuate dimensional stability and enhance at least one desired physical property of said article.

712. The composition of claim 711, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, essentially water-insoluble or crystallizable poly(alkylene oxides), and combinations and mixtures thereof.

713. The composition of claim 712, wherein component (c) is selected from the group consisting of polyethylenes, polypropylenes, polyisobutylenes, poly(vinyl chlorides), poly(vinyl acetates), polystyrenes, polyamides, polyesters, polyurethanes, polycarbonates, poly(alkylene terephthalates) and combinations and mixtures thereof.

714. The composition of claim 711, wherein component (c) is selected from the group consisting of alkylene/vinyl ester-copolymers, alkylene/acrylate or methacrylate copolymers, ABS copolymers styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers block copolymers of amide-ethers, amide-esters; block copolymers of urethane-ethers, urethane-esters and combinations and mixtures thereof.

715. The composition of claim 714, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAM), ethylene/maleic anhydride copolymers, block copolymers of amide-ethers, amide-esters; block copolymers of urethane-ethers, urethane-esters and combinations and mixtures thereof.

716. The composition of claim 711, wherein components (b) and (c) comprise from about 1 percent to about 99 percent by weight of the total composition.

717. The composition of claim 716, wherein components (b) and (c) comprise form about 20 percent to about 80 percent by weight of the total composition.

718. The composition of claim 717, wherein the sum of components (b) and (c) comprises from about 1 percent to about 30 percent by weight of the total composition.

719. The composition of claim 695, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

720. The composition of claim 695, further comprising an agriculturally active compound.

721. The composition of claim 695, in the form of a melt blend.

722. The composition of claim 695, in the form of a cooled solidified blend..

723. The composition of claim 695, in particulate, granular or pelletized form.

724. The composition of claim 711, further comprising at least one material selected from the group consisting of adjuvants, fillers, lubricants, mold release agents, plasticizers, foaming agents, stabilizers, extruders, chemical modifiers, flow accelerators, coloring agents, pigments and mixtures thereof.

725. The composition of claim 711, further comprising an agriculturally active agent.

726. The composition of claim 711, in the form of a melt blend or a cooled solidified blend..

727. The composition of claim 711, in particulate, granulate or pelletized form.

728. A thermoplastic destructurized-starch product having substantial dimensional stability formed by a process comprising the steps of:
1) providing a mixture comprising starch and at least one compound selected from the group consisting of styrene sulfonic acid polymers, styrene sulfonic acid copolymers, and salts thereof (component (b)); said compound being present in an amount effective to enhance the physical properties of an article made from said mixture;
2) heating said mixture in a closed volume under sufficient temperature and pressure for a time long enough to effectuate destructurization of said starch and form a substantially homogenous melt;
3) shaping said melt into an article; and
4) allowing said article to cool to a substantially dimensionally stable thermoplastic product.

729. The product of claim 728, wherein component (b) has a molecular weight form about 2,000 to about 1,500,000.

730. The product of claim 728, wherein component (b) is a block copolymer of sulfonated styrene with an unsaturated monomer.

731. The product of claim 730, wherein said unsaturated monomer is selected from the group consisting of ethylene, butylene, isobutylene, propylene, butadiene, isoprene and styrene.

732. The product of claim 728, wherein component (b) is a copolymer of sulfonated styrene and ethylene or a salt thereof.

733. The product of claim 728, wherein component (b) is a metal salt or an ammonium salt.

734. The product of claim 728, wherein said salt is a sodium or zinc salt.

735. The product of claim 728, wherein component (b) has a degree of substitution from about 5 percent to about 100 percent.

736. The product of claim 728, wherein the weight percent ratio of destructurized starch to component (b) is from about 1:99 to about 99:1.

737. The product of claim 728, wherein destructurization of the starch is carried out at a temperature above its melting point and glass transition temperature.

738. The product of claim 728, wherein the destructurization of the starch is carried out at a temperature from about 105° C. to about 240° C.

739. The product of claim 738, wherein the destructurization of the starch is carried out at a temperature from about 130° C. to about 190° C.

740. The product of claim 738, wherein the melt is formed at a pressure form the minimum pressure necessary to avoid formation of water vapor under the applied temperature to about $150 \times 10^5$ N/m$^2$.

741. The product of claim 740, wherein the heat and pressure are maintained until the starch has undergone the specific narrow endothermic transition just prior to its endothermic change characteristic of oxidative and thermal degradation.

742. A thermoplastic destructurized-starch product having substantial dimensional stability formed by a process comprising the steps of:
1) providing a mixture comprising: (a) starch; (b) at least one compound selected from the group consisting of styrene sulfonic acid polymers, styrene sulfonic acid copolymers, and salts thereof; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

743. The product of claim 742, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, essentially water-insoluble or crystallizable poly(alkylene oxides), and combinations and mixtures thereof.

744. The product of claim 742, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and mixtures thereof.

745. The product of claim 728, wherein said mixture further comprises at least one material selected from the group consisting of adjuvants, lubricants, flow accelerators, mold release agents, plasticizers, foaming agents, 746. The product of claim 728, in the form of a granulate, pellet or powder.

747. The product of claim 742, wherein said mixture further comprises at least one material selected from the group consisting of: adjuvants, lubricants, flow accelerators, mold release agents, plasticizers, foaming agent, stabilizers, extenders, coloring agents, pigments, chemical modifiers and mixtures thereof.

748. The product of claim 742, in the form of a granulate, a pellet or a powder.

749. The product of claim 746, further processed to form a shaped article selected from the group consisting of containers, bottles, pipes, rods, packaging material, sheets, foams, films, sacks, bags and pharmaceutical capsules.

750. The product of claim 748 further processed to form a shaped article selected from the group consisting of containers, bottles, pipes, rods, packaging material, sheets, foams, films, sacks, bags and pharmaceutical capsules.

751. The product of claim 747 wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, essentially water-insoluble or crystallizable poly(alkylene oxides), and combinations and mixtures thereof.

752. The product of the claims 747, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/ acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

753. The product of claim 749, wherein the further processing comprises foaming, filming, compression molding, injection molding, blow molding, extruding, co-extruding, vacuum-forming, thermo-forming and combinations thereof.

754. The product of claim 746, further comprising an agriculturally active compound.

755. The product of claim 747, further comprising an agriculturally active compound.

756. The product of claim 748, further comprising an agriculturally active compound.

757. The product of claim 749, further comprising an agriculturally active compound.

758. The product of claim 728, further comprising an agriculturally active compound.

759. The product of claim 729, further comprising an agriculturally active compound.

760. A thermoplastic destructurized-starch substantially homogenous melt formed by a process comprising the steps of:
1) providing a mixture comprising starch and at least one compound selected from the group consisting of styrene sulfonic acid polymers, styrene sulfonic acid copolymers, and salts thereof; said compound being present in an amount effective to enhance the physical properties of an article made from said mixture; and
2) heating said mixture in a closed volume under sufficient temperature and pressure for a time long enough to destructurize said starch and form said melt.

761. The melt of claim 760 wherein destructurization of the starch is carried out in the presence of at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

762. The melt of claim 760, wherein destructurization of the starch is carried out at a temperature from about 205° C. to about 240° C.

763. The melt of claim 760, wherein destructurization of the starch is carried out at a temperature form about 130° C. to about 90° C.

764. The melt of claim 763, wherein the melt is formed at a pressure form the minimum pressure necessary to avoid formation of water vapor under the applied temperature to about $150 \times 10^5$ N/m$^2$.

765. The melt of claim 764, wherein the heat and pressure are maintained until the starch has undergone the specific narrow endothermic transition just prior to its endothermic change characteristic of oxidative and thermal degradation.

766. A thermoplastic destructurized-starch substantially homogenous melt formed by the process comprising:
1) providing a mixture comprising: (a) starch; (b) at least one compound selected from the group consisting of styrene sulfonic acid, styrene sulfonic acid copolymers, and salts thereof; and (c) at least one substantially water-insoluble thermoplastic polymer that does not fall within the definition of (b);
2) heating said mixture in a closed volume under sufficient temperature and pressure for a time long enough to destructurize said starch and form said melt.

767. The melt of claim 760, wherein said component (c) is selected from the group consisting of: polyolefins, vinyl polymers, polystyrenes, polyacrylonitriles, polyacrylates, polymethacrylates, polyacetals, thermoplastic polycondensates, polyarylethers, thermoplastic polyimides, polyhydroxybutyrate, high molar-mass essentially water-insoluble or crystallizable poly(alkylene oxides) and combinations and mixtures thereof.

768. The melt of claim 766, wherein component (c) is selected from the group consisting of: alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

769. The melt of claim 766, wherein the mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

770. A composition of matter capable of being formed into an article having substantial dimensional stability comprising:
(a) destructurized starch, and
(b) at least one compound selected from the group consisting of polymers and copolymers that contain carboxylic groups at least partially present in the form of salts, wherein said polymers or copolymers do not contain further functional groups, said polymers and copolymers being present in an amount effective to enhance at least one physical property of said article; wherein said polymer is present in an amount sufficient to modify in a desired manner at least one of the properties of: toughness; resistance to deformation in humid atmosphere; and compatibility with a substantially water-insoluble thermoplastic polymer.

771. The composition of claim 770, wherein component (b) is obtained by polymerization of at least one monomer selected from the group consisting of acrylic acid, methacrylic acid, crotonic acid, maleic acid, maleic acid anhydride, itaconic acid, itaconic acid anhydride and combinations and mixtures thereof, with subsequent salt formation of a part or of all the carboxyl groups.

772. The composition of claim 770, wherein component (b) is obtained by copolymerization of at least one monomer selected from the group consisting of acrylic acid, methacrylic acid, crotonic acid, maleic acid, itaconic acid an combinations and mixtures thereof, with at least one monomer selected from the group consisting of ethylene, butylene, isobutylene, propylene, isoprene, butadiene and styrene and combinations and mixtures thereof, with subsequent salt formation.

773. The composition of claim 772, wherein said copolymer is a salt of an ethylene-acrylic-acid copolymer or a salt of an ethylene-methacrylic acid copolymer.

774. The composition of claim 770 wherein the component (b) comprises carboxylate groups of the formula

—COOM wherein M is a monovalent or polyvalent cation, ammonium (NH$_4$)$^+$ or an organic base cation.

775. The composition of claim 774, wherein said cation M is an alkali, magnesium or zinc cation.

776. The composition of claim 775, wherein said cation is sodium.

777. The composition of claim 770, wherein the amount of carboxyl and carboxylate containing monomer in component (b) is from about 5 percent to about 80 percent based on the total amount of monomeric moieties in component (b).

778. The composition of claim 770 wherein the amount of carboxyl and carboxylate containing monomer in component (b) is from about 3 mole percent to about 40 mole percent based on the total amount of monomeric moieties in component (b).

779. The composition of claim 770, wherein the amount of carboxyl and carboxylate containing monomer in component (b) is from about 3.5 mole percent to about 30 mole percent based on the total amount of monomeric moieties.

780. The composition of claim 777, wherein the amount of carboxyl and carboxylate containing monomer in component (b) is from about 3.5 mole percent to about 20 mole percent, based on, the total amount of monomeric moieties in component (b).

781. The composition of claim 777, wherein the degree of neutralization of component (b) is from about 40 percent to about 90 percent.

782. The composition of claim 770, wherein the weight percent ratio of destructurized starch to component (b) is from about 1:99 to about 99:1.

783. The composition of claim 777, wherein destructurized starch comprises from about 50 percent to about 99 percent of the total composition.

784. The composition of claim 770, wherein destructurized starch has a water content from about 5 percent to about 40 percent by weight of the total starch content.

785. The composition of claim 770, wherein destructurized starch has a water content from about 10 percent to about 22 percent by weight of the total starch content.

786. A composition of matter capable of being formed into an article having substantial dimensional stability comprising:
(a) destructurized starch, and
(b) at least one compound selected from the group consisting of polymers and copolymers that contain carboxylic groups at least partially present in the form of salts, wherein said polymers or copolymers do not contain further functional groups, and
(c) at least one substantially water-insoluble thermoplastic polymer that does not fall within the definition of component (b), wherein (b) and (c) are present in a combined amount sufficient to effectuate dimensional stability and enhance at least one desired physical property of said article.

787. The composition of claim 786, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

788. The composition of claim 787, wherein component (c) is selected from the group consisting of polyethylenes, polypropylenes, polyisobutylenes, poly(vinyl chlorides), poly(vinyl acetates), polystyrenes; polyamides, polyesters, polyurethanes, polycarbonates, poly(alkylene terephthalates) and combinations and mixtures thereof.

789. The composition of claim 786, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

790. The composition of claim 789, wherein component (c) is selected from the group consisting of ethylene/vinyl acetate copolymers (EVA), ethylene/vinyl alcohol copolymers (EVAL), ethylene/acrylic acid copolymers (EAA), ethylene/ethyl acrylate copolymers (EEA), ethylene/methacrylate copolymers (EMA), styrene/acrylonitrile copolymers (SAN), ethylene/maleic anhydride copolymers, block copolymers of amide-ethers, amide-esters; clock copolymers of urethane-ethers, urethaneesters and mixtures thereof.

791. The composition of claim 786, wherein components (b) and (c) comprise form about 1 percent to about 99 percent by weight of the total composition.

792. The composition of claim 791, wherein components (b) and (c) comprise from about 80 percent to about 10 percent by weight of the total composition.

793. The composition of claim 792, wherein components (b) and (c) comprise from about 40 percent to about 10 percent by weight of the total composition.

794. The composition of claim 770, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

795. The composition of claim 770, further comprising an agriculturally active compound.

796. The composition of claim 770, in the form of a melt blend.

797. The composition of claim 770, in the form of a cooled, solidified blend.

798. The composition of claim 770, in particulate, granulate or pelletized form.

799. The composition of claim 786, further comprising at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

800. The composition of claim 786, further comprising an agriculturally active compound.

801. The composition of claim 786, in the form of a melt blend or a cooled solidified blend.

802. The composition of claim 786, in particulate, granulate or pelletized form.

803. A thermoplastic destructurized-starch product having substantial dimensional stability formed by a process comprising the steps of:
1) providing a mixture comprising starch and at least one compound selected from the group consisting of polymers and copolymers that contain carboxylic groups at least partially present in the form of salts, wherein said polymers or copolymers do not contain further functional groups, said polymers and copolymers being present in an amount effective to enhance at least one physical property of an article made from said mixture (component (b));
2) heating said mixture in a closed volume under sufficient temperature and pressure for a time long enough to effectuate destructurization of said starch and form a substantially homogenous melt;
3) shaping said melt into an article; and
4) allowing said shaped article to cool to a substantially dimensionally stable thermoplastic product.

804. The product of claim 803, wherein component (b) is obtained by polymerization of at least one monomer selected from the group consisting of acrylic acid, methacrylic acid, crotonic acid, maleic acid, maleic acid anhydride, itaconic acid, itaconic acid anhydride and combinations and mixtures thereof, with subsequent salt formation of at least part of the carboxyl groups.

805. The product of claim 803, wherein component (b) is obtained by copolymerization of at least one monomer selected from the group consisting of acrylic acid, methacrylic acid, crotonic acid, maleic acid, itaconic acid and combinations and mixtures thereof, with at least one monomer selected from the group consisting of ethylene, butylene, isobutylene, propylene, isoprene, butadiene and styrene and combinations and mixtures thereof, with subsequent salt formation.

806. The product or claim 803, wherein said copolymer is a salt of an ethylene-acrylic-acid copolymer or a salt of an ethylene-methacrylic acid copolymer.

807. The product of claim 803, wherein component (b) comprises carboxylate groups of the formula

—COOM wherein M is a monovalent or polyvalent cation, an ammonium cation $(NH_4)^+$ or an organic base cation.

808. The product of claim 803, wherein the amount of carboxyl and carboxylate containing monomer in component (b) is from about 5 percent to about 80 percent based the total amount of component (b).

809. The product of claim 803, wherein the amount of carboxyl and carboxylate containing monomer in component (b) is from about 3 mole percent to about 40 mole percent, based on the total amount of component (b).

810. The product of claim 803, wherein the degree of neutralization is from about 40 percent to about 90 percent.

811. The product of claim 803, wherein the weight percent ratio of destructurized starch to component (b) is from about 1:99 to about 99:1.

812. The product of claim 803, wherein destructurization of the starch is carried out at a temperature above its melting point and glass transition temperature.

813. The product of claim 803, wherein the destructurization of the starch is carried out at a temperature from about 105° C. to about 240° C.

814. The product of claim 812, wherein the destructurization of the starch is carried out at a temperature form about 130° C. to about 190° C.

815. The product of claim 812, wherein the melt is formed at a pressure from the minimum pressure necessary to avoid formation of water vapor under the applied temperature to about $150 \times 10^5$ N/m².

816. The product of claim 815, wherein the heat and pressure are maintained until the starch has undergone the specific narrow endothermic transition just prior to its endothermic change characteristic of oxidative and thermal degradation.

817. A thermoplastic destructurized-starch product having substantial dimensional stability formed by a process comprising the steps of:
1) providing a mixture comprising: (a) starch; (b) at least one compound selected from the group consisting of polymers and copolymers that contain carboxylic groups at least partially present in the form of salts, wherein said polymers or copolymers do not contain further functional groups; and (c) at least one substantially water-insoluble thermoplastic polymer that does not fall within the definition of (b);
2) heating said mixture in a closed volume under sufficient temperature and pressure for a time long enough to effect destructurization of said starch and form a substantially homogenous melt;
3) shaping said melt into an article; and
4) allowing said shaped article to cool to a substantially dimensionally stable thermoplastic product.

818. The product of claim 817, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, substantially water-insoluble or crystallizable poly(alkylene oxides), and combinations and mixtures thereof.

819. The product of claim 817, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

820. The product of claim 803, further comprising at least one material selected from the group consisting of adjuvants, lubricants, flow accelerators, mold release agents, plasticizers, foaming agents, stabilizers, extenders, coloring agents, pigments, chemical modifiers and mixtures thereof.

821. The product of claim 803, in the form of a granulate.

822. The product of claim 803, in the form of a pellet.

823. The product of claim 803, in the form of a powder.

824. The product of claim 817, further comprising at least one material selected form the group consisting of: adjuvants, lubricants, flow accelerators, mold release agents, plasticizers, foaming agents, stabilizers, extenders, coloring agents, pigments, chemical modifiers and mixtures thereof.

825. The product of claim 817, in the form of a granulate, pellet or powder.

826. The product of claim 821, further processed to form a shaped article selected from the group consisting of containers, bottles, pipes, rods, packaging material, sheets, foams, films, sacks, bags and pharmaceutical capsules.

827. The product of claim 822, further processed to form a shaped article selected from the group consisting of containers, bottles, pipes, rods, packaging material, sheets foams, films, sacks, bags and pharmaceutical capsules.

828. The product of claim 823, further processed to form a shaped article selected from the group consisting of containers, bottles, pipes, rods, packaging material, sheets, foams, films, sacks, bags and pharmaceutical capsules.

829. The product of claim 825, further melted and processed to form a shaped article selected from the group consisting of containers, bottles, pipes, rods, packaging material, sheets, foams, films, sacks, bags and pharmaceutical capsules.

830. The product of claim 825, wherein component (c) is selected from the group consisting of polyolefins, vinyl polymers, polystyrenes, polyacrylonitriles, polyacrylates, polymethacrylates, polyacetals, polycondensates, polyarylethers, thermoplastic polyimides, substantially water-insoluble or crystallizable poly(alkylene oxides), and combinations and mixtures thereof.

831. The product of claim 825, wherein component (c) is selected from the group consisting of alkylene/vinyl ester copolymers, alkylene/acrylate or methacrylate copolymers, ABS copolymers, styrene/acrylonitrile copolymers, alkylene/maleic anhydride copolymers, partially hydrolyzed polyacrylates or polymethacrylates, partially hydrolyzed copolymers of acrylates and methacrylates, acrylic acid esters/acrylonitrile copolymers and hydrolysates thereof, acrylamide/acrylonitrile copolymers, block copolymers of amide-ethers, amide-esters; block copolymers of urethane-ethers, urethane-esters and combinations and mixtures thereof.

832. The product of claim 821, 822, or 823 wherein the further processing comprises foaming, filming, compression molding, injection molding, blow molding, extruding, co-extruding, vacuum-forming, thermoforming and combinations thereof.

833. A thermoplastic destructurized-starch substantially homogenous melt formed by a process comprising the steps of:
1) providing a mixture of starch and at least one compound selected from the group consisting of polymers and copolymers that contain carboxylic groups at least partially present in the form of salts, wherein said polymers or copolymers do not contain further functional groups, said polymers and copolymers being present in an amount effective to enhance the physical properties of an article made from said mixture (component (b)); and
2) heating said mixture in a closed volume under sufficient temperature and pressure for a time long enough to destructurize said starch and form said melt.

834. The melt of claim 833, wherein destructurization of the starch is carried out in the presence of at least one material selected from the group consisting of adjuvants, fillers, lubricants, mold release agents, plasticizers, foaming agents, stabilizers, extenders, chemical modifiers, flow accelerators, coloring agents, pigments and mixtures thereof.

835. The melt of claim 833, wherein destructurization of the starch is carried out at a temperature from about 105° C. to about 240° C.

836. The melt of claim 833, wherein destructurization of the starch is carried out at a temperature from about 130° C. to about 190° C.

837. The melt of claim 836, wherein the melt is formed at a pressure from the minimum pressure necessary to avoid formation of water vapor under the applied temperature to about $150 \times 10^5$ N/m$^2$.

838. The melt of claim 837, wherein the heat and pressure are maintained until the starch has undergone the specific narrow endothermic transition just prior to its endothermic change characteristic of oxidative and thermal degradation.

839. A thermoplastic destructurized-starch substantially homogenous melt formed by the process comprising:
1) providing a mixture comprising: (a) starch; (b) at least one compound selected from the group consisting of polymers and copolymers that contain carboxylic groups at least partially present in the form of salts, wherein said polymers or copolymers do not contain further functional groups; and (c) at least one substantially water-insoluble thermoplastic polymer that does not fall within the definition of (b);
2) heating said mixture in a closed volume under sufficient temperature and pressure for a time long enough to destructurize said starch and form said melt.

840. The melt of claim 839, wherein component (c) is selected from the group consisting of polyolefins, vinyl polymers, polystyrenes, polyacrylonitriles, polyacrylates, polymethacrylates, polyacetals, thermoplastic polycondensates, polyarylethers, thermoplastic polyimides, polyhydroxybutyrate, high molar-mass substantially water-insoluble or crystallizable poly(alkylene oxides) and combinations and mixtures thereof.

841. The melt of claim 839, wherein component (c) is selected from the group consisting of alkylene/vinyl ester-copolymers, alkylene/acrylate or methacrylate copolymers, ABS copolymers, styrene/acrylonitrile copolymers, alkylene/maleic anhydride copolymers, partially hydrolyzed polyacrylates of polymethacrylates, partially hydrolyzed copolymers of acrylates and methacrylates, acrylic acid esters/acrylonitrile copolymers and hydrolysates thereof, acrylamide/acrylonitrile copolymers block copolymers of amide-ethers, amide-esters; block copolymers of urethane-ethers, urethaneesters and combinations and mixtures thereof.

842. The melt of claim 839, wherein the mixture further comprises at least one material selected from the group consisting of adjuvants, lubricants, flow accelerators, mold release agents, plasticizers, foaming agents, stabilizers, extenders, coloring agents, pigments, chemical modifiers and mixtures thereof.

843. A blended polymeric material obtained from a melt comprising a water-containing destructurized starch and at least one essentially water-insoluble synthetic thermoplastic polymer.

844. The polymeric material of claim 843, wherein thermoplastic polymer is selected from the group consisting of polyolefins, vinylpolymers, polyacetals (POM); polycondensates, thermoplastic polyesters, polycarbonates, poly(alkylene terephthalates) polyarylethers; thermoplastic polyimides; polyhydroxybutyrate (PHB) and high molecular weight essentially water-insoluble polyalkylene oxides, and combinations and mixtures thereof and copolymers comprises thereof.

845. The polymeric material of claim 844, wherein said thermoplastic polymer is selected from the group consisting of: polyethylene (PE), polyisobutylenes, polypropylenes, poly(vinyl chloride) (PVC), poly(vinyl acetates), polystyrenes, polyacrylonitriles (PAN), polyvinylcarbazols (PVK), polyamides (PA), essentially water-insoluble poly(acrylic acid esters) and essentially water-insoluble poly(methacrylic acid esters), copolymers, combinations and mixtures thereof.

846. The polymeric material of claim 844, wherein said thermoplastic polymer is selected from the group consisting of ethylene/vinyl acetate-copolymers (EVA), ethylene/vinyl alcohol-copolymers (EVAL), ethylene/acrylic acid-copolymers (EAA), ethylene/ethyl acrylate-copolymers (EEA), ethylene/methyl acrylate-copolymers (EMA), Acrylonitrile-butadiene-styrene-copolymers (ABS), styrene/acrylonitrile-copolymers (SAN), polyacetals and copolymers, combinations and mixtures thereof.

847. The polymeric material of claim 843, wherein the ratio of the water-containing destructurized starch to synthetic polymer is from about 0.1:99.9 to about 99.9:0.1, wherein the water-containing starch comprises at least about 50 percent by weight of the entire composition.

848. The polymeric material of claim 847, wherein the ratio of the synthetic polymer to the starch/water component is from about 0.5 to about 5% and about 99.5 to about 95% by weight.

849. The polymeric material of claim 848, wherein said starch is selected from the group consisting of chemically substantially non-modified starch in the form of carbohydrates of natural, vegetable origin composed mainly of amylose or amylopectin or amylose and amylopectin.

850. The polymeric material of claim 849, wherein said starch is mixed with at least one synthetic polymer and heated for destructurization in a closed volume for a time long enough to effect destructurization at a temperature from about 105° C. to about 190° C.

851. The polymeric material of claim 850, wherein destructurization is carried out at a pressure form about zero to about $150 \times 10^5$ N/m².

852. The polymeric material of claim 851, wherein the pressure is less than or equal to about $75 \times 10^5$ N/m².

853. The polymeric material of claim 852, wherein the pressure is less than or equal to about $50 \times 10^5$ N/m².

854. The polymeric material of claim 843, wherein the starch has a water content in the range from about 10 to about 20 percent by weight of the starch/water component.

855. The polymeric material of claim 854, wherein the starch/synthetic polymer mixture contains extenders, fillers, lubricants, plasticizers or coloring agents.

856. The polymeric material of claim 855, comprising up to about 50% by weight of the total composition of at least one extender.

857. The polymeric material of claim 856, comprising from about 0.02 percent to about 3 percent, by weight of at least one organic filler.

858. The polymeric material of claim 857, comprising from about 0.5 weight percent to about 15 weight percent plasticizer.

859. The polymeric material of claim 858, comprising from about 0.001 weight percent to about 10 weight percent coloring agent.

860. The polymeric material of claim 859, wherein the plasticizer and water content does not exceed about 25% by weight of the total composition.

861. The polymeric material of claim 860, wherein the blended starch contains at least one active ingredient selected from the group consisting of pharmaceuticals, agriculturally active compounds and combinations and mixtures thereof.

862. The polymeric material of claim 843, in the form of a melt.

863. The polymeric material of claim 862, in the form of a cooled, solidified melt.

864. A method of producing a polymeric material comprising a modified destructurized starch and a substantially water-insoluble synthetic thermoplastic polymer comprising the steps of heating a starch having a water content from about 5 to about 30 percent by weight based on the starch/water component in a closed volume to elevated temperatures thereby at elevated pressures for a time long enough to form a melt; and mixing into said starch at least one essentially water-insoluble synthetic thermoplastic polymer before or during melt formation to make a blend.

865. The polymeric material of claim 843, in the form of a carrier for active ingredients.

866. The process of claim 864, further comprising the step of shaping said blend by injection molding, blow molding, extrusion or coextrusion, compression molding or vacuum forming.

867. Shaped articles produced by the process of claim 866.

868. The articles of claim 867, in the form of bottles, sheets, films, packaging materials, pipes, rods, laminates, sacks, bags or pharmaceutical capsules, granules or powders.

* * * * *

EX PARTE REEXAMINATION CERTIFICATE (7812th)

United States Patent
Lay et al.

(10) Number: US 5,095,054 C1
(45) Certificate Issued: Oct. 19, 2010

(54) POLYMER COMPOSITIONS CONTAINING DESTRUCTURIZED STARCH

(75) Inventors: Gustav Lay, Bad Bellingen (DE); Johannes Rehm, Bad Krozingen (DE); Robert F. Stepto, Cheshire (GB); Markus Thoma, Reihen (CH); Jean-Pierre Sachetto, Arlesheim (CH); David J. Lentz, Randolph, NJ (US); Jakob Silbiger, Basel (CH)

(73) Assignee: Novon International, Inc., Tonawanda, NY (US)

Reexamination Request:
No. 90/009,037, Feb. 11, 2008

Reexamination Certificate for:
Patent No.: 5,095,054
Issued: Mar. 10, 1992
Appl. No.: 07/539,846
Filed: Jun. 18, 1990

Related U.S. Application Data

(63) Continuation-in-part of application No. 07/431,715, filed on Oct. 2, 1989, now abandoned, which is a continuation-in-part of application No. 07/430,764, filed on Oct. 2, 1989, now abandoned, which is a continuation-in-part of application No. 07/431,672, filed on Oct. 2, 1989, now abandoned, which is a continuation-in-part of application No. 07/449,313, filed on Dec. 8, 1989, now abandoned, which is a continuation-in-part of application No. 07/447,741, filed on Dec. 8, 1989, now abandoned, which is a continuation-in-part of application No. 07/440,955, filed on Dec. 22, 1989, now abandoned, which is a continuation-in-part of application No. 07/447,979, filed on Dec. 8, 1989, now abandoned, which is a continuation-in-part of application No. 07/449,095, filed on Dec. 8, 1989, now abandoned, which is a continuation-in-part of application No. 07/447,747, filed on Dec. 8, 1989, now abandoned, which is a continuation-in-part of application No. 07/449,314, filed on Dec. 8, 1989, now abandoned, which is a continuation-in-part of application No. 07/443,791, filed on Oct. 22, 1989, now abandoned, which is a continuation-in-part of application No. 07/447,730, filed on Dec. 8, 1989, now abandoned, which is a continuation-in-part of application No. 07/298,603, filed on Jan. 18, 1989, now abandoned, which is a continuation-in-part of application No. 07/368,486, filed on Jun. 19, 1989, now abandoned, which is a continuation-in-part of application No. 07/369,978, filed on Jun. 22, 1989, now abandoned, which is a continuation-in-part of application No. 07/369,983, filed on Jun. 22, 1989, now abandoned, which is a continuation-in-part of application No. 07/407,643, filed on Jul. 18, 1989, now abandoned, which is a continuation-in-part of application No. 07/376,057, filed on Jul. 6, 1989, now abandoned, which is a continuation-in-part of application No. 07/378,120, filed on Jul. 11, 1989, now abandoned, which is a continuation-in-part of application No. 07/377,981, filed on Jul. 11, 1989, now abandoned, which is a continuation-in-part of application No. 07/378,536, filed on Jul. 11, 1989, now abandoned, which is a continuation-in-part of application No. 07/381,620, filed on Jul. 18, 1989, now abandoned, which is a continuation-in-part of application No. 07/407,644, filed on Jul. 18, 1989, now abandoned, which is a continuation-in-part of application No. 07/382,870, filed on Jul. 20, 1989, now abandoned, which is a continuation-in-part of application No. 07/382,869, filed on Jul. 20, 1989, now abandoned.

(51) Int. Cl.
| | |
|---|---|
| A61K 47/32 | (2006.01) |
| A61K 47/36 | (2006.01) |
| A61K 47/30 | (2006.01) |
| C08J 5/18 | (2006.01) |
| C08L 3/00 | (2006.01) |
| C08L 3/02 | (2006.01) |
| C08L 23/04 | (2006.01) |
| C08L 25/04 | (2006.01) |
| C08L 101/00 | (2006.01) |
| A01N 25/10 | (2006.01) |

(52) U.S. Cl. ............................. 524/47; 524/52; 524/53; 264/328.14; 424/451

(58) Field of Classification Search ........................ None
See application file for complete search history.

(56) References Cited

U.S. PATENT DOCUMENTS 3,884,892 A    5/1975    Winkler et al. ............. 260/91.3

(Continued)

OTHER PUBLICATIONS

Grant of Grant & Hackh's Chemical Dictionary, Fifth Edition, p. 228, 2nd column for the word "extender", 1987.*

(Continued)

*Primary Examiner*—Dwayne C Jones

(57) ABSTRACT

A thermoplastic polymer composition comprising:

(a) a destructurized starch, and either (b) an effective amount of at least one compound selected from the following: (1) a polymer which contains at least two different types of functional groups, one of said types of these groups being hydroxyl groups; (2) at least one polymer which does not contain hydroxyl groups and is selected from the group consisting of polymers which contain at least two types of functional groups bound to the same molecule one type of these groups being carboxylate groups; (3) at least one polymer selected from the group consisting of polymers which contain tertiary amino groups and/or salts thereof and/or quaternary ammonium groups; (4) at least one polymer selected from the group of polysaccharides which have been chemically modified to contain added hydroxyalkyl groups and/or contain alkyl ether groups, and/or contain ester groups; (5) at least one compound selected from the group consisting of copolymers of vinyl pyrrolidone; (6) at least one compound selected from the group consisting of cationically modified polysaccharides; (7) at least one compound selected from the group consisting of anionically modified polysaccharides; (8) at least one polymer selected from the group of copolymers containing vinyl alcohol units together with aliphatic chain units as are obtained by copolymerization of vinyl esters, preferably vinyl acetate, with unsaturated monomers containing no functional group with subsequent hydrolysis of the vinyl ester group; (9) at least one compound selected from the group consisting of polysaccharide graft copolymers and graft copolymers of polysaccharide derivatives; (10) at least one compound selected from the group consisting of polyalkyleneimine polymers and polyalkyleneimine copolymers; (11) at least one compound selected from the group consisting of styrene sulfonic acid polymers, styrene sulfonic acid copolymers, and salts thereof; and (12) at least one compound selected from the group consisting of polymers and copolymers which contain carboxylic groups which partially or wholly are present in the form of their salts and wherein said polymers or copolymers do not contain further functional groups; or (c) At least one substantially water-insoluble thermoplastic polymer. combinations of (a), (b) and (c) are also disclosed.

U.S. PATENT DOCUMENTS

| | | | |
|---|---|---|---|
| 4,424,642 A | 1/1984 | Stubler et al. | 43/114 |
| 4,432,965 A | 2/1984 | Keith et al. | 424/19 |
| 4,673,438 A | 6/1987 | Wittwer et al. | 106/126 |
| 4,900,361 A | 2/1990 | Sachetto et al. | 106/213 |
| 5,554,577 A | 9/1996 | Kempf et al. | 504/116 |

OTHER PUBLICATIONS

Nwufo, et al., "Extrusion of Starch–Extended Water–Soluble Polyvinyl Alcohol," Ind. Eng. Chem. Prod. Res. Dev., 1984, pp. 594–595.

* cited by examiner

EX PARTE REEXAMINATION CERTIFICATE ISSUED UNDER 35 U.S.C. 307

THE PATENT IS HEREBY AMENDED AS INDICATED BELOW

AS A RESULT OF REEXAMINATION, IT HAS BEEN DETERMINED THAT:

Claims 29-31, 39-42, 54-59, 67-72 and 76-88 are cancelled.

Claims 1-28, 32-38, 43-53, 60-66, 73-75 and 89-868 were not reexamined.

\* \* \* \* \*